United States Patent
Kang et al.

(10) Patent No.: US 9,698,355 B2
(45) Date of Patent: Jul. 4, 2017

(54) ORGANIC ELECTROLUMINESCENT COMPOUNDS AND ORGANIC ELECTROLUMINESCENT DEVICE COMPRISING THE SAME

(71) Applicant: Rohm and Haas Electronic Materials Korea Ltd., Cheonan (KR)

(72) Inventors: Hee-Ryong Kang, Seoul (KR);
Hyun-Ju Kang, Gwangmyeong (KR);
Doo-Hyeon Moon, Hwaseong (KR);
Young-Mook Lim, Cheonan (KR);
Bitnari Kim, Cheonan (KR);
Nam-Kyun Kim, Yongin (KR)

(73) Assignee: Rohm and Haas Electronic Materials Korea Ltd., Cheonan-si (KR)

( * ) Notice: Subject to any disclaimer, the term of this patent is extended or adjusted under 35 U.S.C. 154(b) by 0 days.

(21) Appl. No.: 15/318,099

(22) PCT Filed: Jun. 26, 2015

(86) PCT No.: PCT/KR2015/006574
§ 371 (c)(1),
(2) Date: Dec. 12, 2016

(87) PCT Pub. No.: WO2015/199493
PCT Pub. Date: Dec. 30, 2015

(65) Prior Publication Data
US 2017/0125692 A1  May 4, 2017

(30) Foreign Application Priority Data

Jun. 27, 2014 (KR) .......... 10-2014-0079487
Jun. 9, 2015 (KR) .......... 10-2015-0081430

(51) Int. Cl.
*H01L 51/00* (2006.01)
*C07D 491/22* (2006.01)
*C09K 11/02* (2006.01)
*C09K 11/06* (2006.01)

(52) U.S. Cl.
CPC ........ *H01L 51/0071* (2013.01); *C07D 491/22* (2013.01); *C09K 11/02* (2013.01); *C09K 11/06* (2013.01); *C09K 2211/1062* (2013.01)

(58) Field of Classification Search
CPC . C09K 2211/1062; C09K 11/02; C09K 11/06; C07D 491/22; H01L 51/0071
See application file for complete search history.

(56) References Cited

U.S. PATENT DOCUMENTS

2011/0303901 A1  12/2011  Cheng et al.

FOREIGN PATENT DOCUMENTS

| JP | 2014-73965 | * 10/2012 | ........... C07D 487/06 |
|---|---|---|---|
| JP | 2014-073965 A | 4/2014 | |
| KR | 2012-0087935 A | 8/2012 | |
| KR | 20120095997 A | 8/2012 | |

* cited by examiner

*Primary Examiner* — Erich A Leeser
(74) *Attorney, Agent, or Firm* — Jae-Choon You

(57) ABSTRACT

The present invention relates to a novel organic electroluminescent compound and an organic electroluminescent device comprising the same. The organic electroluminescent compound of the present invention has high luminous efficiency, and thus can be used as a host in a light-emitting layer; and an organic electroluminescent device comprising the organic electroluminescent compounds of the present invention has long operating lifespan, provides improved current efficiency and power efficiency, and gives colors having high purity.

6 Claims, No Drawings

ORGANIC ELECTROLUMINESCENT COMPOUNDS AND ORGANIC ELECTROLUMINESCENT DEVICE COMPRISING THE SAME

TECHNICAL FIELD

The present invention relates to novel organic electroluminescent compounds and an organic electroluminescent device comprising the same.

BACKGROUND ART

An electroluminescent (EL) device is a self-light-emitting device with the advantages of providing a wider viewing angle, a greater contrast ratio, and a faster response time. The first organic EL device was developed by Eastman Kodak, by using small aromatic diamine molecules and aluminum complexes as materials for forming a light-emitting layer (see Appl. Phys. Lett. 51, 913, 1987).

An organic EL device changes electric energy into light by the application of electric current to an organic light-emitting material, and commonly comprises an anode, a cathode, and an organic layer formed between the two electrodes. The organic layer of the organic EL device may be composed of a hole injection layer (HIL), a hole transport layer (HTL), an electron blocking layer (EBL), a light-emitting layer (EML) (containing host and dopant materials), an electron buffer layer, a hole blocking layer (HBL), an electron transport layer (ETL), an electron injection layer (EIL), etc.; the materials used in the organic layer can be classified into a hole injection material, a hole transport material, an electron blocking material, a light-emitting material, an electron buffer material, a hole blocking material, an electron transport material, an electron injection material, etc., depending on functions. In the organic EL device, holes from an anode and electrons from a cathode are injected into a light-emitting layer by the application of electric voltage, and an exciton having high energy is produced by the recombination of holes and electrons. The organic light-emitting compound moves into an excited state by the energy and emits light from energy when the organic light-emitting compound returns to the ground state from the excited state.

The most important factor determining luminous efficiency in an organic EL device is light-emitting materials. The light-emitting materials are required to have the following features: high quantum efficiency, high movement degree of an electron and a hole, and formability of a uniform and stable layer. The light-emitting materials are classified into blue light-emitting materials, green light-emitting materials, and red light-emitting materials according to the light-emitting color, and further include yellow light-emitting materials or orange light-emitting materials. Furthermore, the light-emitting material is classified into a host material and a dopant material in a functional aspect. Recently, an urgent task is the development of an organic EL device having high efficiency and long lifespan. In particular, the development of highly excellent light-emitting material compared to conventional light-emitting materials is urgently required considering the EL properties necessary for medium- and large-sized OLED panels. For this, preferably, as a solvent in a solid state and an energy transmitter, a host material should have high purity and a suitable molecular weight in order to be deposited under vacuum. Furthermore, a host material is required to have high glass transition temperature and pyrolysis temperature for guaranteeing thermal stability, high electrochemical stability for long lifespan, easy formability of an amorphous thin film, good adhesion with adjacent layers, and no movement between layers.

Until now, Iridium(III) complexes have been widely known as phosphorescent materials, including bis(2-(2'-benzothienyl)-pyridinato-N,C3')iridium(acetylacetonate) ((acac)Ir(btp)$_2$), tris(2-phenylpyridine)iridium (Ir(ppy)$_3$), and bis(4,6-difluorophenylpyridinato-N,C2)picolinatoiridium (Firpic) as red, green, and blue light-emitting materials, respectively.

A mixed system of dopant/host materials can be used as light-emitting materials to improve color purity, luminous efficiency, and stability. If the dopant/host material system is used, the selection of the host materials is important since the host materials greatly influence the efficiency and performance of a light-emitting device. In conventional technique, 4,4'-N,N'-dicarbazol-biphenyl (CBP) is the most widely known phosphorescent host material. Pioneer (Japan) et al., currently developed a high performance organic EL device by employing bathocuproine (BCP), aluminum (III) bis(2-methyl-8-quinolinato)(4-phenylphenolate) (BAlq), etc., which were used in a hole blocking layer, as host materials.

Although these phosphorescent host materials provide good light-emitting characteristics, they have the following disadvantages: (1) Due to their low glass transition temperatures and poor thermal stability, their degradation may occur during a high-temperature deposition process in a vacuum. (2) The power efficiency of an organic EL device is given by [($\pi$/voltage)×current efficiency], and the power efficiency is inversely proportional to voltage. An organic EL device comprising phosphorescent host materials provides higher current efficiency (cd/A) and has a higher driving voltage than one comprising fluorescent host materials. Thus, the organic EL device using conventional phosphorescent host materials has no advantage in terms of power efficiency (lm/W). (3) Furthermore, the operating lifespan and luminous efficiency of the organic EL device are not satisfactory.

Thus, in order to embody excellent properties of the organic EL device, materials constituting the organic layers in the device, in particular host or dopant materials constituting a light-emitting material, should be suitably selected. In this regard, Korean Patent Application Laying-open Nos. 10-2012-0087935 and 10-2012-0095997 disclose fused heterocyclic compounds used as a matrix material, a hole transport or an electron blocking material, an exciton blocking material, or an electron transport or a hole blocking material of a phosphorescent OLED. In addition, U.S. Patent Application Laying-open No. 2011-0303901 discloses indole-quinoline derivatives used as a host or dopant material, a hole transport material, an electron transport material, a hole blocking material, an electron blocking material, a hole injection material, or an electron injection material. However, the organic EL devices comprising the compounds recited in the above publications still do not satisfy power efficiency, luminous efficiency, lifespan, etc. Thus, the present inventors have tried to find organic electroluminescent compounds that can provide an organic EL device with properties superior to the compounds recited in the above publications and have found compounds providing a device with high luminous efficiency and excellent device properties.

DISCLOSURE OF THE INVENTION

Problems to be Solved

The object of the present invention is to provide organic electroluminescent compounds which can provide an organic EL device with long lifespan and improved luminous efficiency.

Solution to Problems

The present inventors found that the above objective can be achieved by a compound represented by the following formula 1 or 2:

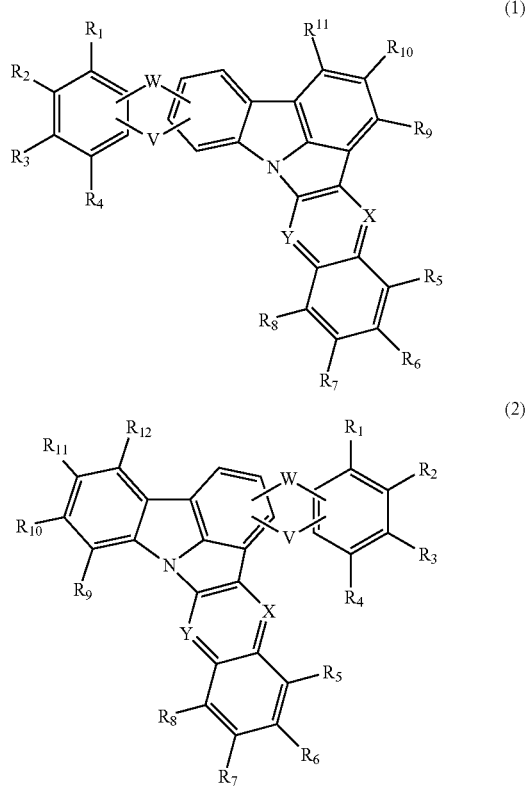

wherein

X and Y each independently represent —$CR_{13}$— or —N—, with the proviso that X and Y do not simultaneously represent —$CR_{13}$—;

W and V each independently represent a single bond, O or S; and $R_1$ to $R_{13}$ each independently represent hydrogen, deuterium, a halogen, a cyano group, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted (C1-C30)alkoxy group, a substituted or unsubstituted tri(C1-C30)alkylsilyl group, a substituted or unsubstituted di(C1-C30)alkyl(C6-C30)arylsilyl group, a substituted or unsubstituted (C1-C30)alkyldi(C6-C30)arylsilyl group, a substituted or unsubstituted tri(C6-C30)arylsilyl group, a substituted or unsubstituted mono- or di(C1-C30)alkylamino group, a substituted or unsubstituted mono- or di(C6-C30)arylamino group, or a substituted or unsubstituted (C1-C30)alkyl(C6-C30)arylamino group; or are linked to an adjacent substituent(s) to form a substituted or unsubstituted mono- or polycyclic (C3-C30) alicyclic or aromatic ring whose carbon atom(s) may be replaced with at least one hetero atom selected from nitrogen, oxygen, and sulfur.

Effects of the Invention

The organic electroluminescent compounds according to the present invention have better luminous efficiency than that of conventional compounds. Thus, an organic EL device comprising the organic electroluminescent compounds of the present invention as a host material for light-emitting has long operating lifespan, provides improved current efficiency and power efficiency, reduces electric power consumption, and gives colors having high purity.

EMBODIMENTS OF THE INVENTION

Hereinafter, the present invention will be described in detail. However, the following description is intended to explain the invention, and is not meant in any way to restrict the scope of the invention.

The present invention relates to an organic electroluminescent compound represented by formula 1 or 2 above, an organic electroluminescent material comprising the organic electroluminescent compound, and an organic EL device comprising the material.

In formulae 1 and 2 above, each of $R_1$ to $R_{13}$ may preferably represent hydrogen, a substituted or unsubstituted (C6-C20)aryl group, or a substituted or unsubstituted 5- to 20-membered heteroaryl group; and more preferably, hydrogen, or a substituted or unsubstituted (C6-C12)aryl group.

Herein, "(C1-C30)alkyl(ene)" is meant to be a linear or branched alkyl(ene) having 1 to 30 carbon atoms, in which the number of carbon atoms is preferably 1 to 20, more preferably 1 to 10, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 carbon atoms, in which the number of carbon atoms is preferably 3 to 20, more preferably 3 to 7, and includes cyclopropyl, cyclobutyl, cyclopentyl, cyclohexyl, etc. "3- to 7-membered heterocycloalkyl" is a cycloalkyl having at least one heteroatom selected from the group consisting of B, N, O, S, P(=O), Si, and P, preferably O, S, and N, and 3 to 7, preferably 5 to 7 ring backbone atoms, and includes tetrahydrofuran, pyrrolidine, thiolan, tetrahydropyran, etc. "(C6-C30)aryl(ene)" is a monocyclic or fused ring derived from an aromatic hydrocarbon having 6 to 30 carbon atoms, in which the number of carbon atoms is preferably 6 to 20, more preferably 6 to 15, and includes phenyl, biphenyl, terphenyl, naphthyl, fluorenyl, phenanthrenyl, anthracenyl, indenyl, triphenylenyl, pyrenyl, tetracenyl, perylenyl, chrysenyl, naphthacenyl, fluoranthenyl, etc. "3- to 30-membered heteroaryl(ene)" is an aryl group having at least one, preferably 1 to 4 heteroatom selected from the group consisting of B, N, O, S, P(=O), Si, and P, and 3 to 30 ring backbone atoms; is a monocyclic ring, or a fused ring condensed with at least one benzene ring; has preferably 3 to 20, more preferably 3 to 15 ring backbone atoms; may be partially saturated; may be one formed by linking at least one heteroaryl or aryl group to a heteroaryl group via a single bond(s); and includes a monocyclic ring-type heteroaryl, such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl, such as benzofuranyl, benzothiophenyl, isobenzofuranyl, dibenzofuranyl, dibenzothiophenyl, benzoimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or group, i.e., a substituent. Substituents of the substituted alkyl group, the substituted cycloalkyl group, the substituted aryl group, the substituted heteroaryl group, the substituted alkoxy group, the substituted alkylsilyl group, the substituted arylsilyl group, the substituted alkylamino group, the substituted arylamino group, or the substituted mono- or polycyclic (C3-C30) alicyclic or aromatic ring in formulae 1 and 2 above are each independently at least one selected from the group consisting of deuterium; a halogen; a cyano group; a carboxyl group; a nitro group; a hydroxyl group; a (C1-C30) alkyl group; a halo(C1-C30)alkyl group; a (C2-C30)alkenyl group; a (C2-C30)alkynyl group; a (C1-C30)alkoxy group; a (C1-C30)alkylthio group; a (C3-C30)cycloalkyl group; a (C3-C30)cycloalkenyl group; a 3- to 7-membered heterocycloalkyl group; a (C6-C30)aryloxy group; a (C6-C30)arylthio group; a 3- to 30-membered heteroaryl group which is unsubstituted or substituted with a (C6-C30)aryl group; a (C6-C30)aryl group which is unsubstituted or substituted with a 3- to 30-membered heteroaryl group; a tri(C1-C30) alkylsilyl group; a tri(C6-C30)arylsilyl group; a di(C1-C30) alkyl(C6-C30)arylsilyl group; a (C1-C30)alkyldi(C6-C30) arylsilyl group; an amino group; a mono- or di(C1-C30) alkylamino group; a mono- or di(C6-C30)arylamino group; a (C1-C30)alkyl(C6-C30)arylamino group; a (C1-C30)alkylcarbonyl group; a (C1-C30)alkoxycarbonyl group; a (C6-C30)arylcarbonyl group; a di(C6-C30)arylboronyl group; a di(C1-C30)alkylboronyl group; a (C1-C30)alkyl(C6-C30) arylboronyl group; a (C6-C30)aryl(C1-C30)alkyl group; and a (C1-C30)alkyl(C6-C30)aryl group.

The compound of formula 1 or 2 above may be selected from the group consisting of the following compounds, but is not limited thereto:

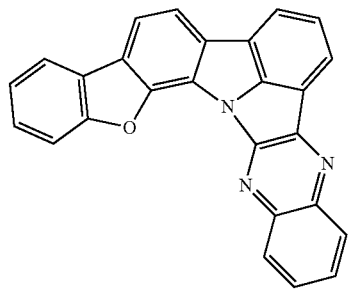

A-1

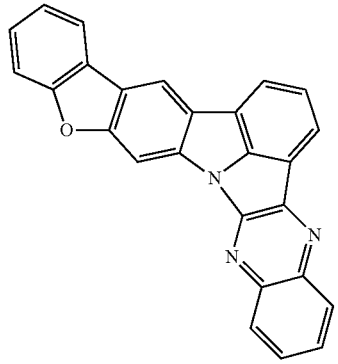

A-2

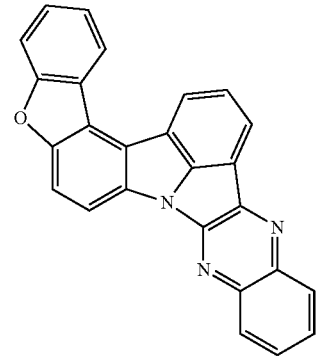

A-3

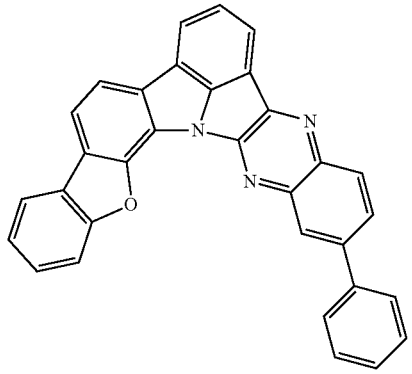

A-4

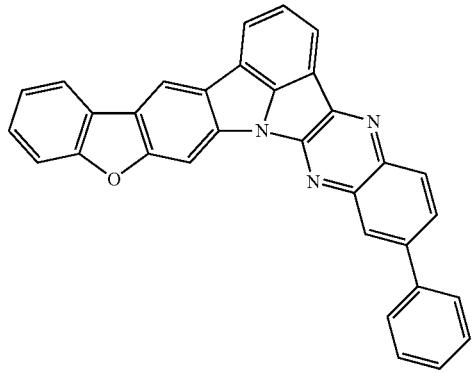

A-5

A-6
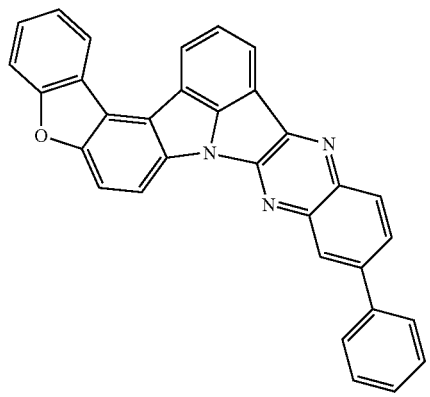
A-7
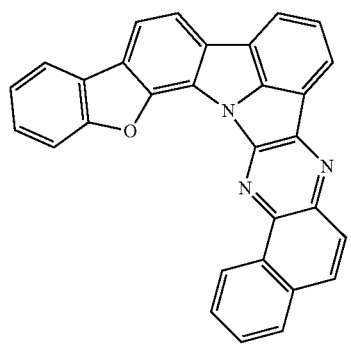
A-8
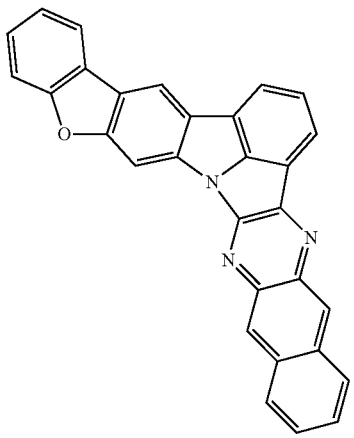
A-9
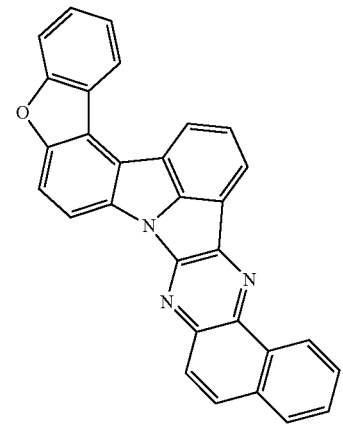
A-10
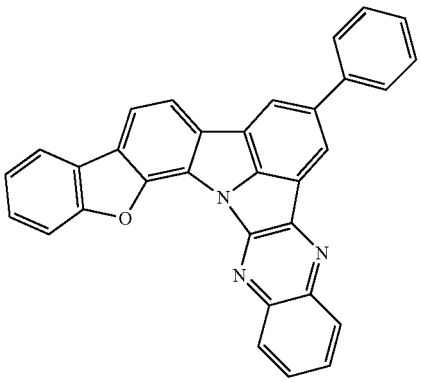
A-11
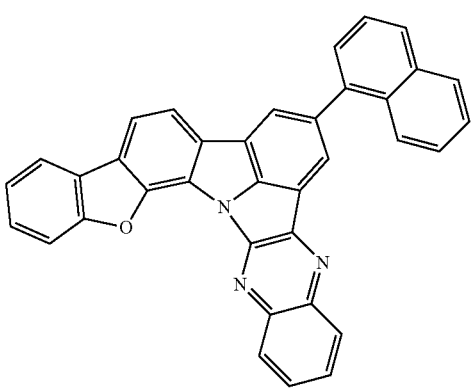
A-12
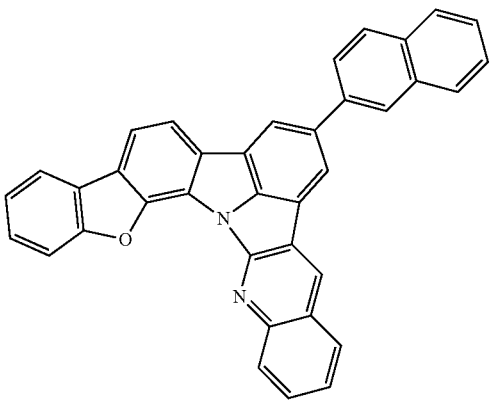
A-13
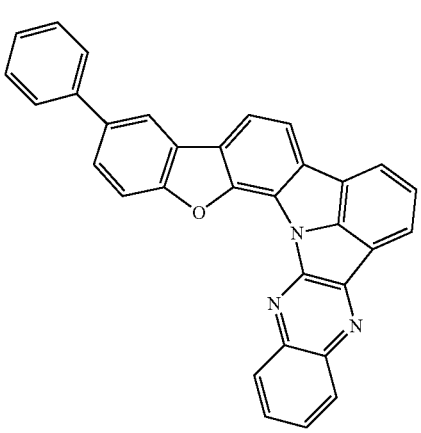

A-14
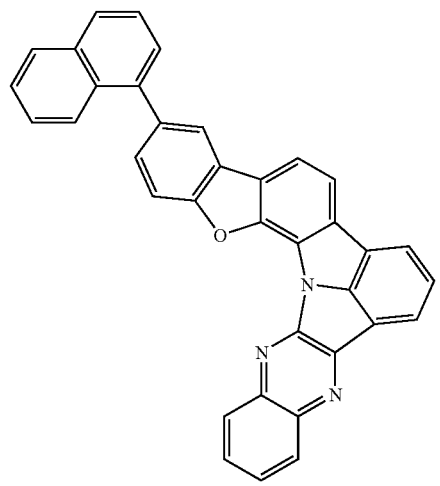
A-15
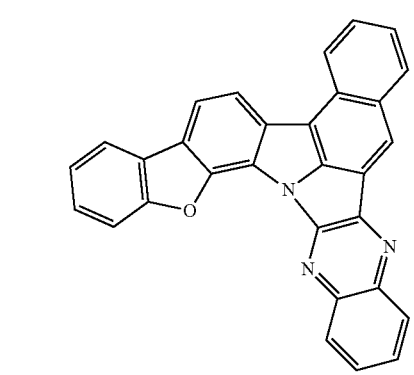
A-16
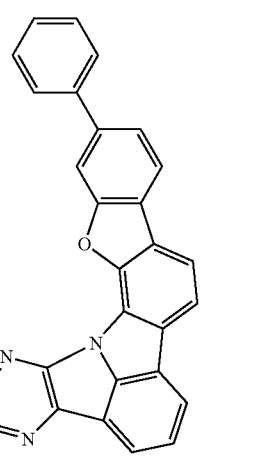
A-17
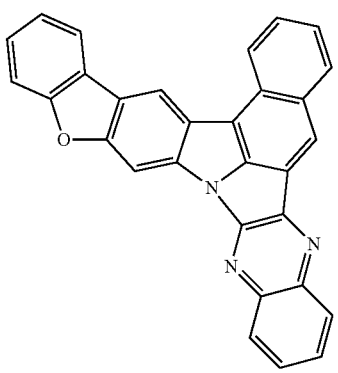
A-18
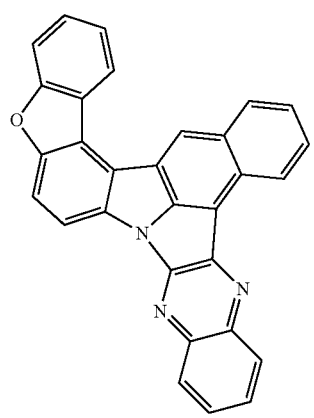
A-19
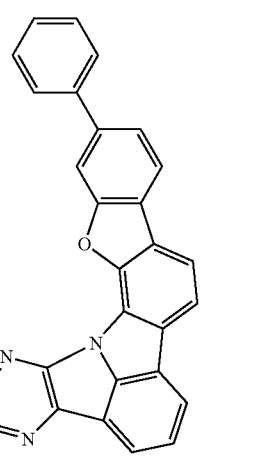

A-20
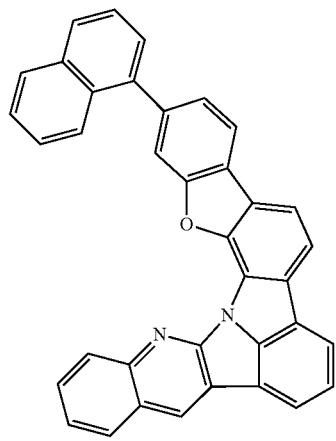
A-21
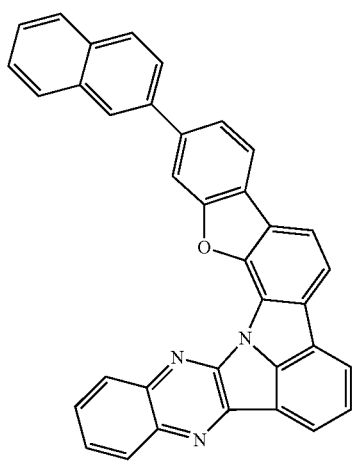
A-22
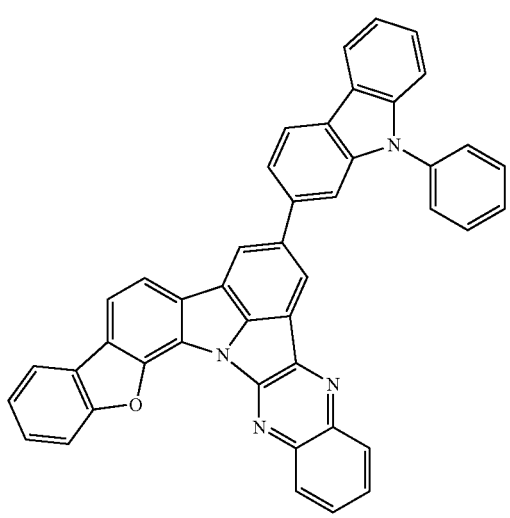
A-23
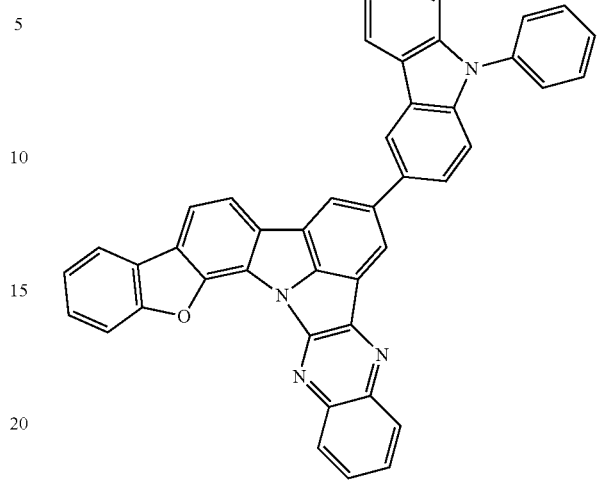
A-24
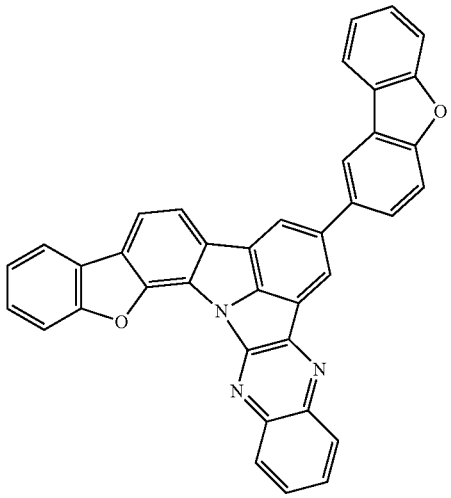
A-25
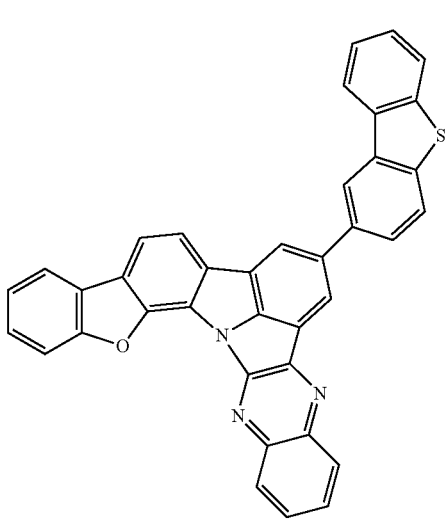

A-26
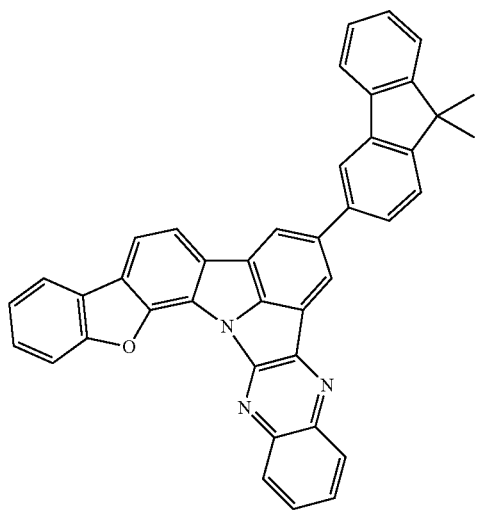
A-27
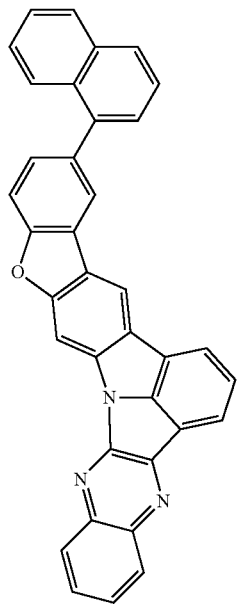
A-28
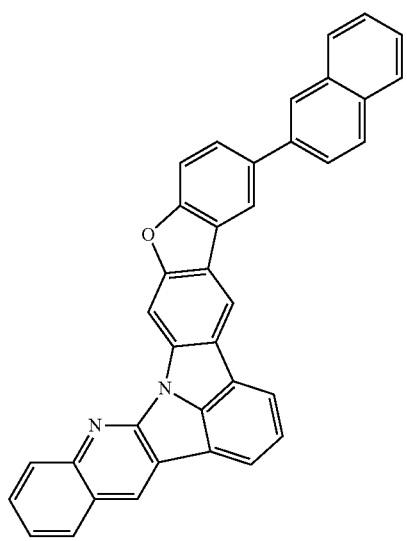
A-29
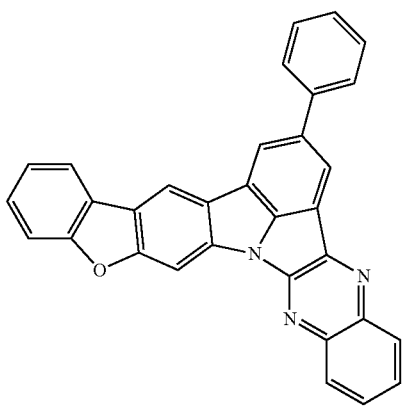
A-30
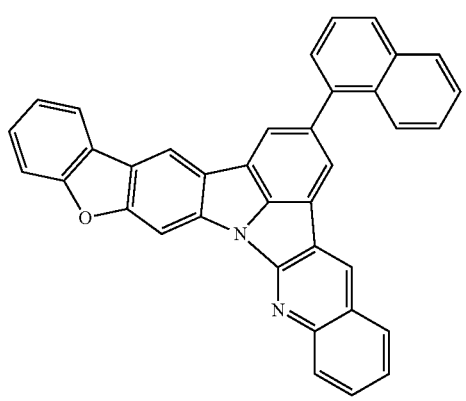
A-31
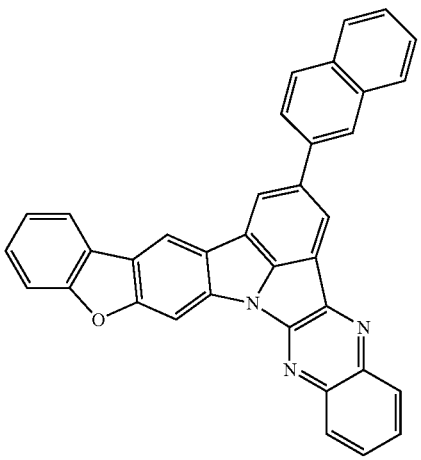

-continued
A-32
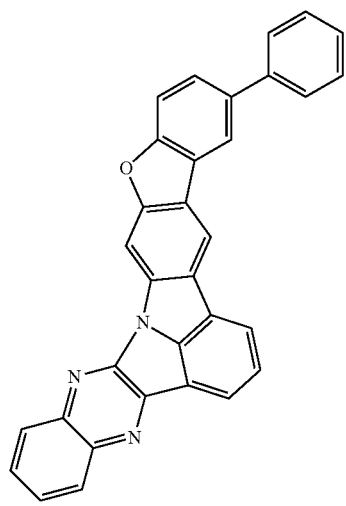
A-33
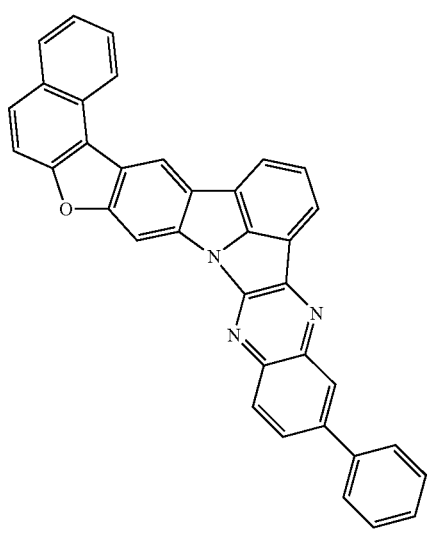
A-34
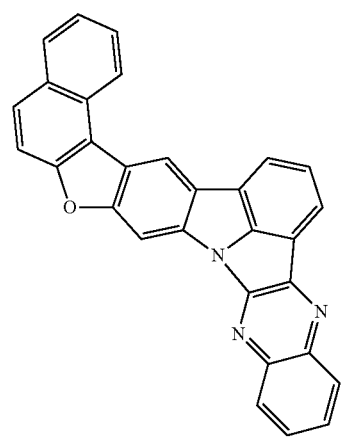
A-35
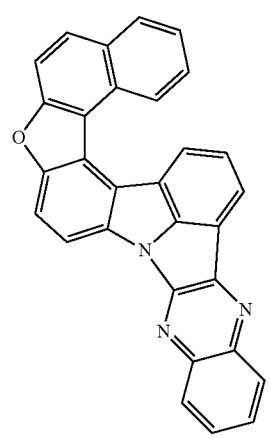
A-36
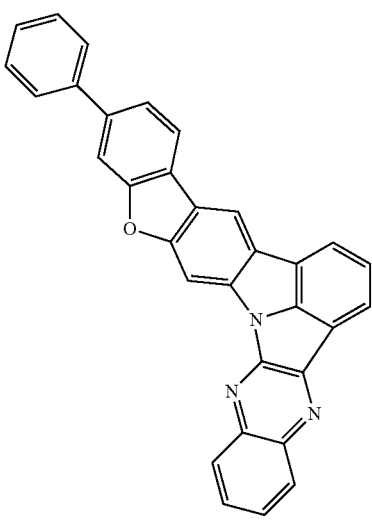
A-37
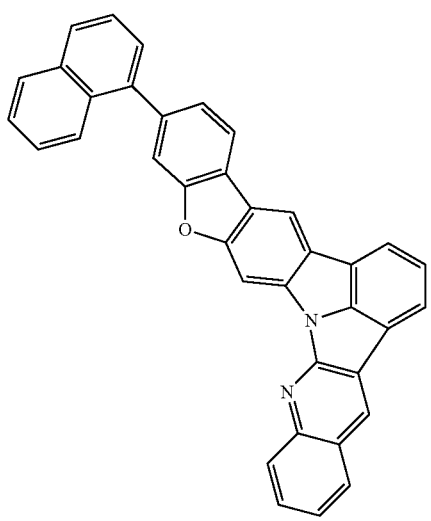

A-38
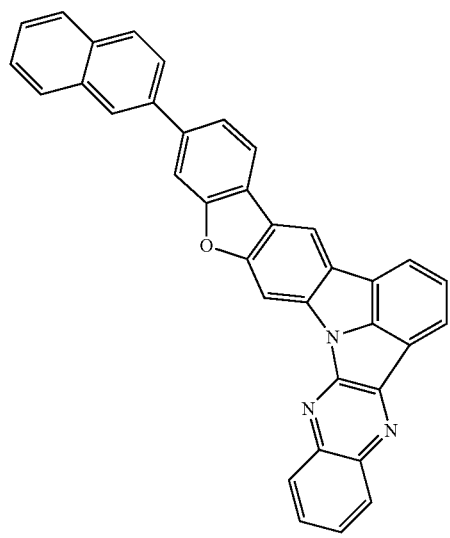
A-39
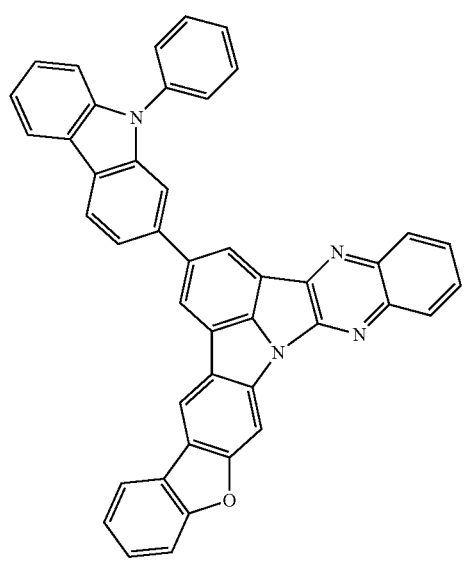
A-40
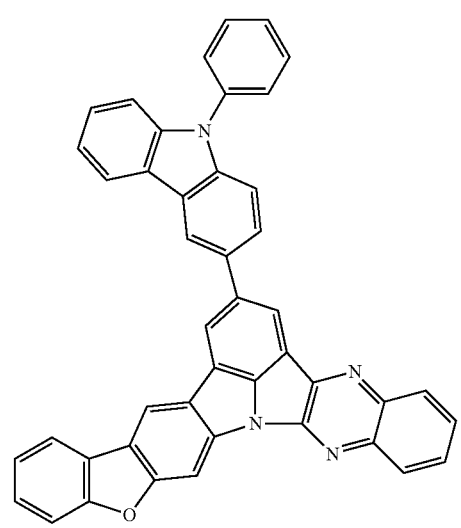
A-41
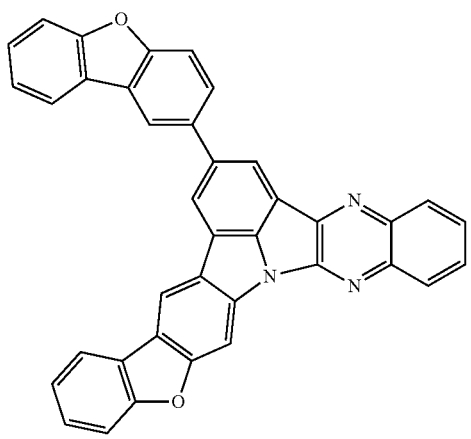
A-42
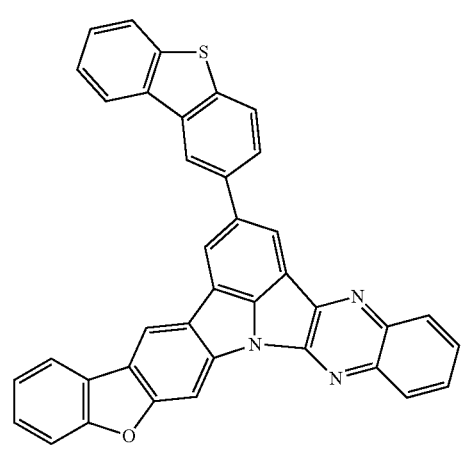
A-43
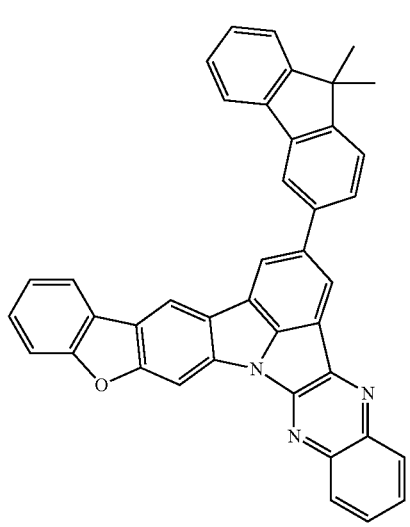

-continued
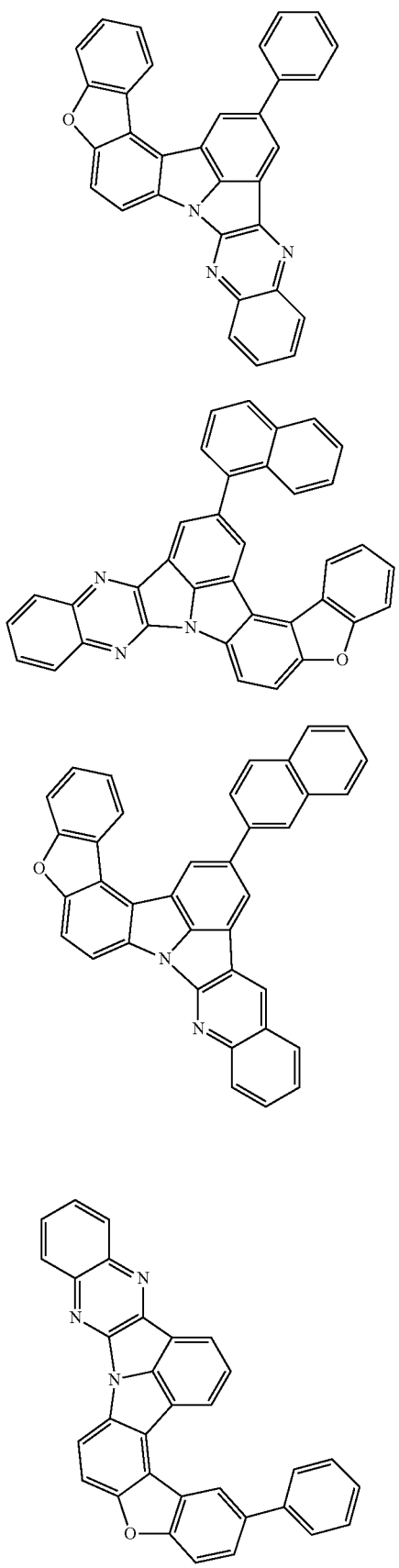
A-44
A-45
A-46
A-47
-continued
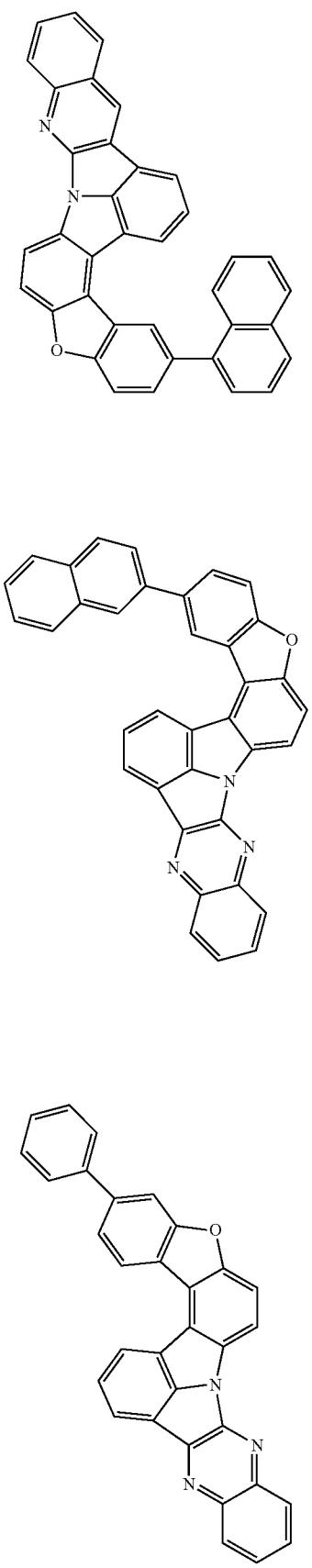
A-48
A-49
A-50

A-51
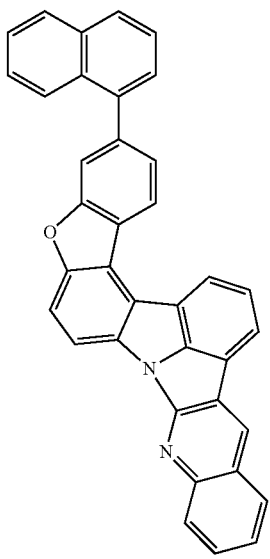
A-54
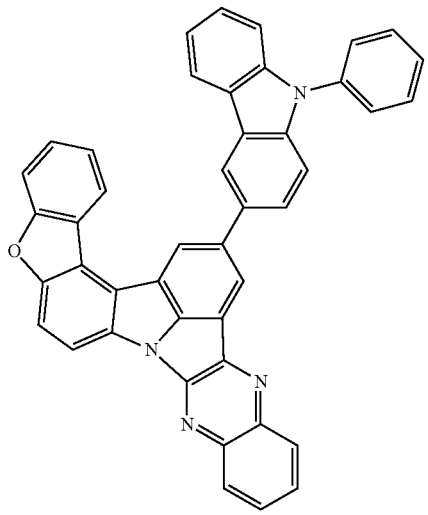
A-52
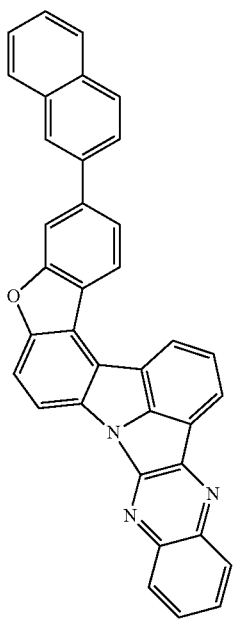
A-55
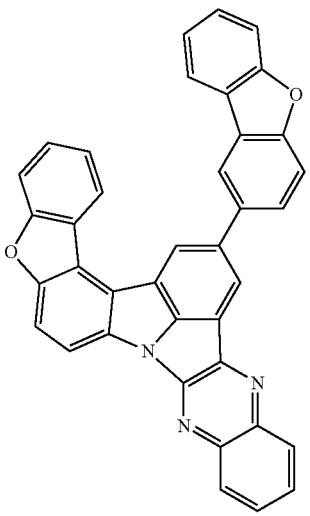
A-53
A-56
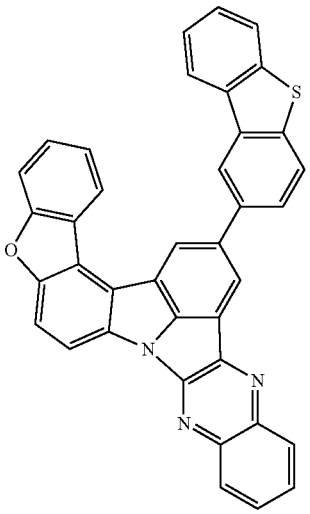

A-57
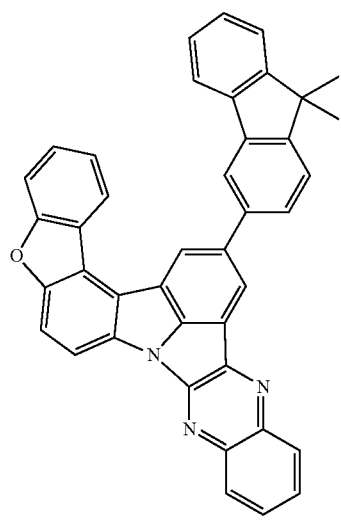
A-58
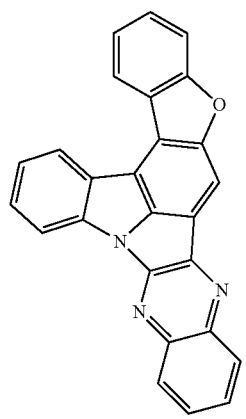
A-59
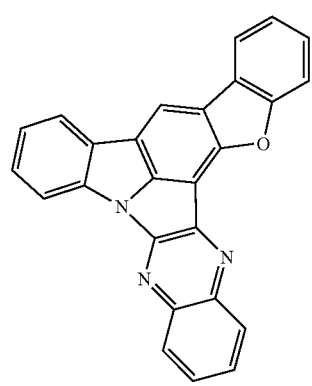
A-60
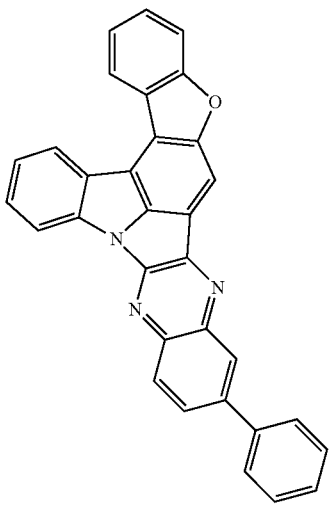
A-61
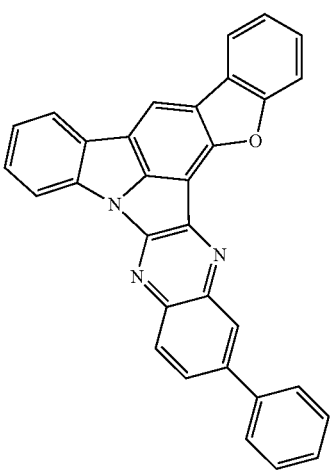
A-62
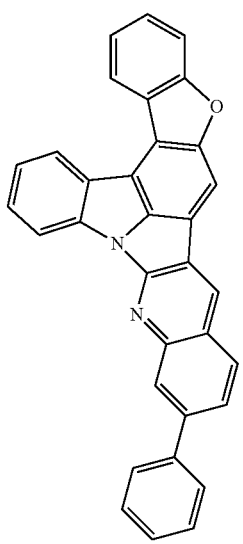

A-63
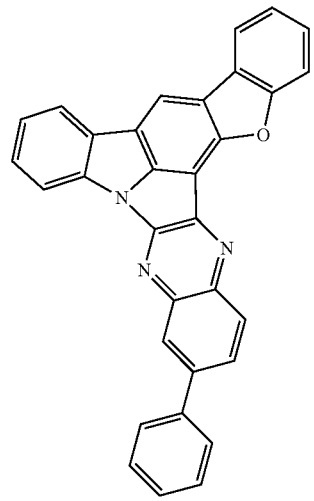
A-64
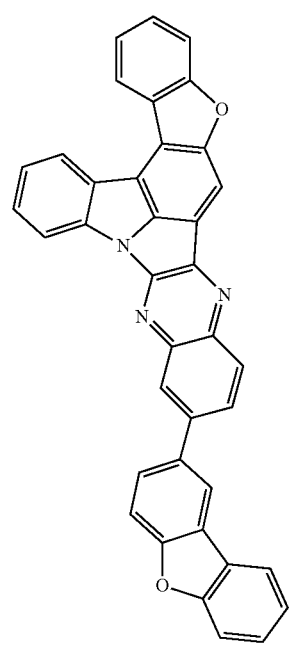
A-65
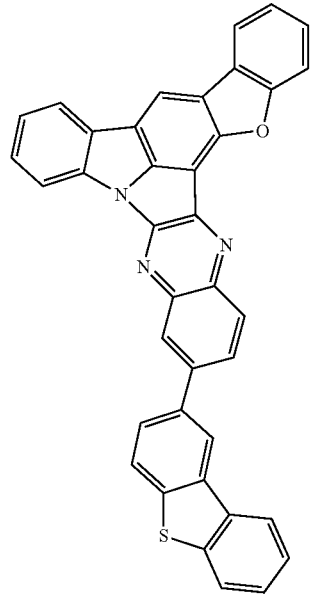
A-66
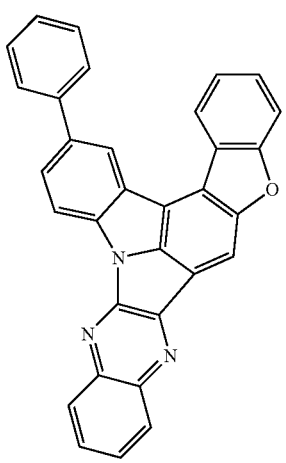
A-67
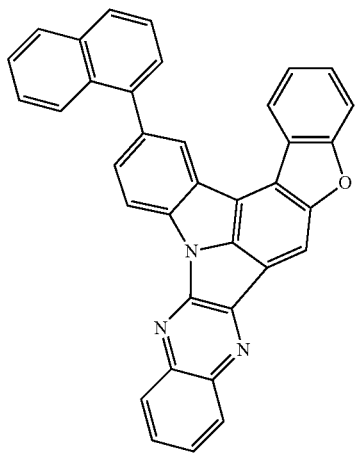

A-68
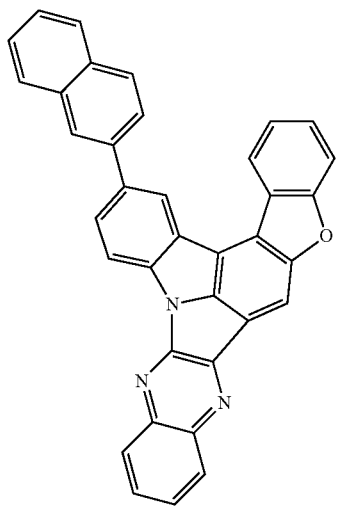
A-71
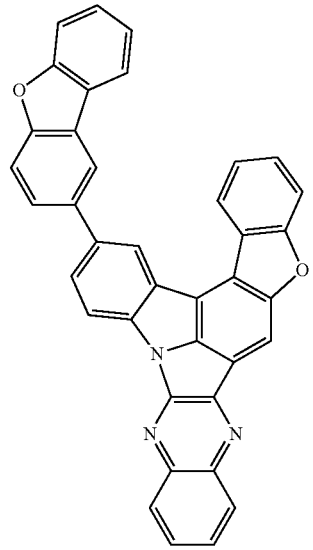
A-69
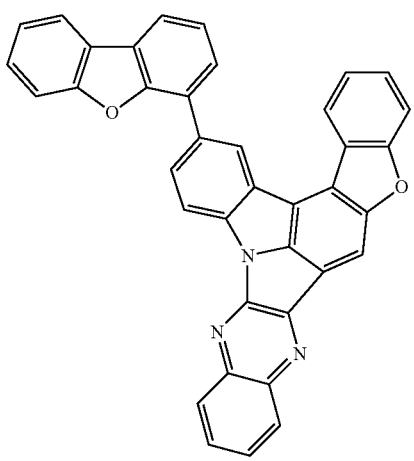
A-72
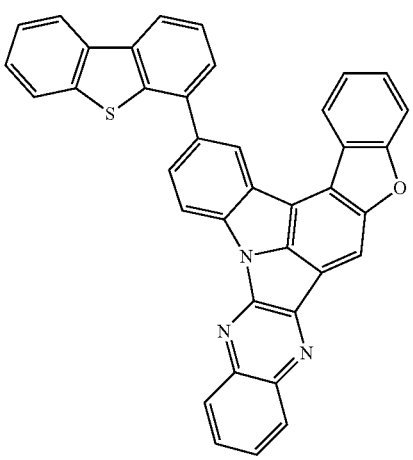
A-70
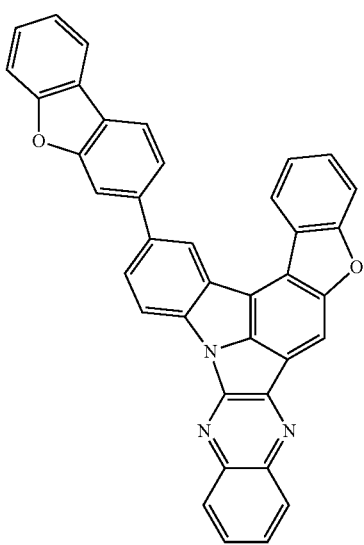
A-73
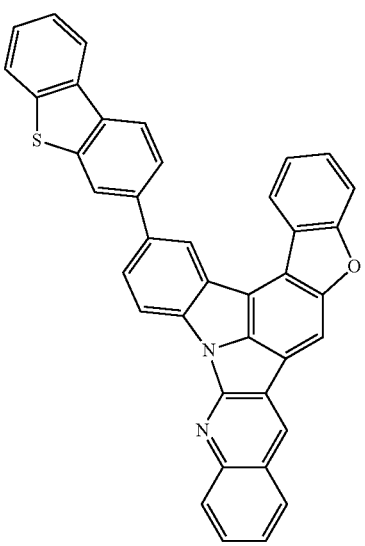

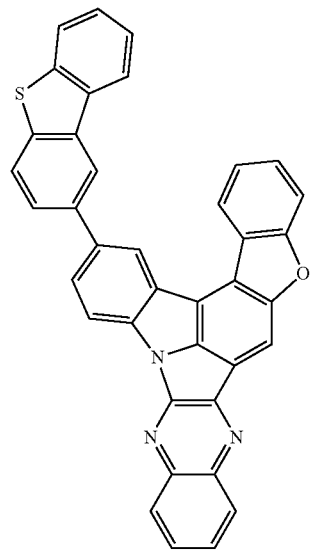
A-74
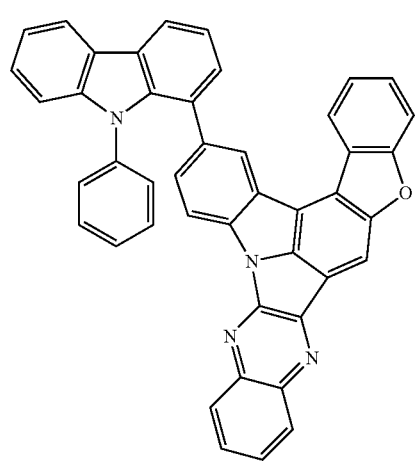
A-75
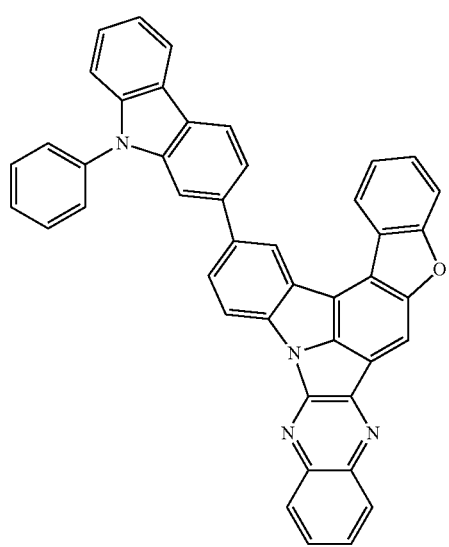
A-76
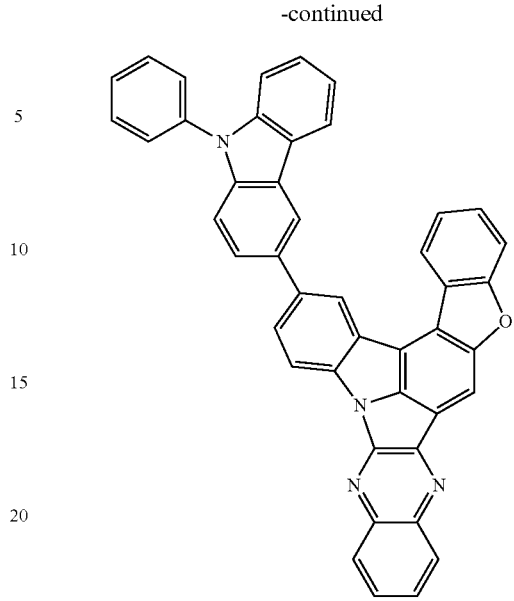
A-77
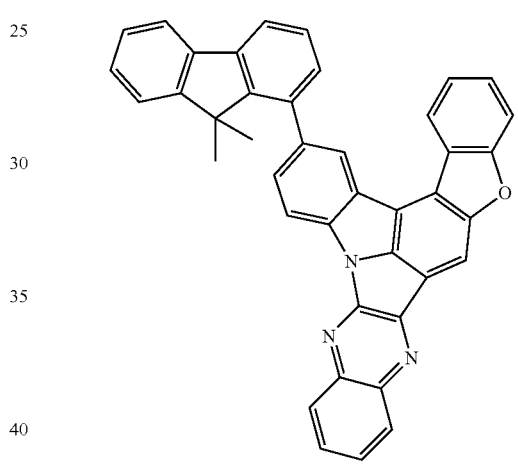
A-78
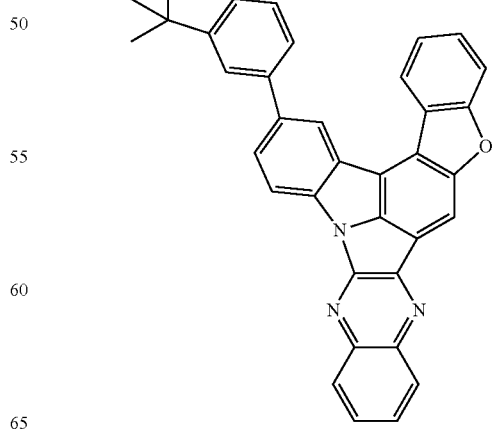
A-79

-continued
A-80
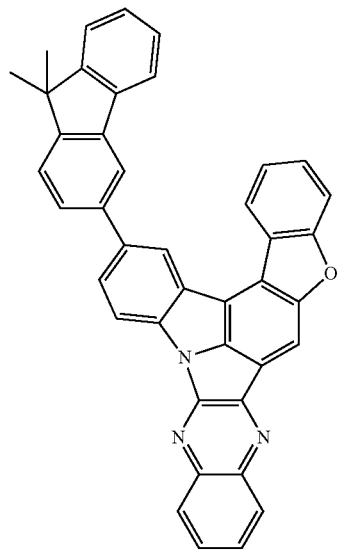
A-81
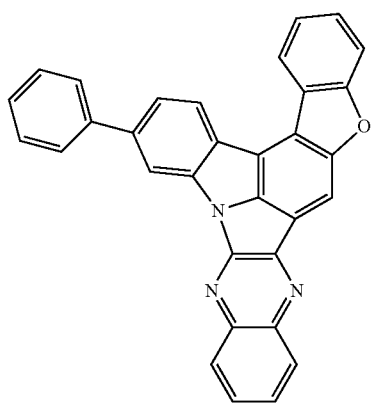
A-82
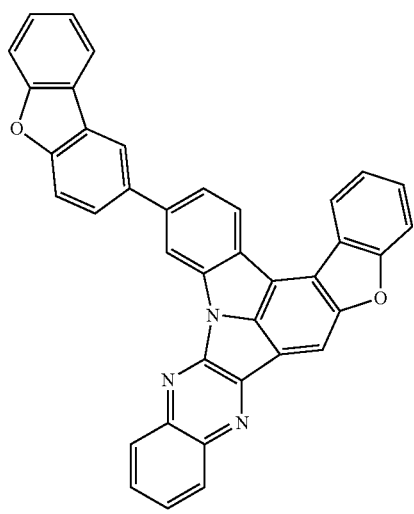
A-83
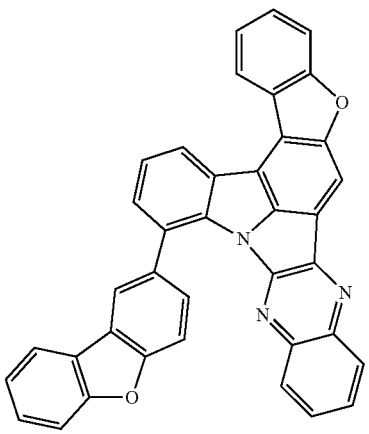
A-84
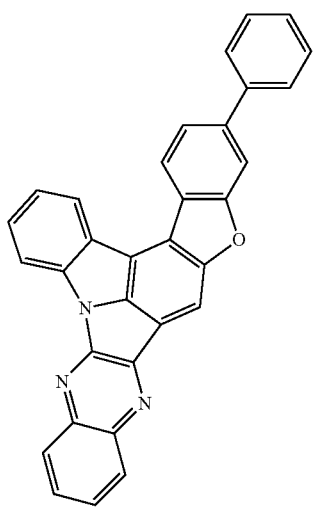
A-85
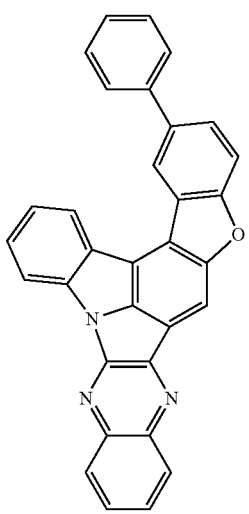

A-86
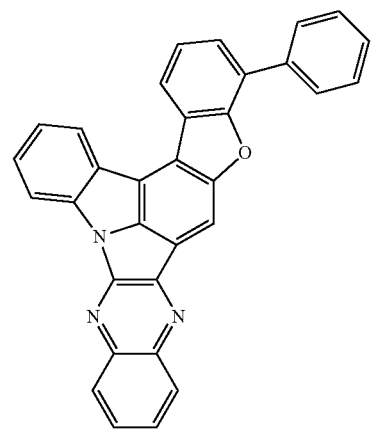
A-87
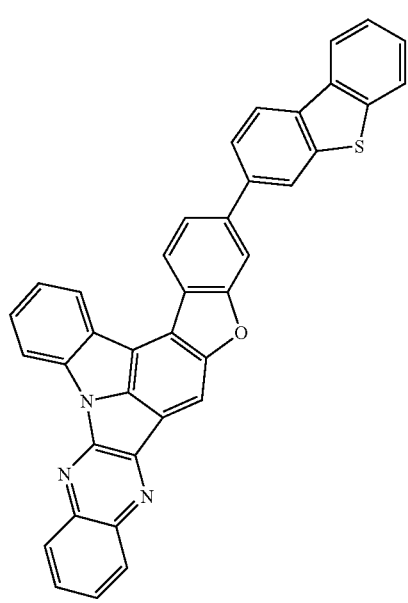
A-88
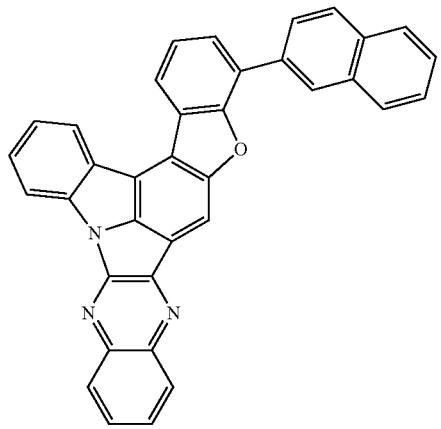
A-89
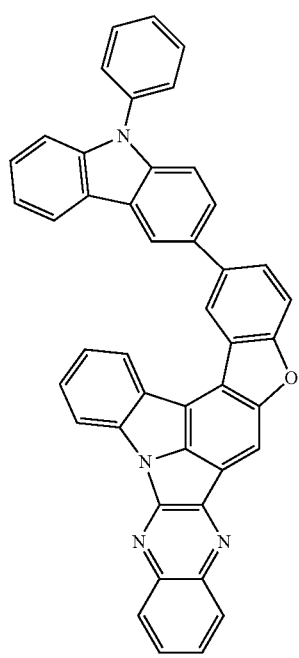
A-90
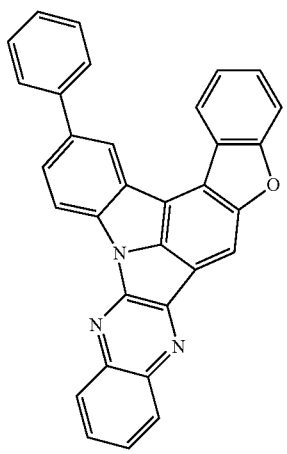
A-91
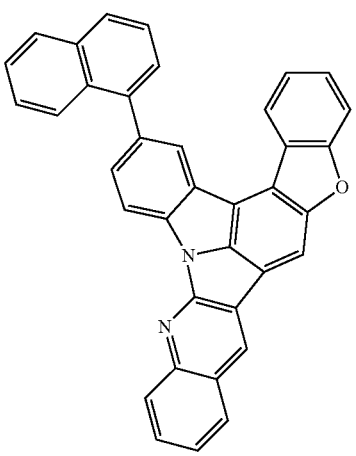

A-92
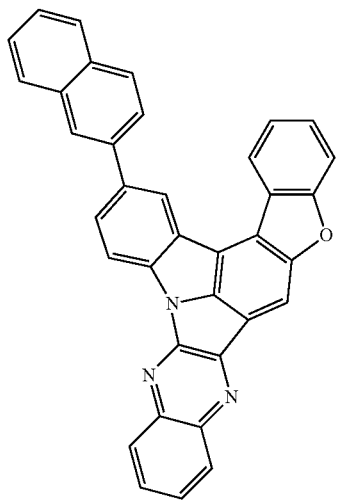
A-93
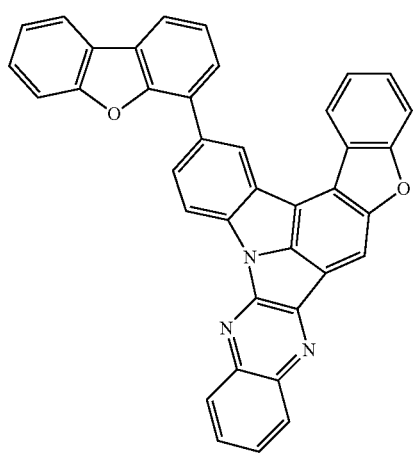
A-94
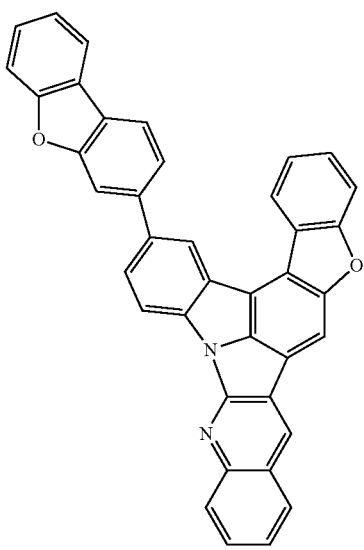
A-95
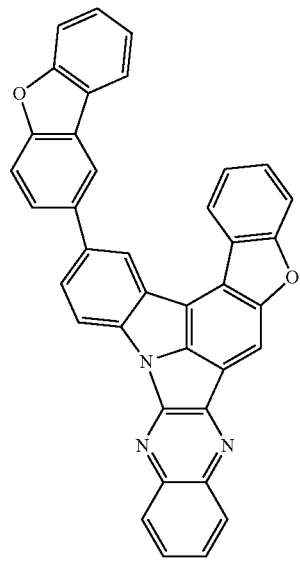
A-96
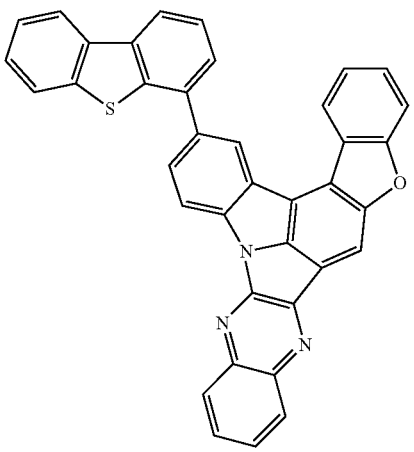
A-97
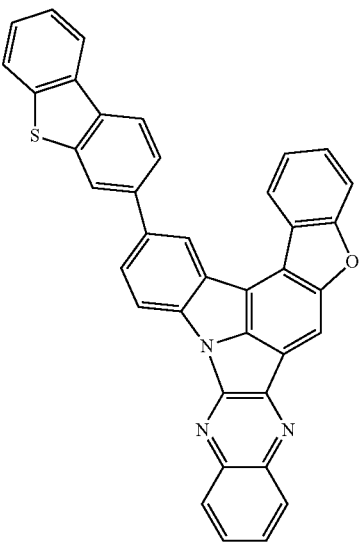

A-98
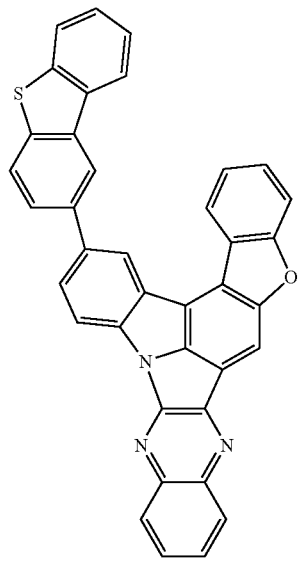
A-99
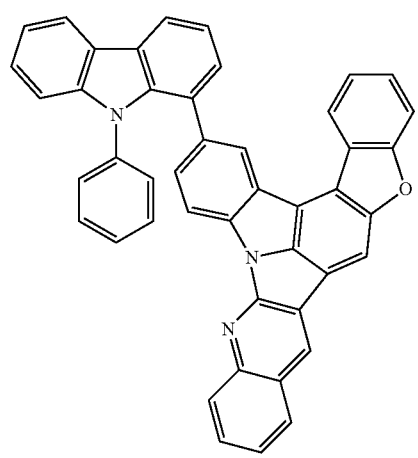
A-100
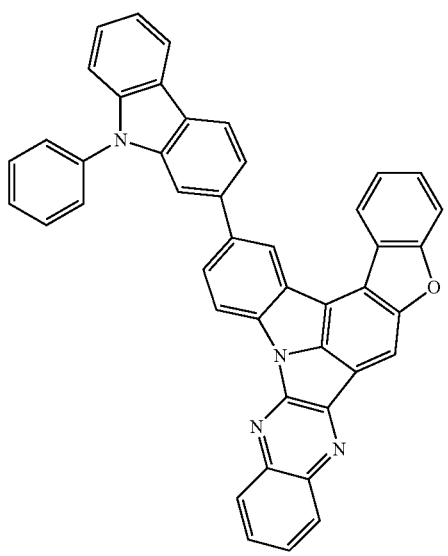
A-101
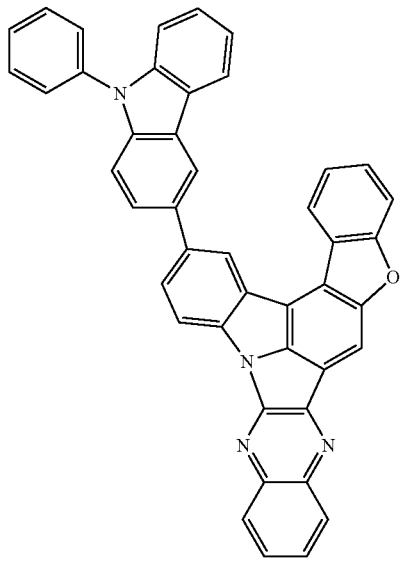
A-102
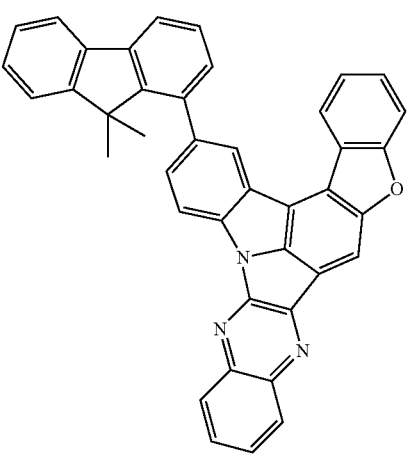
A-103
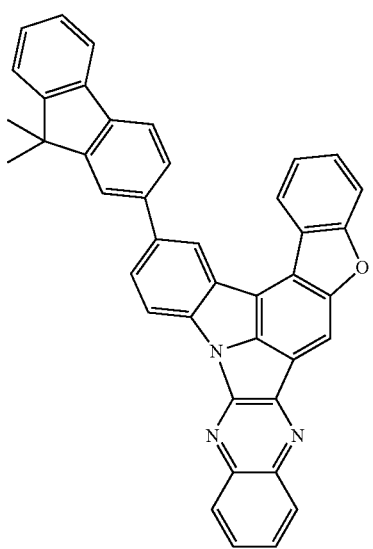

A-104
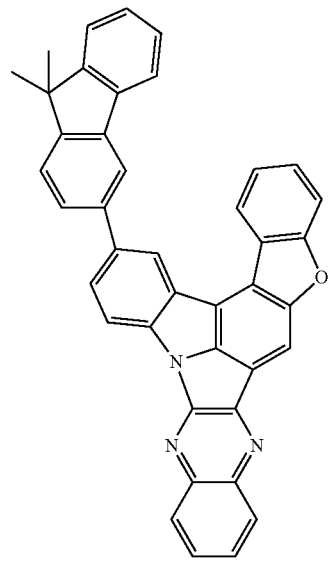
A-105
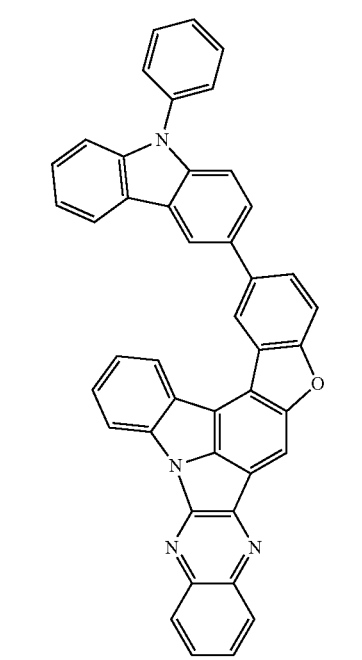
A-106
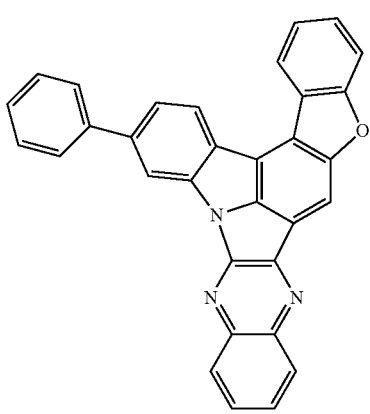
A-107
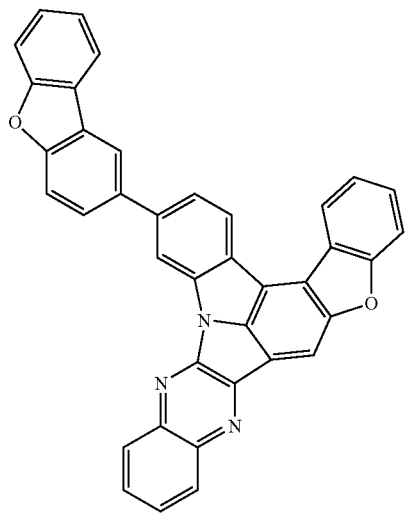
A-108
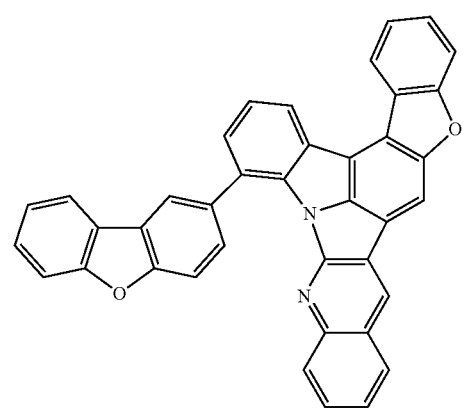
A-109
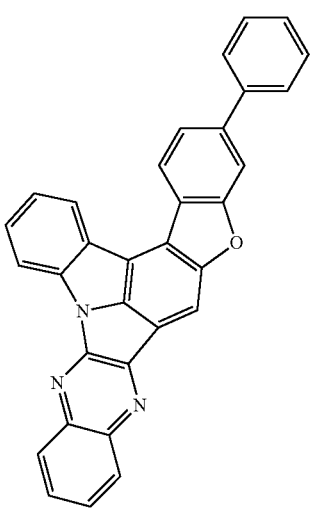

A-110
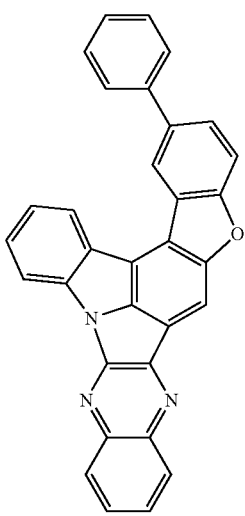
A-111
A-112
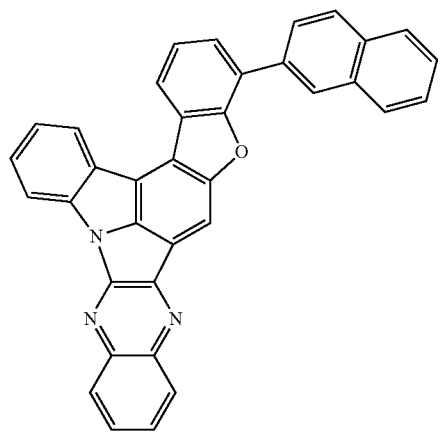
A-113
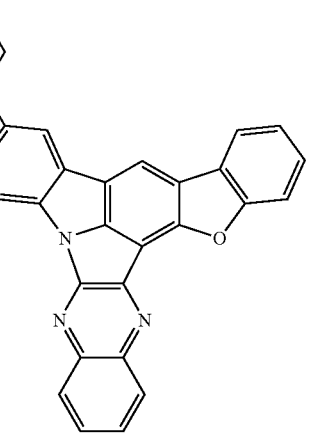
A-114
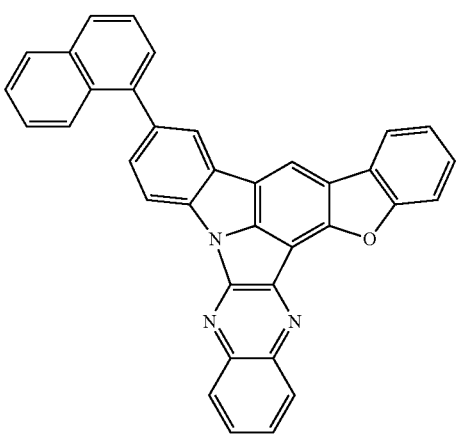
A-115
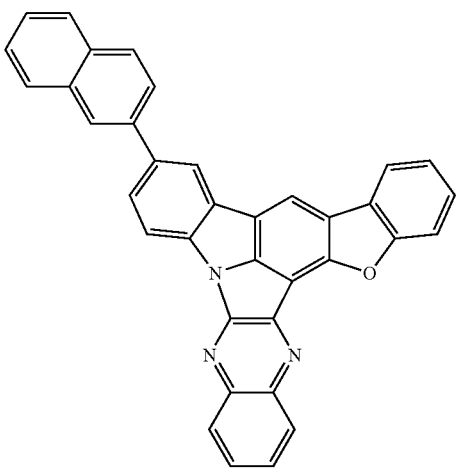

A-116
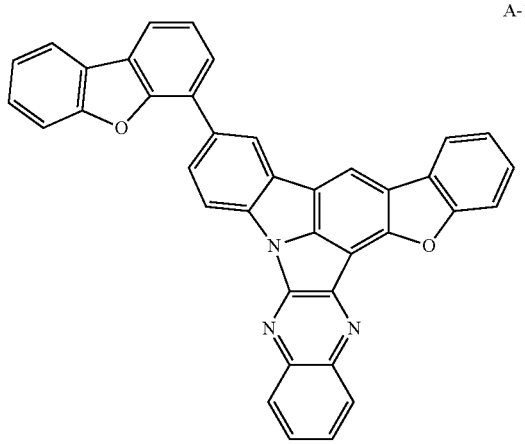
A-117
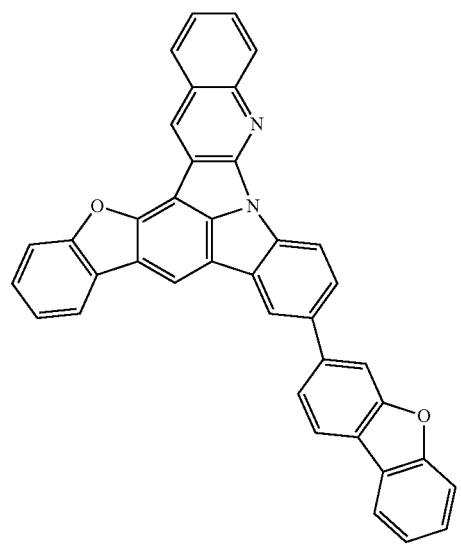
A-118
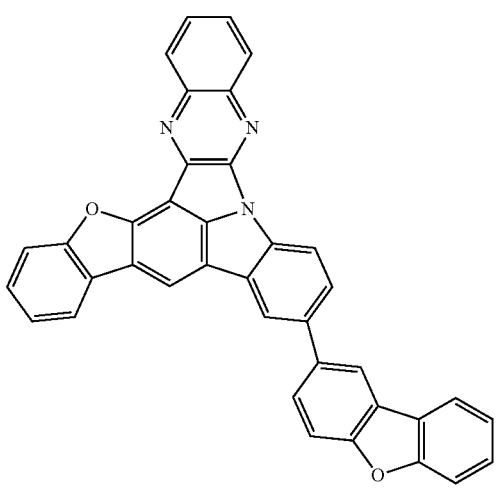
A-119
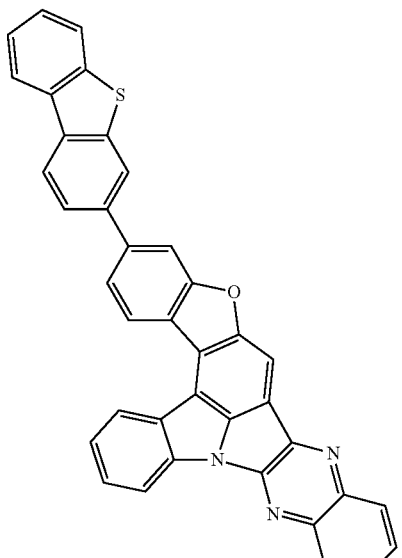
A-120
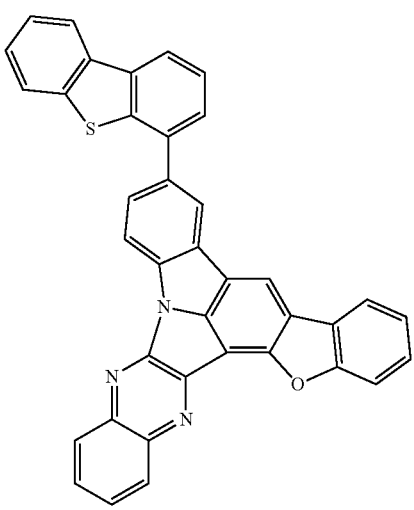
A-121
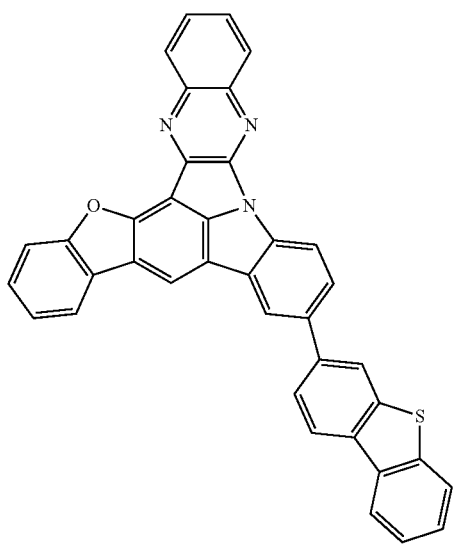

A-122
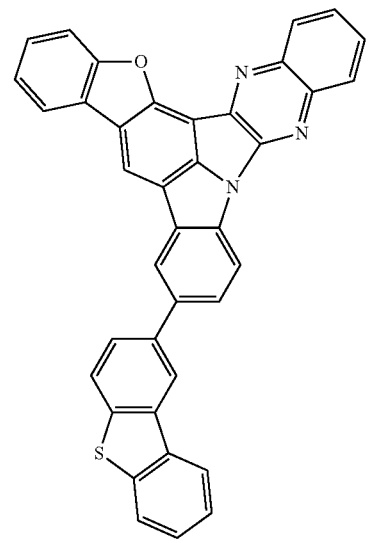
A-123
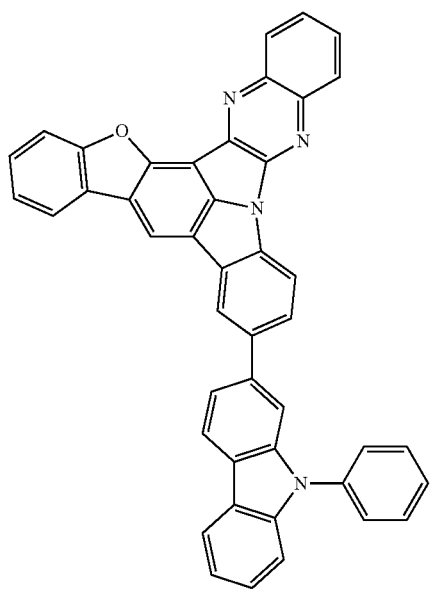
A-124
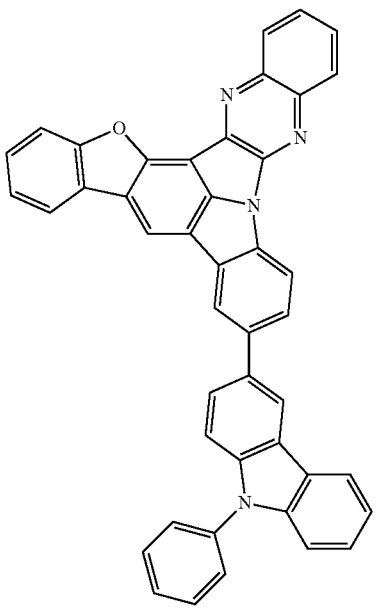
A-125
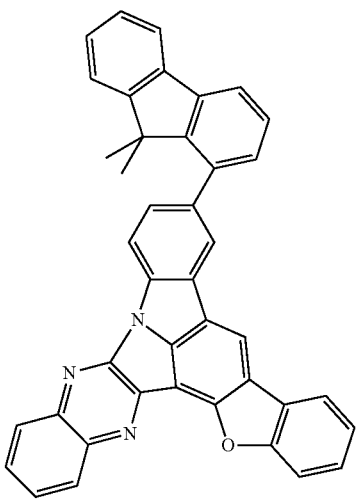
A-126
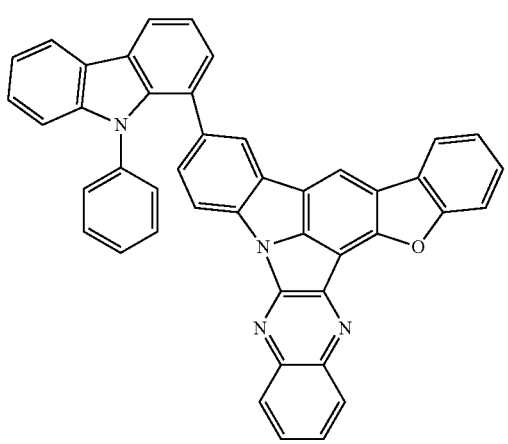

A-127
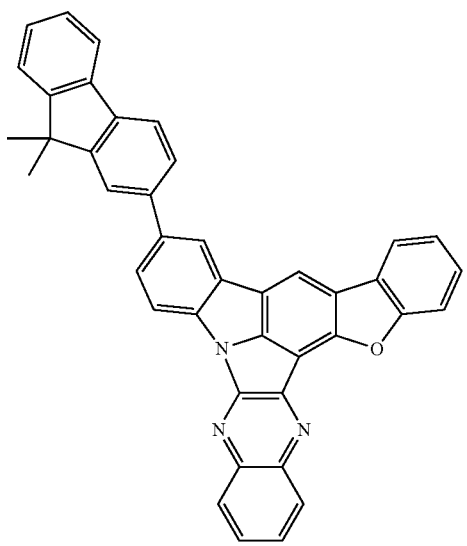
A-128
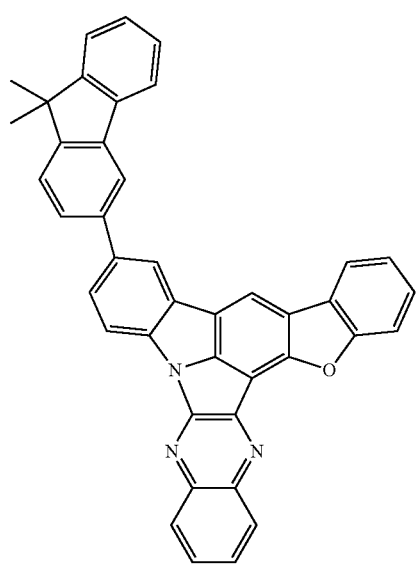
A-129
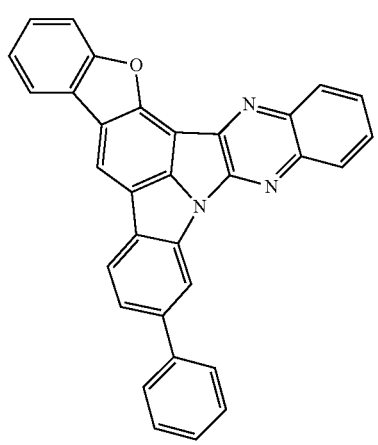
A-130
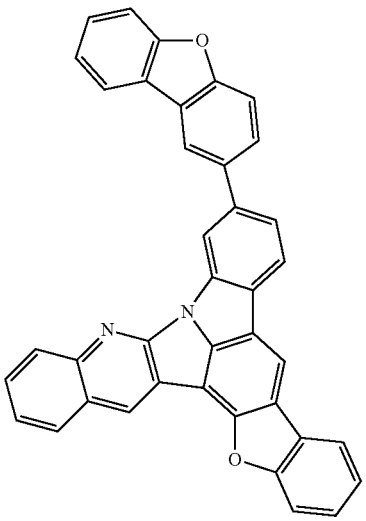
A-131
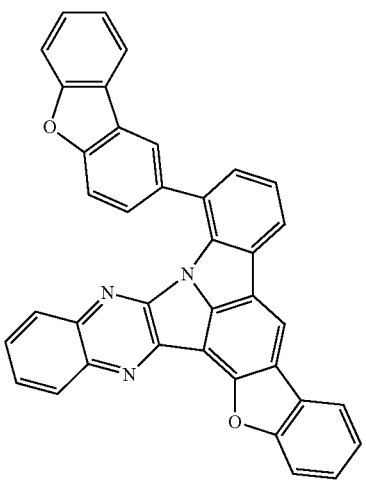
A-132
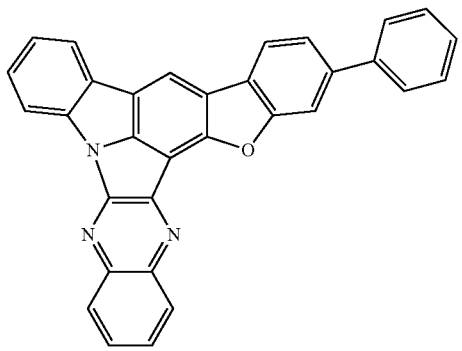

-continued
A-133
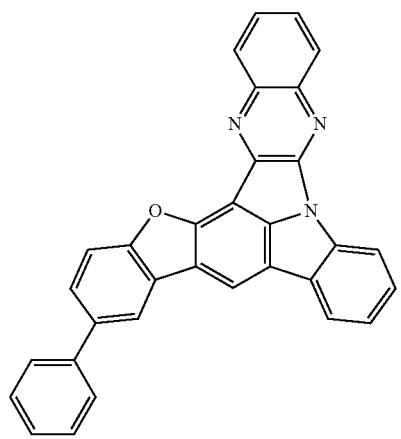
A-134
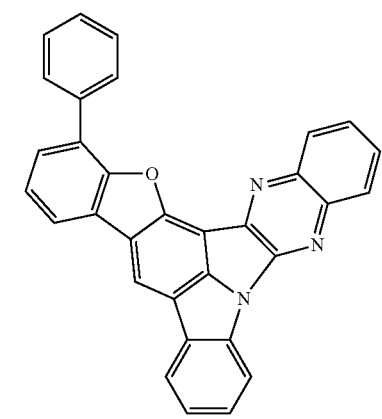
A-135
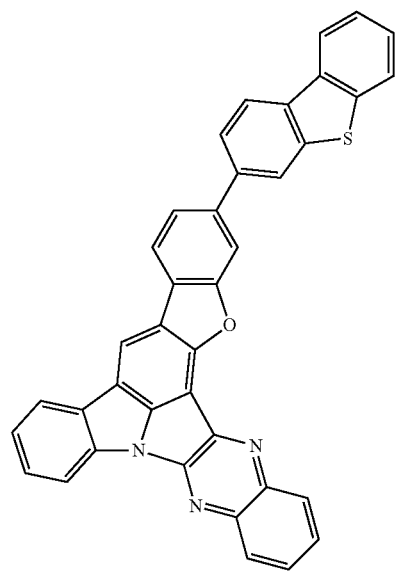
A-136
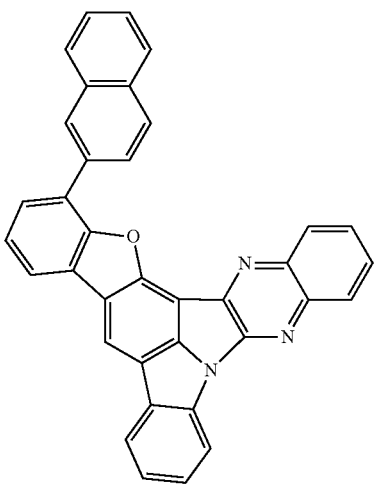
A-137
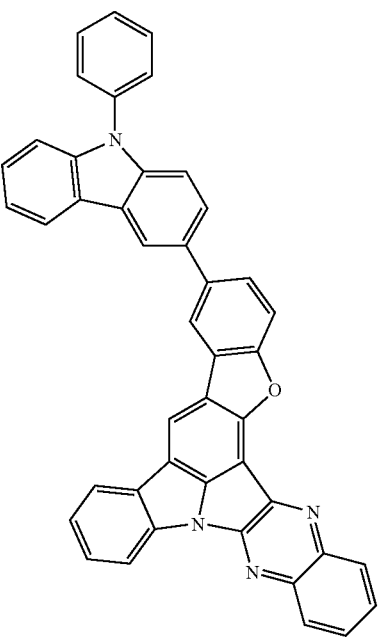
A-138
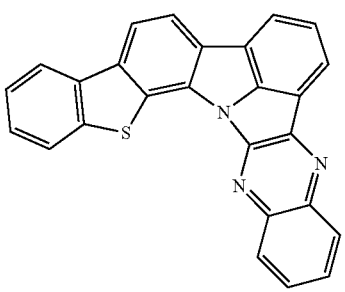

-continued
A-139
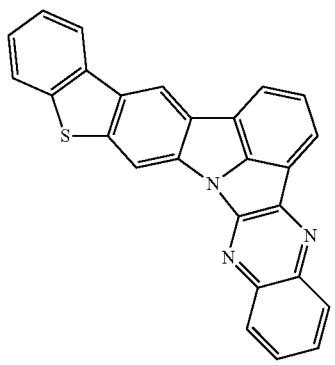
A-140
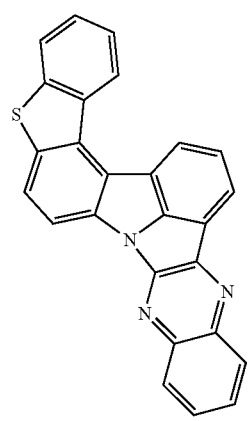
A-141
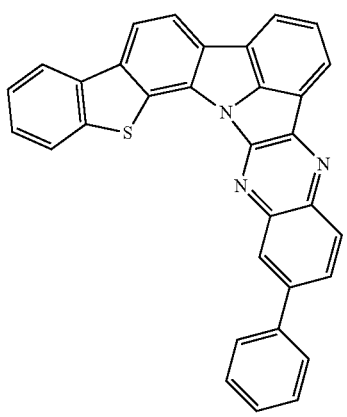
-continued
A-142
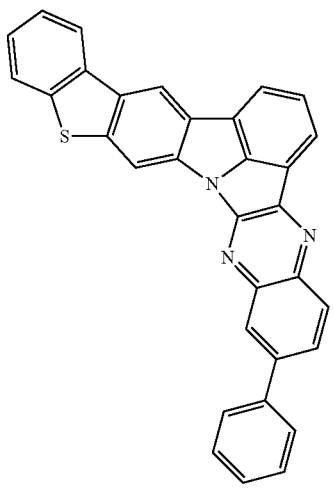
A-143
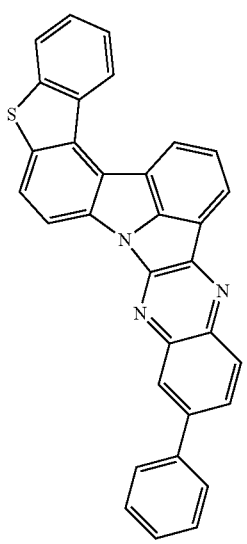
A-144
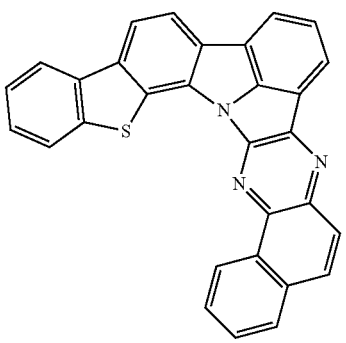

A-145
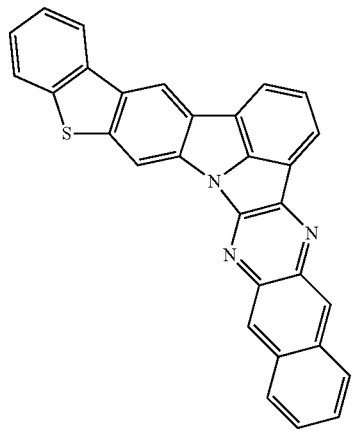
A-146
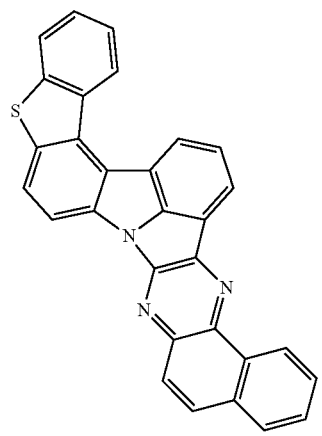
A-147
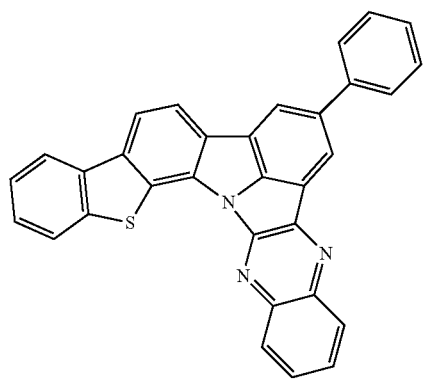
A-148
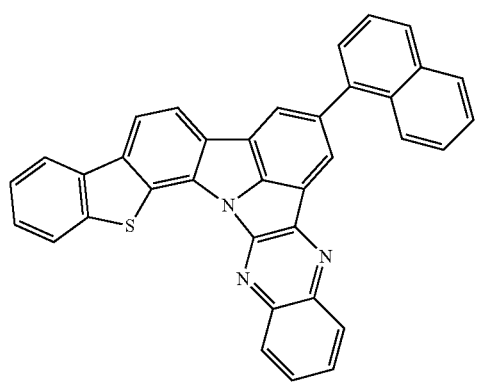
A-149
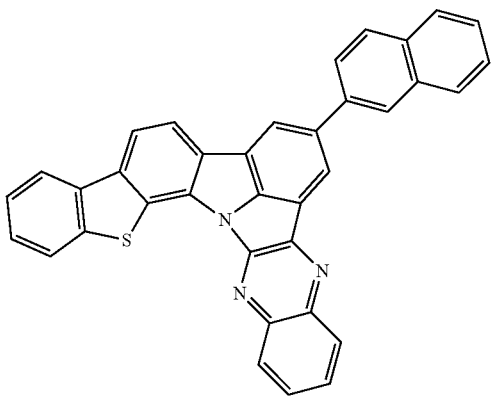
A-150
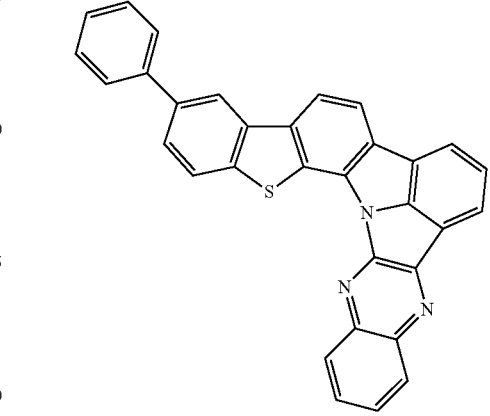
A-151
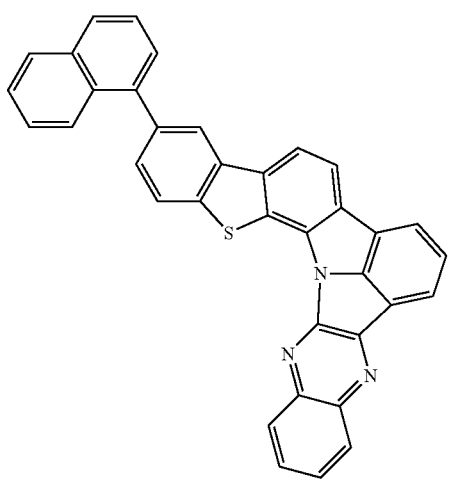

A-152
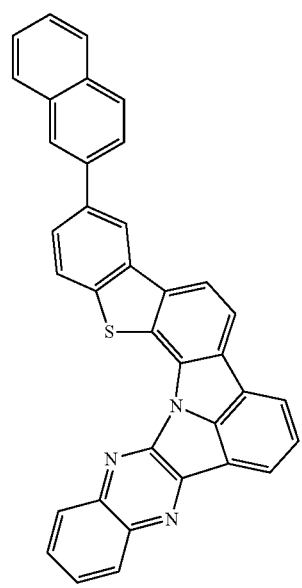
A-153
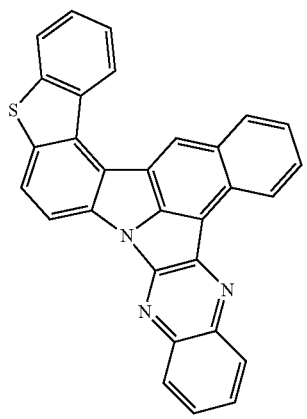
A-154
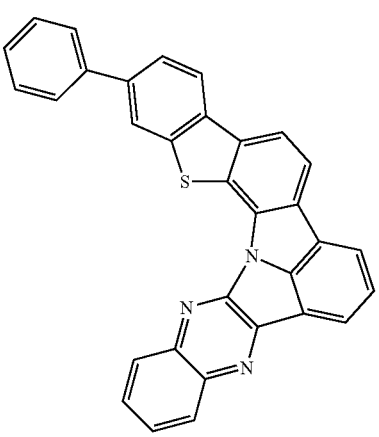
A-155
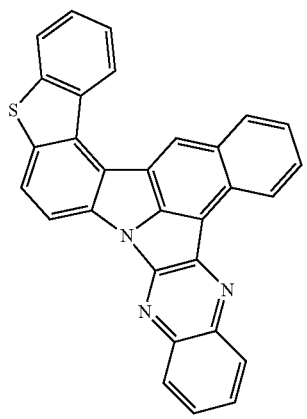
A-156
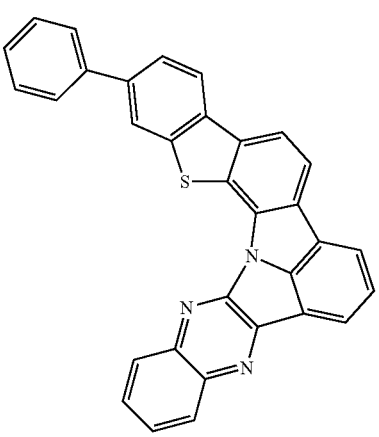
A-157
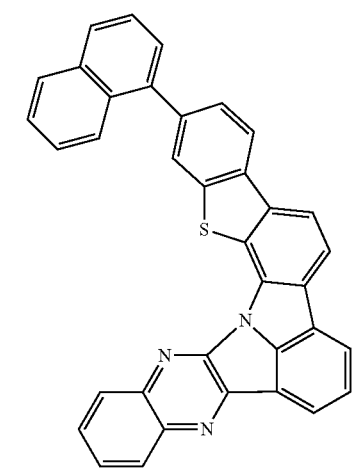

-continued
A-158
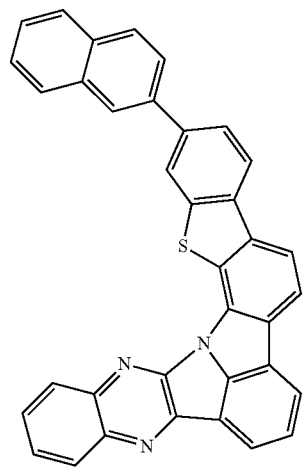
A-159
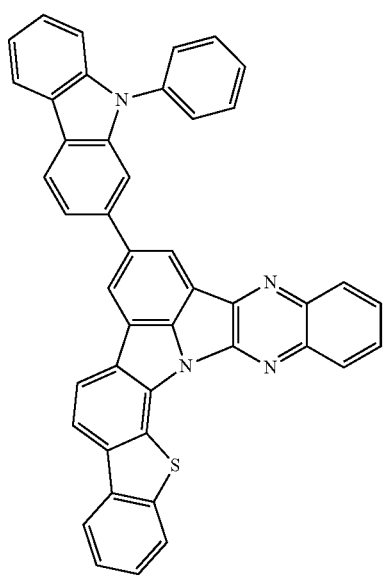
A-160
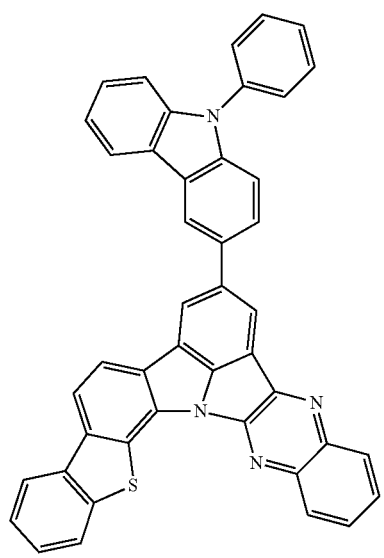
-continued
A-161
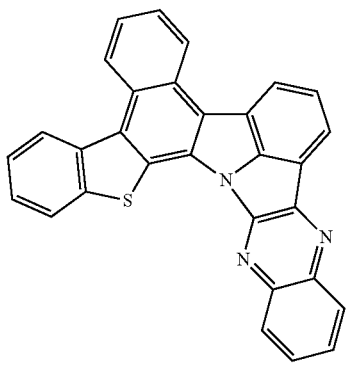
A-162
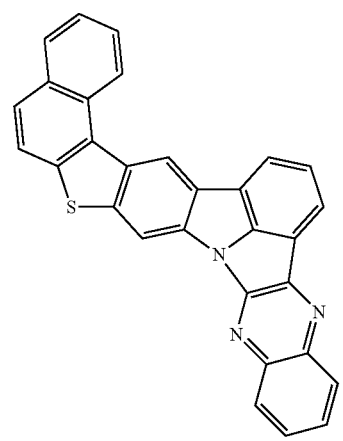
A-163
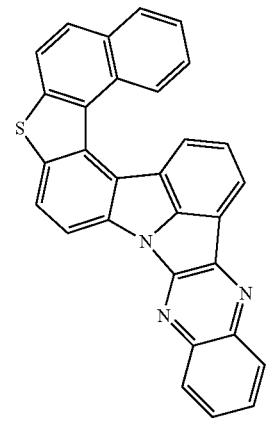

A-164
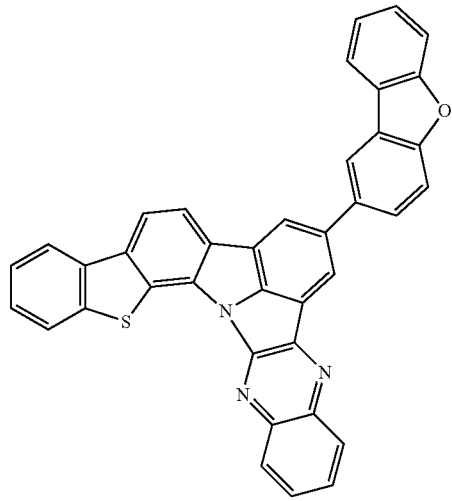
A-165
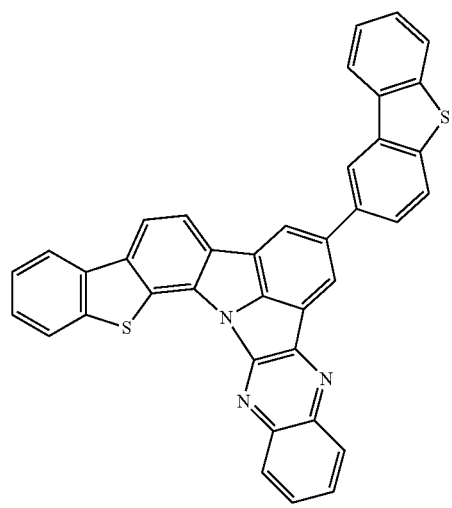
A-166
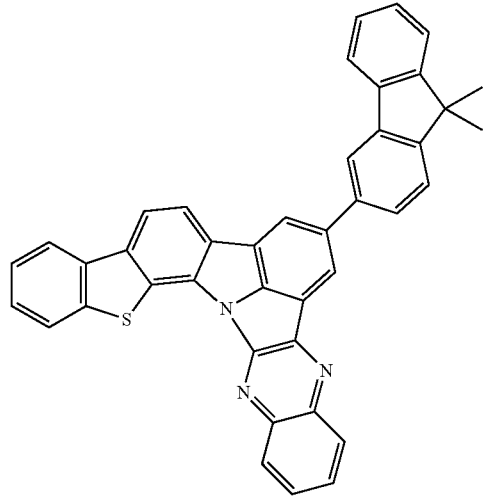
A-167
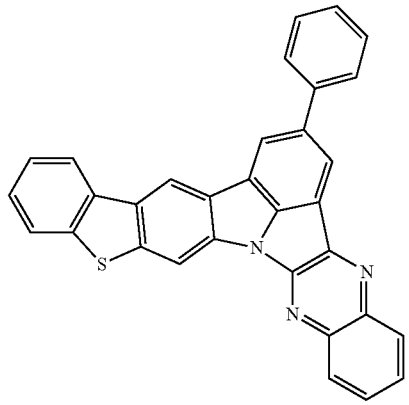
A-168
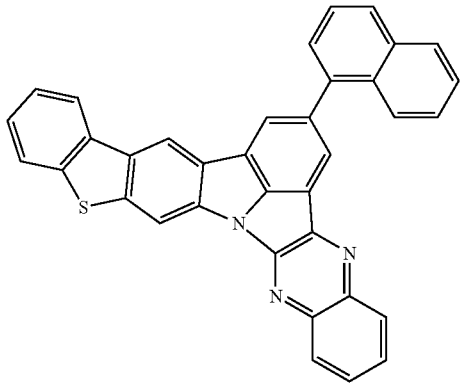
A-169
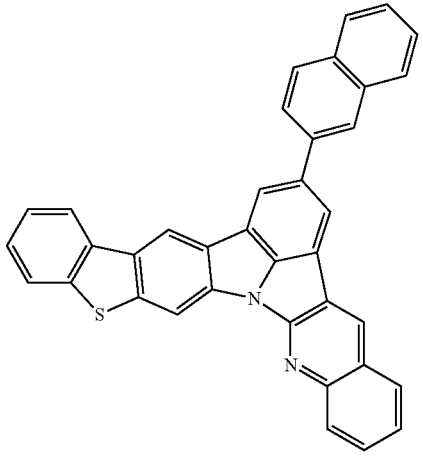

A-170
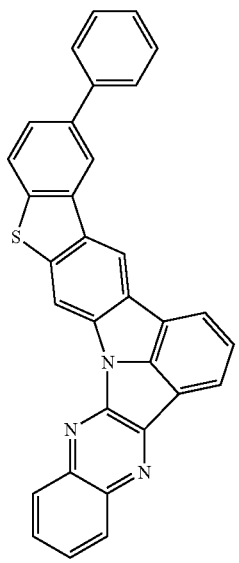
A-172
A-173
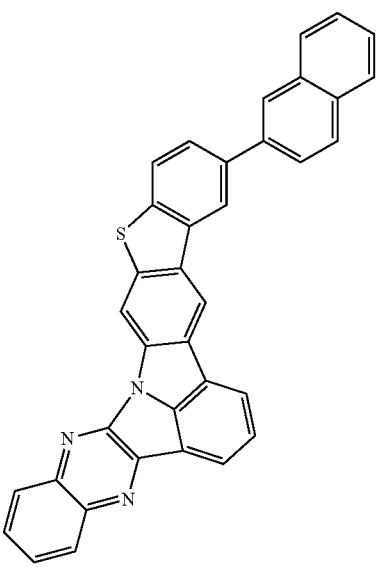
A-171
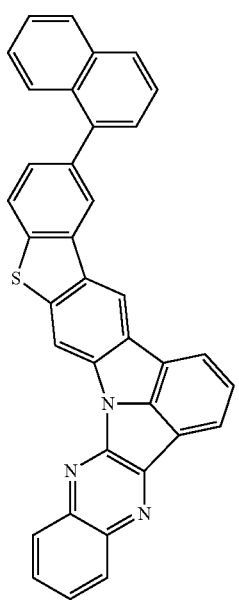
A-174
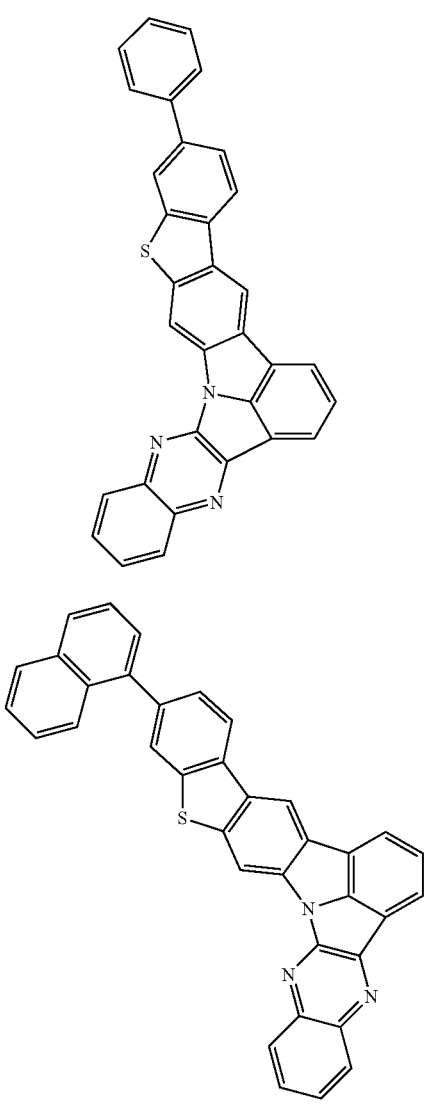

A-175
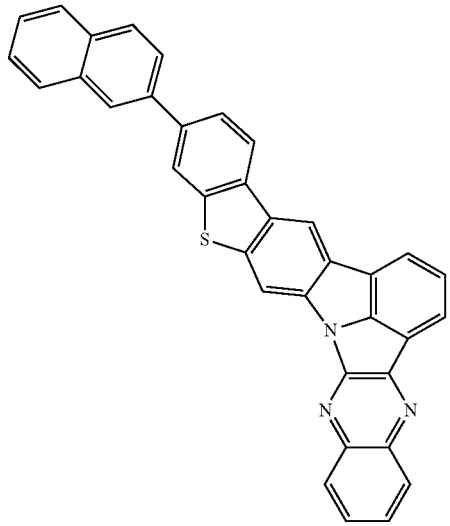
A-176
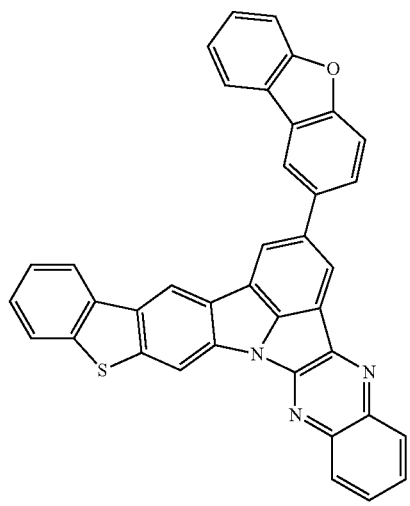
A-177
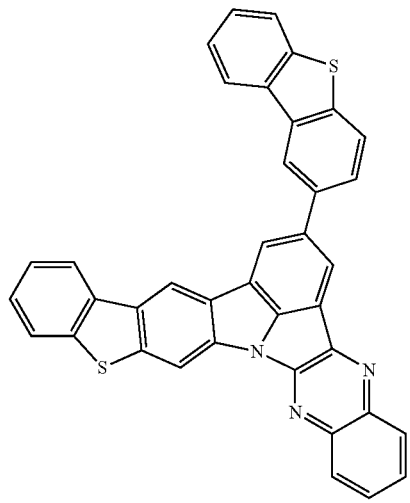
A-178
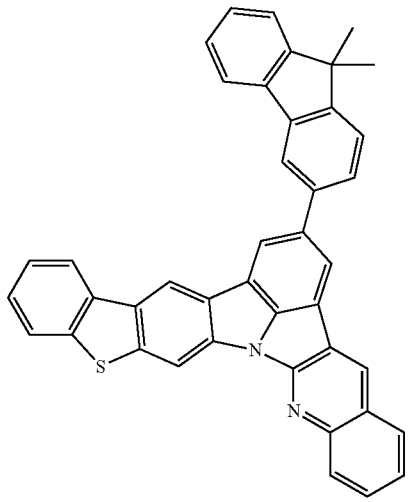
A-179
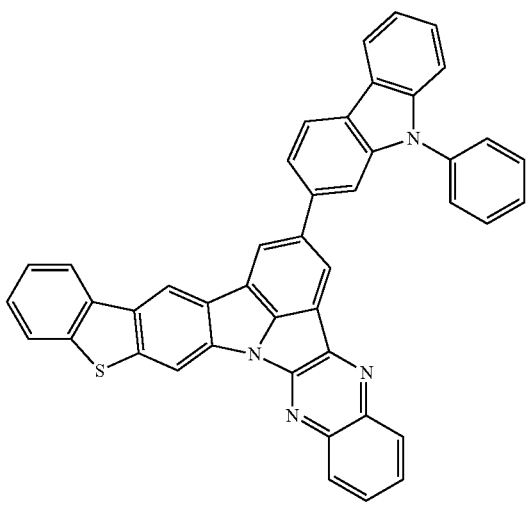
A-180
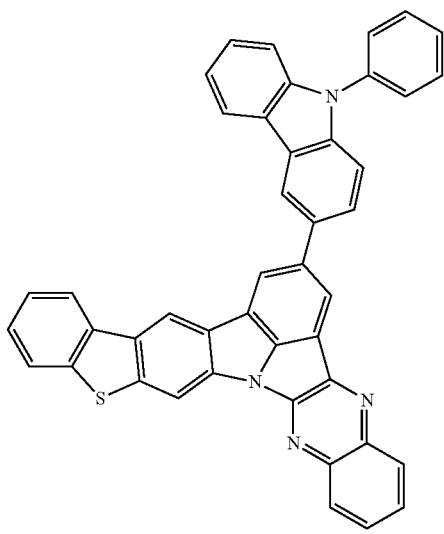

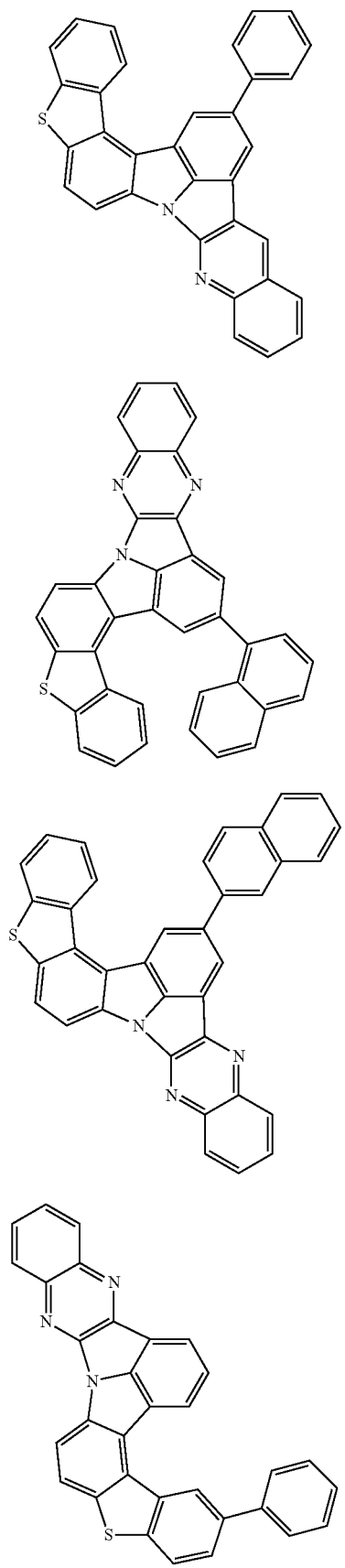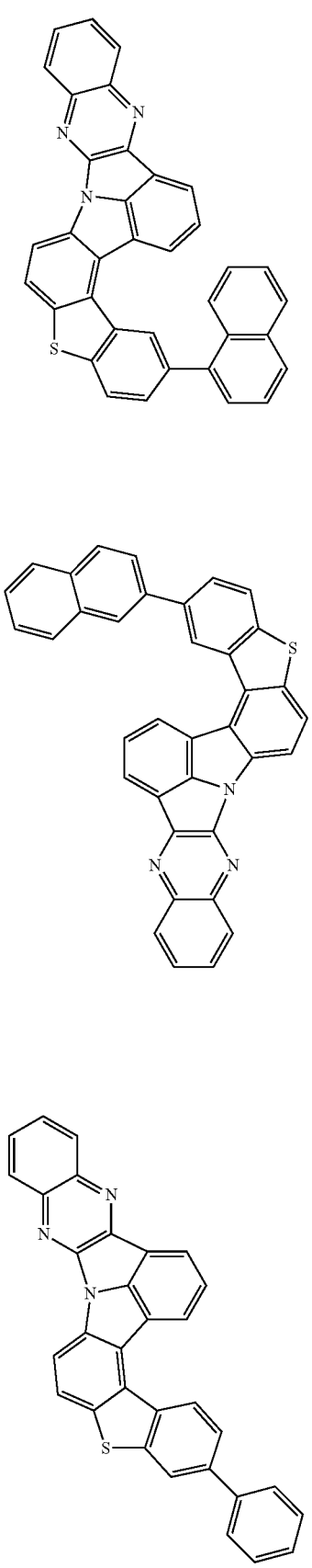

A-188
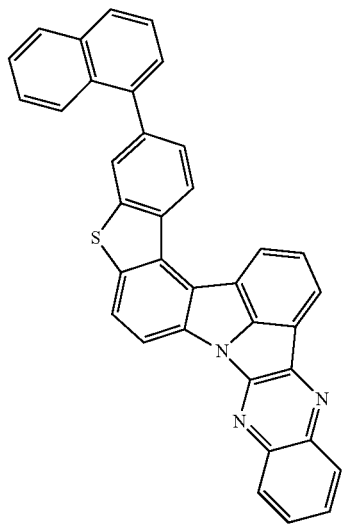
A-189
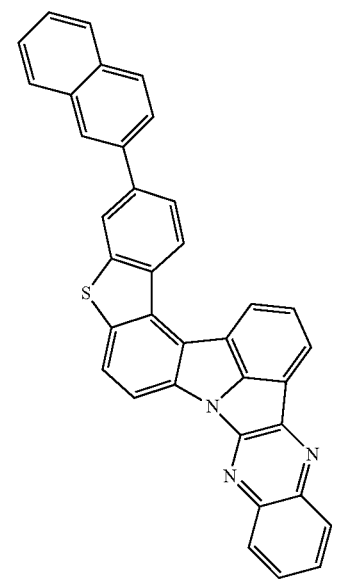
A-190
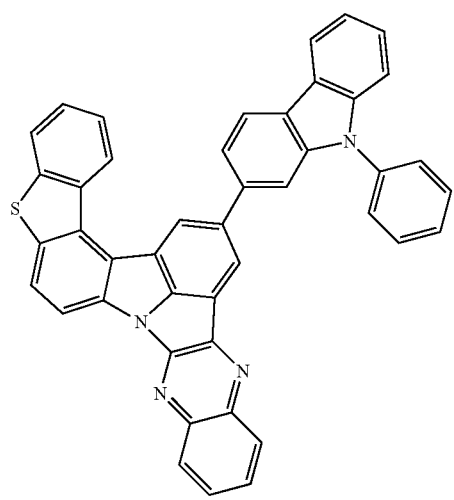
A-191
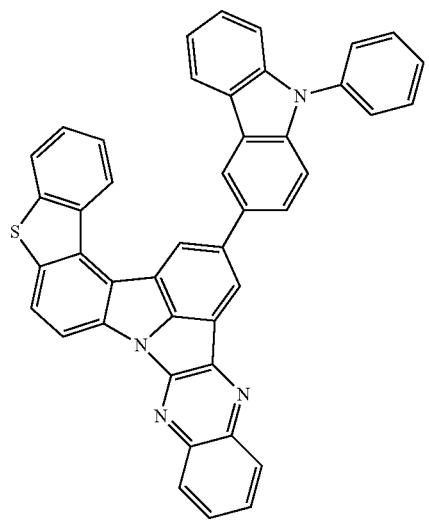
A-192
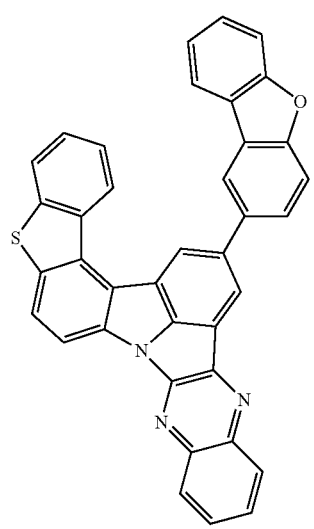
A-193
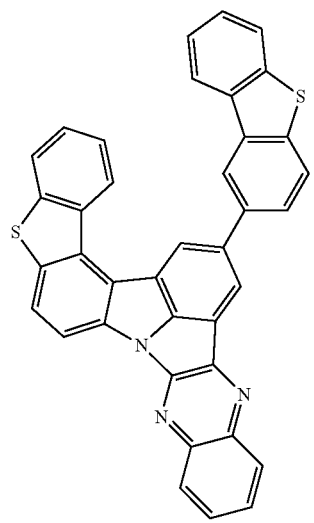

A-194
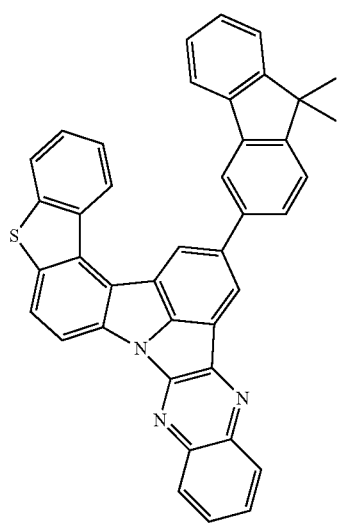
A-195
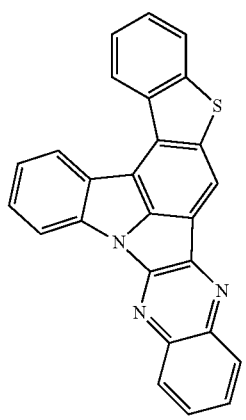
A-196
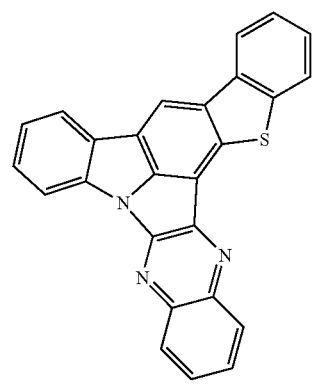
A-197
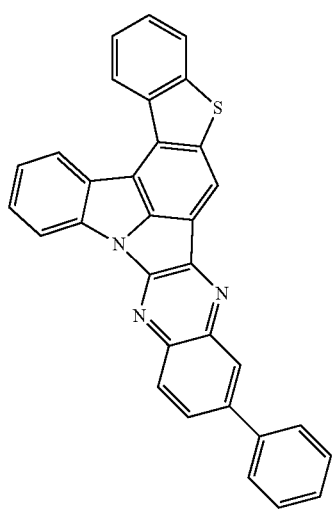
A-198
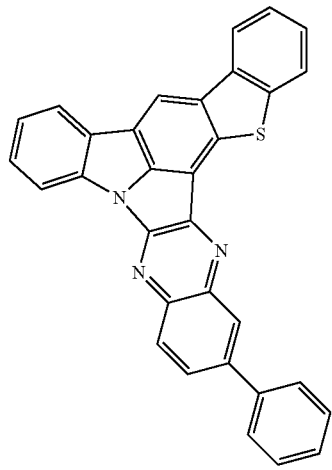
A-199
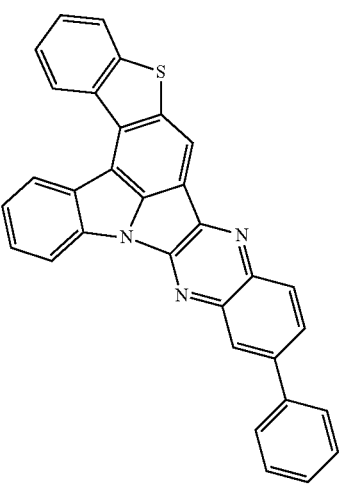

-continued
A-200
A-201
A-202
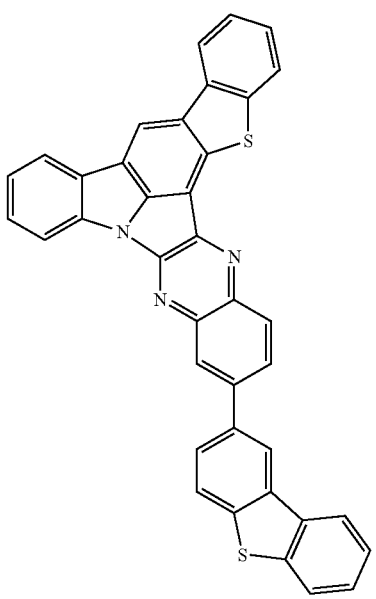
A-203
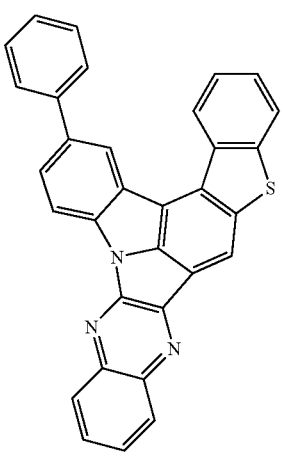
A-204
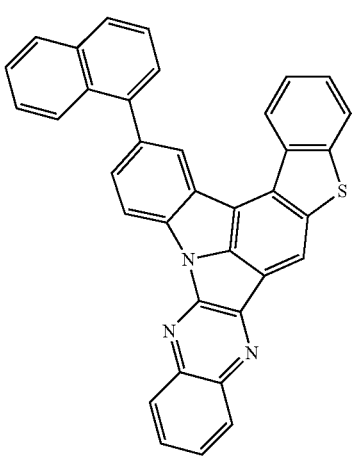

-continued
A-205
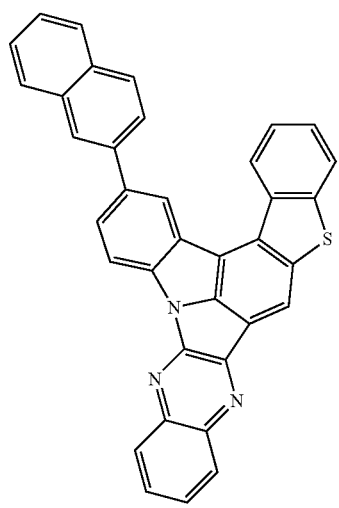
A-206
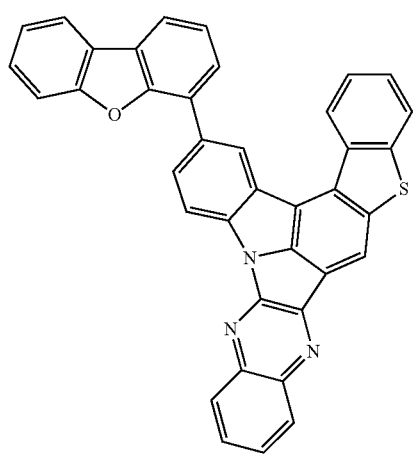
A-207
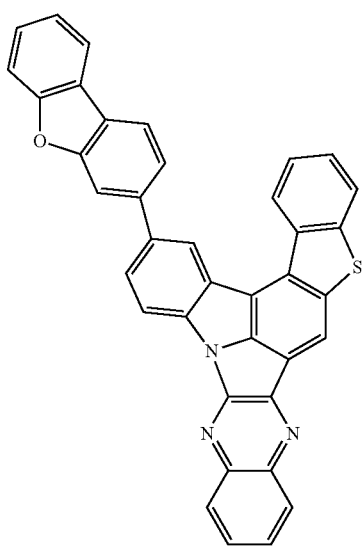
-continued
A-208
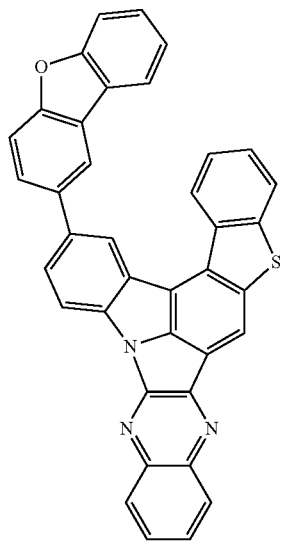
A-209
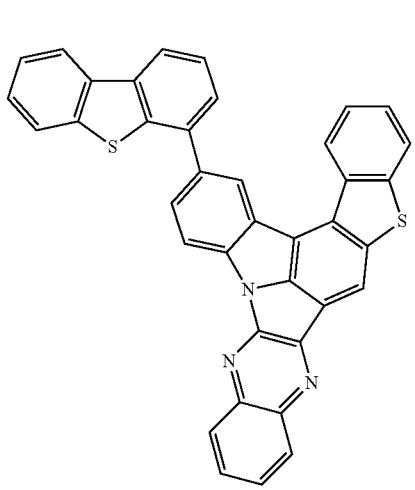
A-210
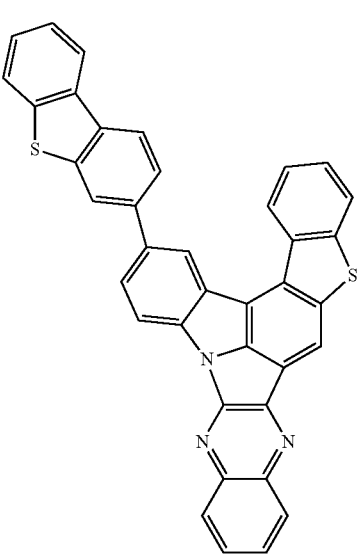

A-211
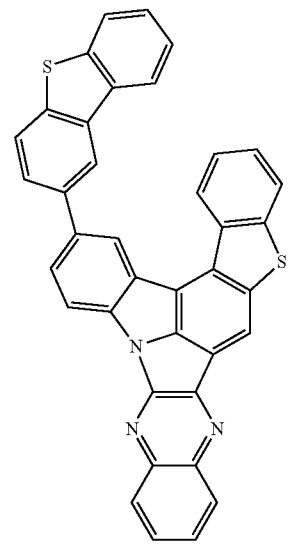
A-212
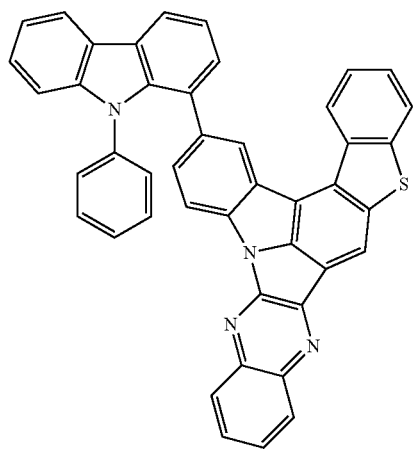
A-213
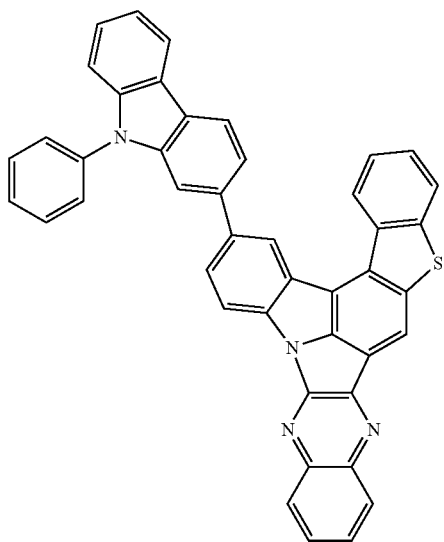
A-214
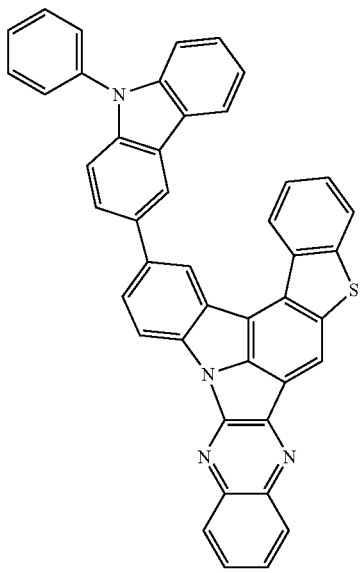
A-215
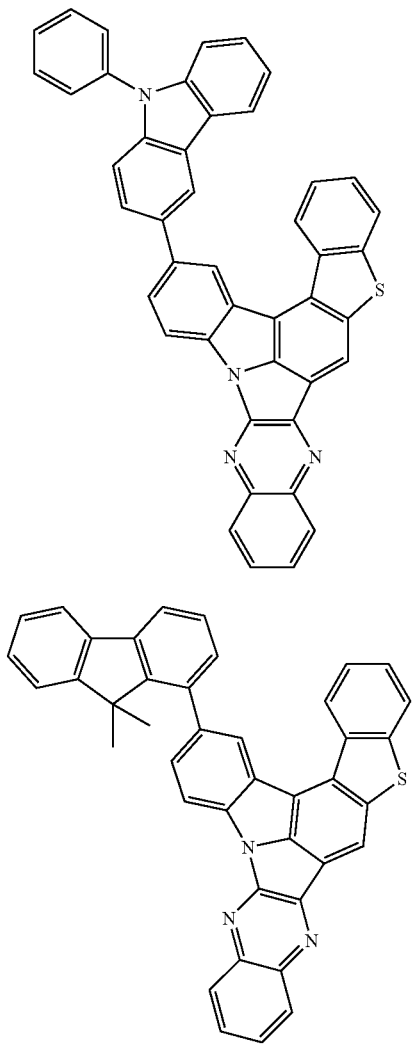
A-216
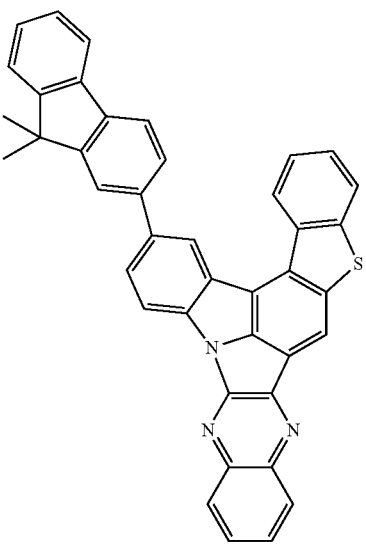

A-217
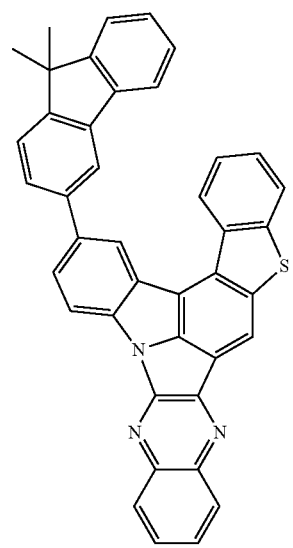
A-218
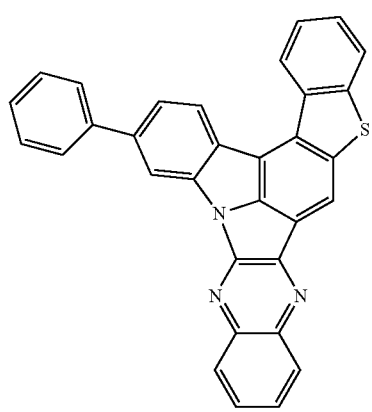
A-219
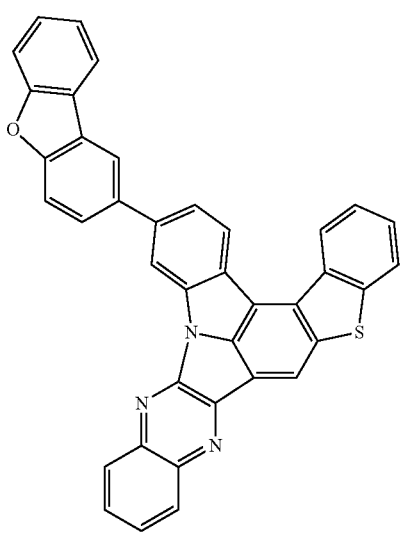
A-220
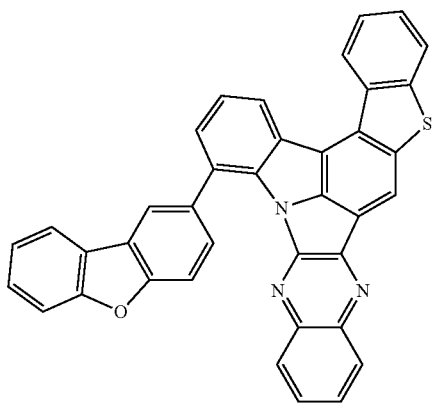
A-221
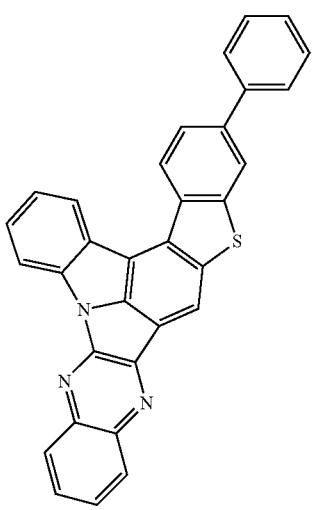
A-223
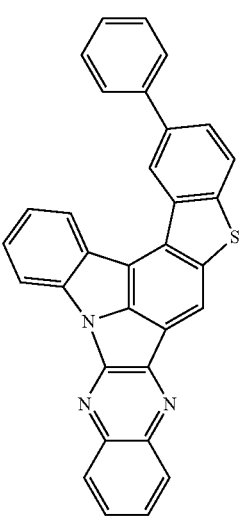

-continued
A-224
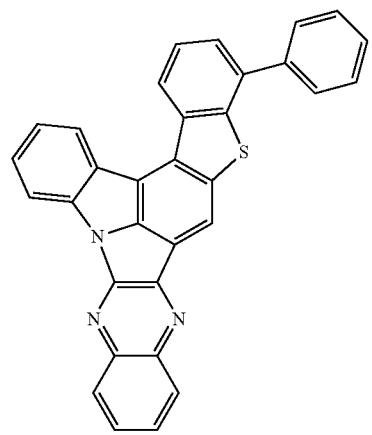
A-225
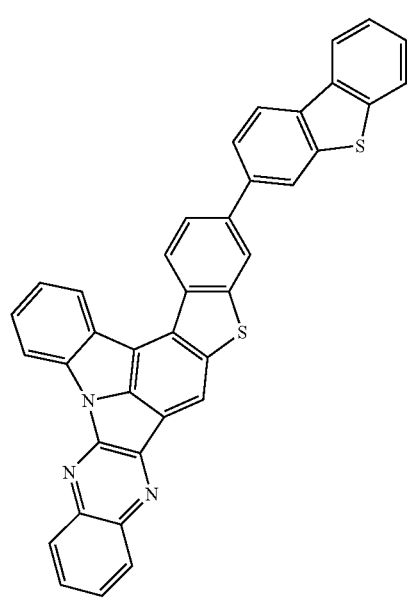
A-226
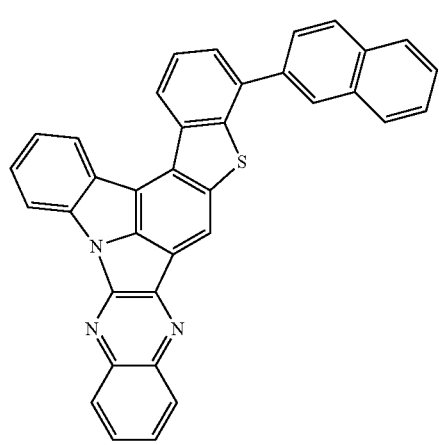
-continued
A-227
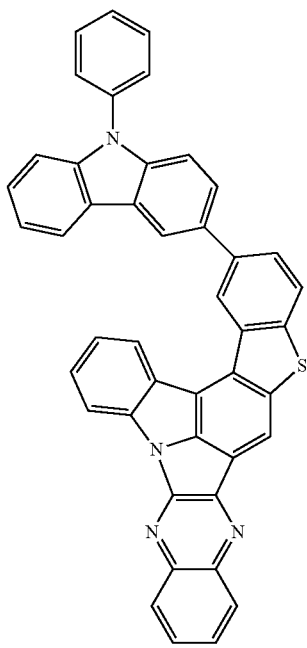
A-228
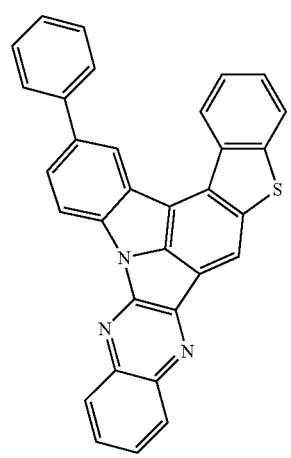
A-229
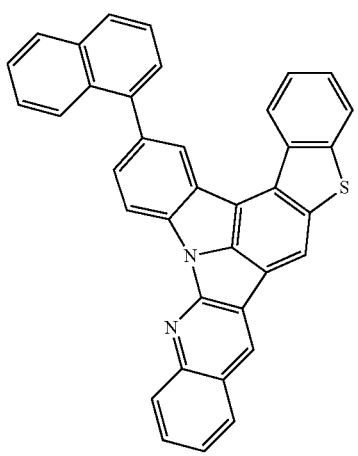

-continued
A-230
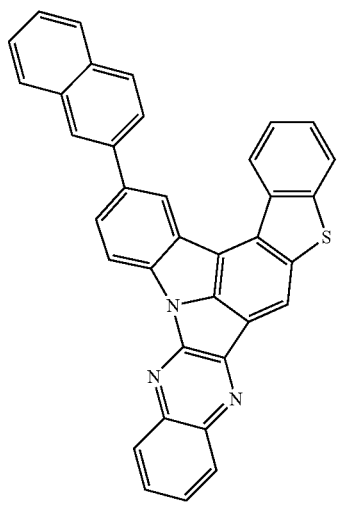
A-231
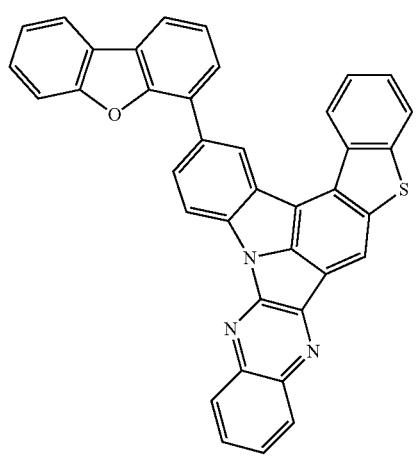
A-232
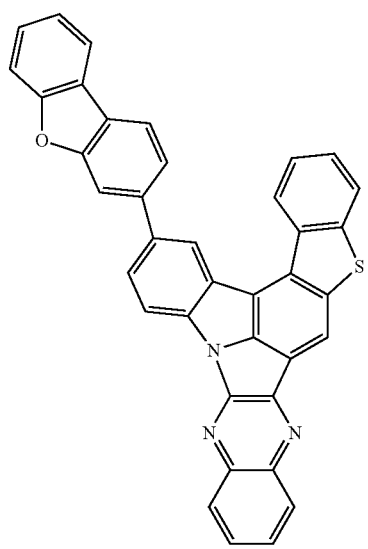
-continued
A-233
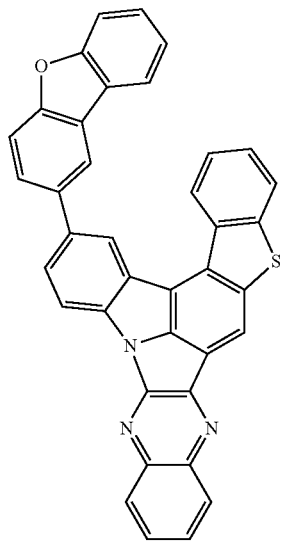
A-234
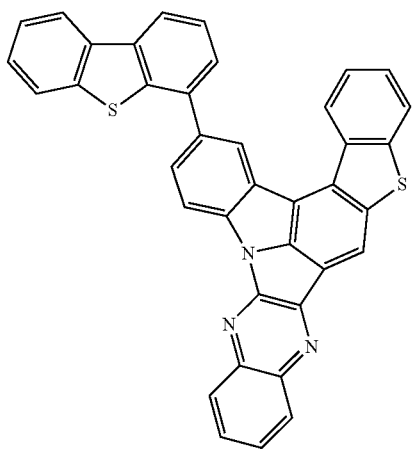
A-235
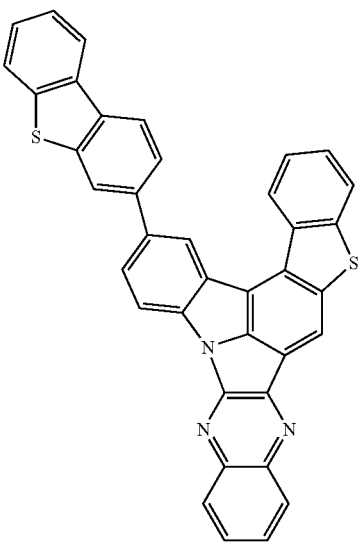

-continued
A-236
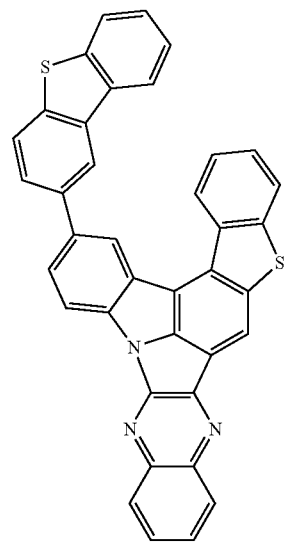
A-237
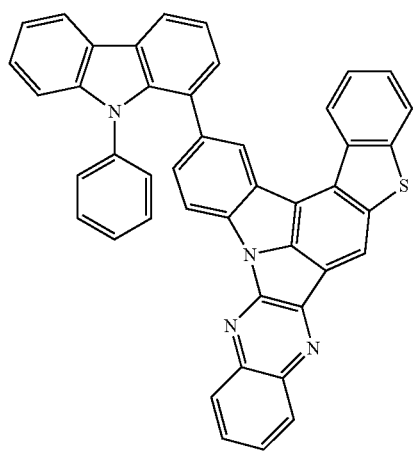
A-238
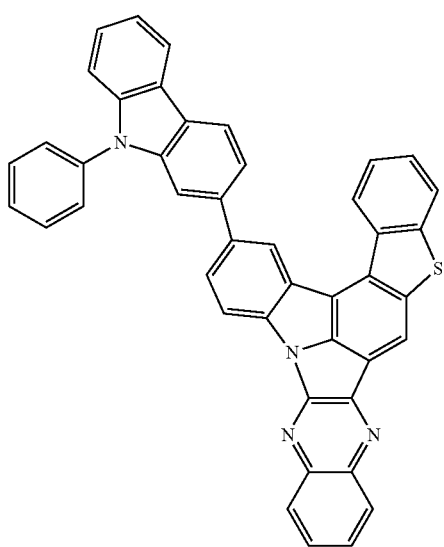
-continued
A-239
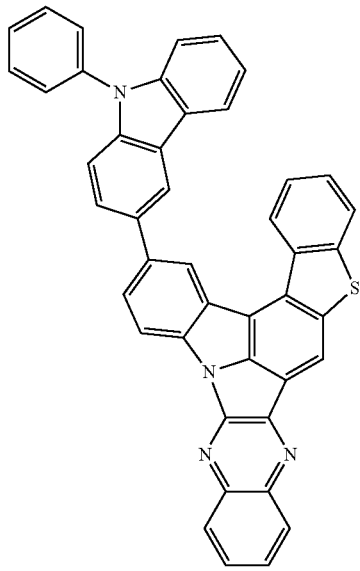
A-240
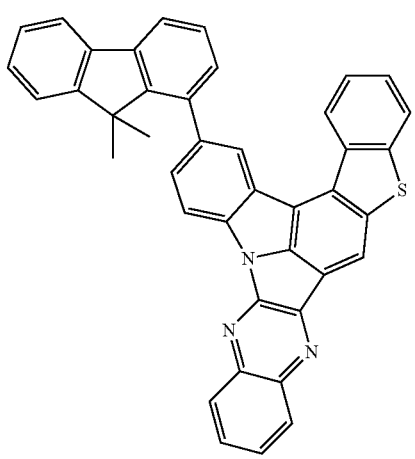
A-241
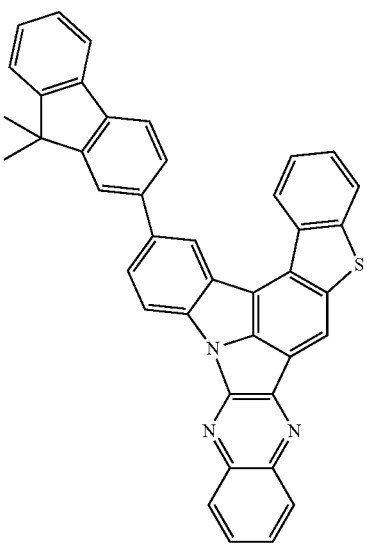

A-242
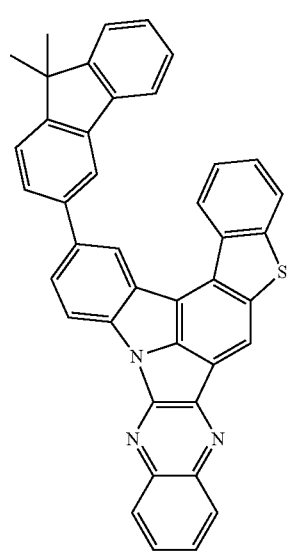
A-243
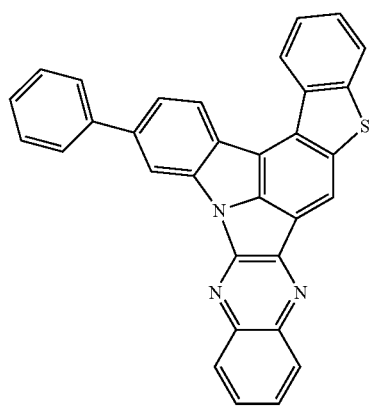
A-244
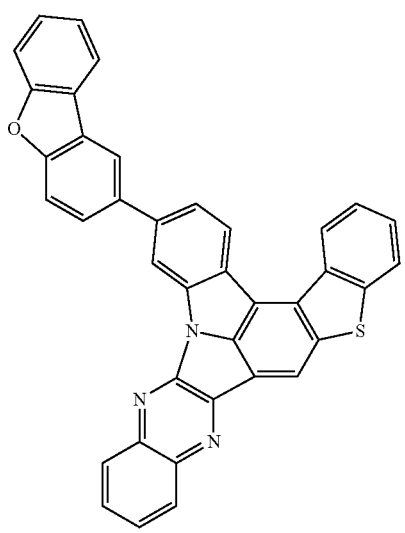
A-245
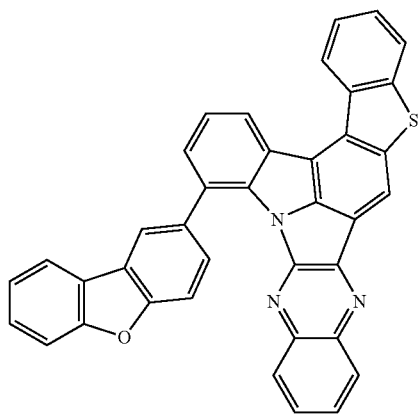
A-246
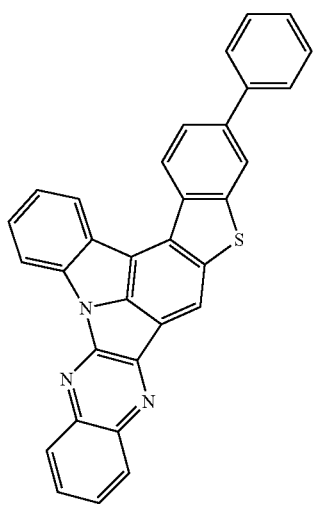
A-247
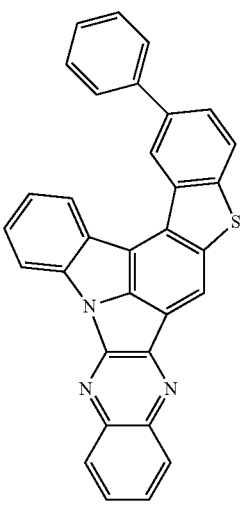

-continued
A-248
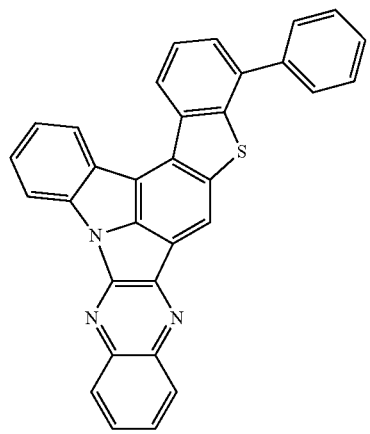
A-249
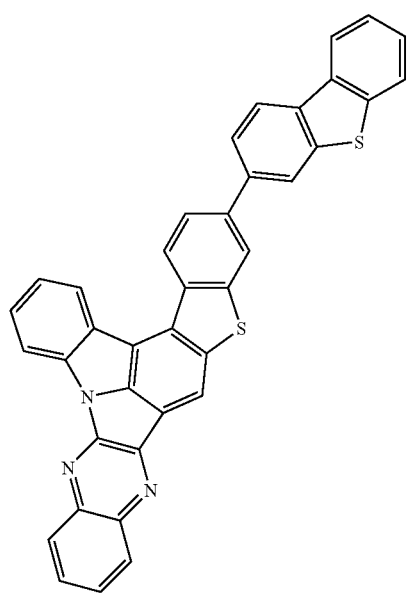
A-250
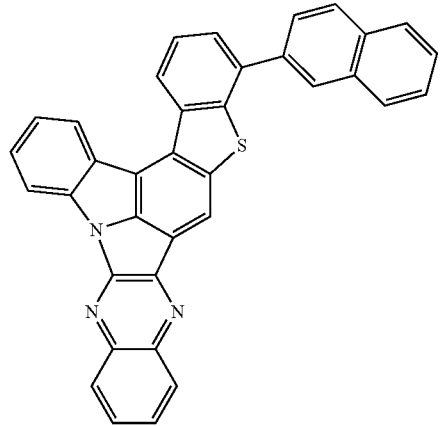
-continued
A-251
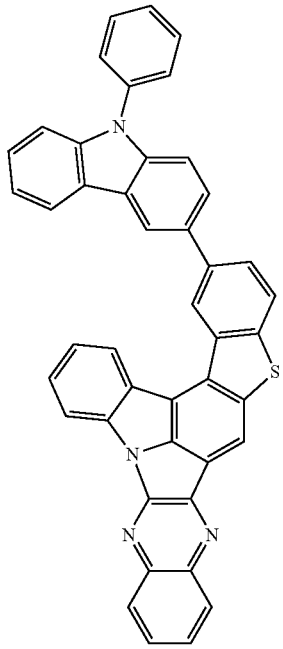
A-252
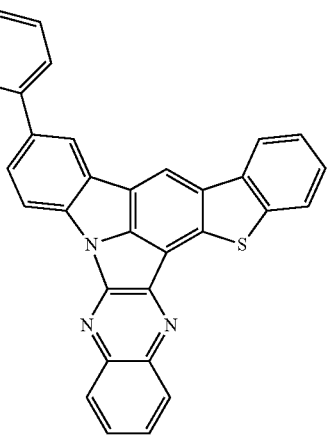
A-253
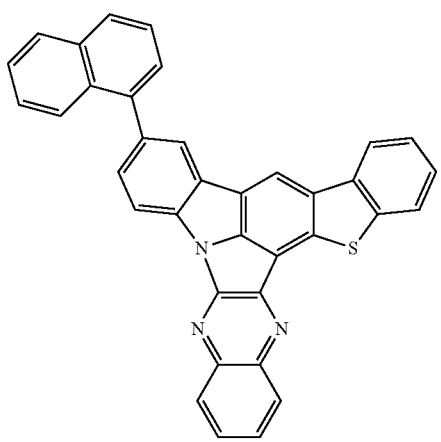

A-254
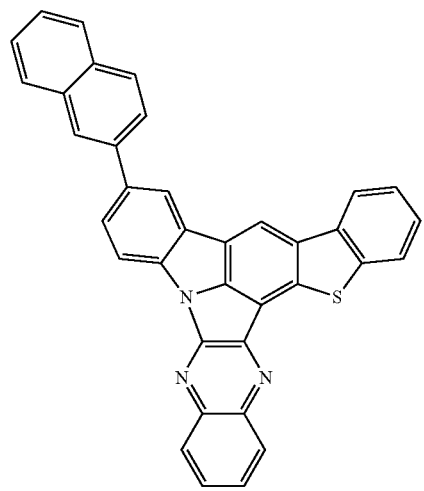
A-255
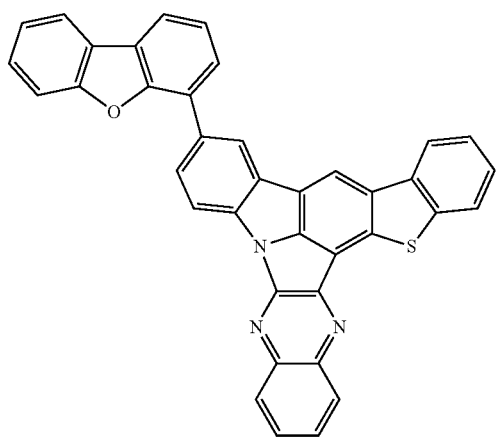
A-256
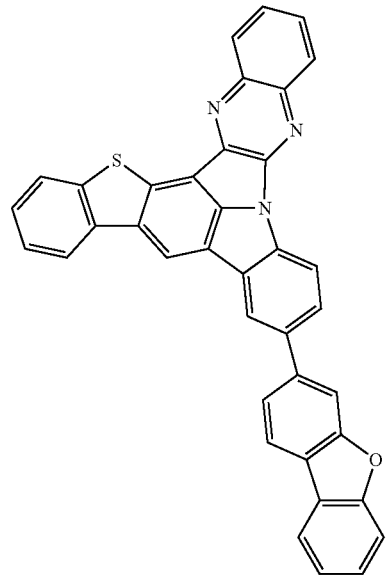
A-257
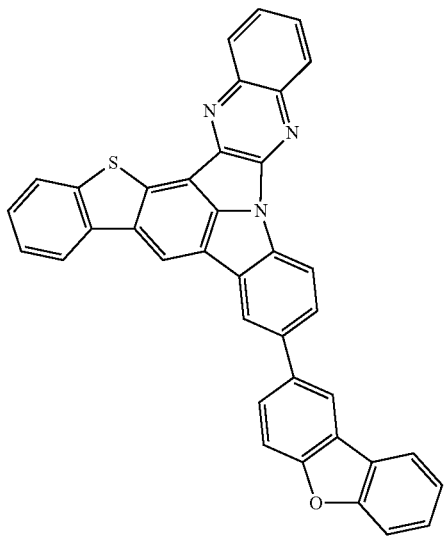
A-258
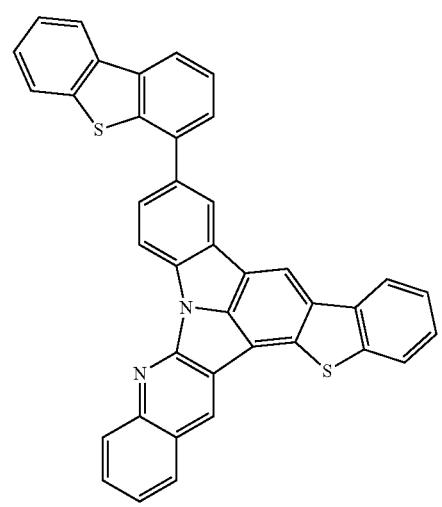
A-259
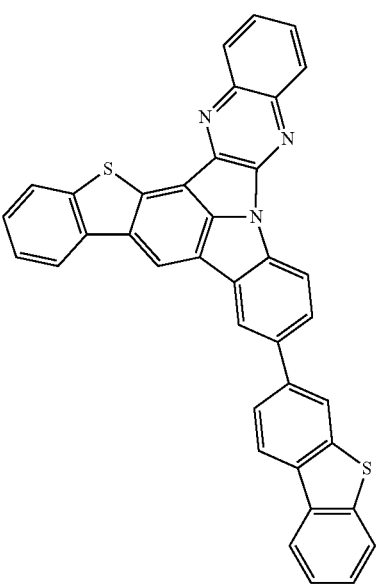

-continued
A-260
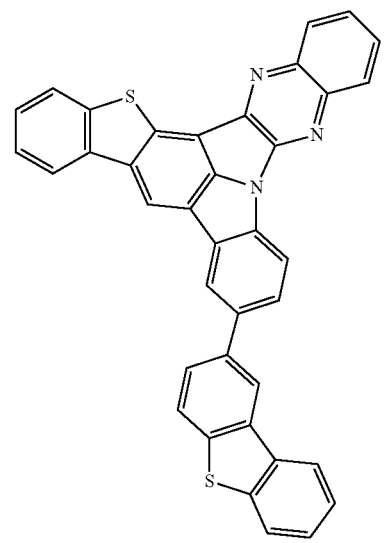
A-261
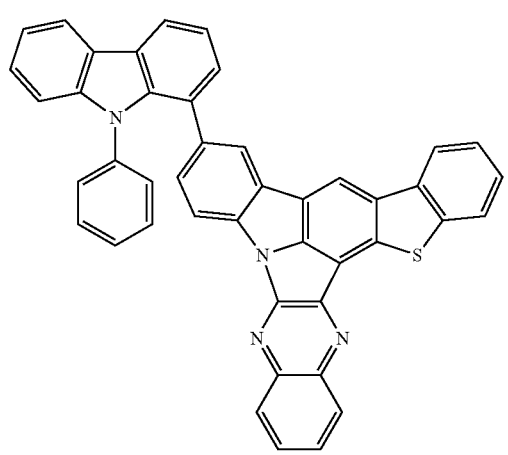
A-262
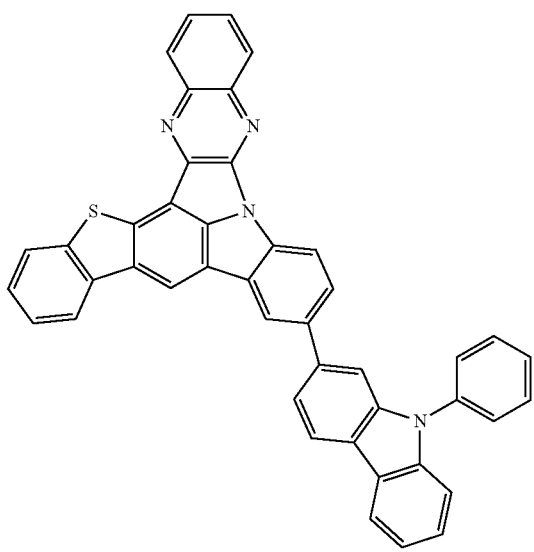
-continued
A-263
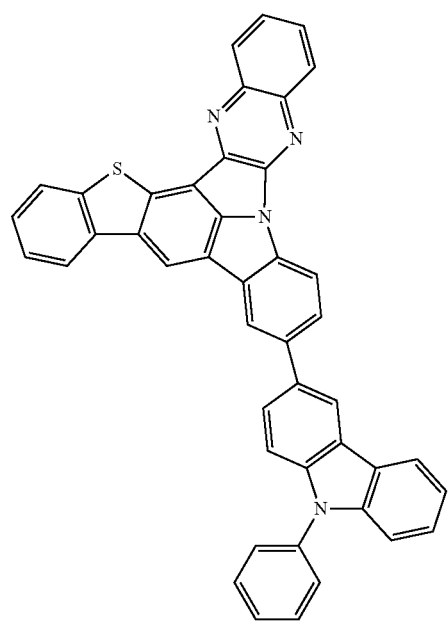
A-264
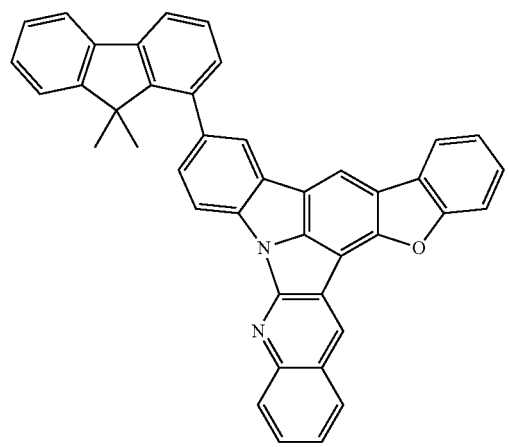
A-265
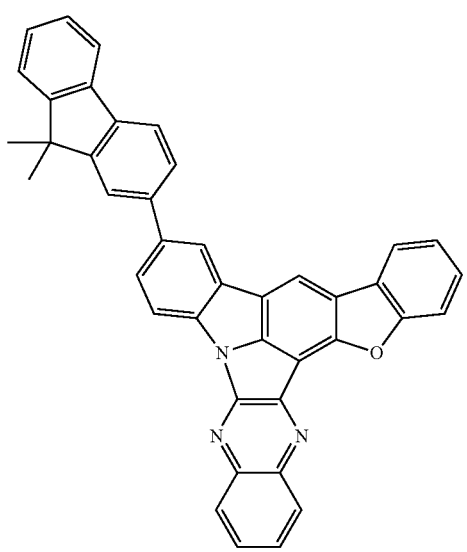

A-266
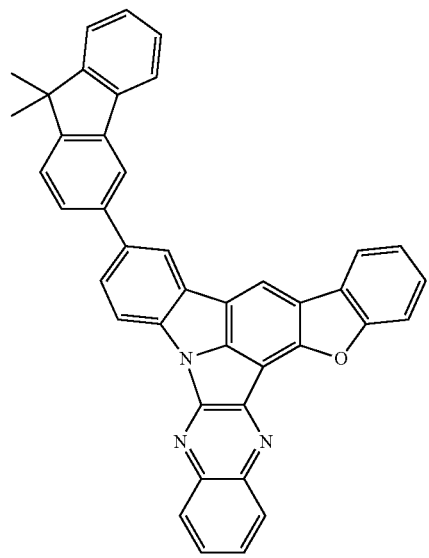
A-267
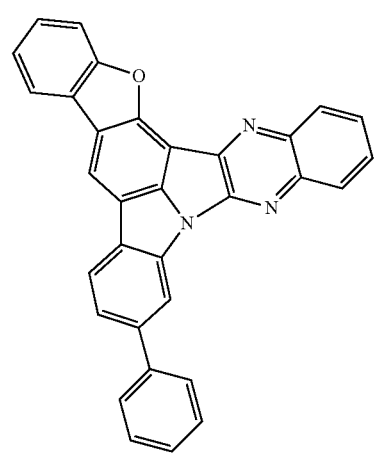
A-268
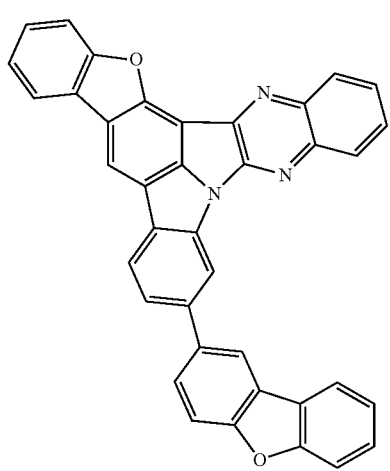
A-269
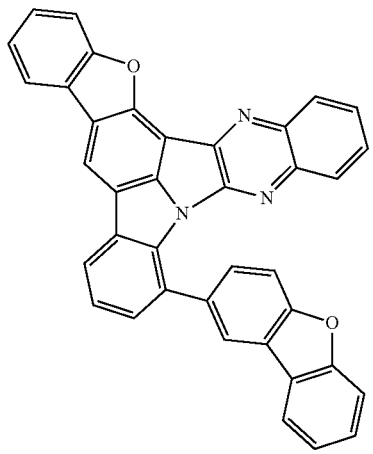
A-270
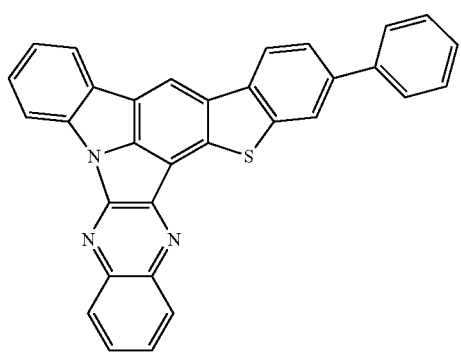
A-271
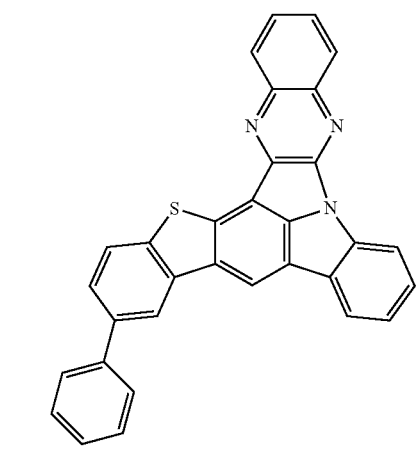
A-272
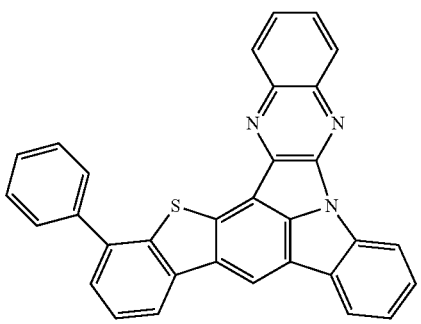

-continued
A-273
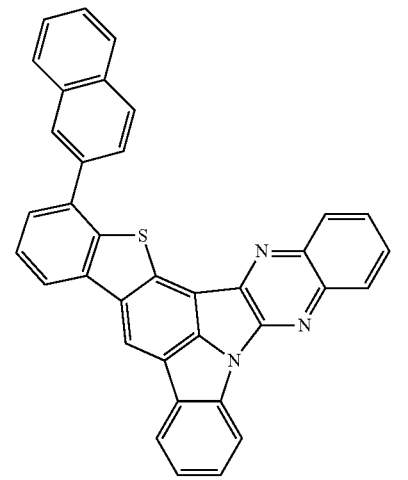
A-274
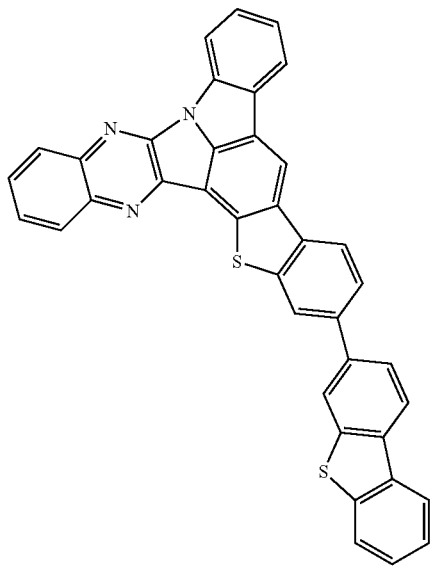
A-275
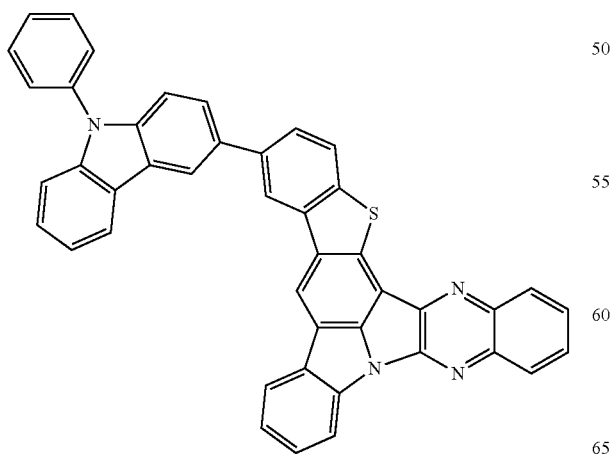
-continued
A-276
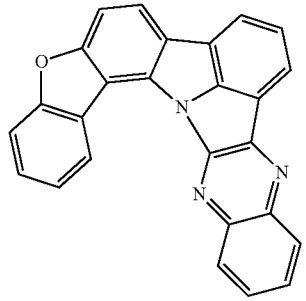
A-277
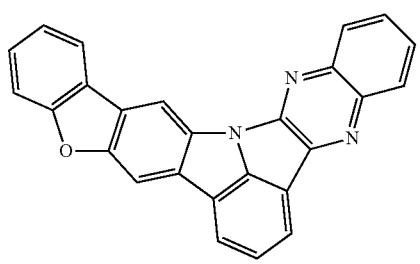
A-278
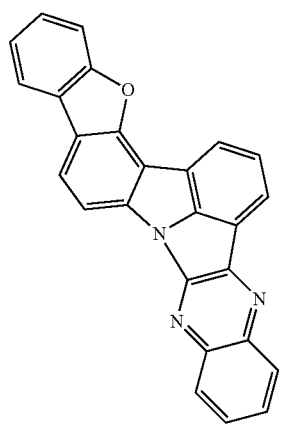
A-279
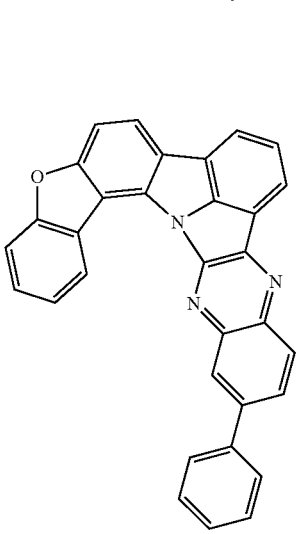

A-280
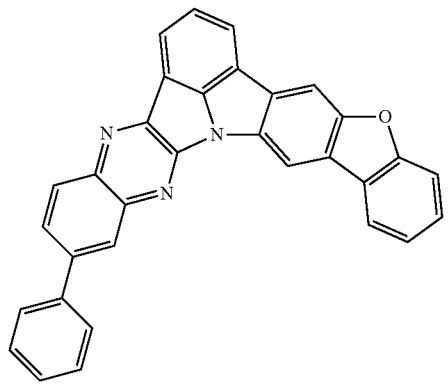
A-281
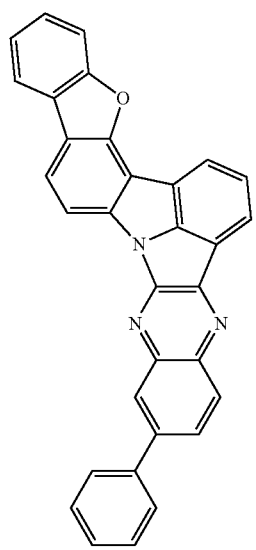
A-282
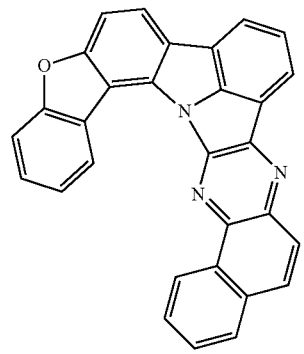
A-283
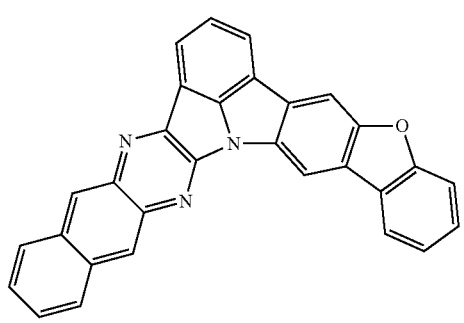
A-284
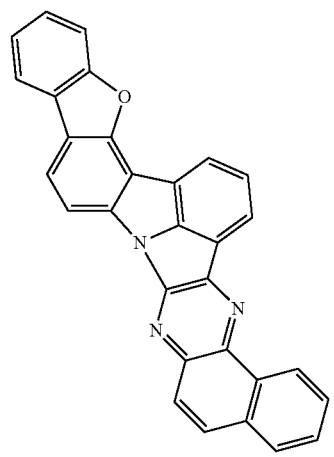
A-285
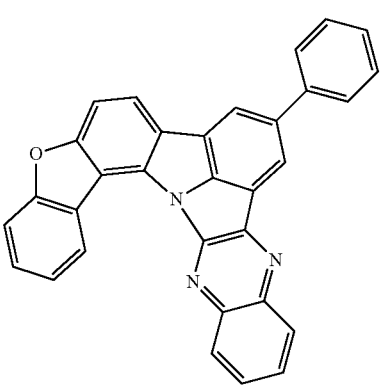
A-286
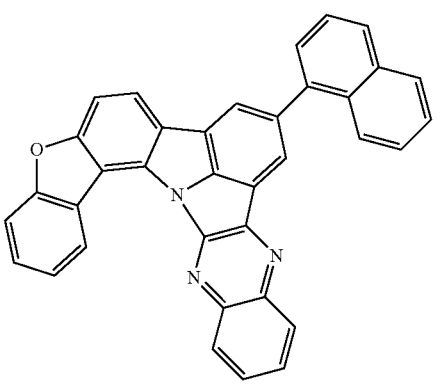
A-287
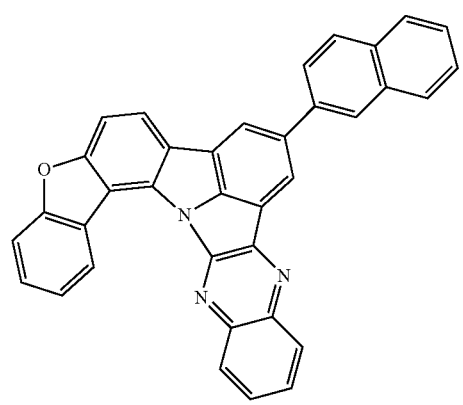

A-288
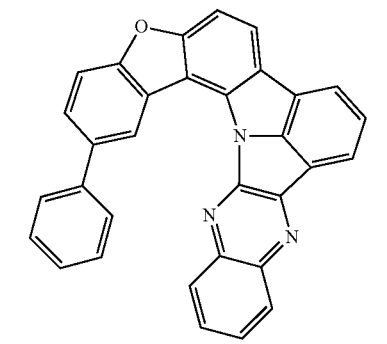
A-289
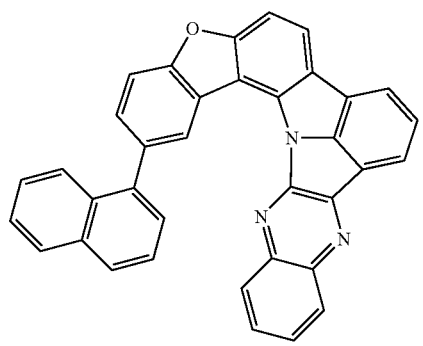
A-290
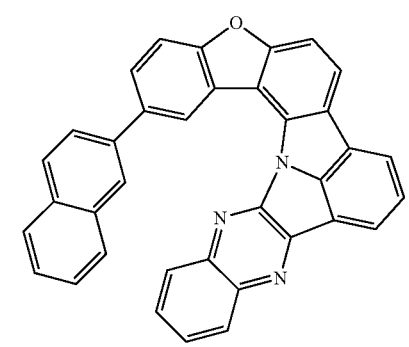
A-291
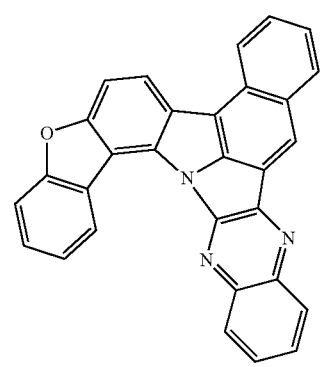
A-292
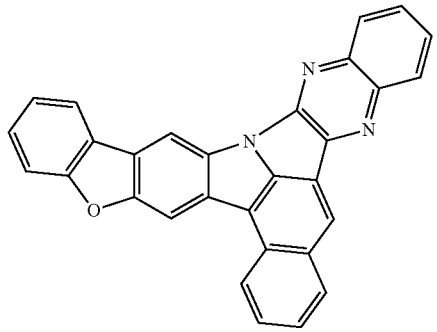
A-293
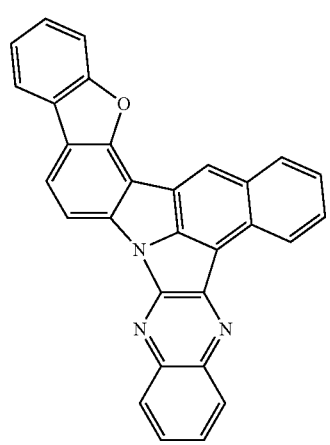
A-294
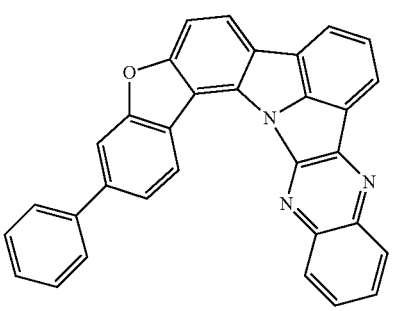
A-295
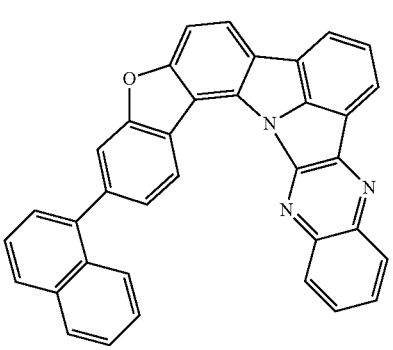

-continued
A-296
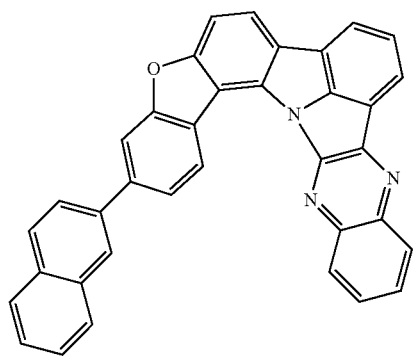
A-297
A-298
A-299
-continued
A-300
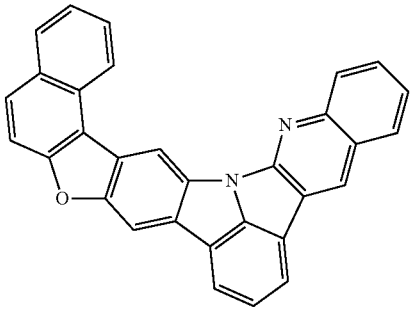
A-301
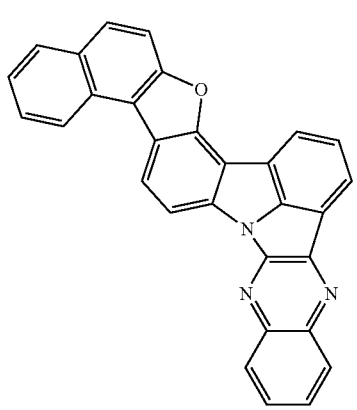
A-302
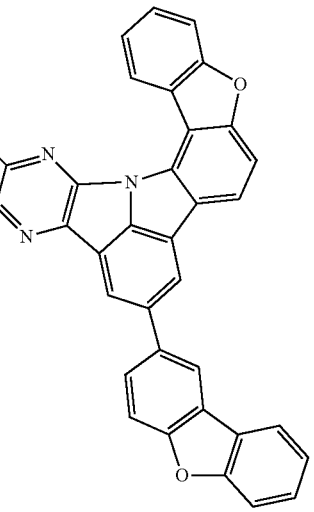

A-303
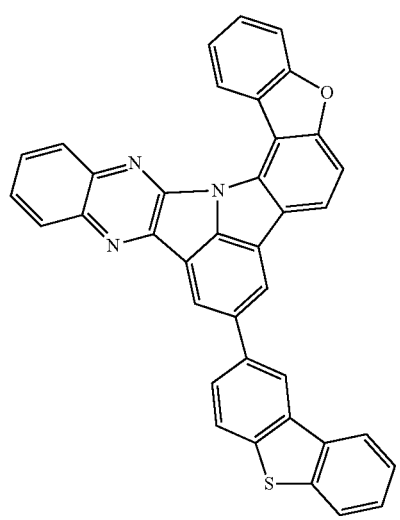
A-304
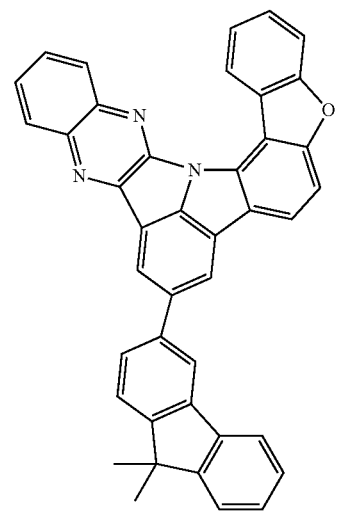
A-305
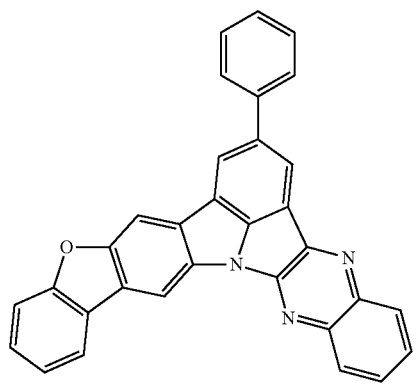
A-306
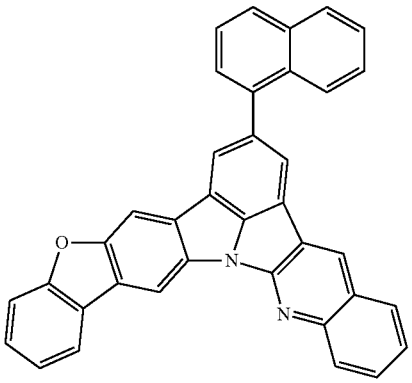
A-307
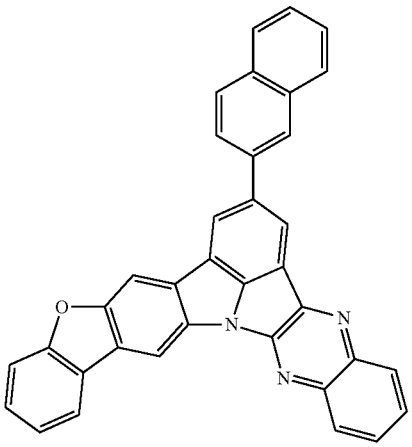
A-308
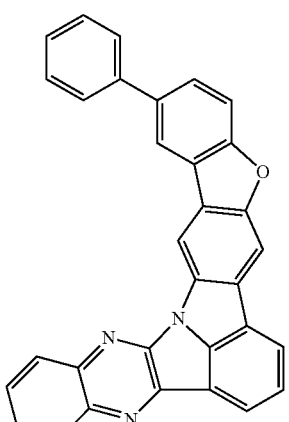

A-309
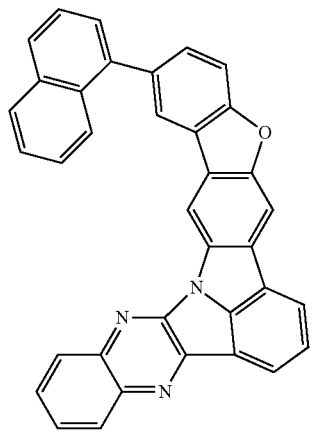
A-310
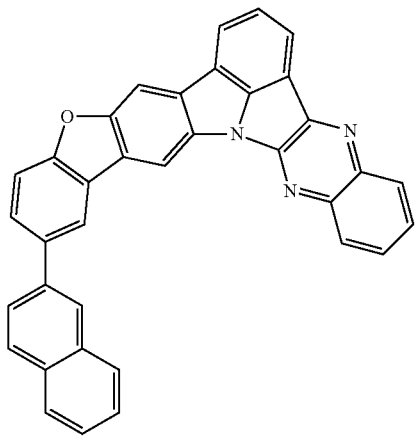
A-311
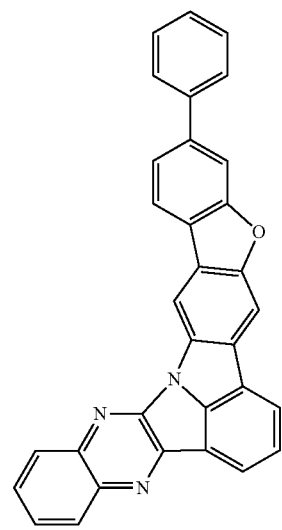
A-312
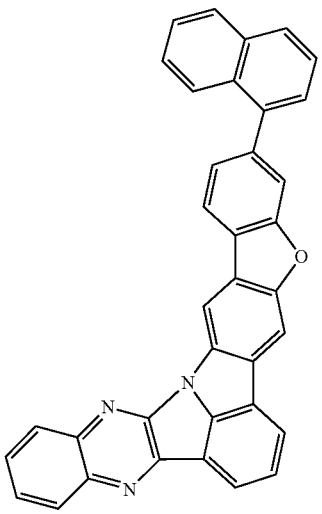
A-313
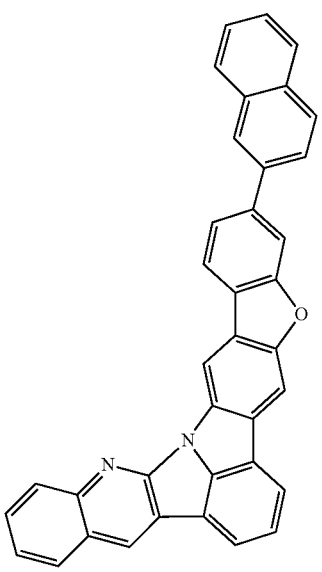
A-314
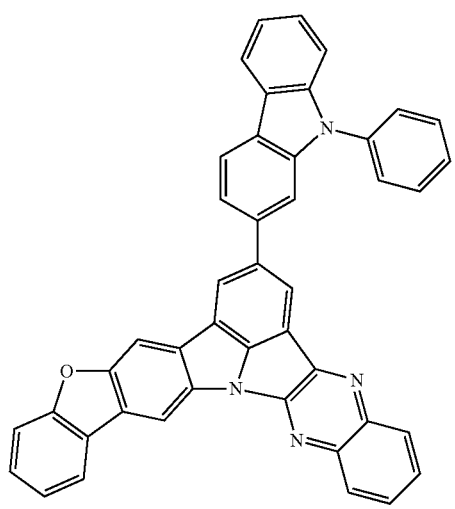

A-315
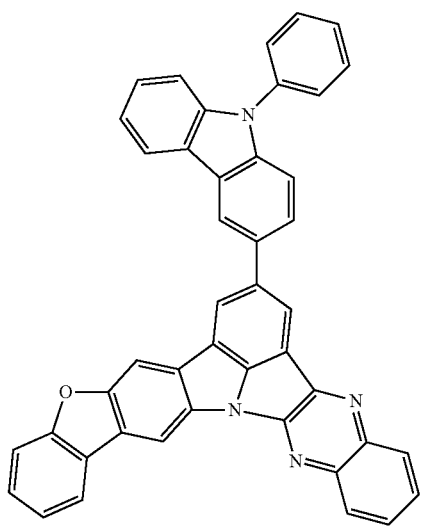
A-316
A-318
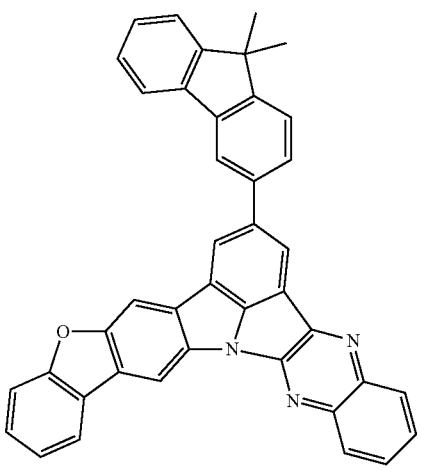
A-319
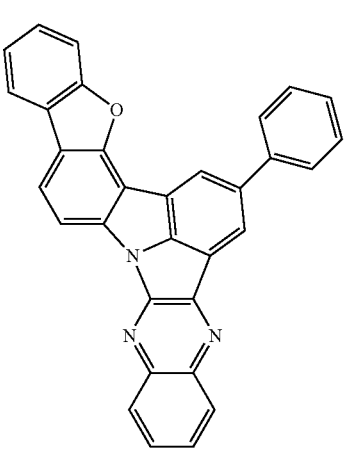
A-317
A-320
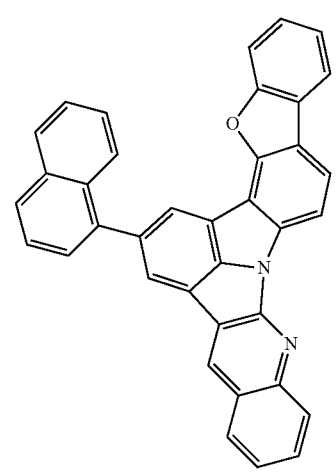

A-321
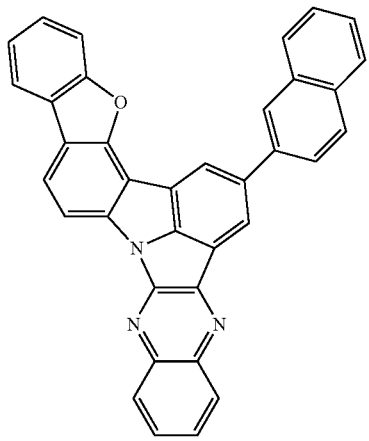
A-322
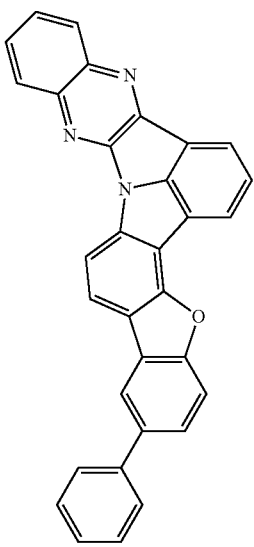
A-323
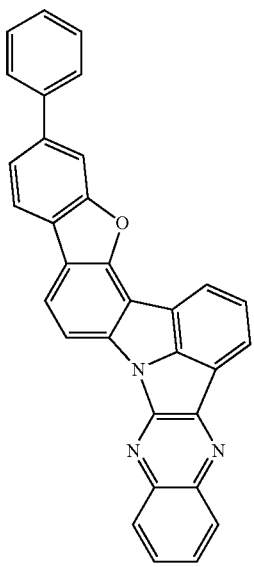
A-324
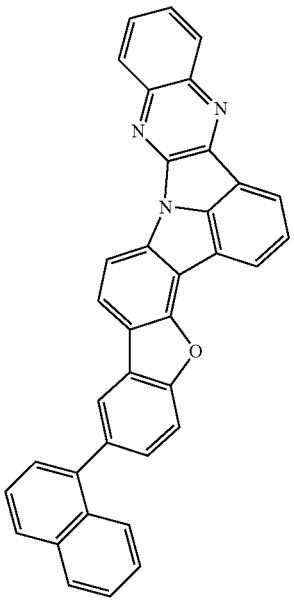
A-325
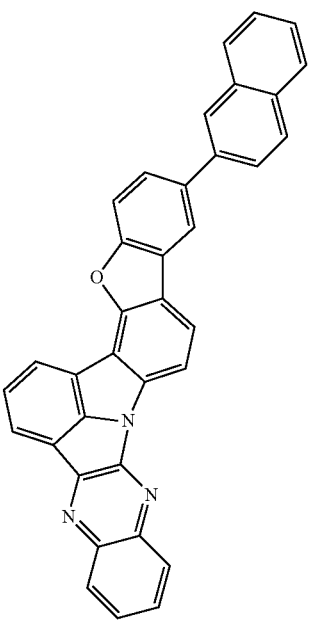

A-326
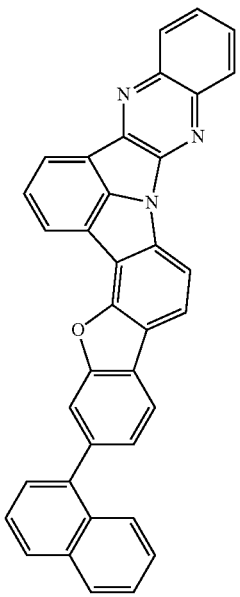
A-327
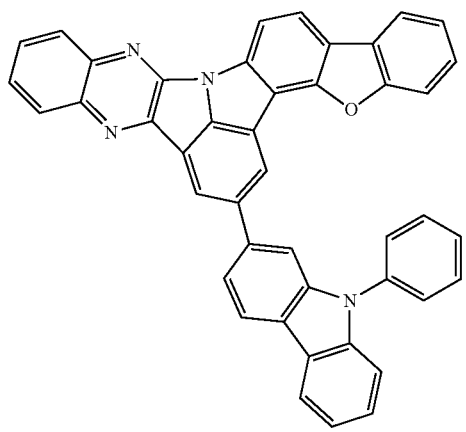
A-328
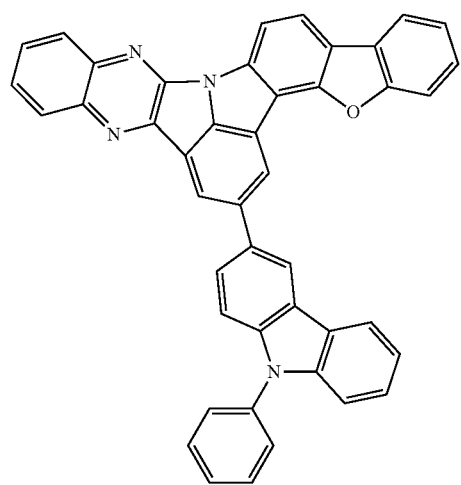
A-329
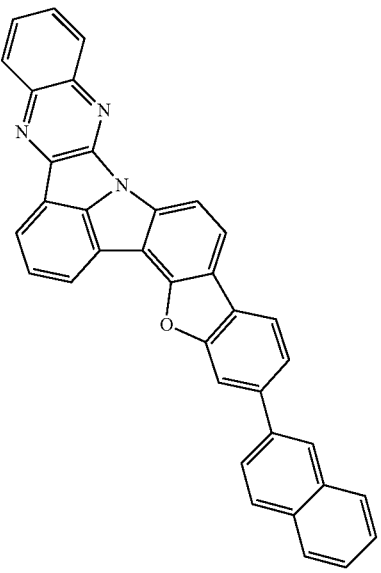
A-330
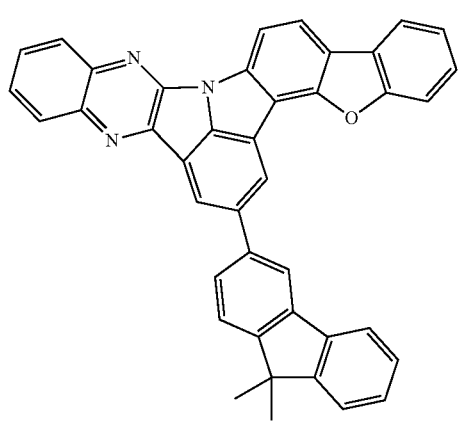
A-331
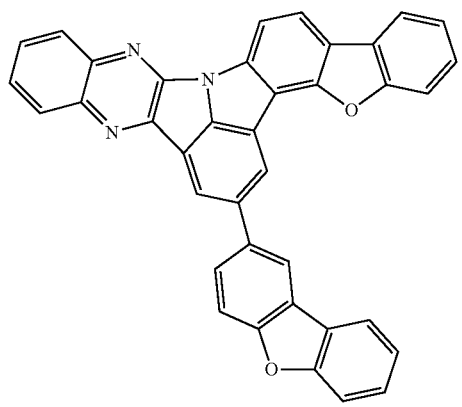

A-332
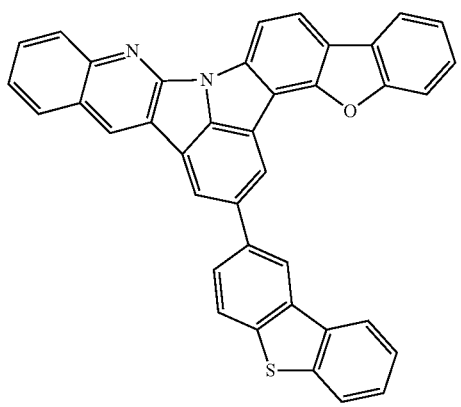
A-333
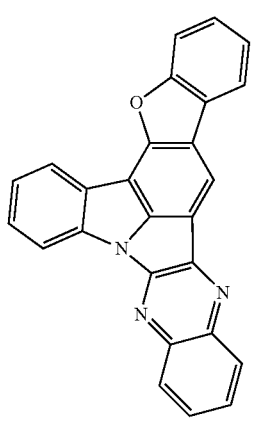
A-334
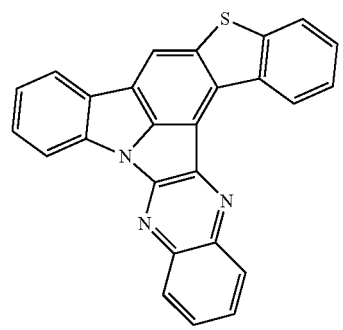
A-335
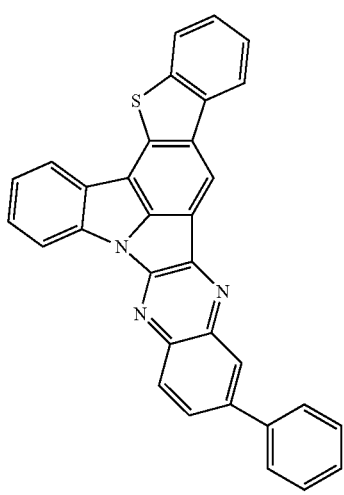
A-336
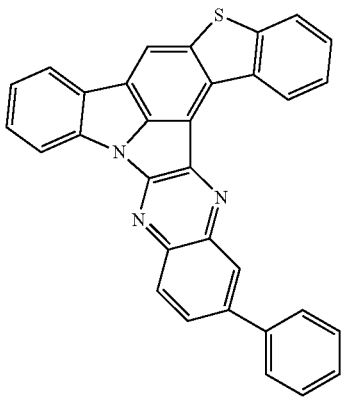
A-337
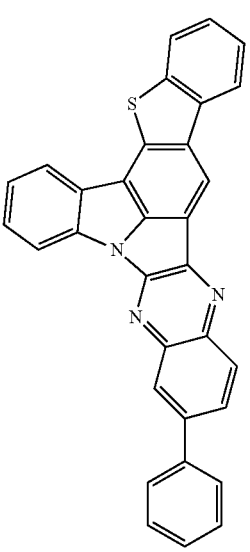
A-338
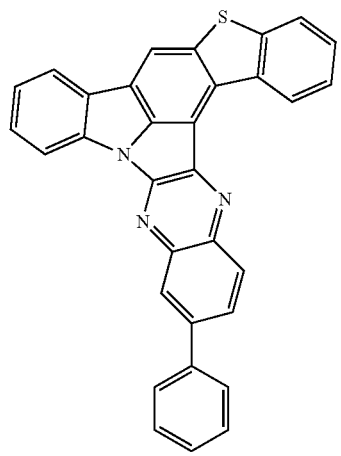

-continued
A-339
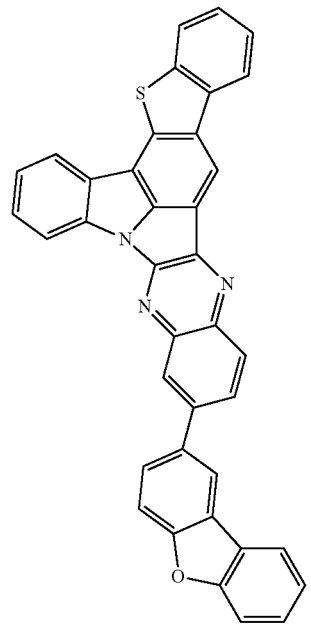
A-339-1
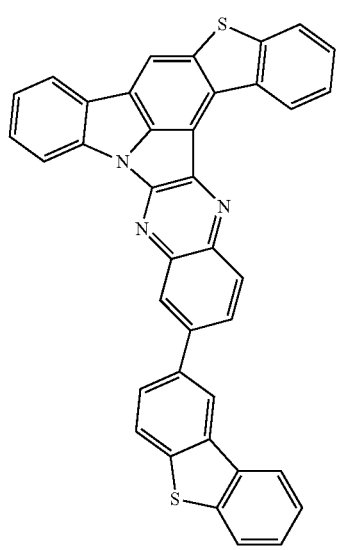
A-340
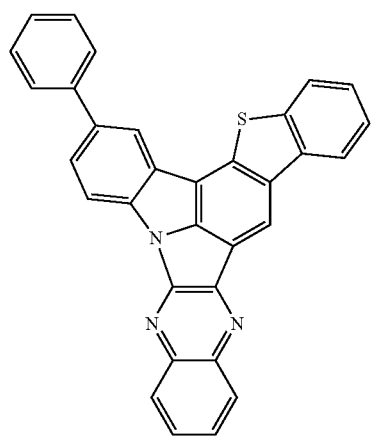
-continued
A-341
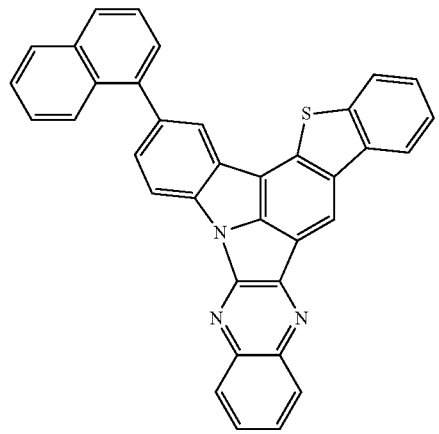
A-342
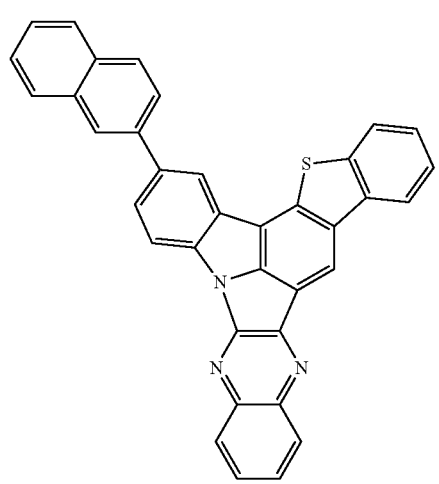
A-343
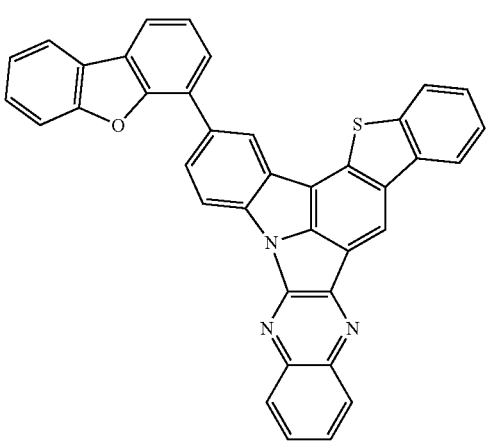

A-344
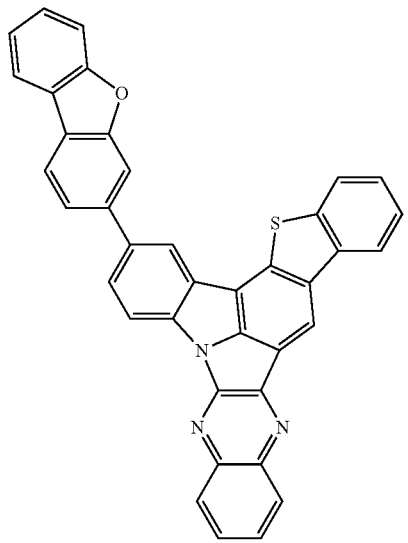
A-345
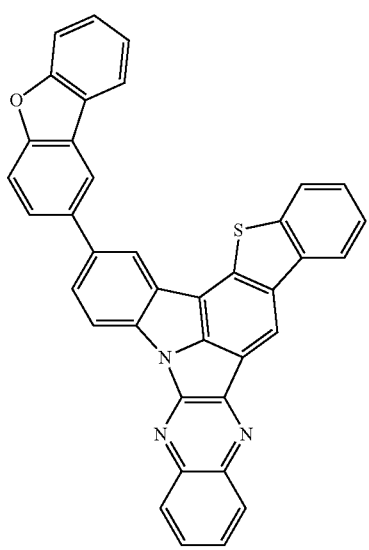
A-346
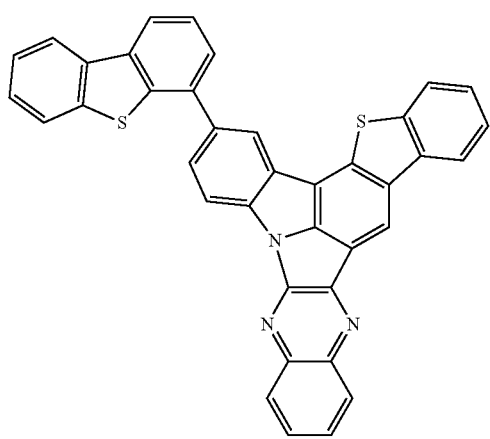
A-347
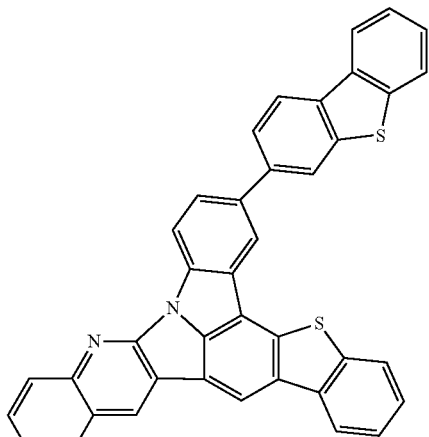
A-348
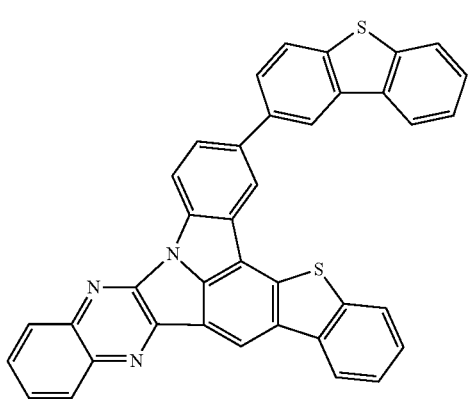
A-349
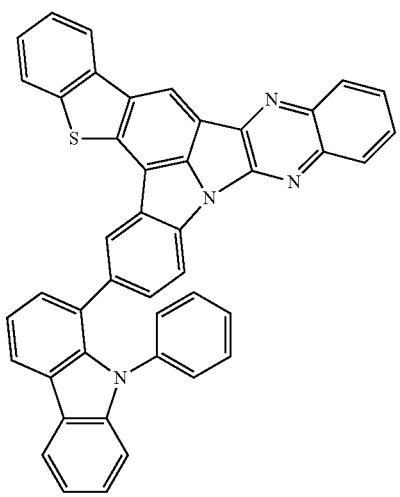

A-350
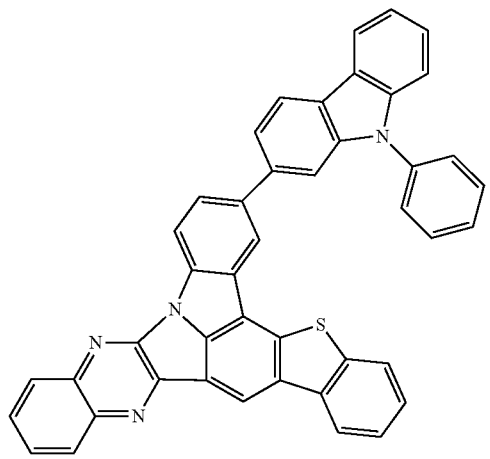
A-351
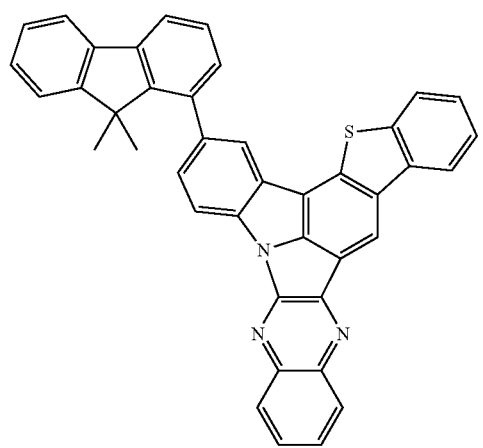
A-352
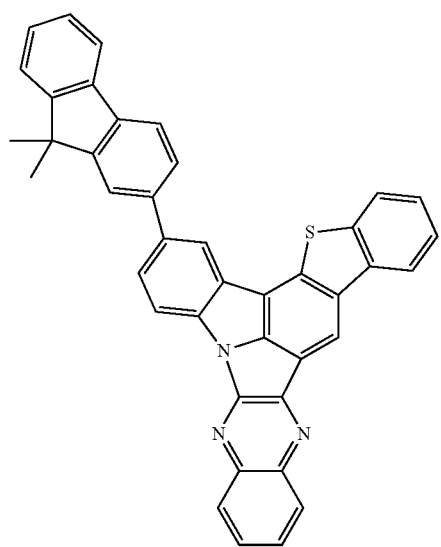
A-353
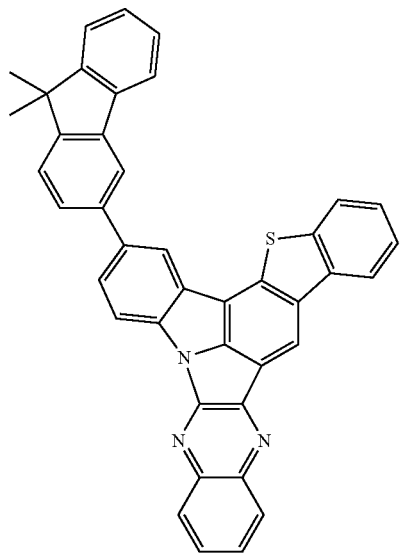
A-354
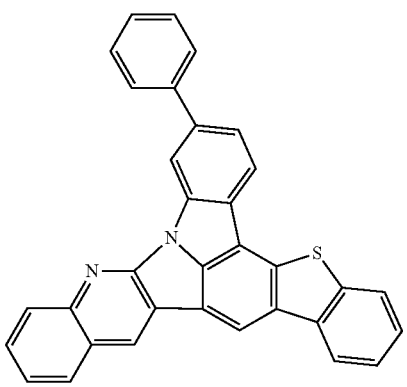
A-355
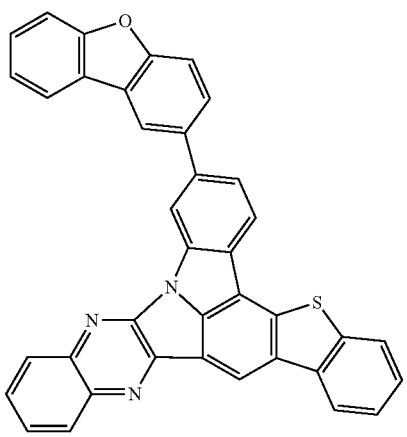
A-356
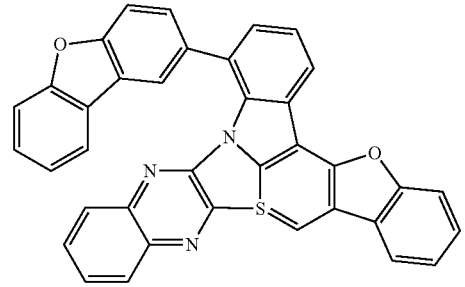

A-357
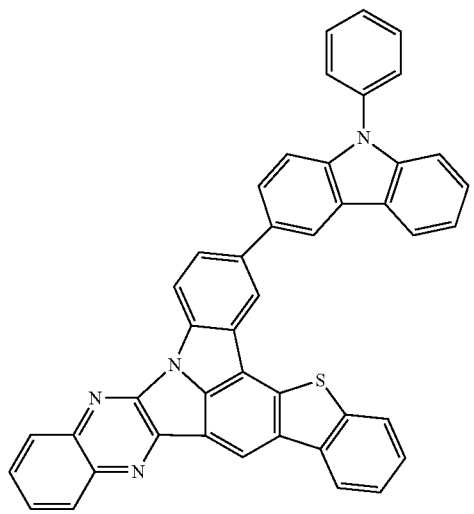
A-358
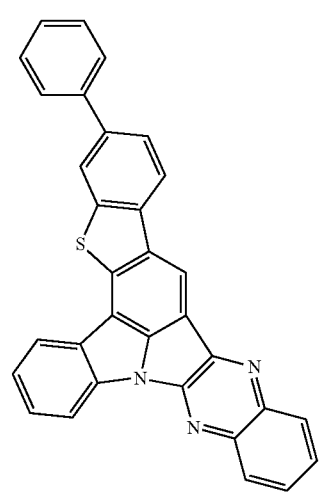
A-359
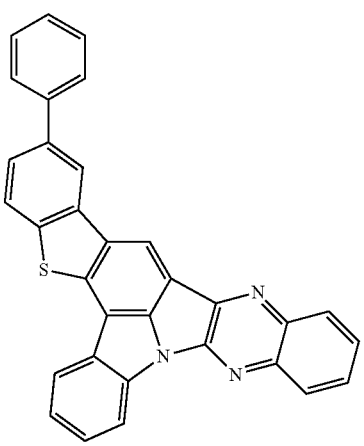
A-360
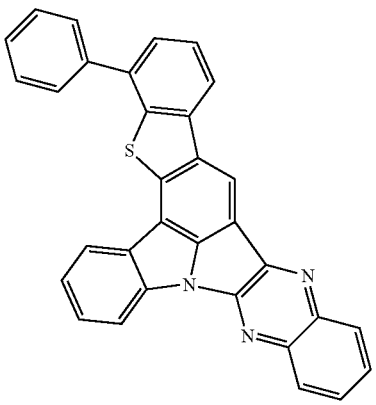
A-361
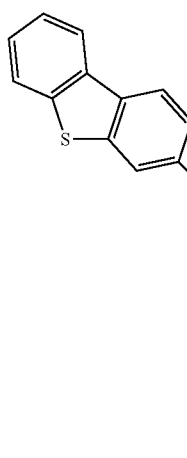
A-362
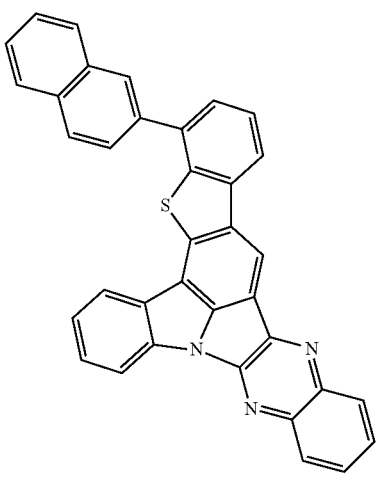

A-363
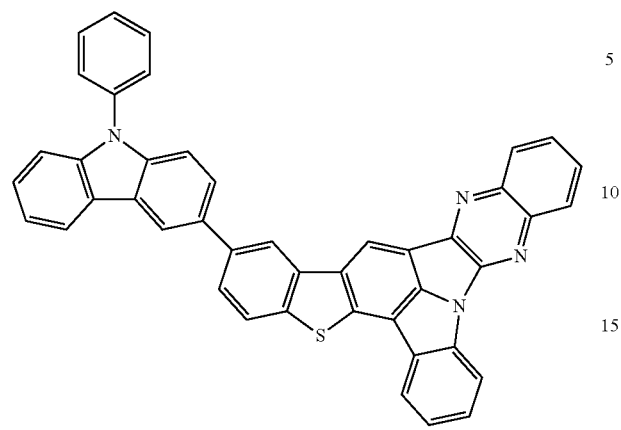
A-364
A-365
A-366
A-367
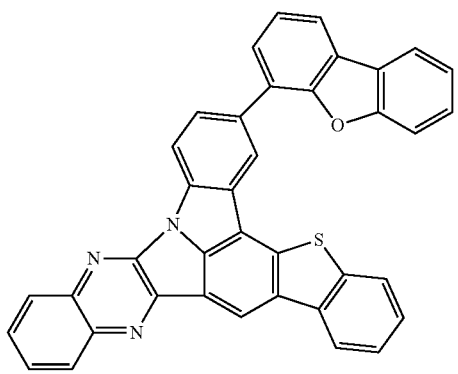
A-368
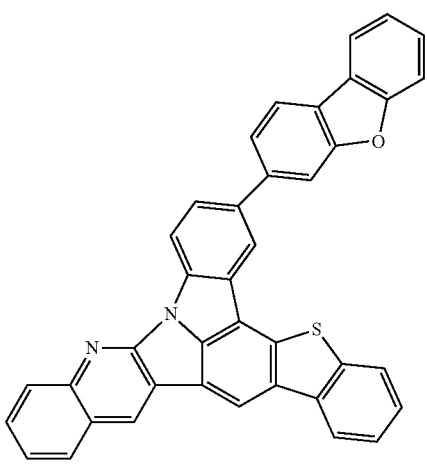
A-369
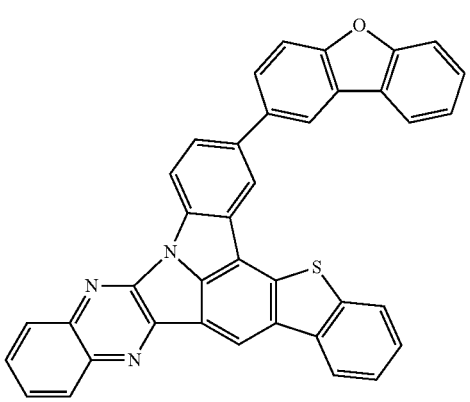
A-370
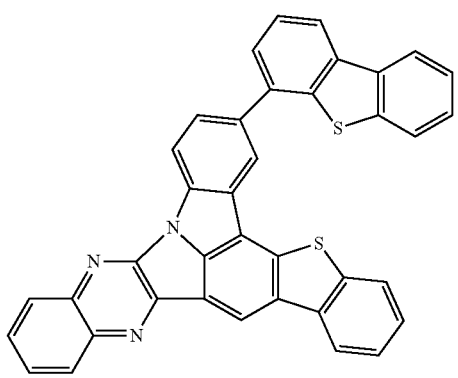

-continued
A-371
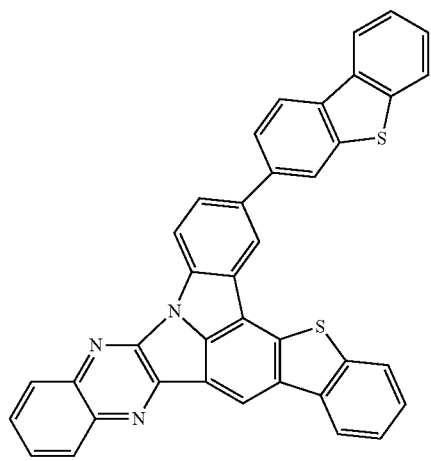
A-374
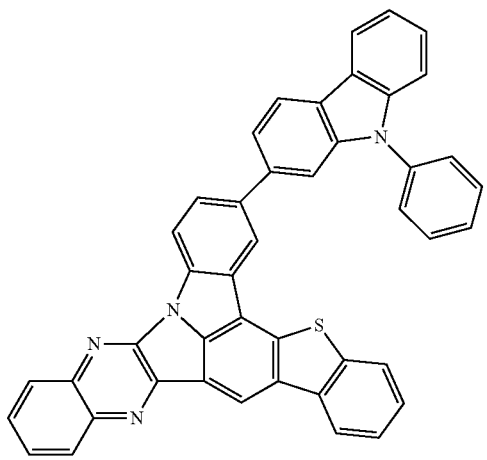
A-372
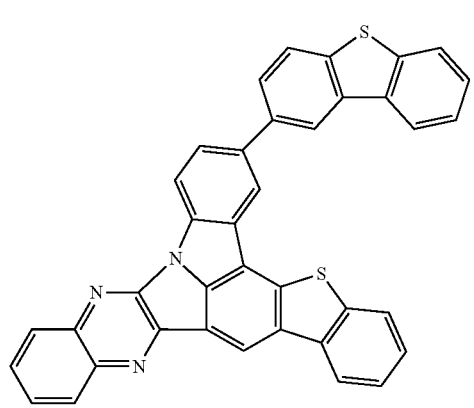
A-375
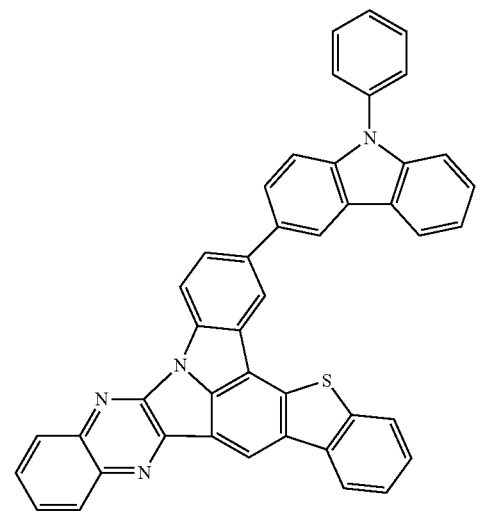
A-373
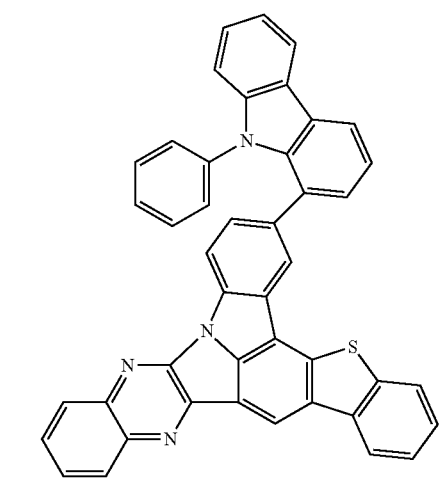
A-376
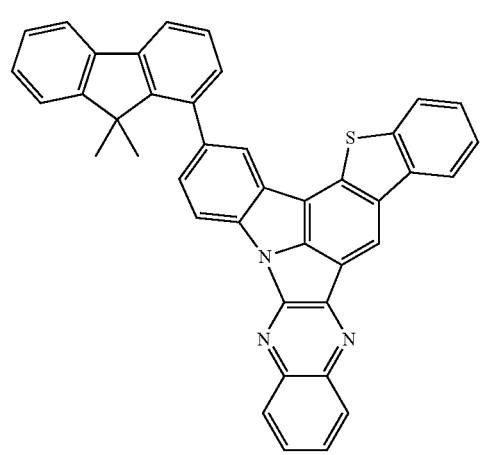

-continued
A-377
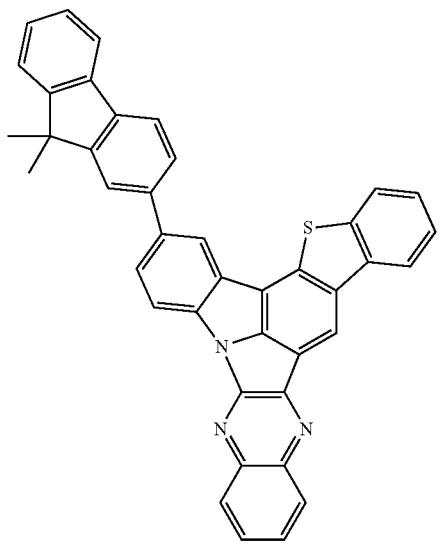
A-378
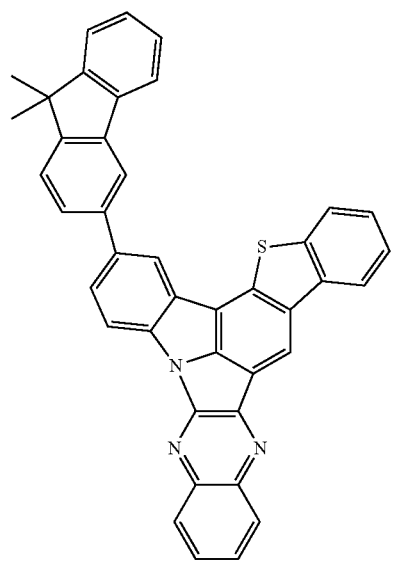
A-379
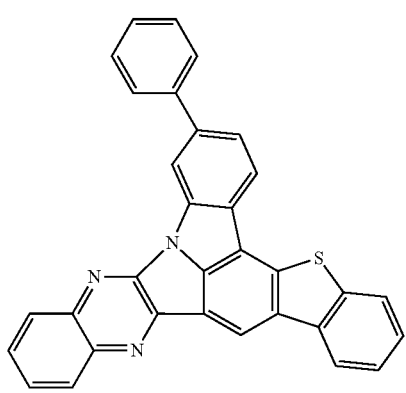
-continued
A-380
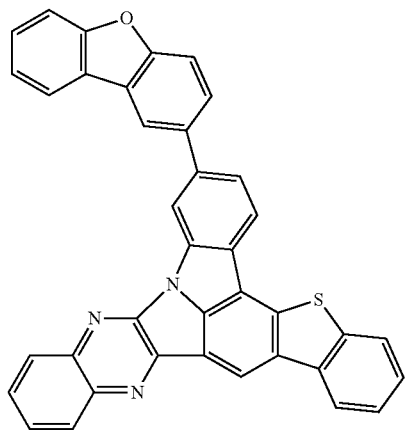
A-381
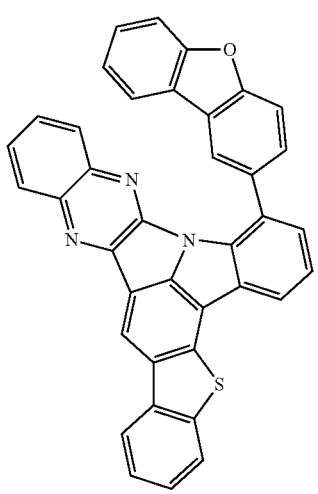
A-382
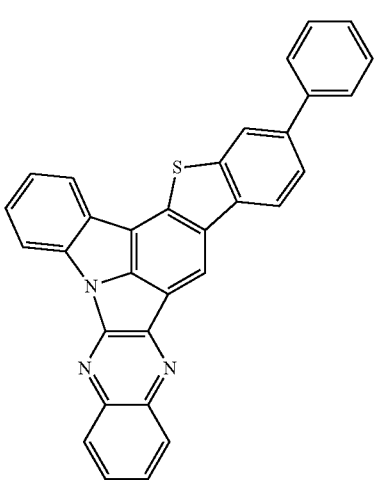

-continued
A-383
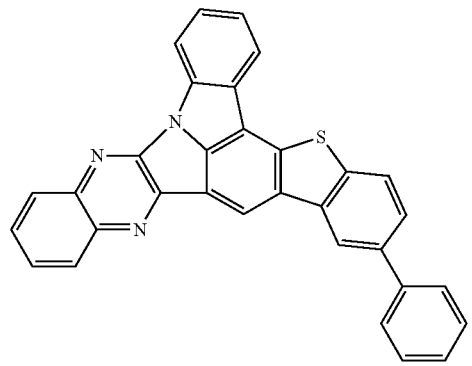
A-384
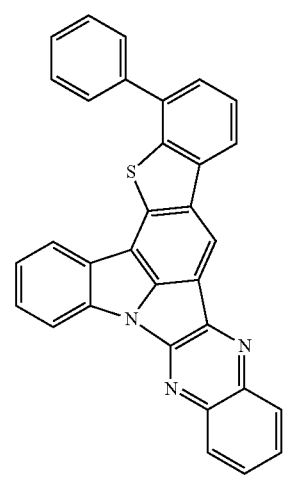
A-385
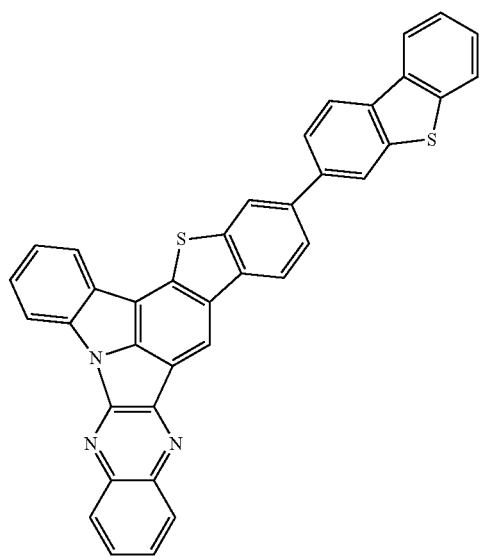
-continued
A-386
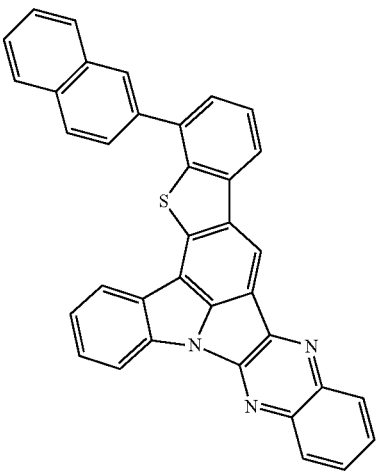
A-387
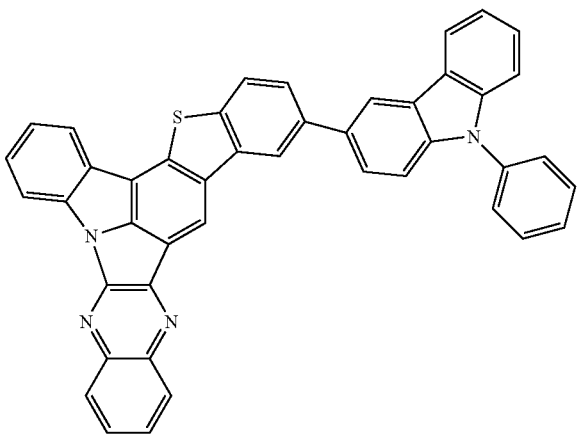
A-388
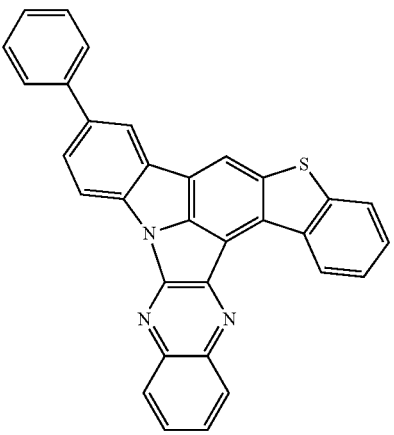

-continued
A-389
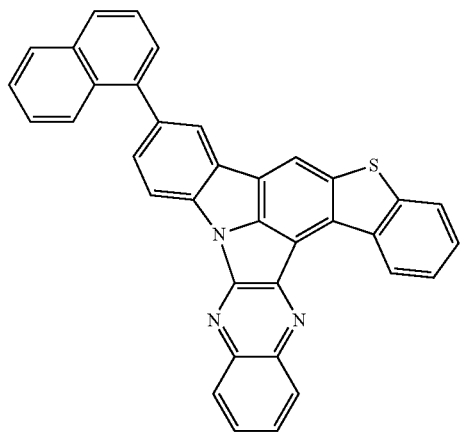
A-390
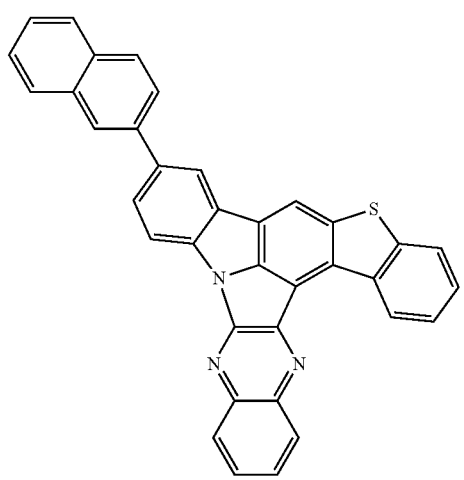
A-391
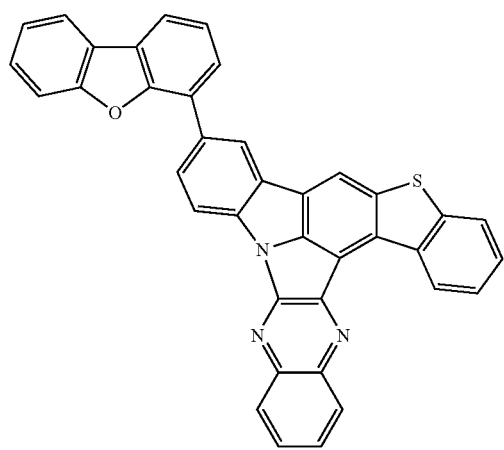
-continued
A-392
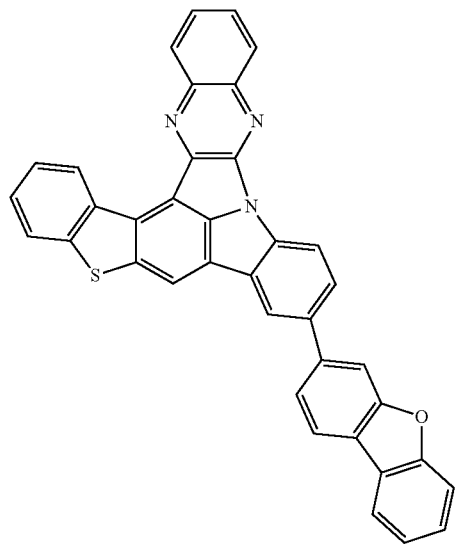
A-393
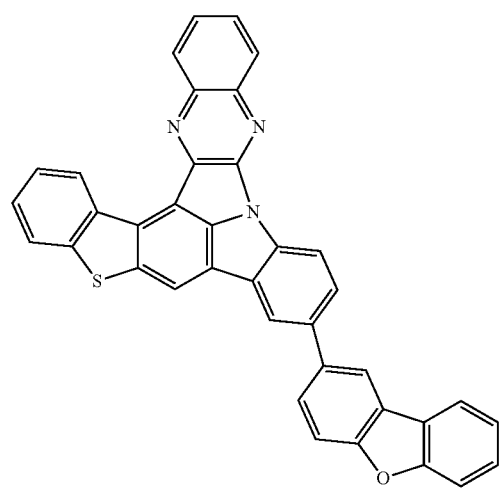
A-394
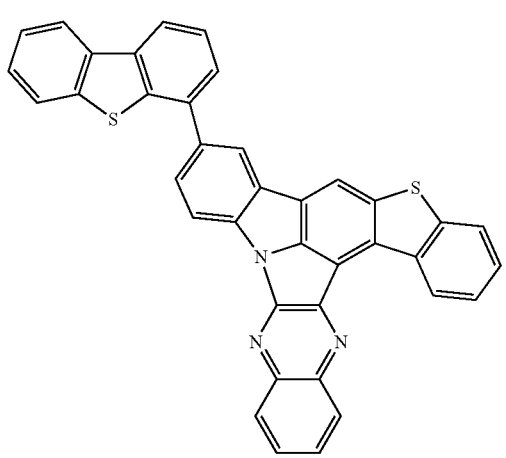

A-395
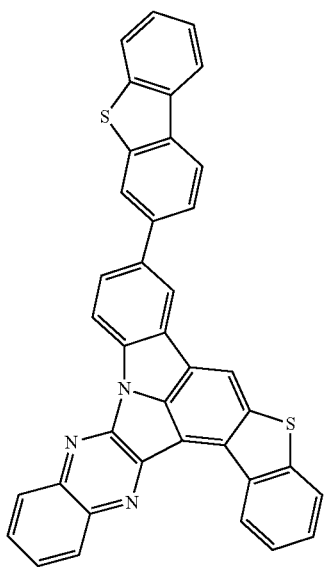
A-396
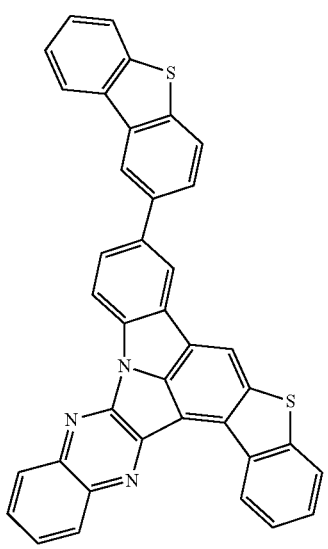
A-397
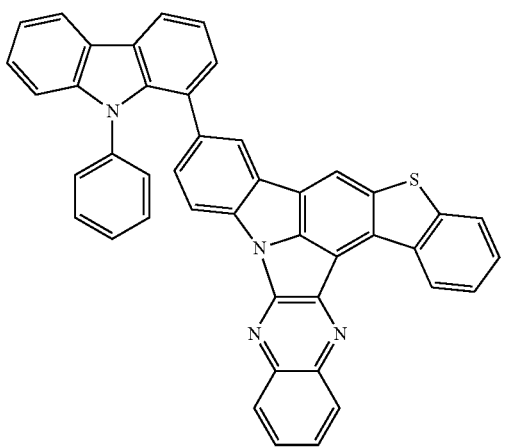
A-398
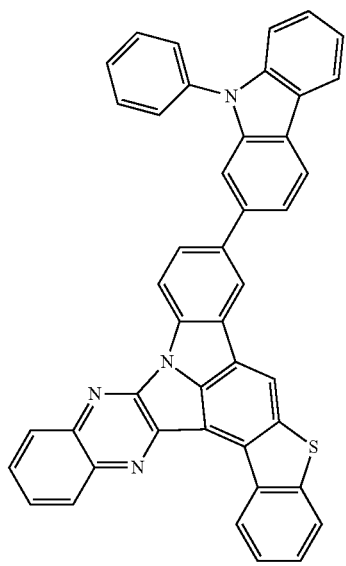
A-399
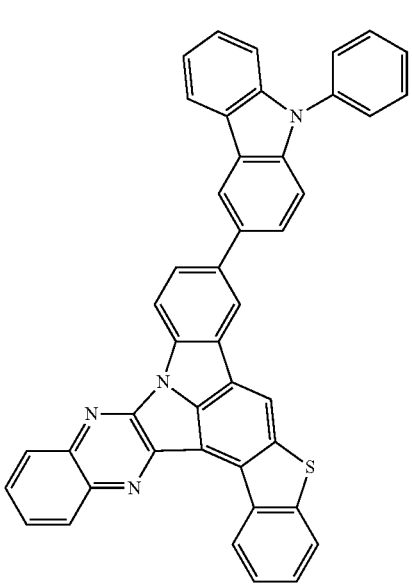
A-400
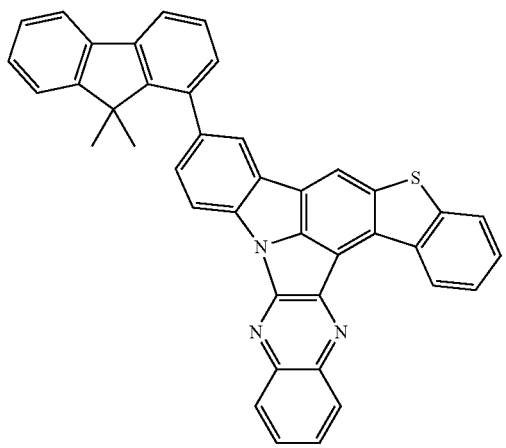

A-401
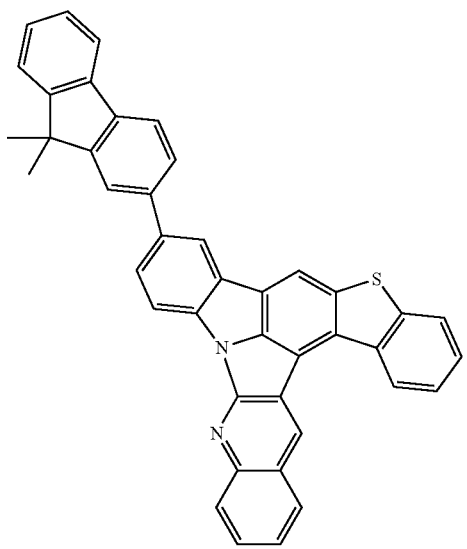
A-402
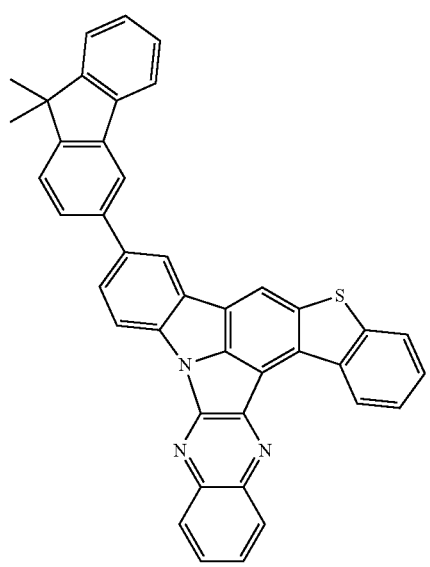
A-403
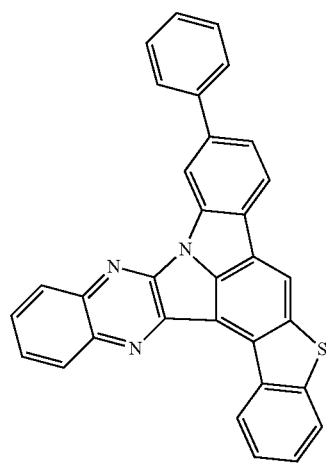
A-404
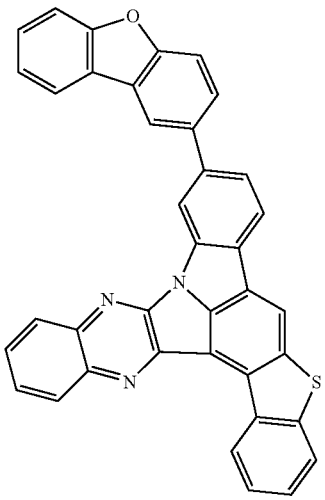
A-405
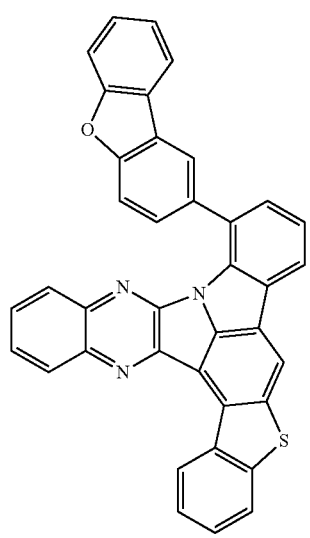
A-406
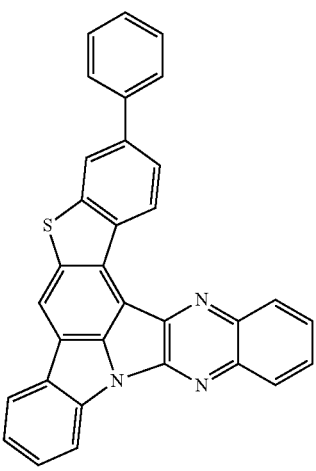

A-407
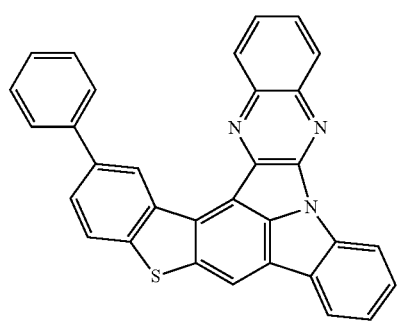
A-408
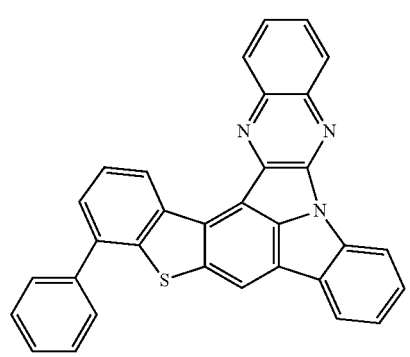
A-409
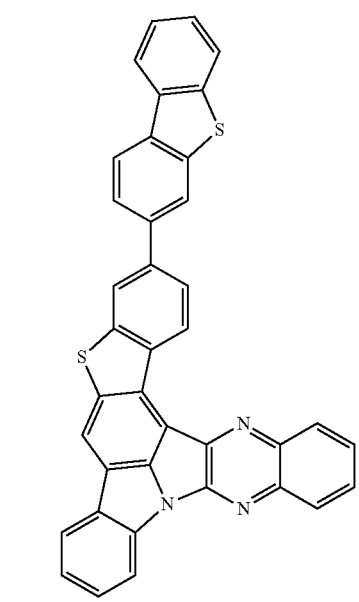
A-410
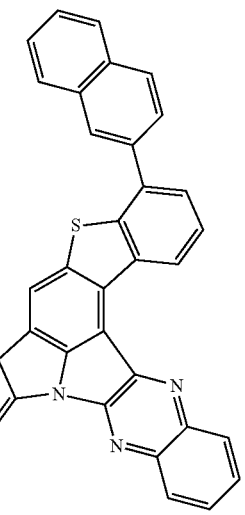
A-411
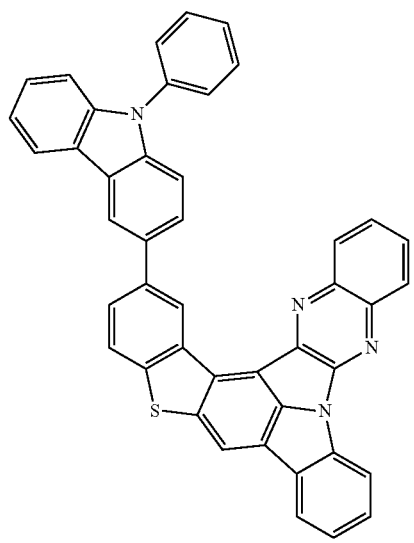
A-412
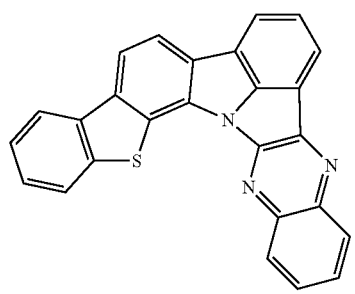
A-413
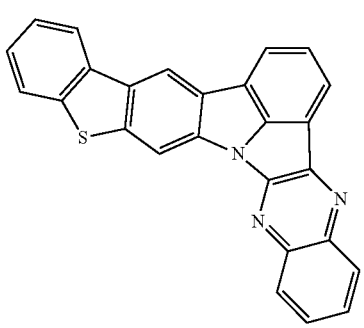

A-414
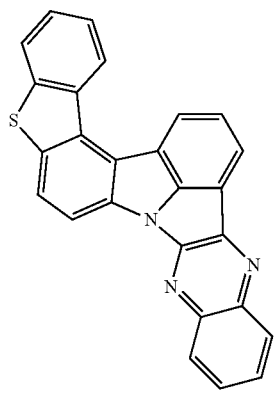
A-415
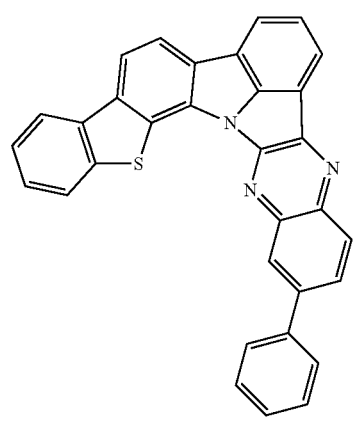
A-416
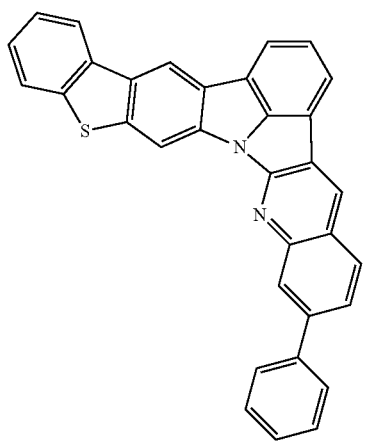
A-417
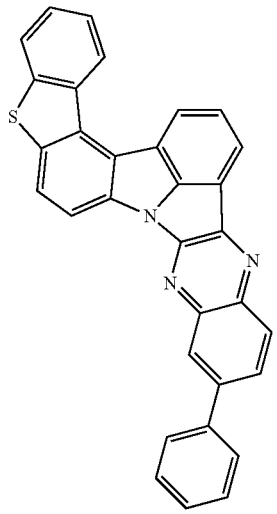
A-418
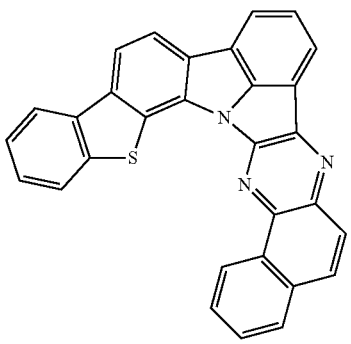
A-419
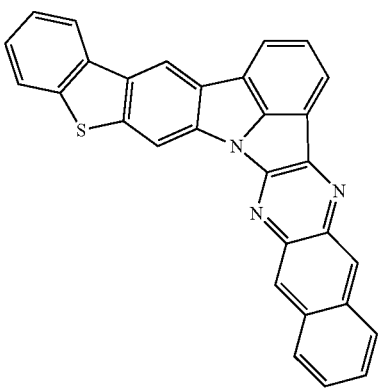
A-420
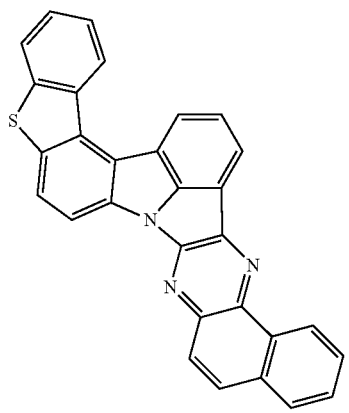

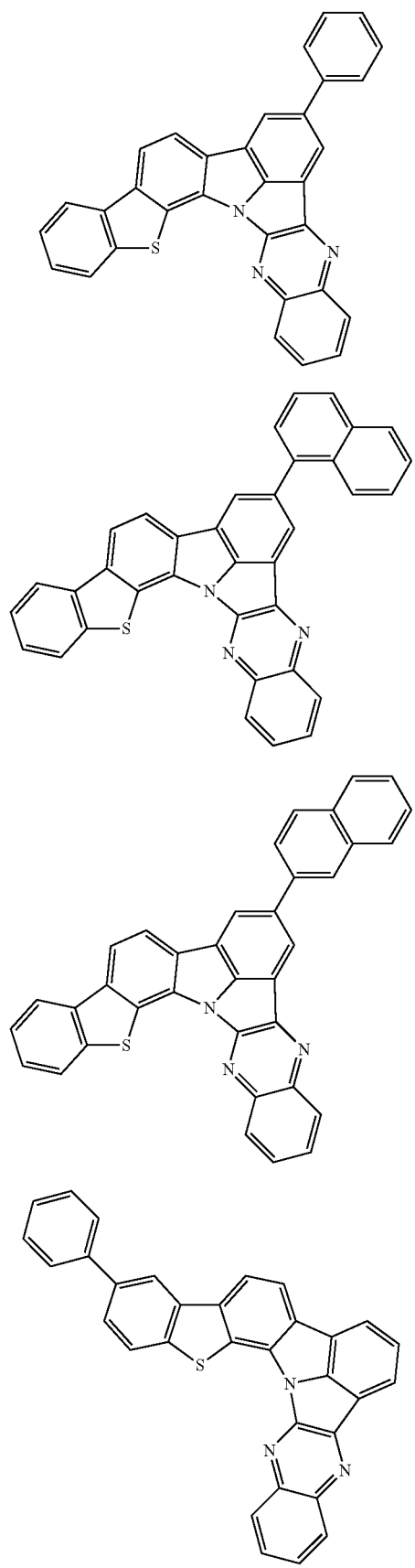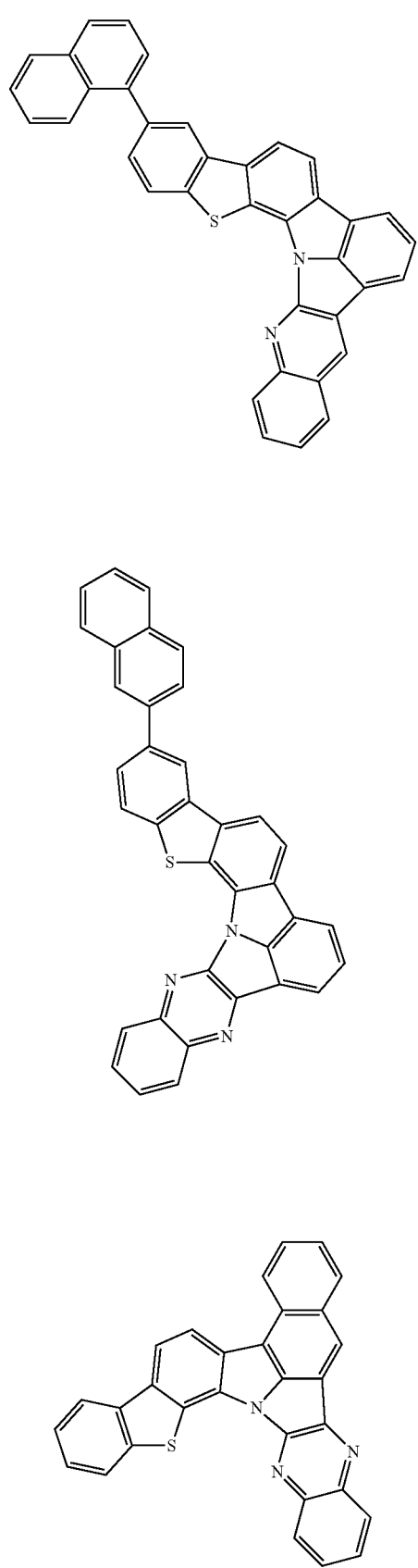

A-428
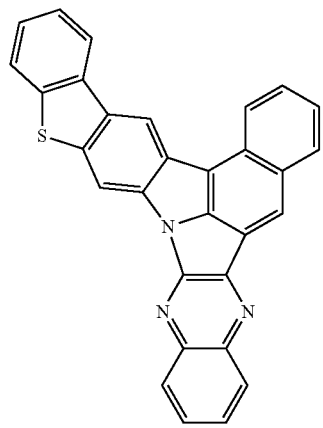
A-429
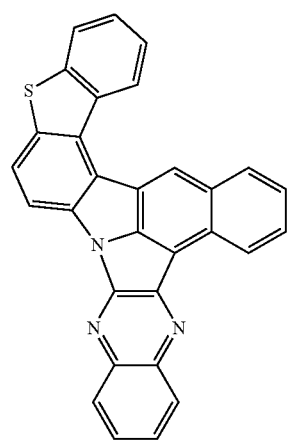
A-430
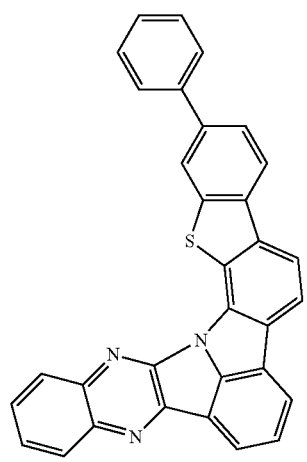
A-431
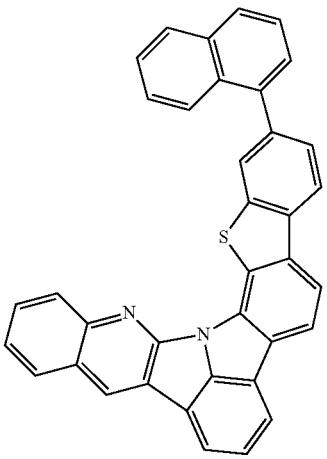
A-432
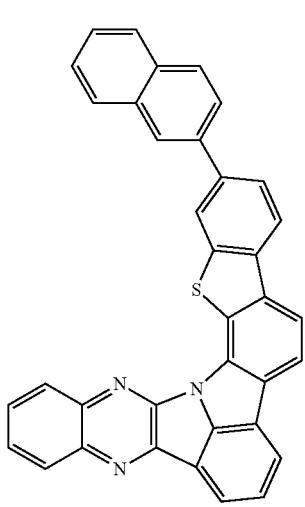
A-433
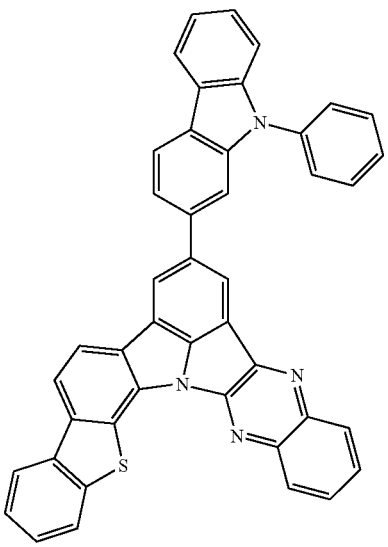

A-434
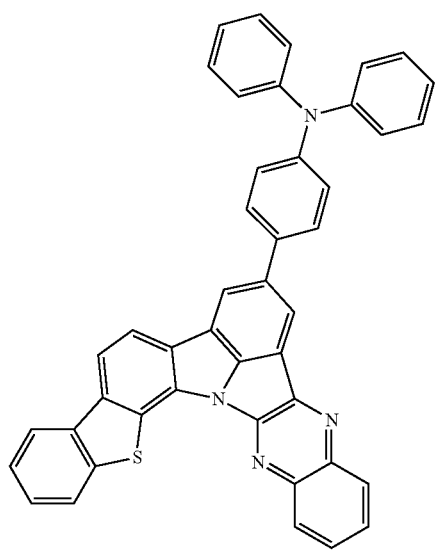
A-435
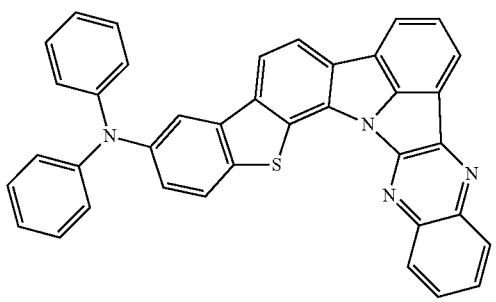
A-436
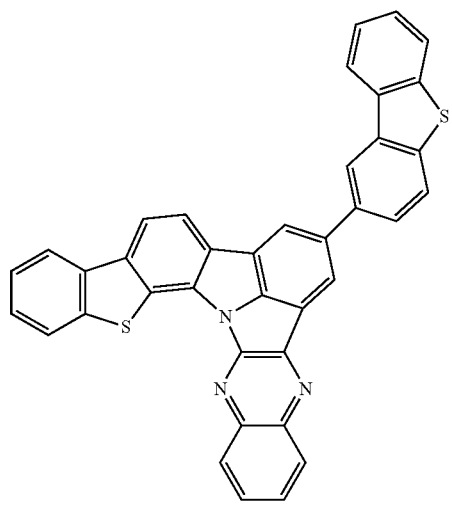
A-437
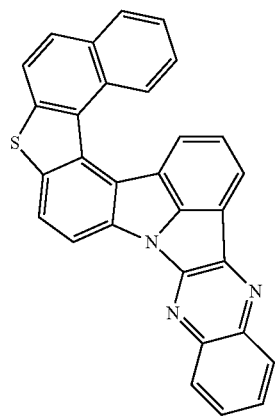
A-438
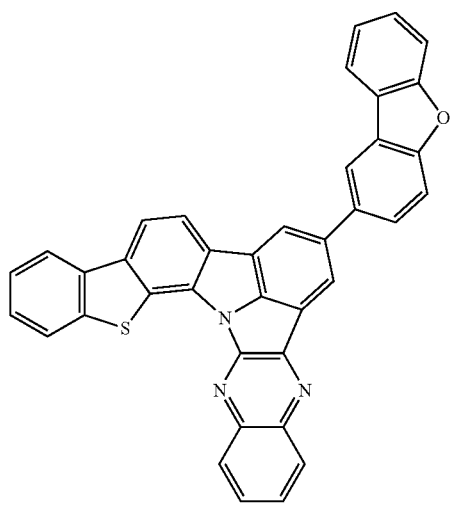
A-439

A-440
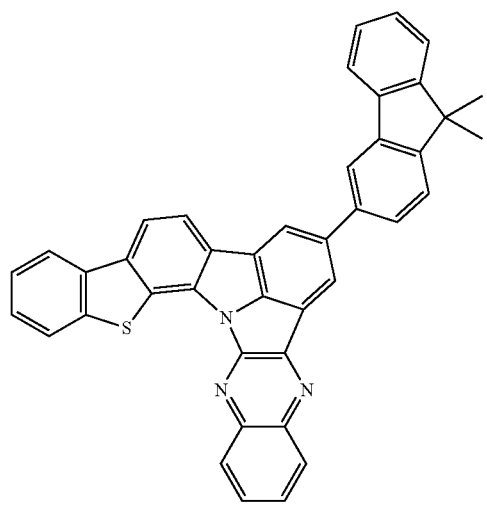
A-441
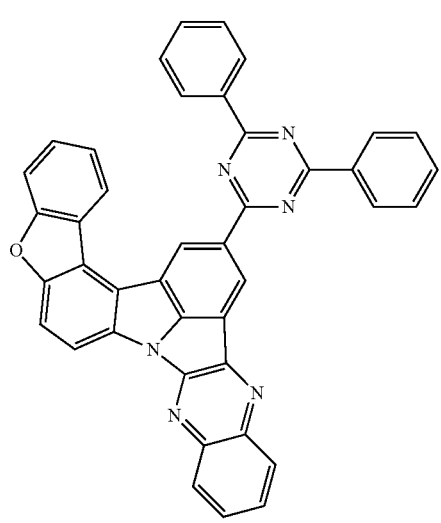
A-442
A-443
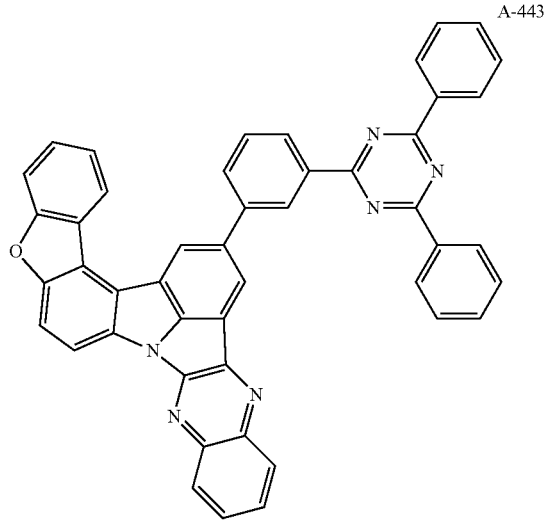
A-444
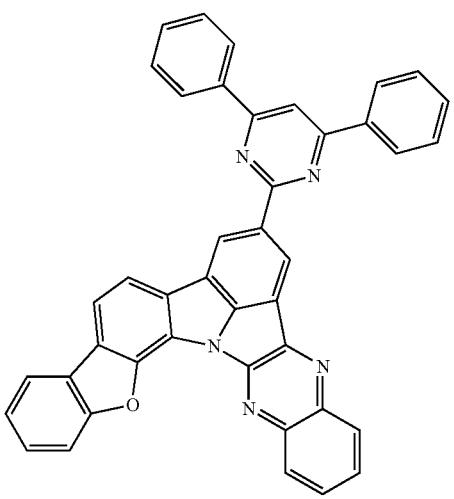
A-445
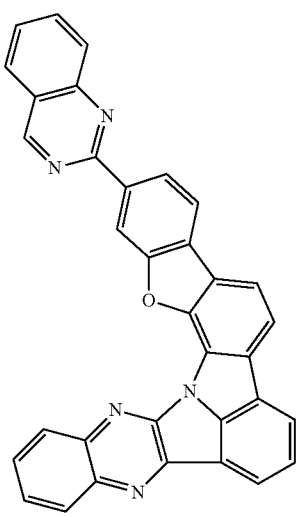

A-446
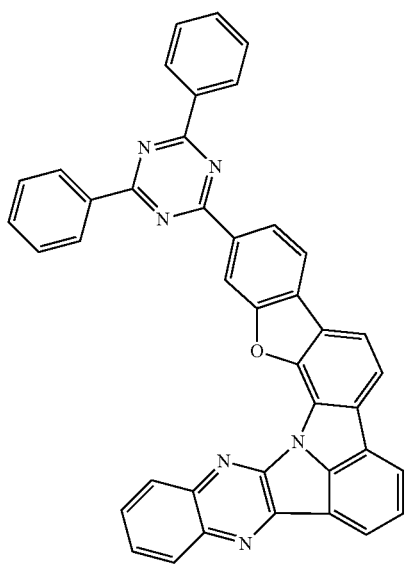
A-447
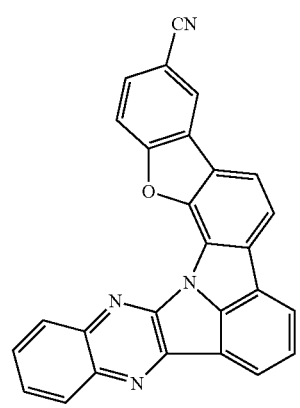
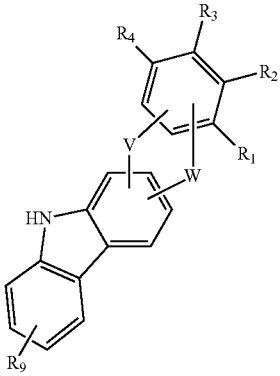
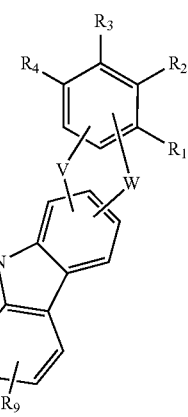
The organic electroluminescent compounds according to the present invention can be prepared by known methods to one skilled in the art, and can be prepared, for example, according to the following reaction scheme 1:
Reaction scheme 1
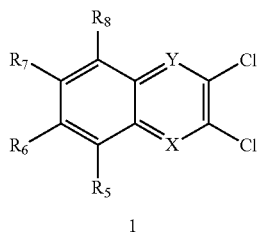
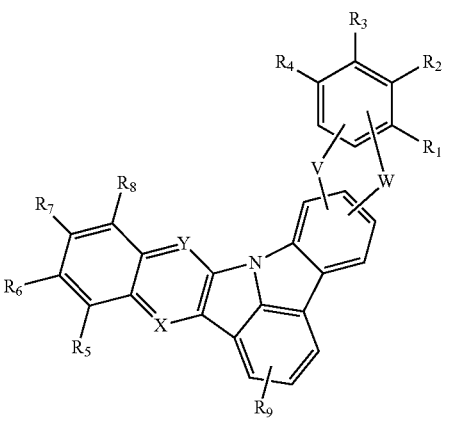
Or -continued

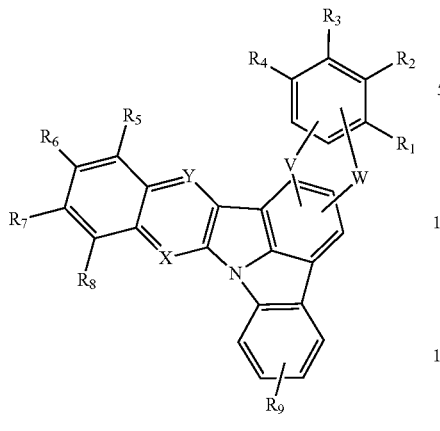

(5)

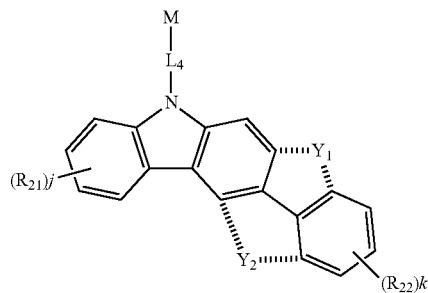

(6)

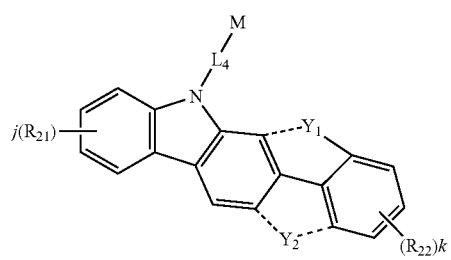

(7)

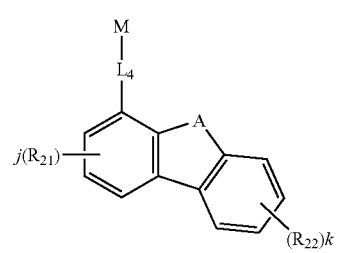

wherein,

R₁ to R₉, X, Y, V, and W are as defined in formula 1.

The present invention further provides an organic electroluminescent material comprising the organic electroluminescent compound of formula 1 or 2, and an organic EL device comprising the material. The material can be comprised of the organic electroluminescent compound of formula 1 or 2 of the present invention alone, or can further include conventional materials generally used in organic electroluminescent materials.

The organic EL device of the present invention may comprise an anode, a cathode, and at least one organic layer disposed between the two electrodes, wherein the organic layer comprises a light-emitting layer, and may further comprise at least one layer selected from the group consisting of a hole injection layer (HIL), a hole transport layer (HTL), an electron blocking layer (EBL), an electron buffer layer, a hole blocking layer (HBL), an electron transport layer (ETL), an electron injection layer (EIL), etc.

The organic electroluminescent compound of formula 1 or 2 according to the present invention may be included in a light-emitting layer. If used in a light-emitting layer, the organic electroluminescent compound of formula 1 or 2 of the present invention may be included as a host material. The light-emitting layer may preferably comprise at least one dopant and further comprise other compounds as the second host material, in addition to the organic electroluminescent compound of formula 1 or 2 of the present invention.

The second host material can be any of the known phosphorescent hosts and preferably, is selected from the group consisting of the compounds of the following formulae 3 to 7 in view of luminous efficiency:

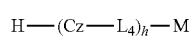

(3)

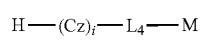

(4)

wherein
Cz represents the following structure:

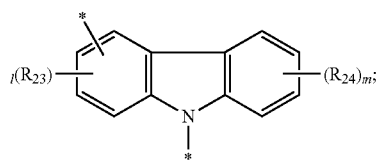

A represents O or S;

$R_{21}$ to $R_{24}$ each independently represent hydrogen, deuterium, a halogen, a substituted or unsubstituted (C1-C30) alkyl group, a substituted or unsubstituted (C6-C30)aryl group, a substituted or unsubstituted 5- or 30-membered heteroaryl group, or $R_{25}R_{26}R_{27}Si$—; or are linked to an adjacent substituent(s) to form a mono- or polycyclic (C5-C30) alicyclic or aromatic ring whose carbon atom(s) may be replaced with at least one hetero atom selected from nitrogen, oxygen, and sulfur;

$R_{25}$ to $R_{27}$ each independently represent a substituted or unsubstituted (C1-C30)alkyl group, or a substituted or unsubstituted (C6-C30)aryl group;

$L_4$ represents a single bond, a substituted or unsubstituted (C6-C30)arylene group, or a substituted or unsubstituted 5- or 30-membered heteroarylene group;

M represents a substituted or unsubstituted (C6-C30)aryl group, or a substituted or unsubstituted 5- or 30-membered heteroaryl group;

$Y_1$ and $Y_2$ each independently represent —O—, —S—, —N($R_{31}$)—, or —C($R_{32}$)($R_{33}$)—; and $Y_1$ and $Y_2$ are not simultaneously present;

$R_{31}$ to $R_{33}$ each independently represent a substituted or unsubstituted (C1-C30)alkyl group, a substituted or unsubstituted (C6-C30)aryl group, or a substituted or unsubstituted 5- or 30-membered heteroaryl group; or are linked to an adjacent substituent(s) to form a mono- or polycyclic (C5-C30) alicyclic or aromatic ring whose carbon atom(s) may be replaced with at least one hetero atom selected from nitrogen, oxygen, and sulfur; and $R_{32}$ and $R_{33}$ may be the same or different;

h and i each independently represent an integer of 1 to 3;

j, k, l, and m each independently represent an integer of 0 to 4;

where h, i, j, k, l, or m is an integer of 2 or more, each (Cz-$L_4$), each (Cz), each $R_{21}$, each $R_{22}$, each $R_{23}$, or each $R_{24}$ may be the same or different.

Specifically, the second host material preferably includes the following:

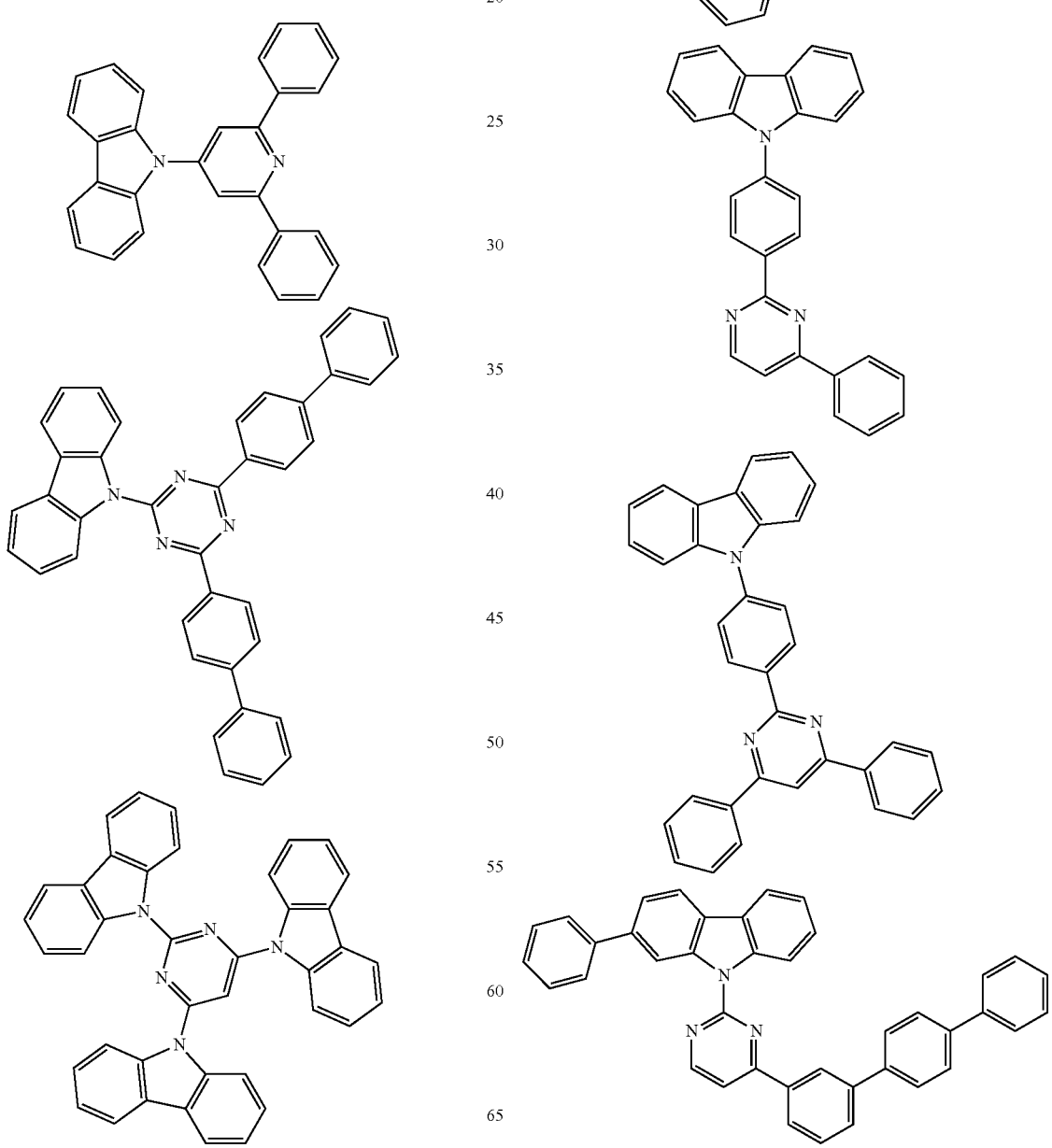
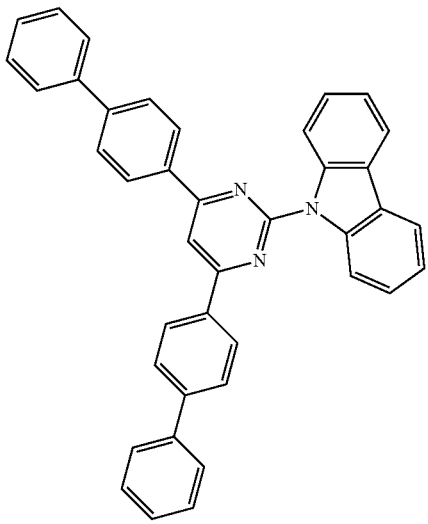
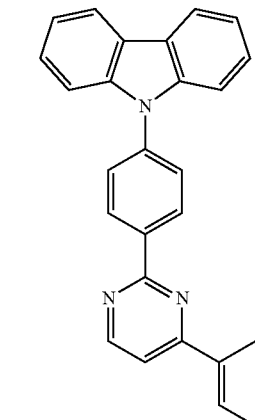
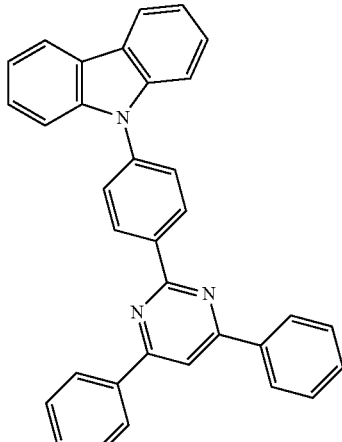
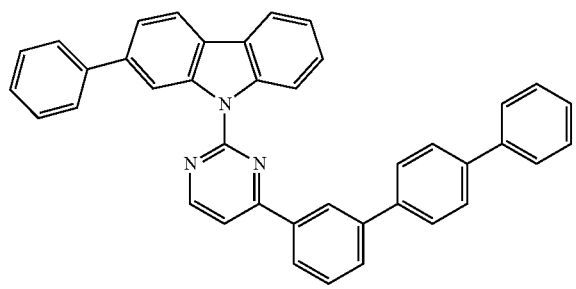

155
-continued
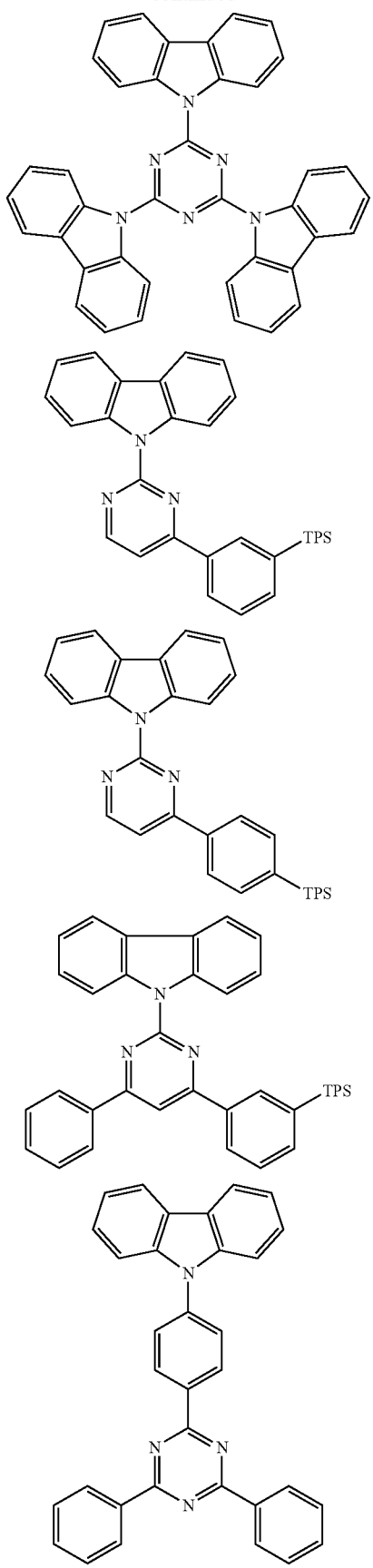
156
-continued
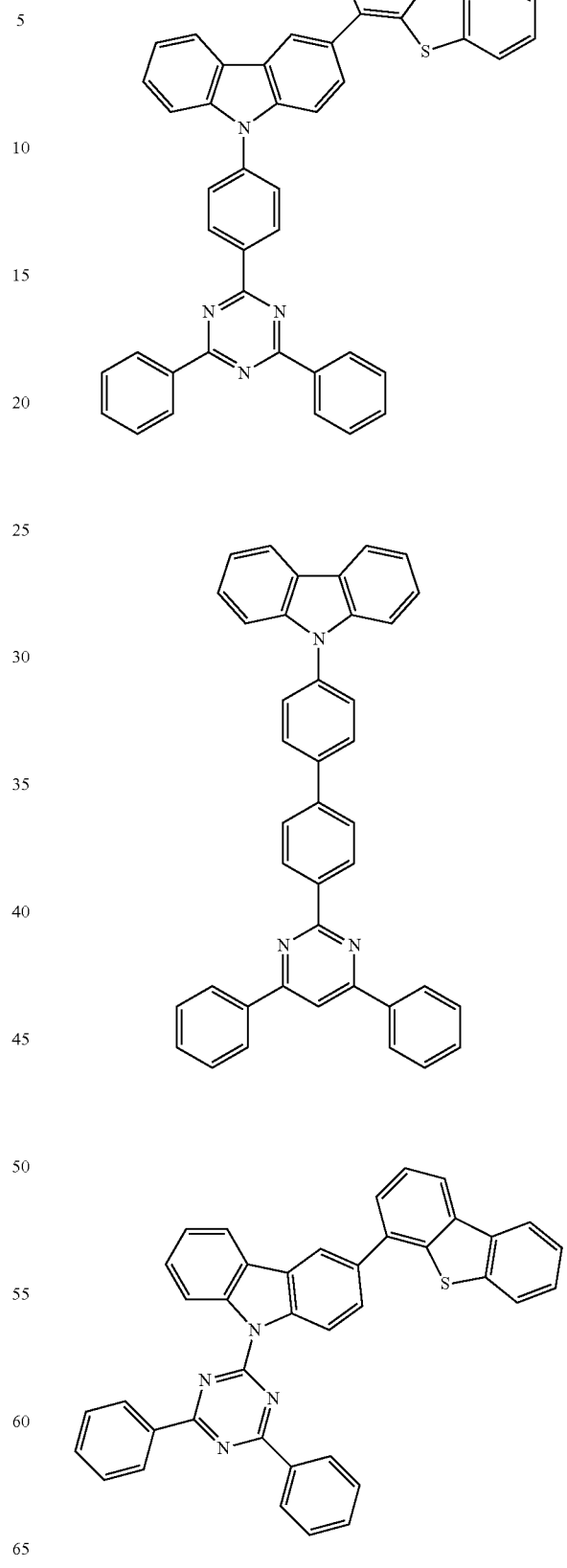

157
-continued
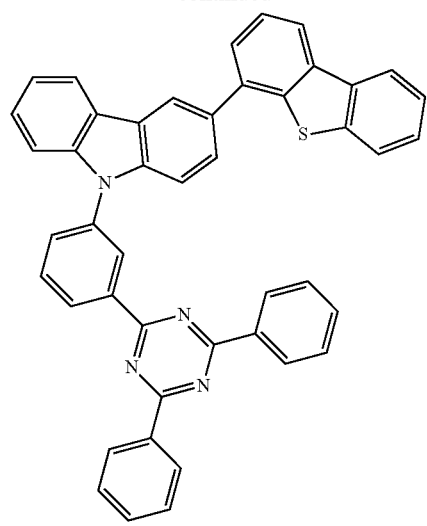
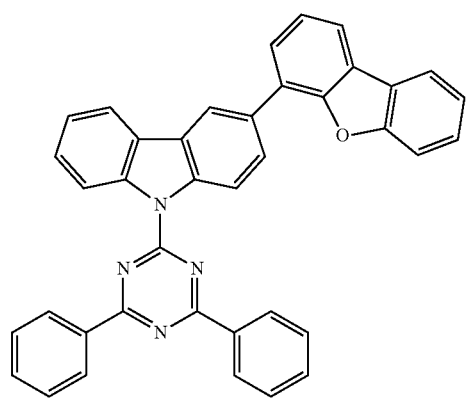
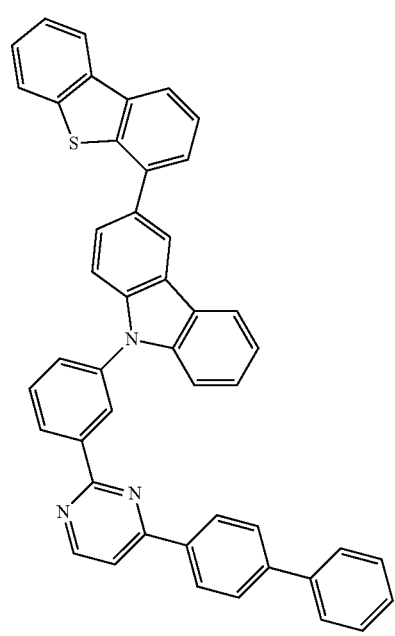
158
-continued
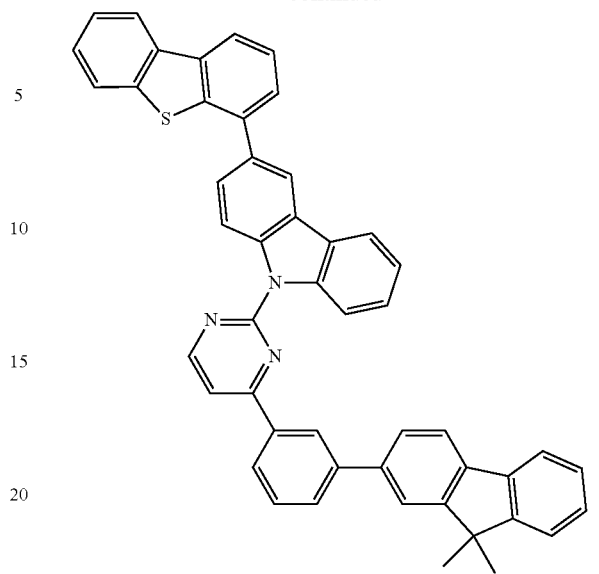
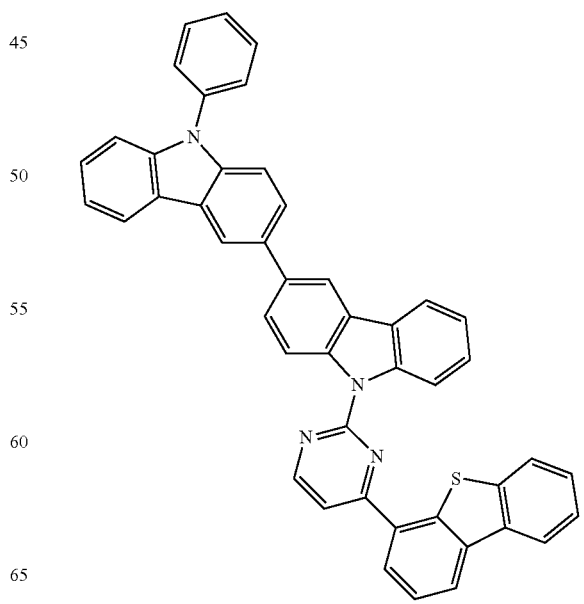

159
-continued
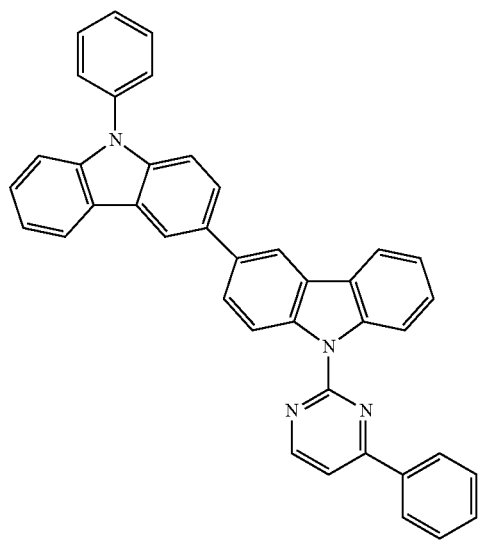
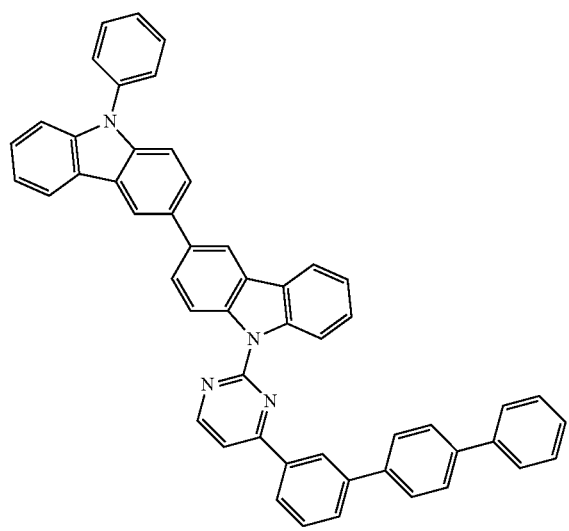
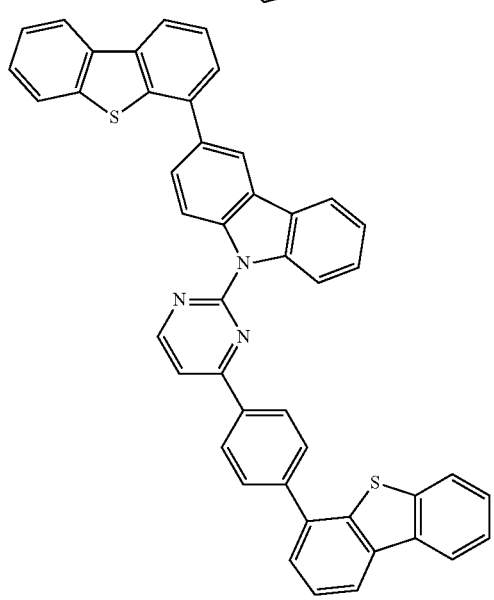
160
-continued
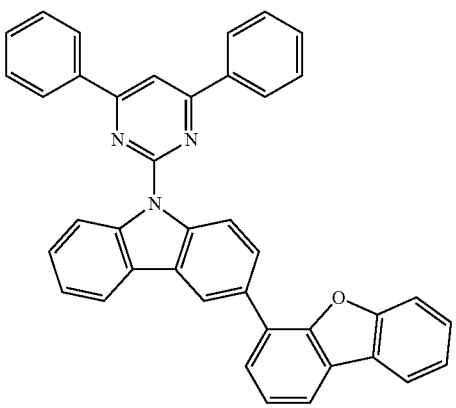
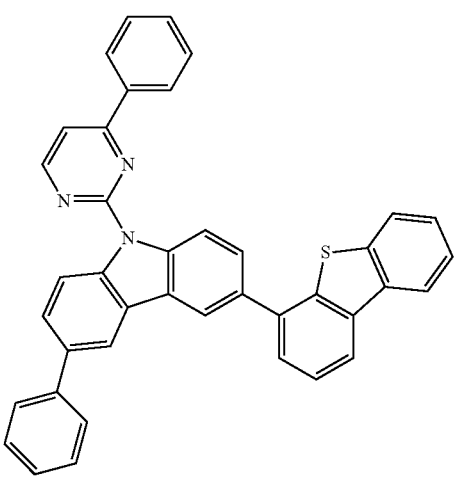
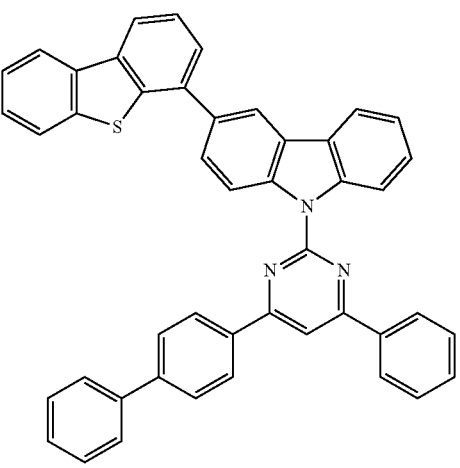

161
-continued
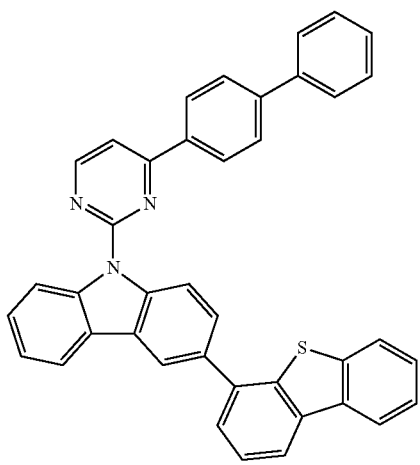
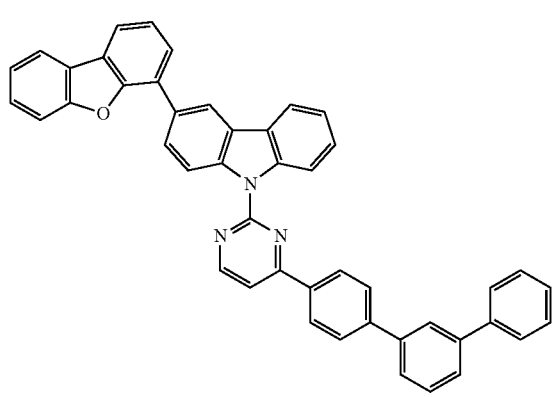
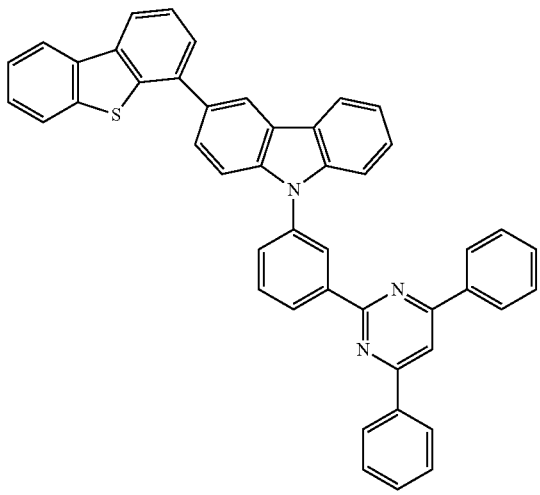
162
-continued
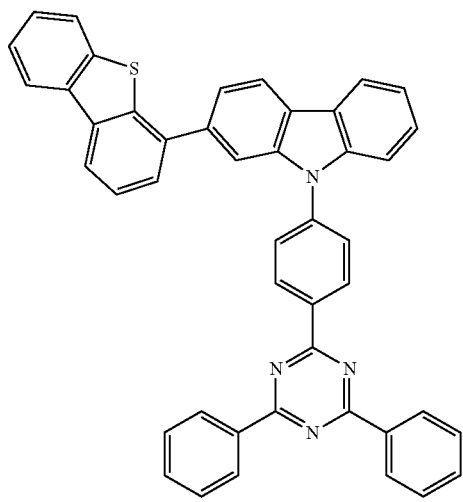
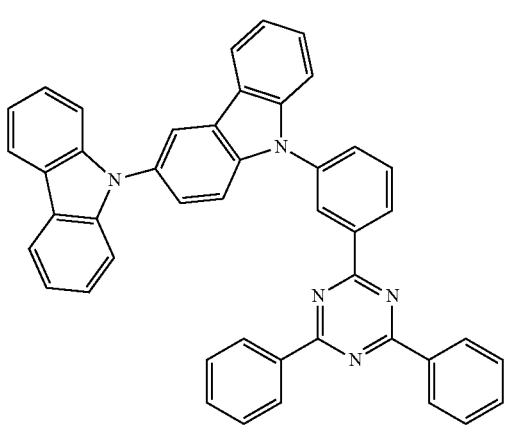
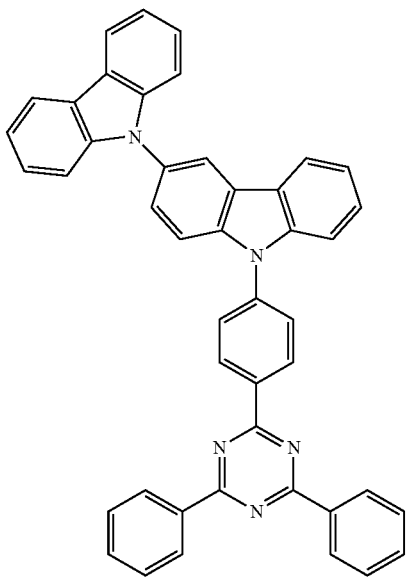

163
-continued
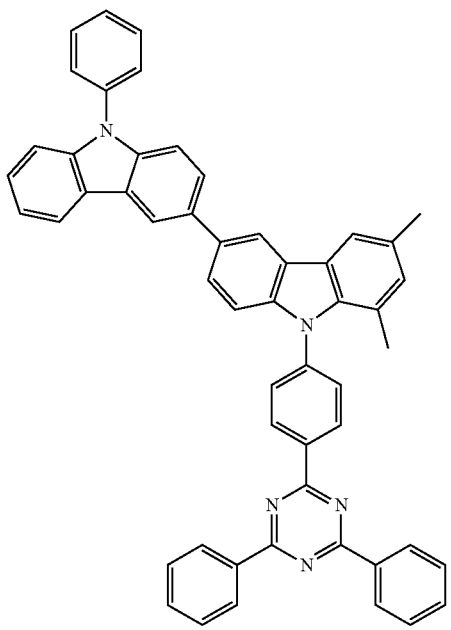
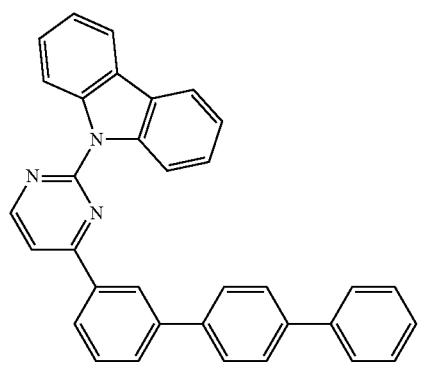
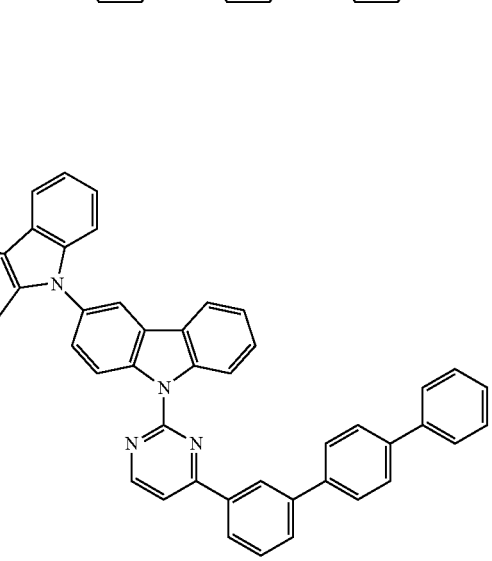
164
-continued
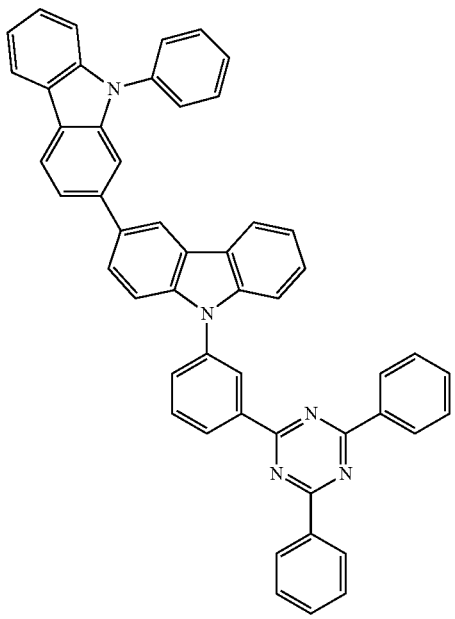
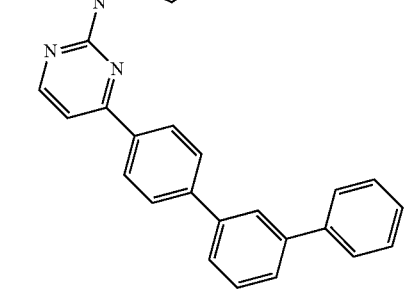

165
-continued
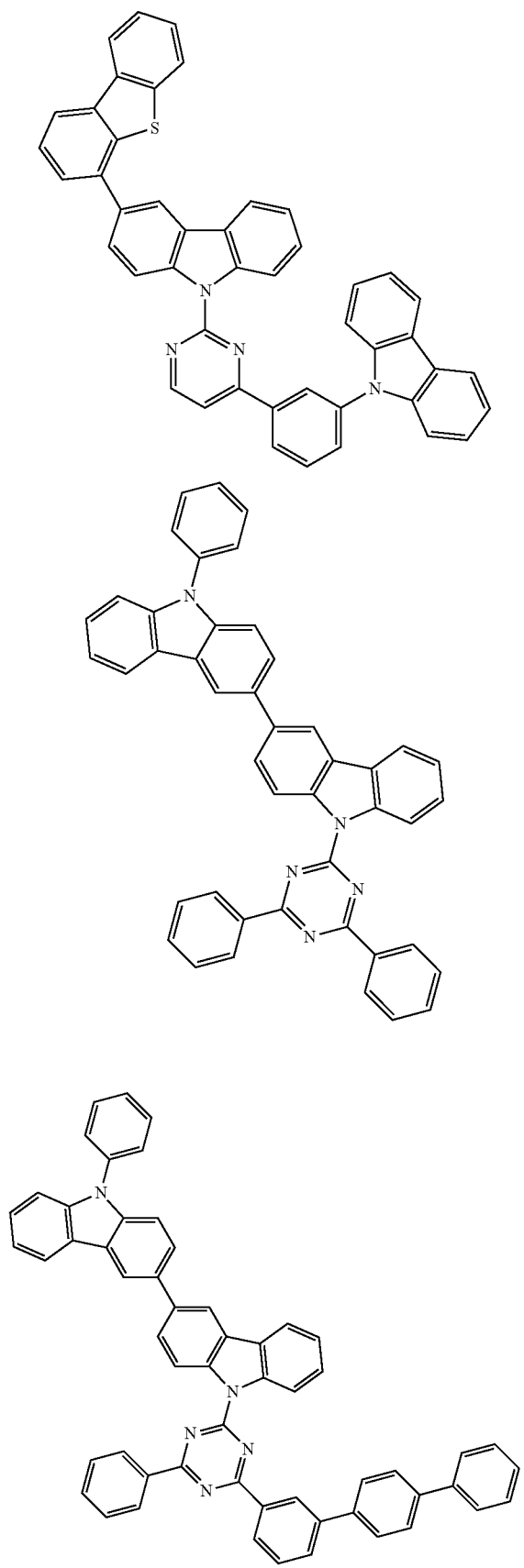
166
-continued
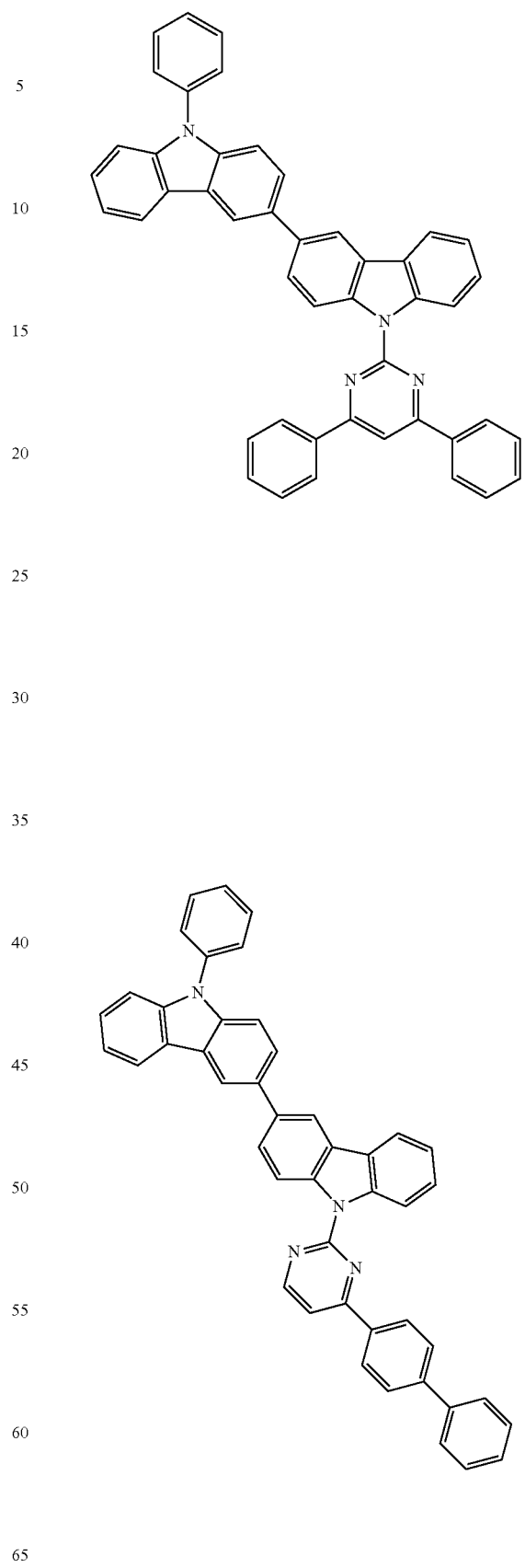

167
-continued
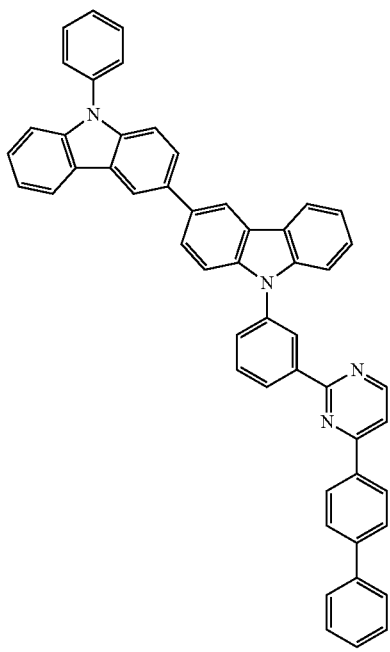
168
-continued
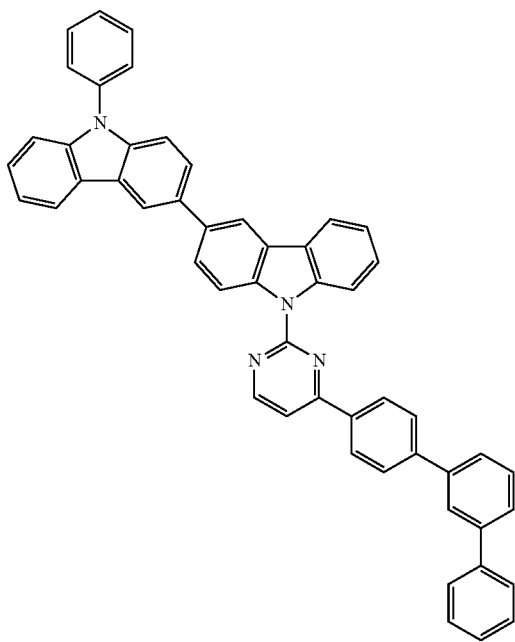
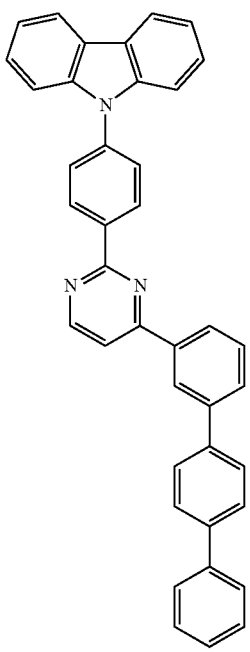
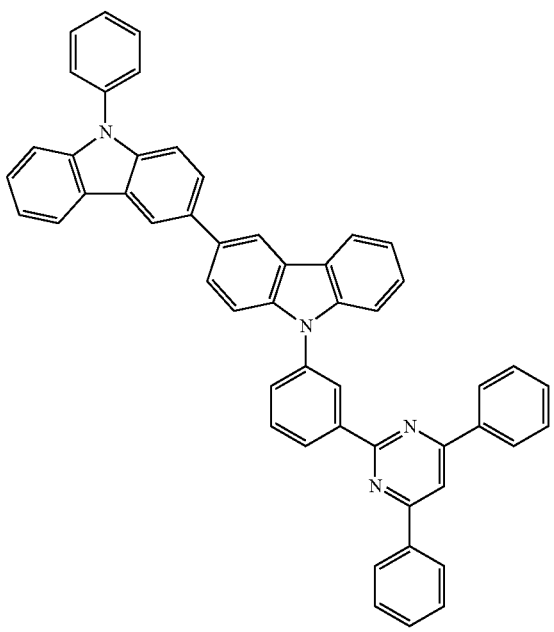

169
-continued
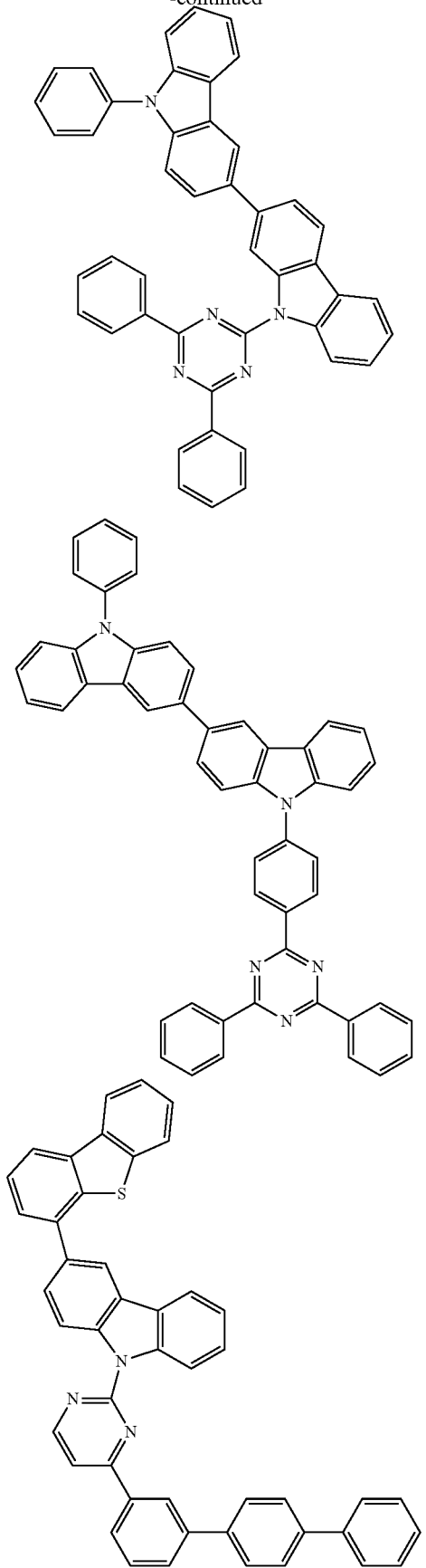
170
-continued
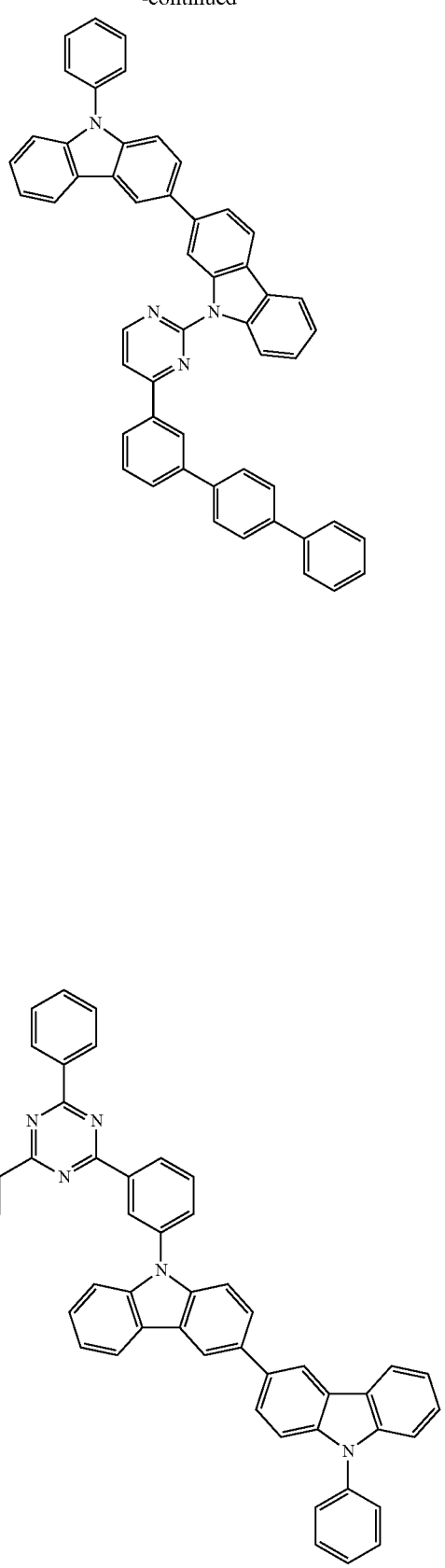

171
-continued
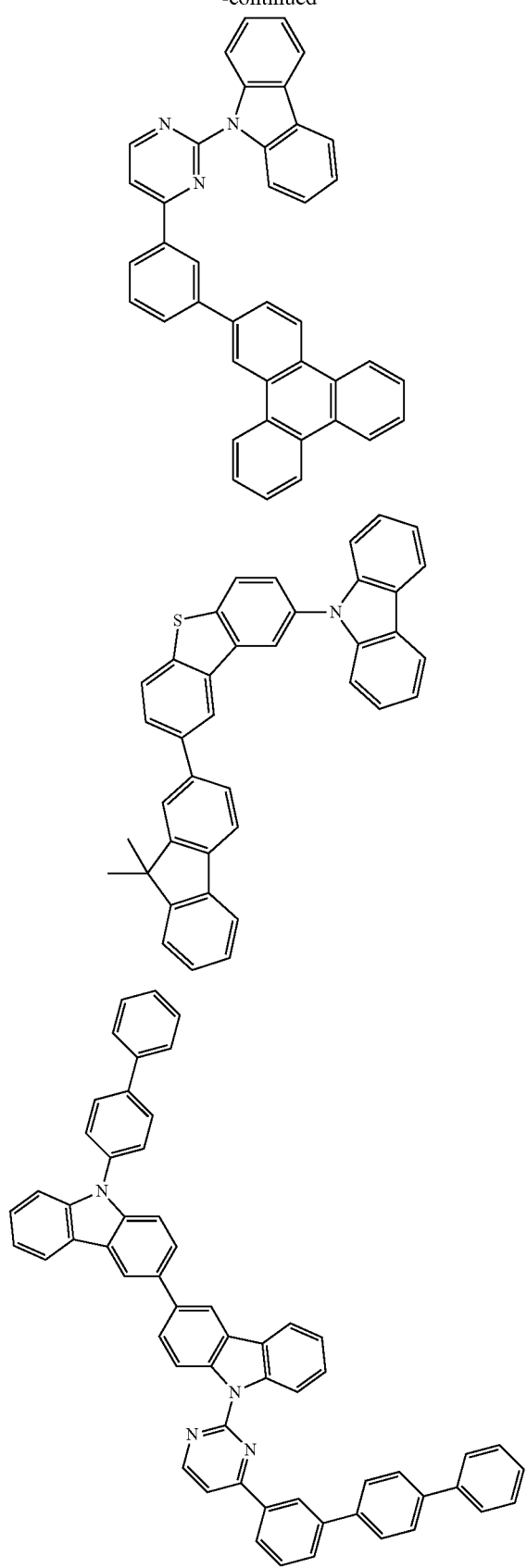
172
-continued
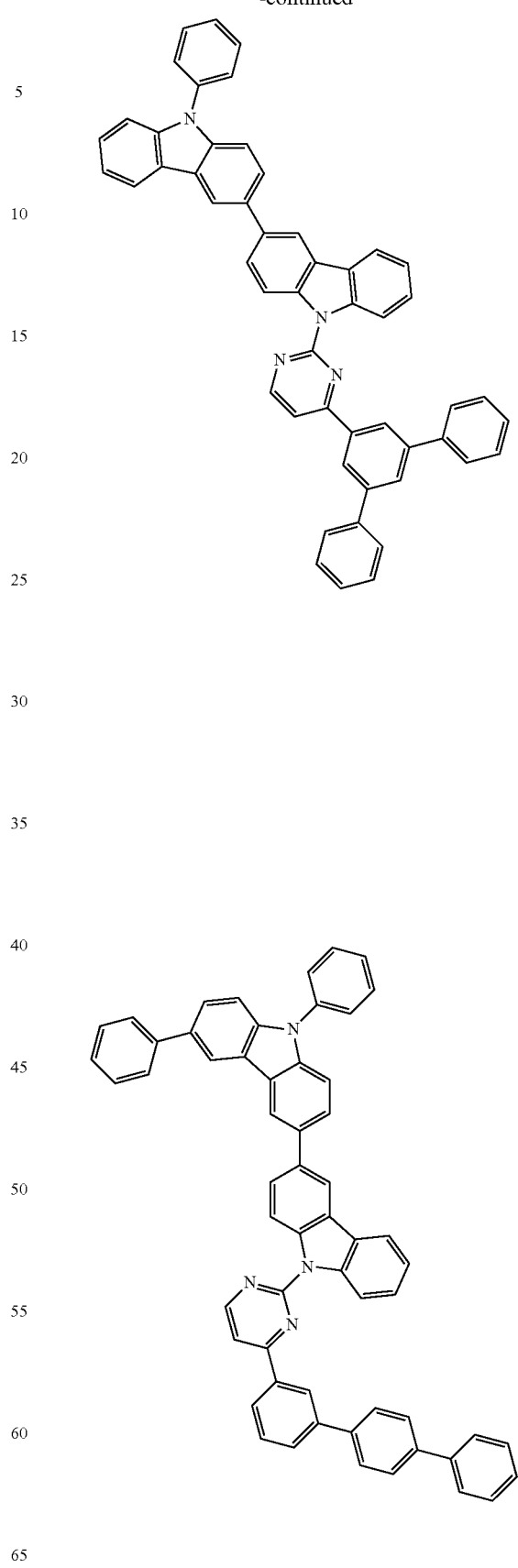

173
-continued
174
-continued
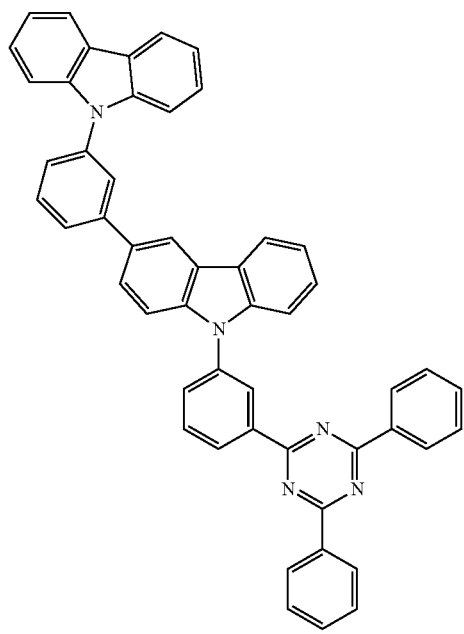
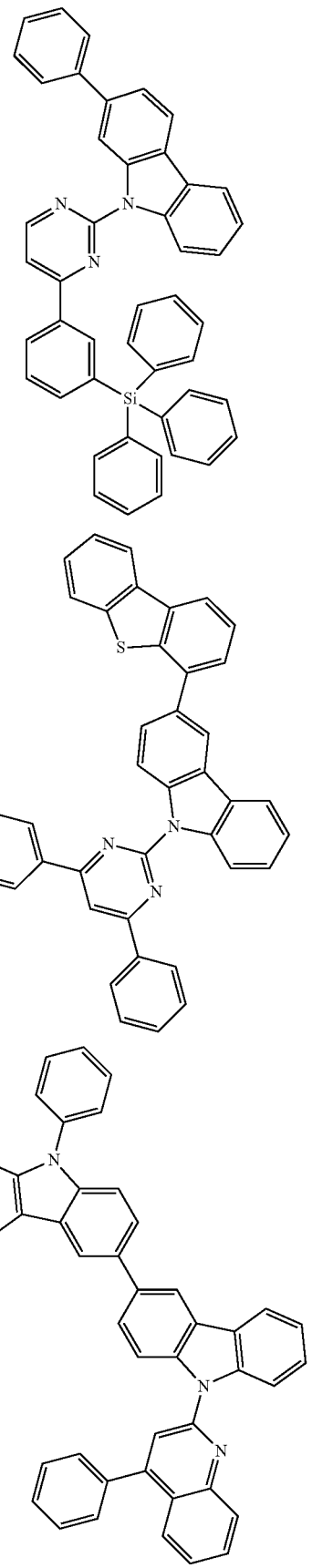

175
-continued
176
-continued
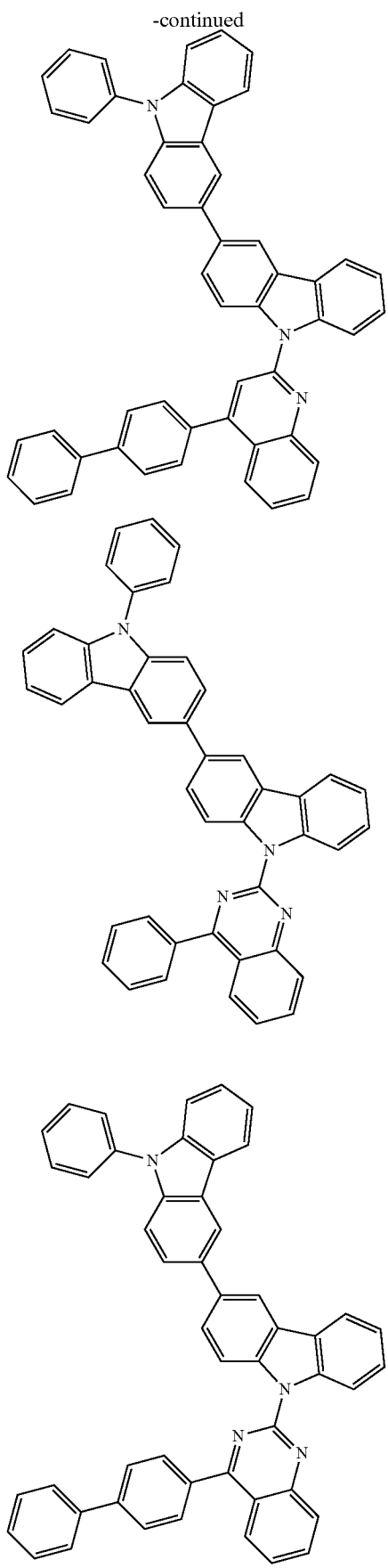
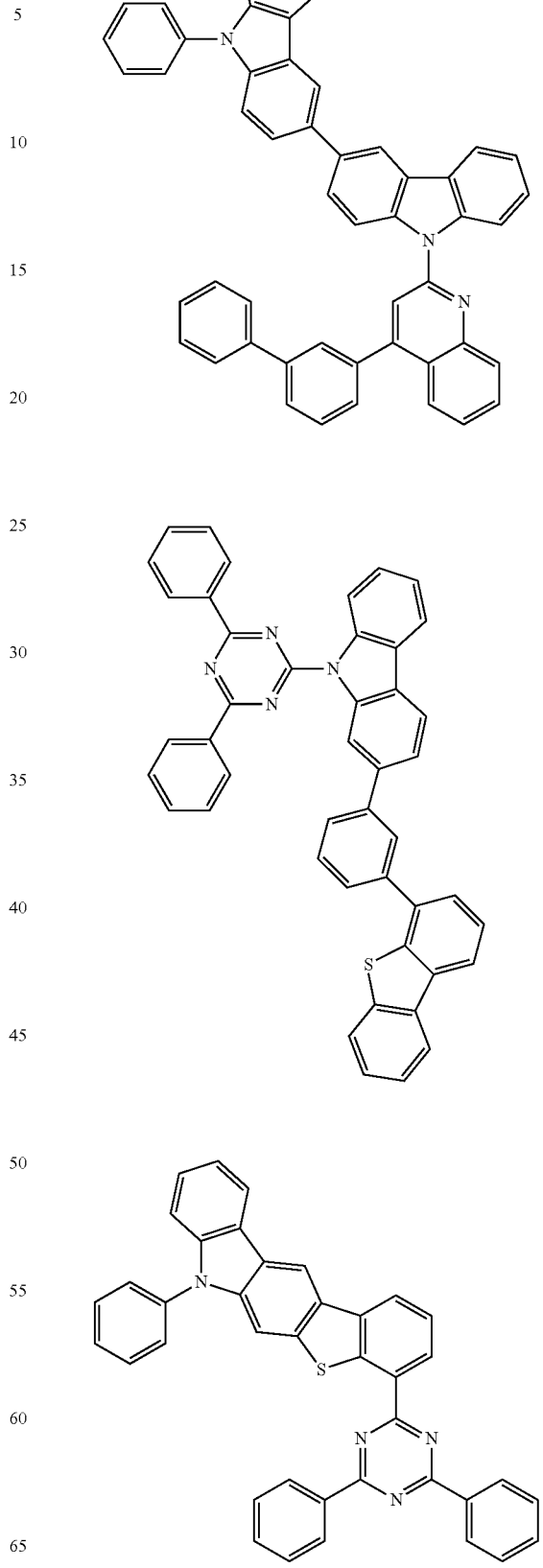

177
-continued
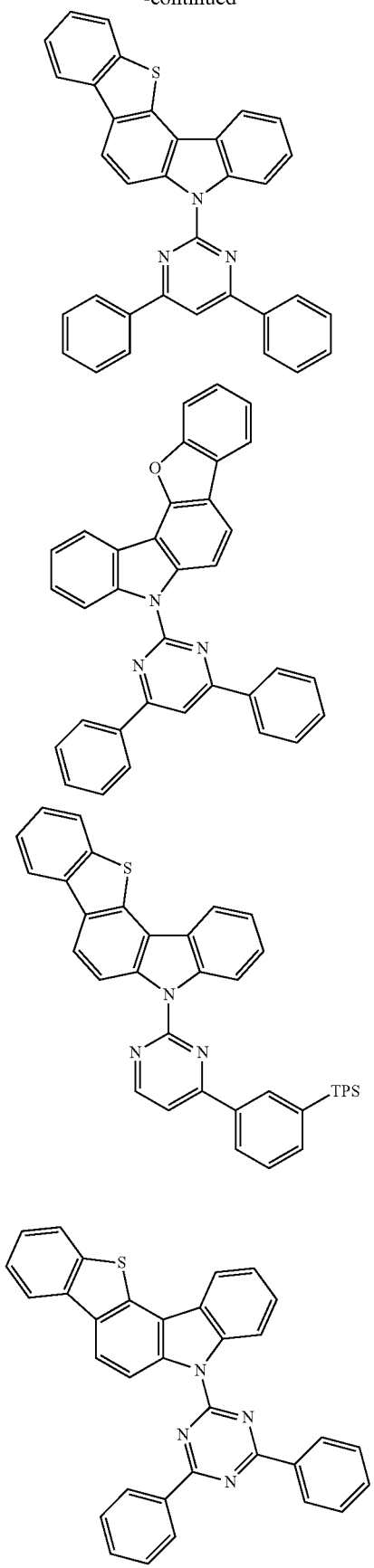
178
-continued
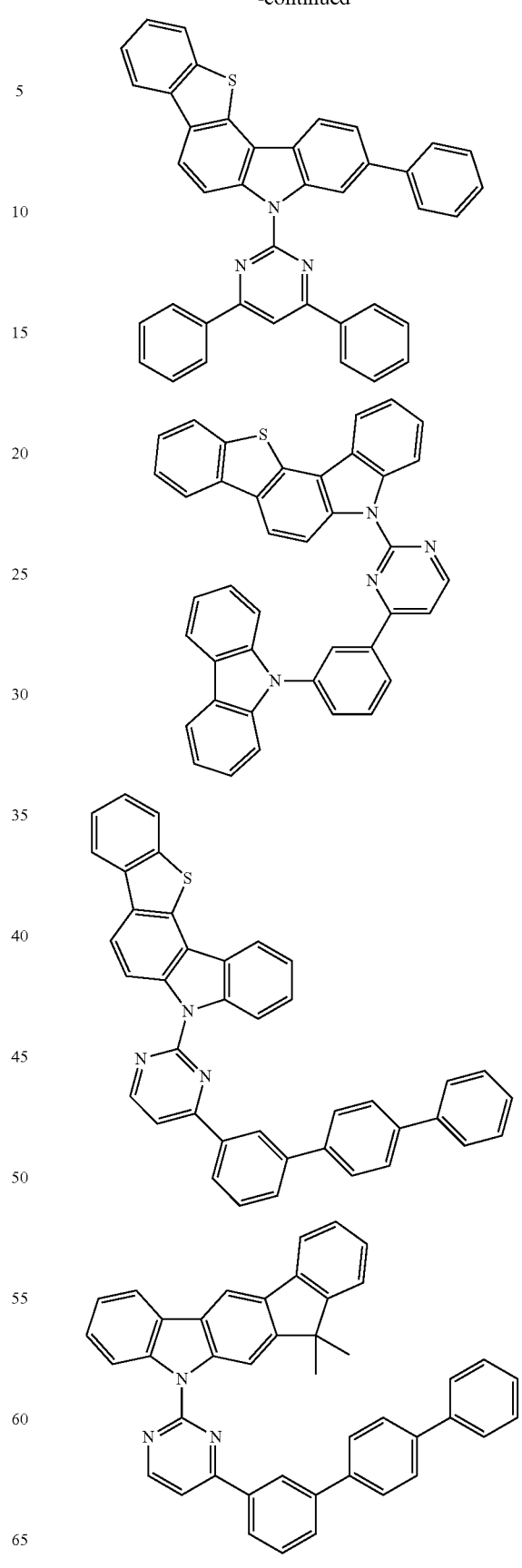

179
-continued
180
-continued
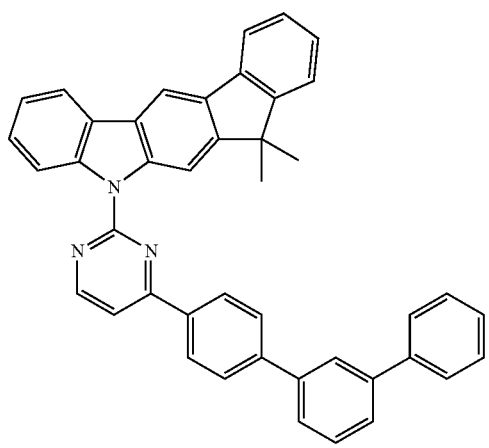
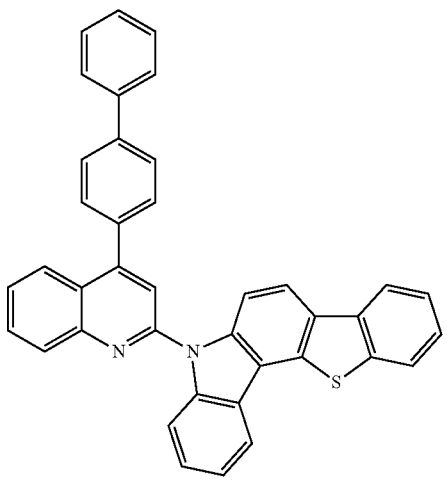
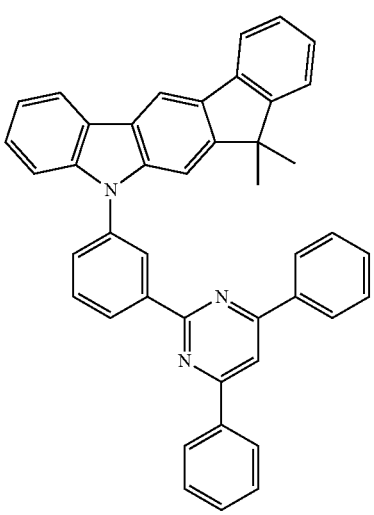
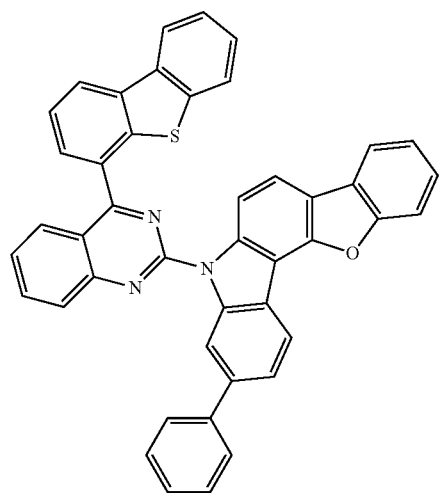
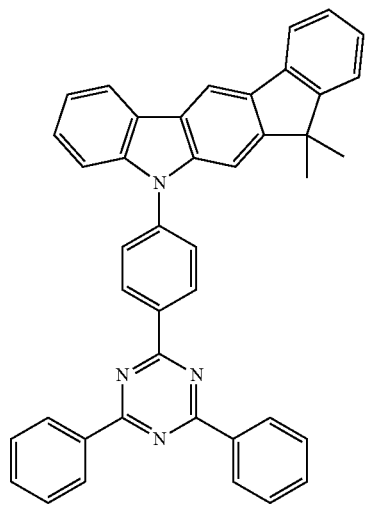
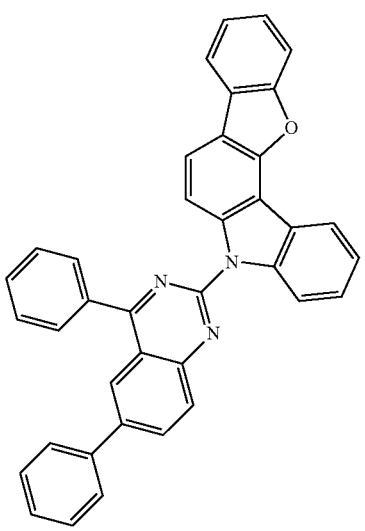

181
-continued
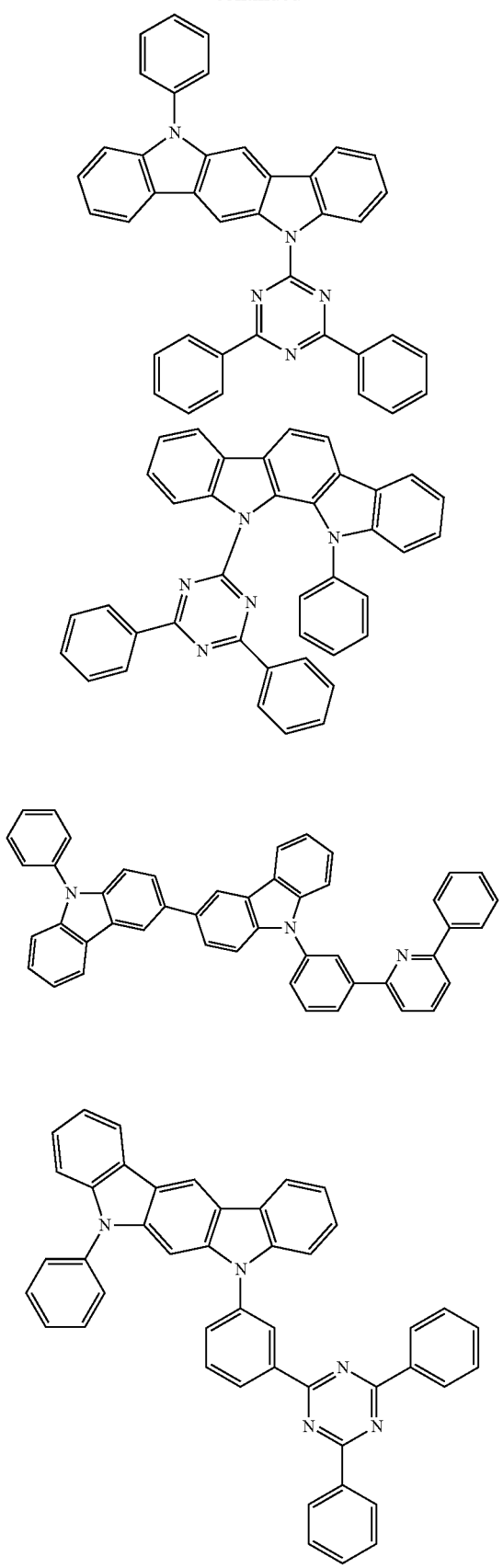
182
-continued
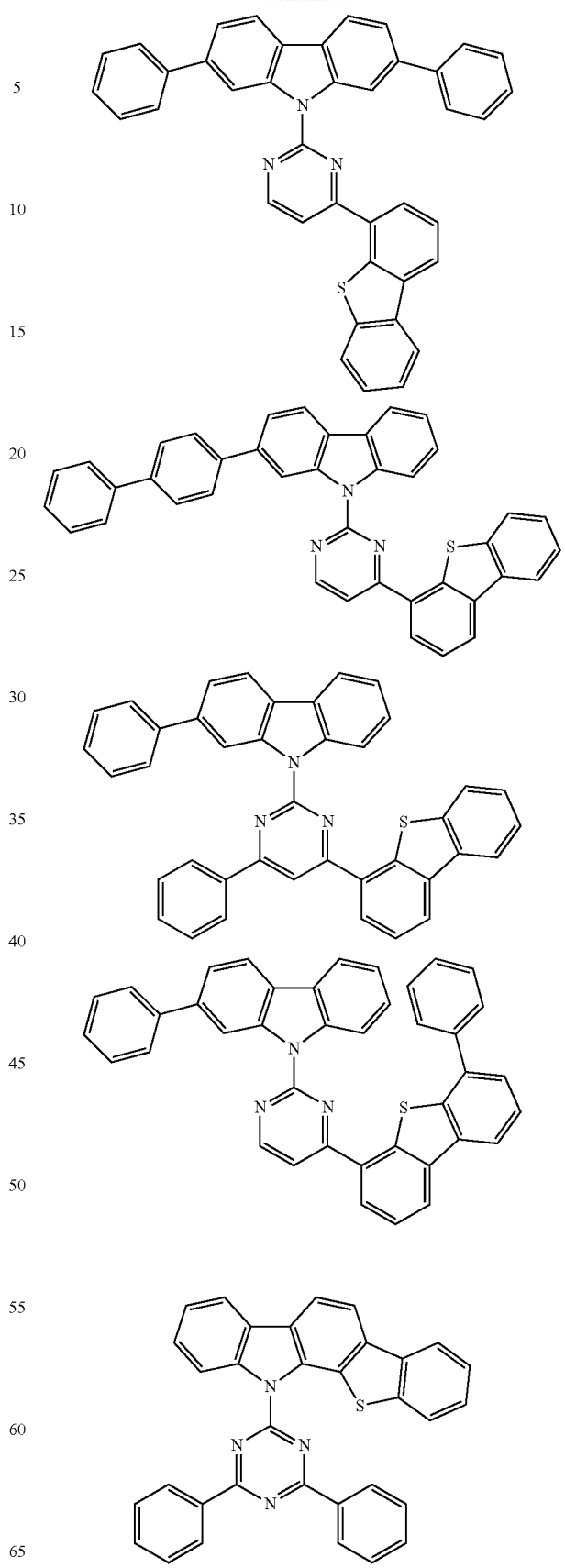

183
-continued
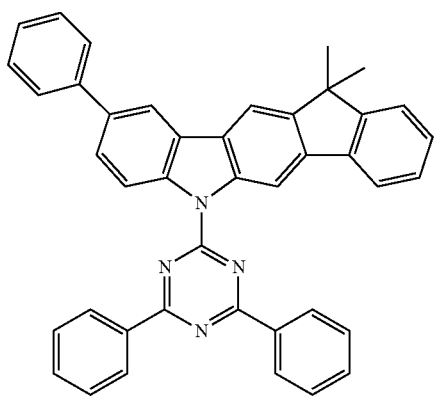
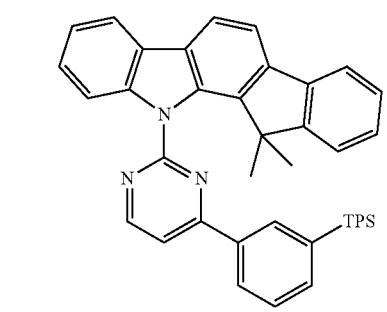
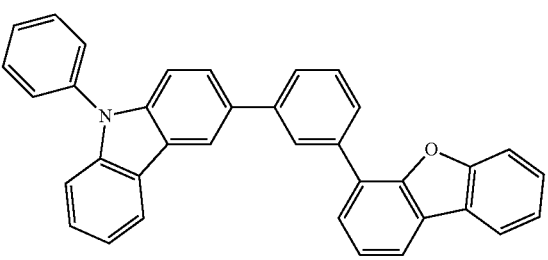
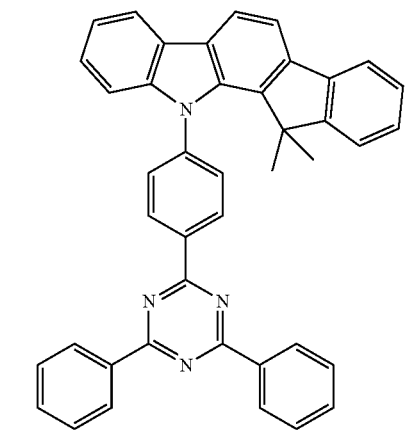
184
-continued
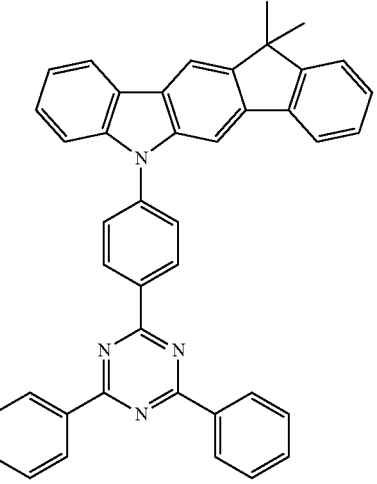
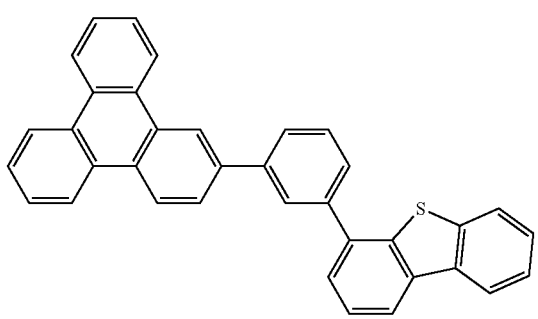
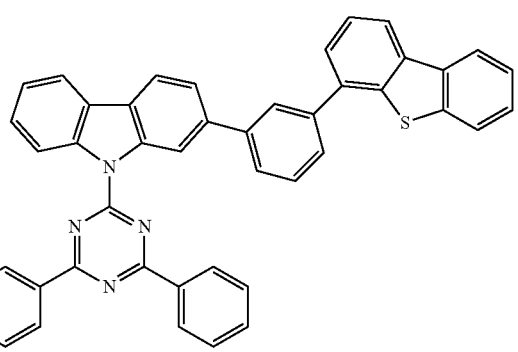
wherein TPS represents a triphenylsilyl group.
The dopants included in the organic EL device of the present invention may be selected from the group consisting of the compounds represented by the following formulae 8 to 10:

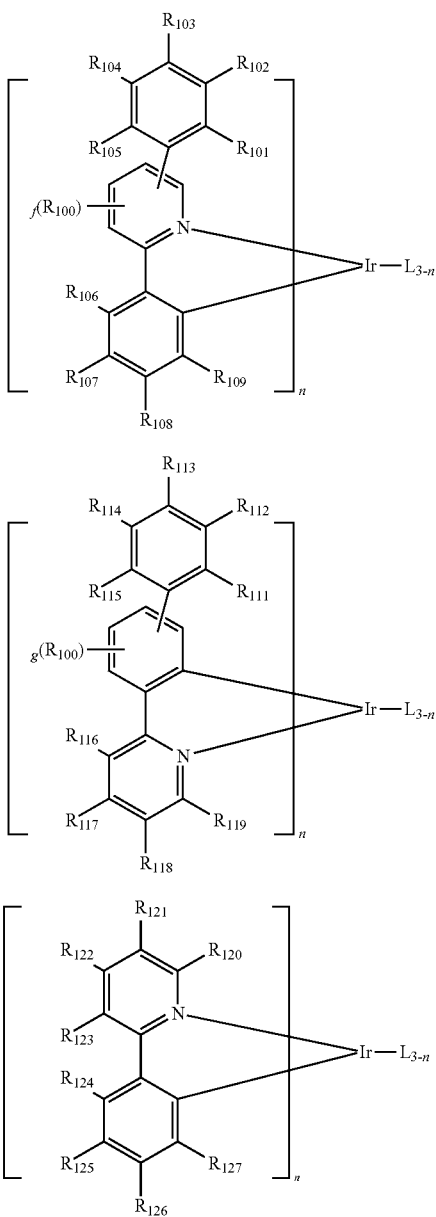

(8)

(9)

(10)

wherein
L is selected from the following structures:

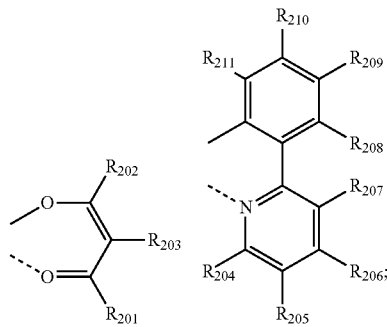

$R_{100}$ represents hydrogen, a substituted or unsubstituted (C1-C30)alkyl group, or a substituted or unsubstituted (C3-C30)cycloalkyl group;

$R_{101}$ to $R_{109}$ and $R_{111}$ to $R_{123}$ each independently represent hydrogen, deuterium, a halogen, a (C1-C30)alkyl group which is unsubstituted or substituted with a halogen(s), a substituted or unsubstituted (C3-C30)cycloalkyl group, a cyano group, a substituted or unsubstituted (C1-C30)alkoxy group, or a substituted or unsubstituted (C6-C30)aryl group; $R_{120}$ to $R_{123}$ may be linked to an adjacent substituent(s) to form a substituted or unsubstituted fused ring, for example, quinoline;

$R_{124}$ to $R_{127}$ each independently represent hydrogen, deuterium, a halogen, a substituted or unsubstituted (C1-C30) alkyl group, or a substituted or unsubstituted (C6-C30)aryl group; when $R_{124}$ to $R_{127}$ are aryl groups, they may be linked to an adjacent substituent(s) to form a substituted or unsubstituted fused ring, for example, fluorene, benzofuran, or benzothiophene;

$R_{201}$ to $R_{211}$ each independently represent hydrogen, deuterium, a halogen, a (C1-C30)alkyl group which is unsubstituted or substituted with a halogen(s), or a substituted or unsubstituted (C6-C30)aryl group; $R_{208}$ to $R_{211}$ may be linked to an adjacent substituent(s) to form a substituted or unsubstituted mono- or polycyclic (C3-C30) alicyclic, aromatic, or heteroaromatic ring, for example, fluorene, dibenzothiophene, or dibenzofuran;

f and g each independently represent an integer of 1 to 3; where f or g is an integer of 2 or more, each of $R_{100}$ may be the same or different; and n represents an integer of 1 to 3.

The dopant material includes the following:

D-1

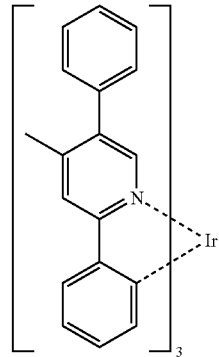

D-2

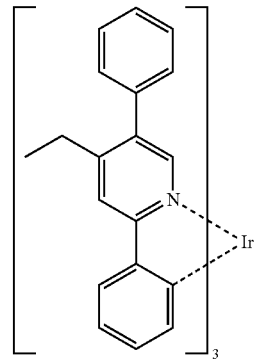

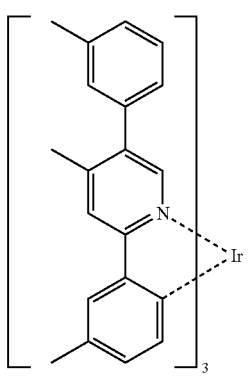
D-3
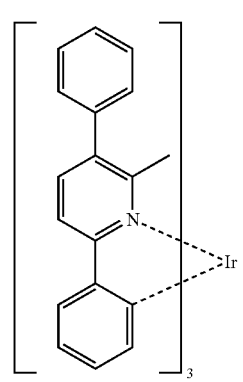
D-4
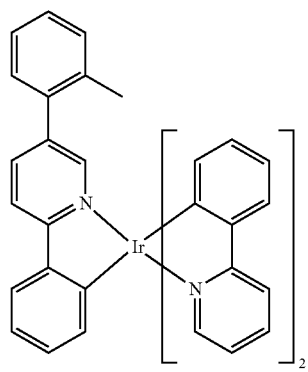
D-5
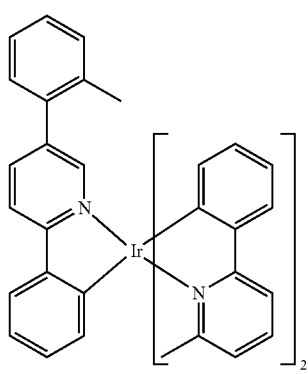
D-6
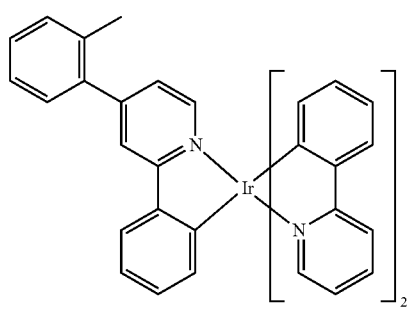
D-7
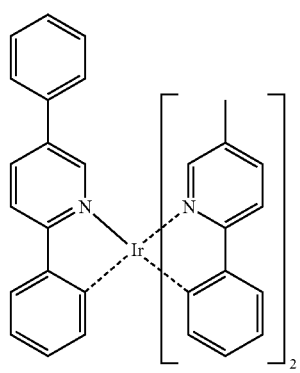
D-8
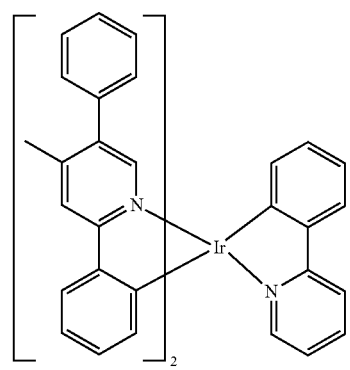
D-9
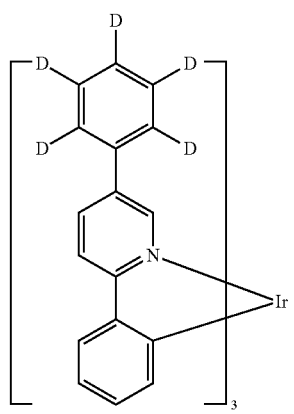
D-10

-continued
D-11
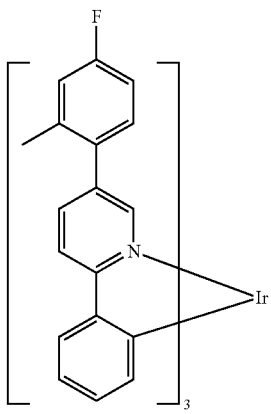
D-12
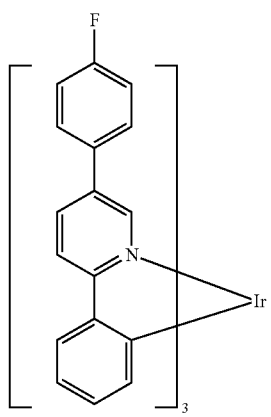
D-13
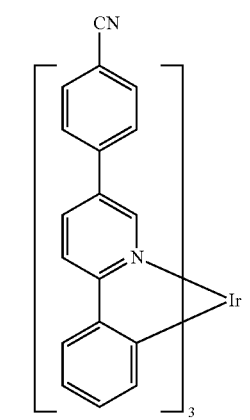
D-14
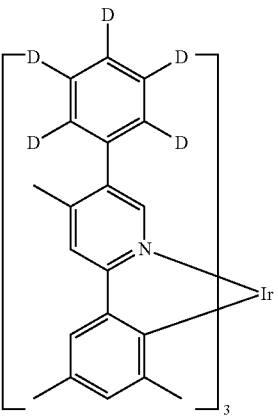
-continued
D-15
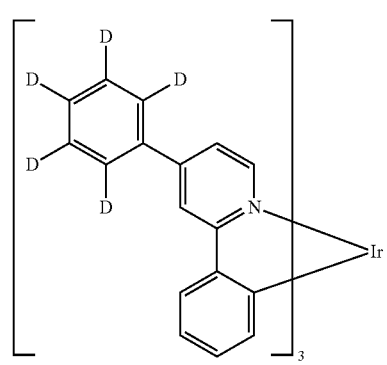
D-16
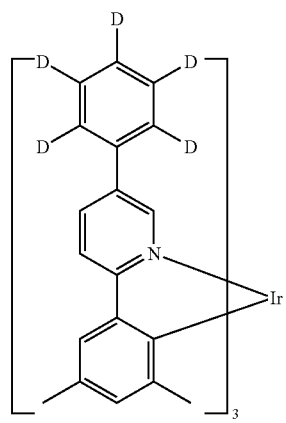
D-17
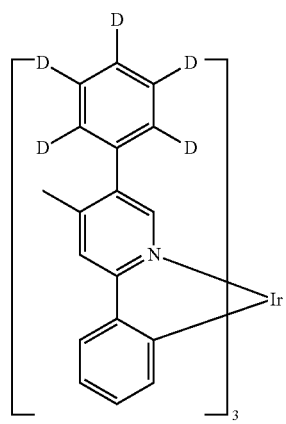
D-18
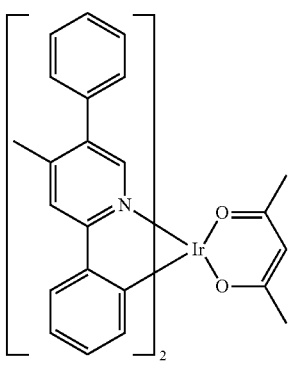

D-19
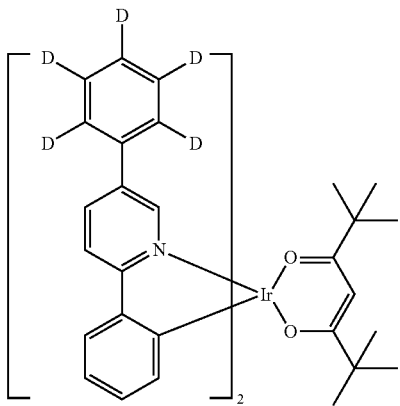
D-20
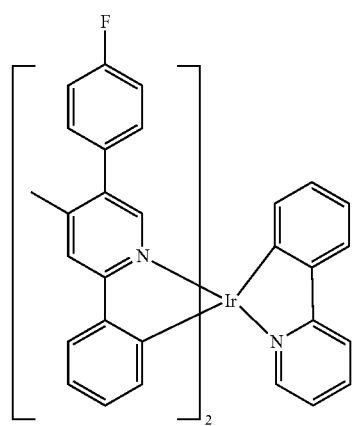
D-21
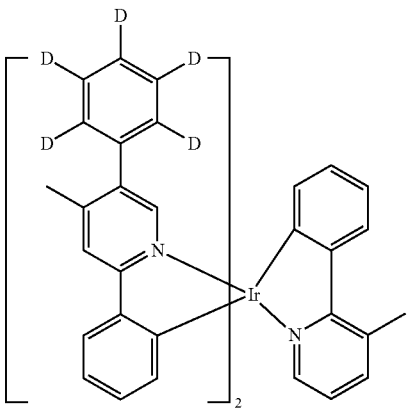
D-22
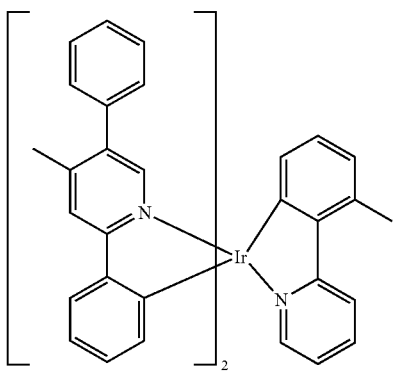
D-23
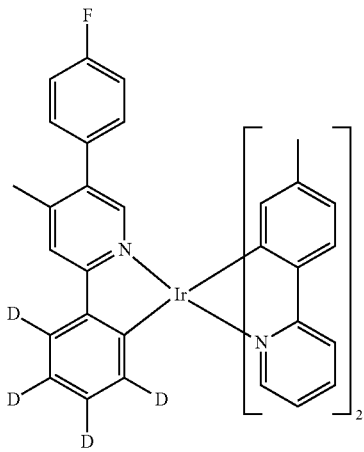
D-24
D-25
D-26
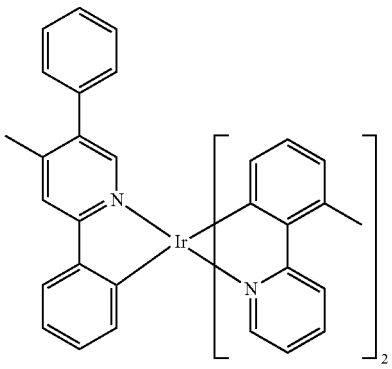

D-27
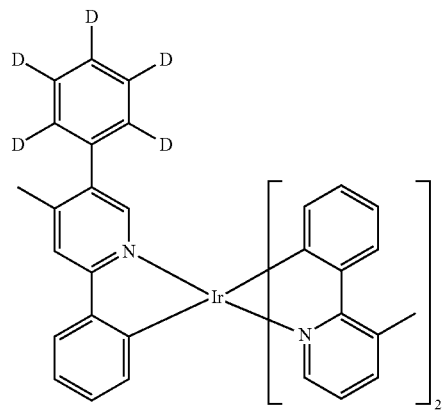
D-28
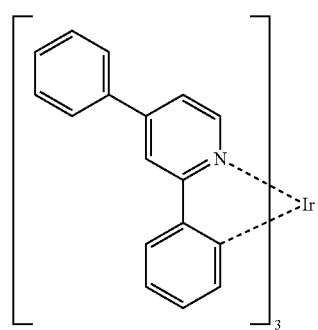
D-29
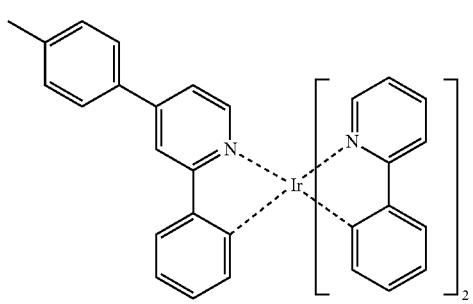
D-30
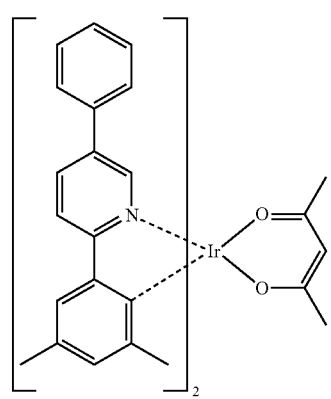
D-31
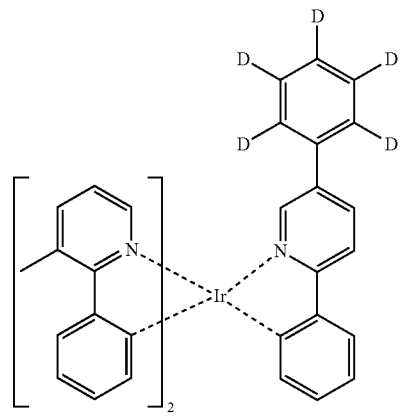
D-32
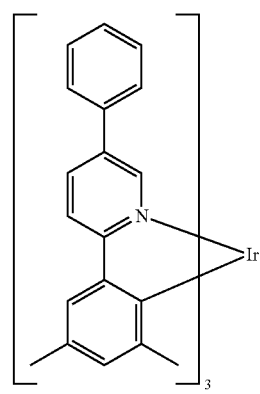
D-33
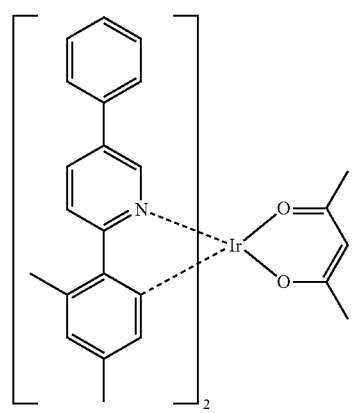
D-34
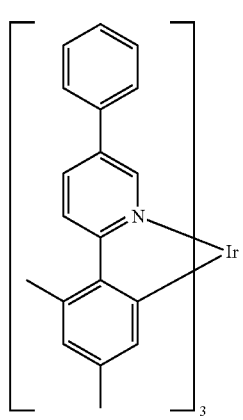

-continued
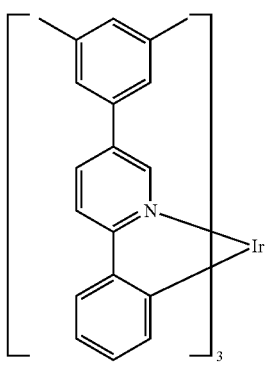
D-35
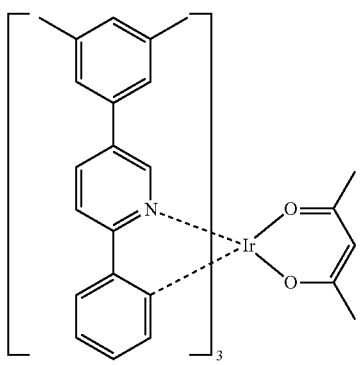
D-36
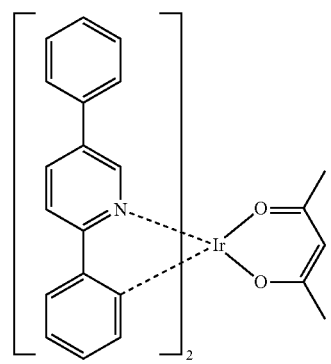
D-37
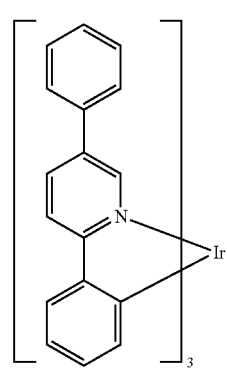
D-38
-continued
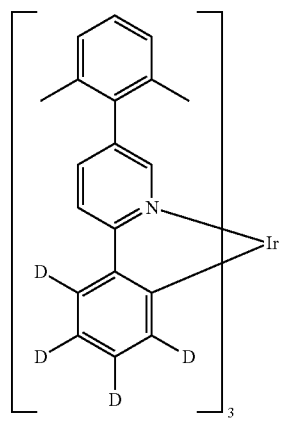
D-39
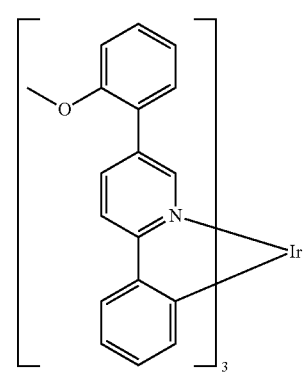
D-40
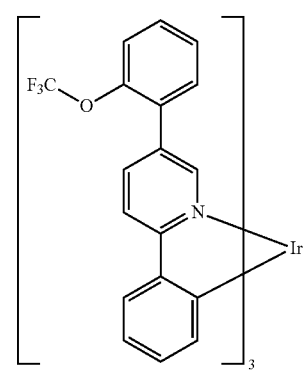
D-41
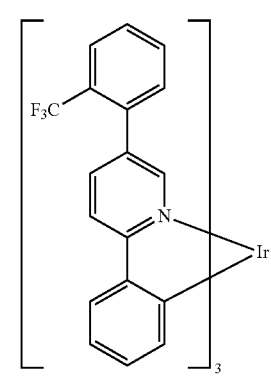
D-42

-continued
D-43
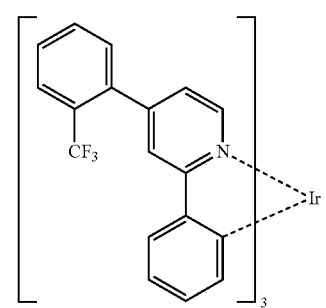
D-44
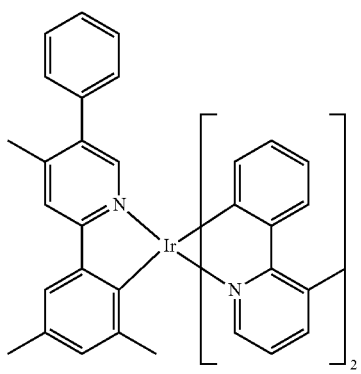
D-45
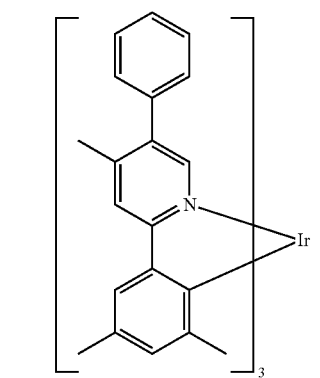
D-46
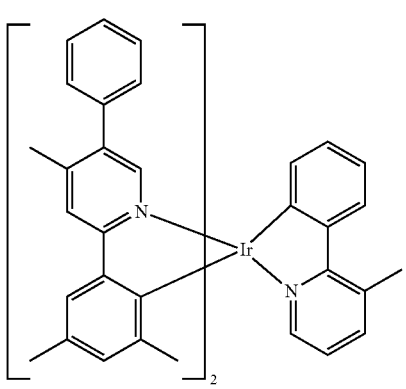
-continued
D-47
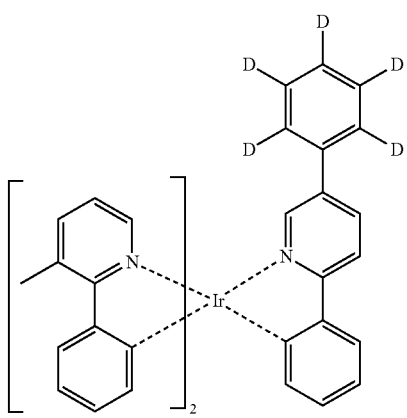
D-48
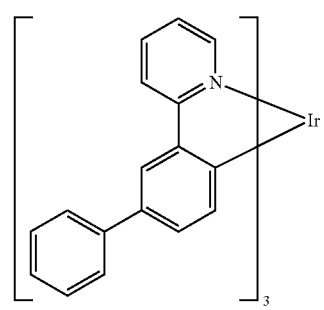
D-49
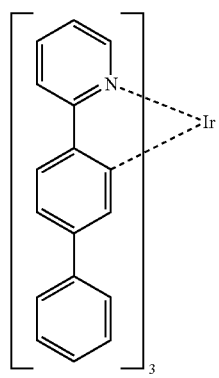
D-50
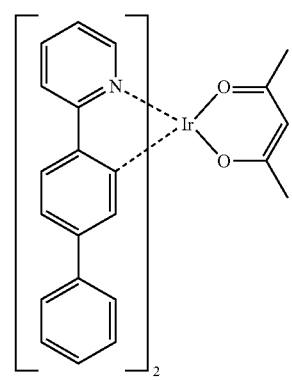

D-51 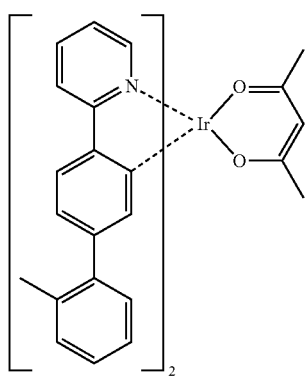
D-52 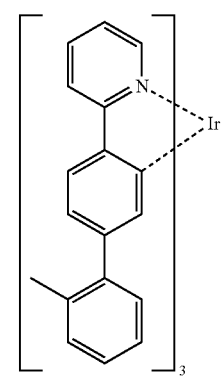
D-53 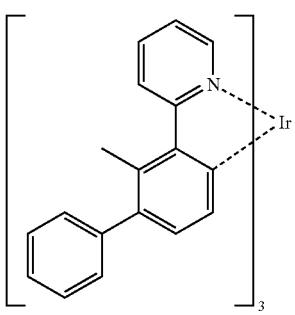
D-54 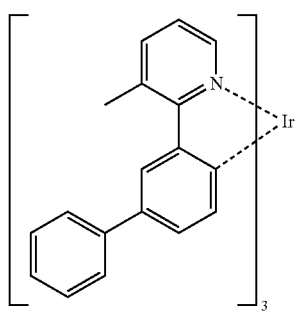
D-55 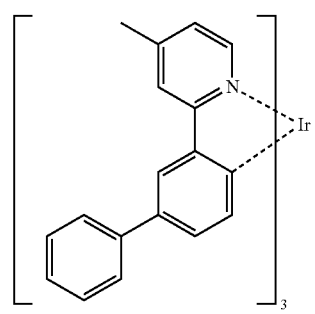
D-56 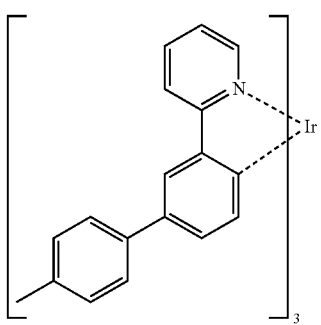
D-57 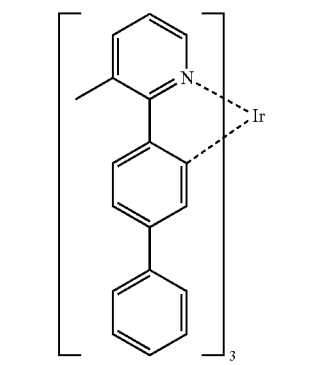
D-58 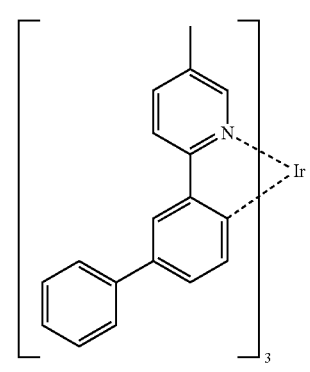

-continued
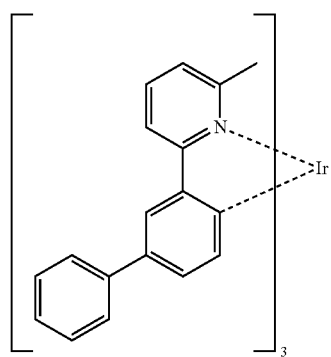 D-59
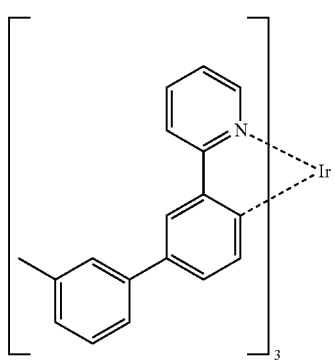 D-60
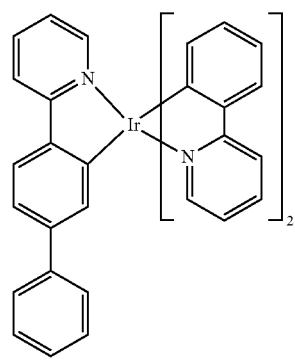 D-61
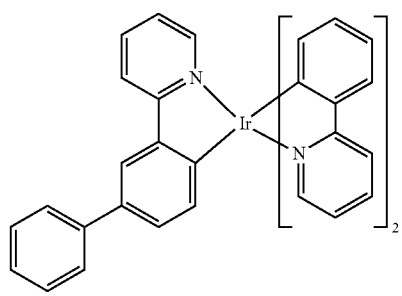 D-62
-continued
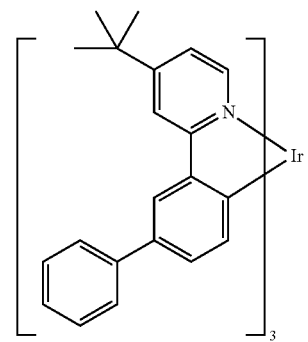 D-63
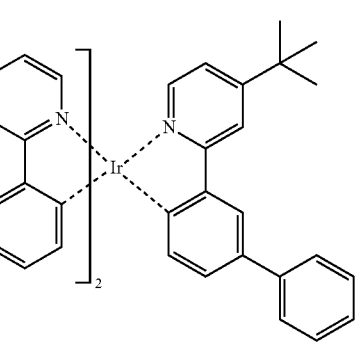 D-64
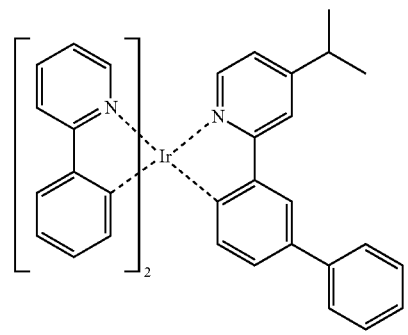 D-65
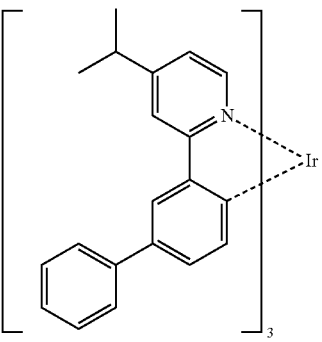 D-66

-continued
D-67
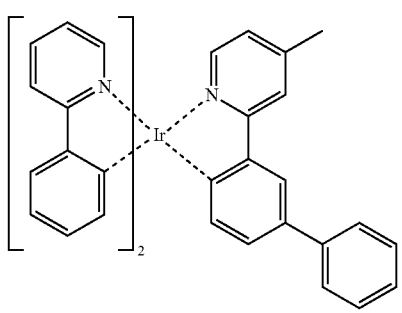
D-68
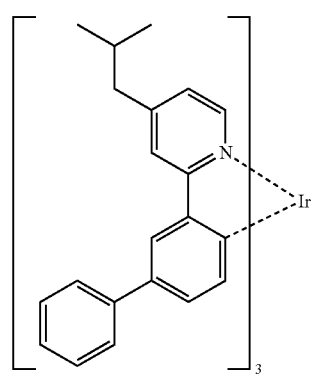
D-69
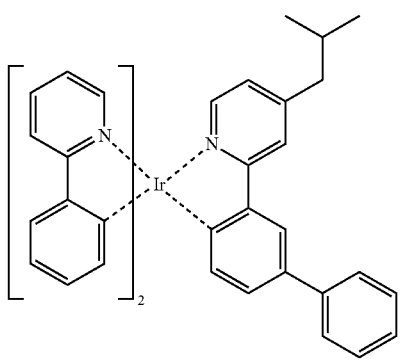
D-70
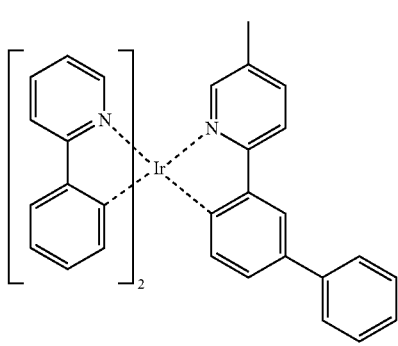
-continued
D-71
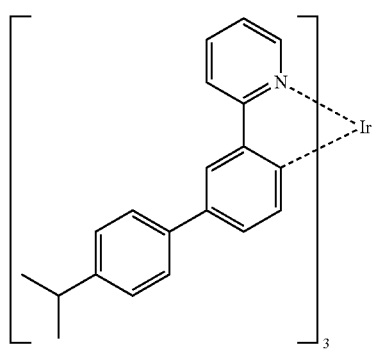
D-72
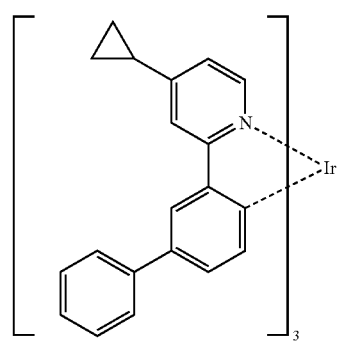
D-73
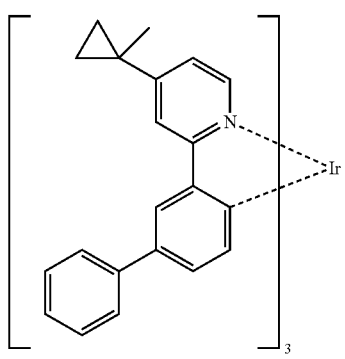
D-74
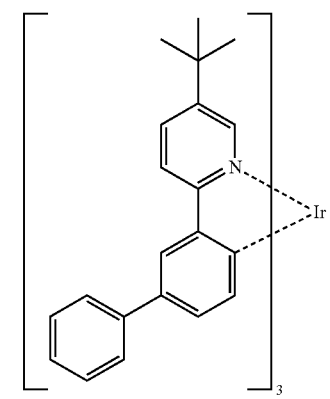

D-75 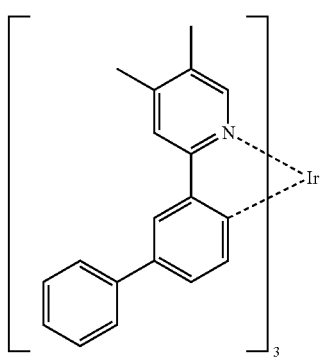
D-76 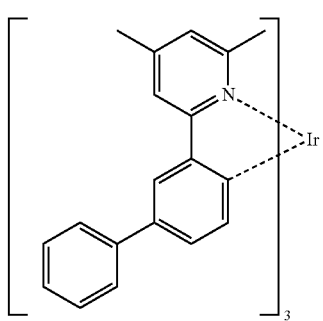
D-77 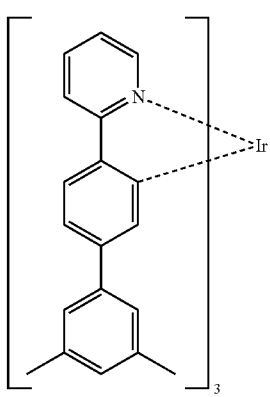
D-78 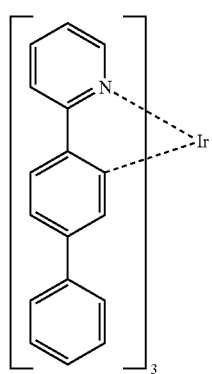
D-79 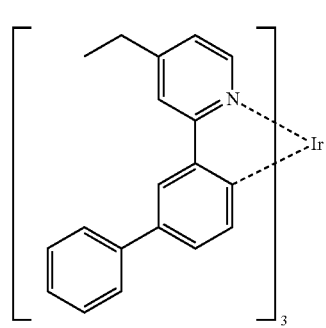
D-80 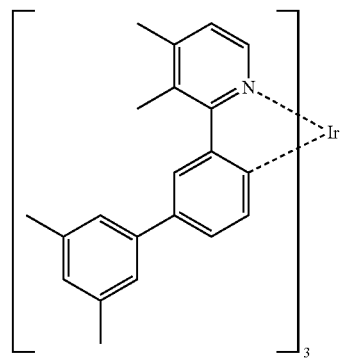
D-81 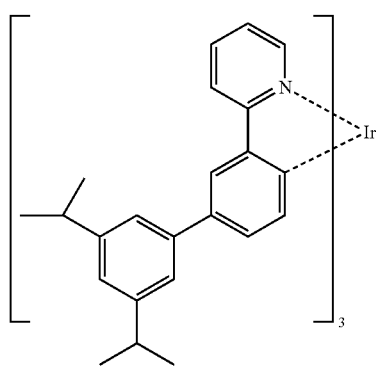
D-82 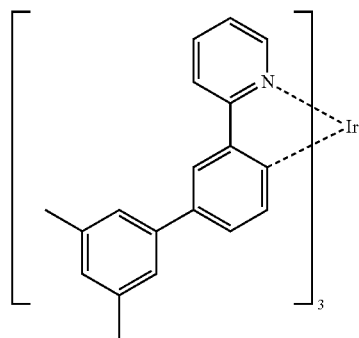

D-83
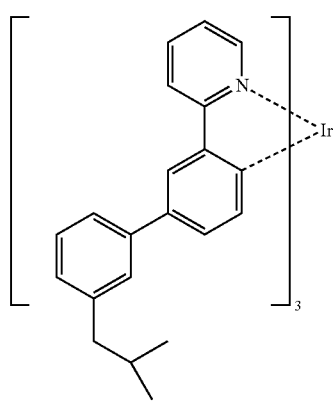
D-84
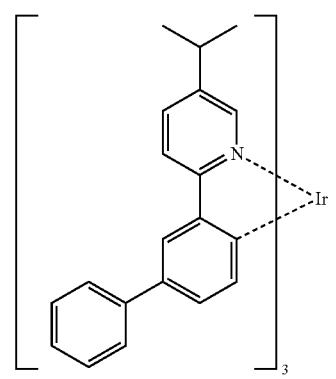
D-85
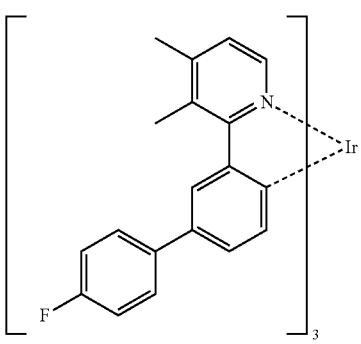
D-86
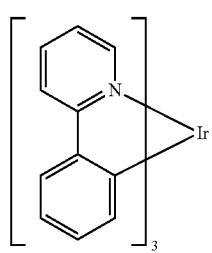
D-87
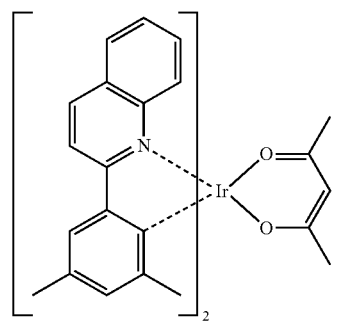
D-88
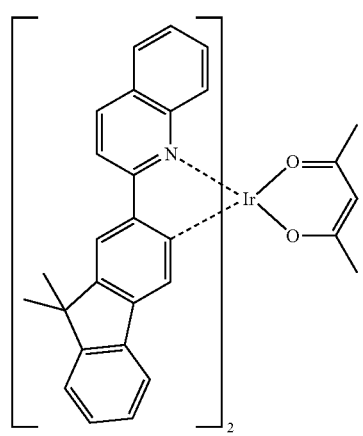
D-89
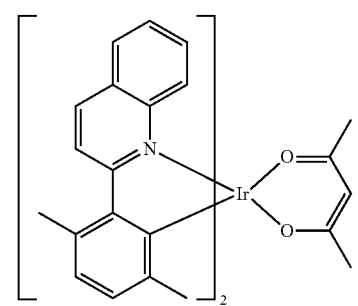
D-90
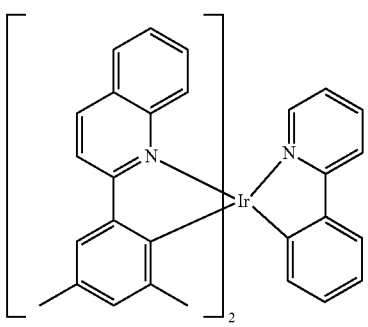

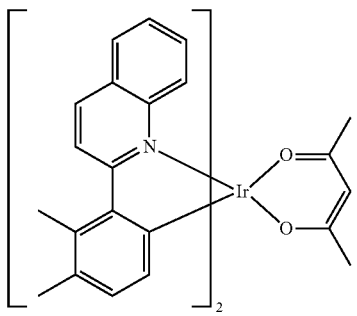
D-91
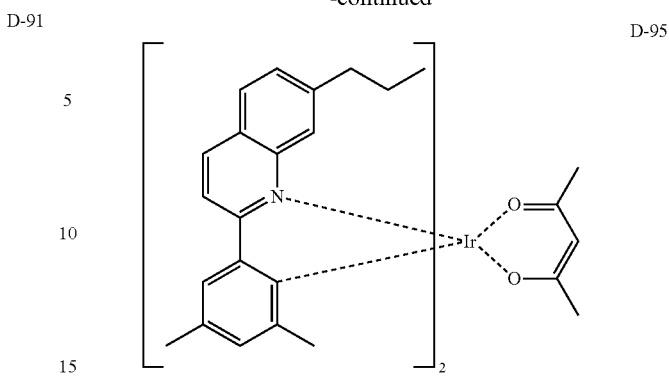
D-95
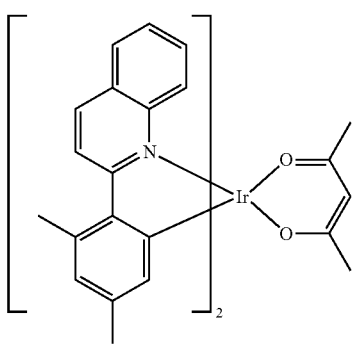
D-92
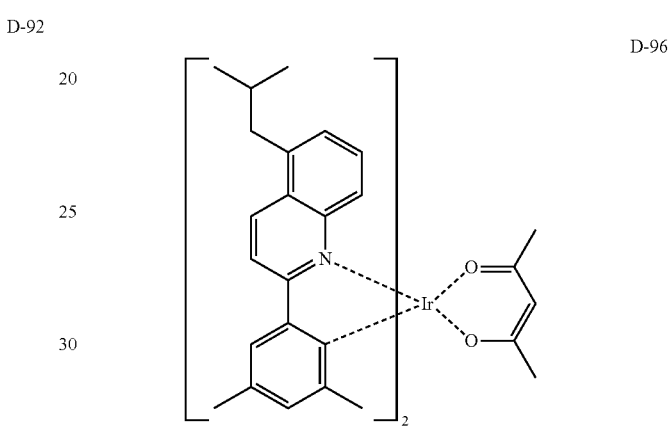
D-96
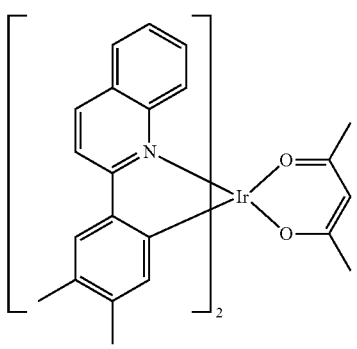
D-93
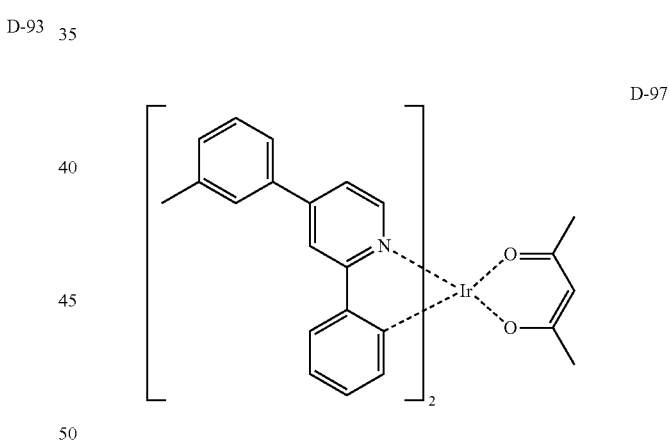
D-97
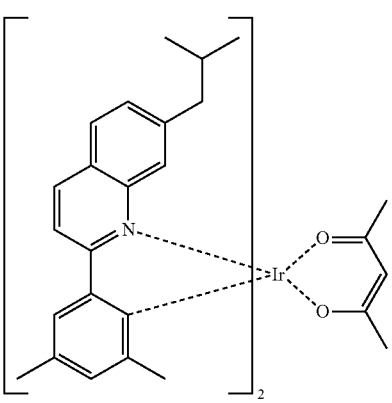
D-94
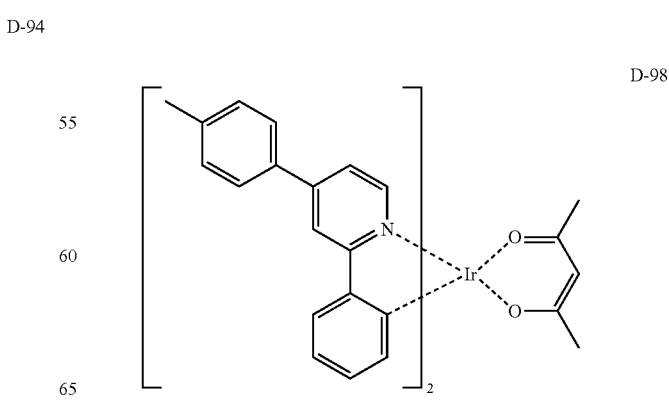
D-98

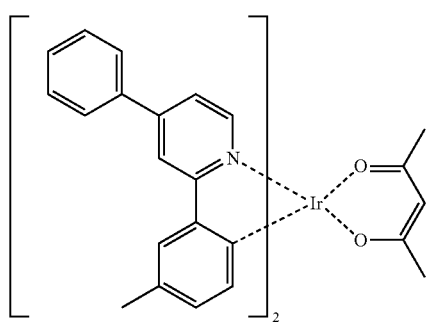
D-99
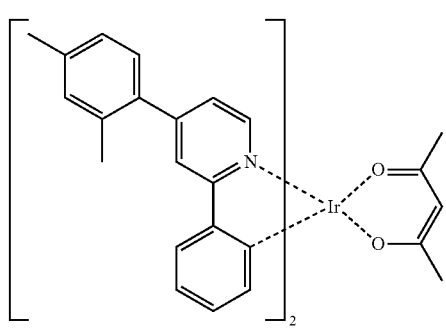
D-100
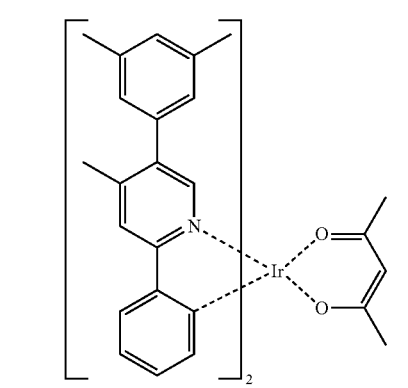
D-101
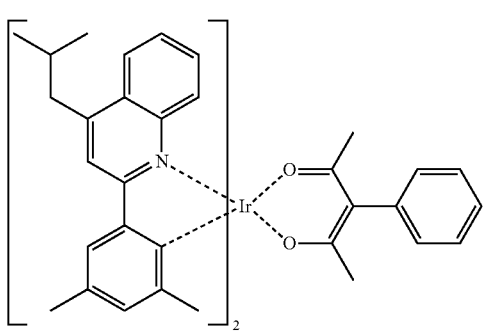
D-102
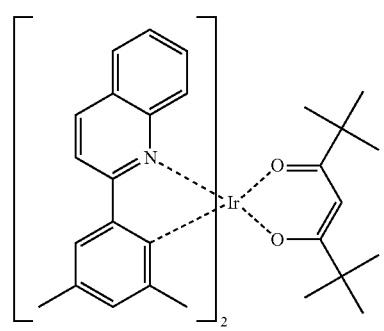
D-103
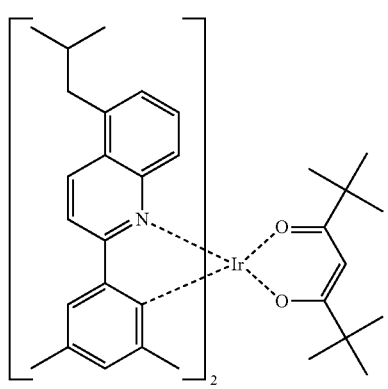
D-104
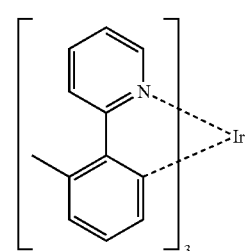
D-105
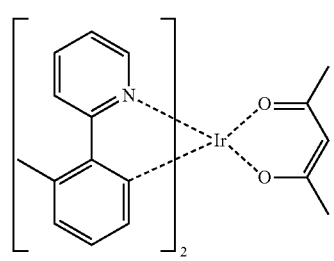
D-106
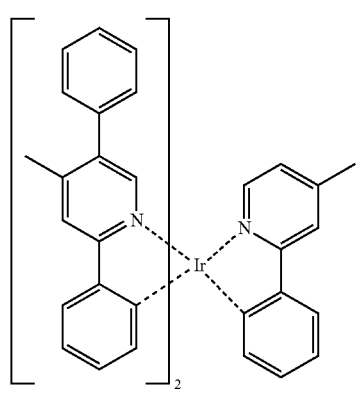
D-107

-continued
D-108
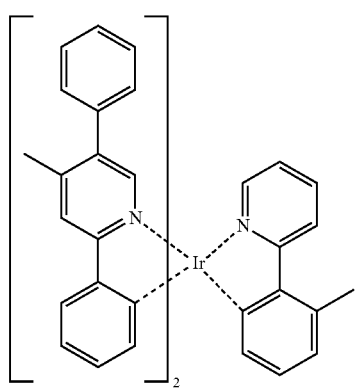
D-109
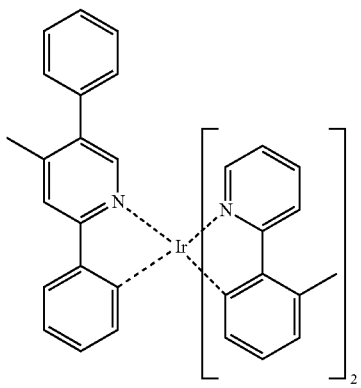
D-110
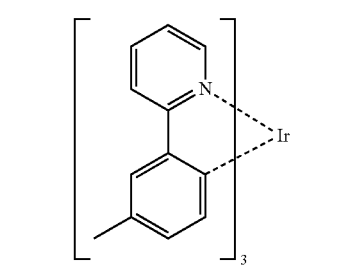
D-111
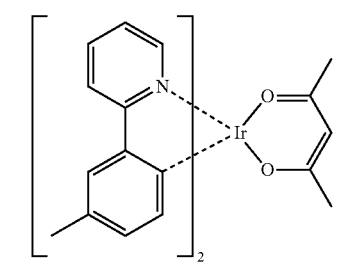
-continued
D-112
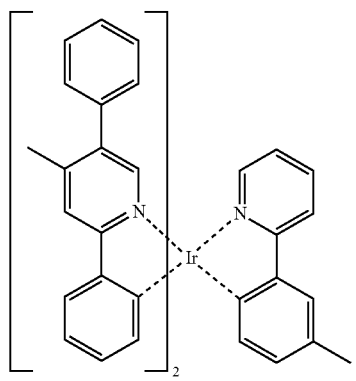
D-113
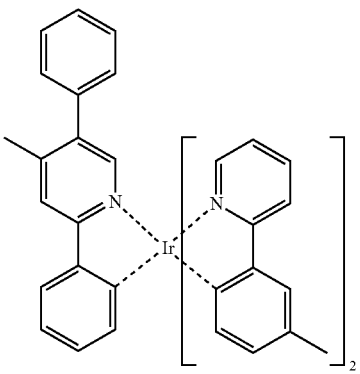
D-114
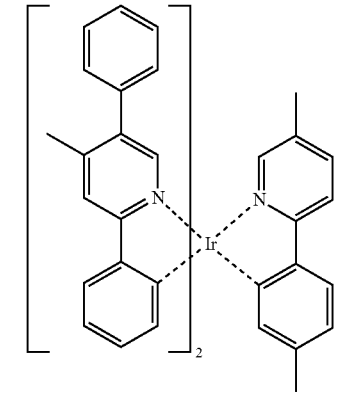
D-115
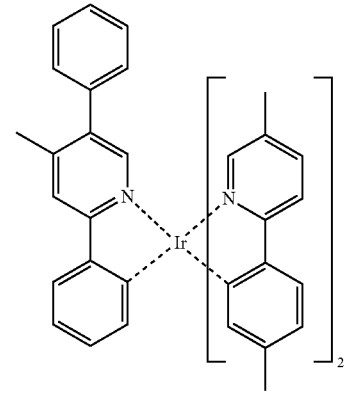

D-116
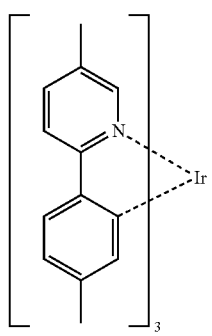
D-117
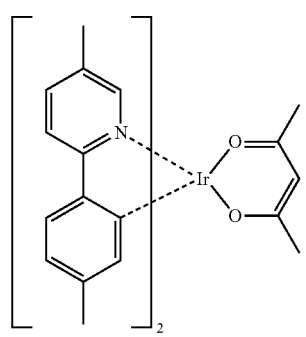
D-118
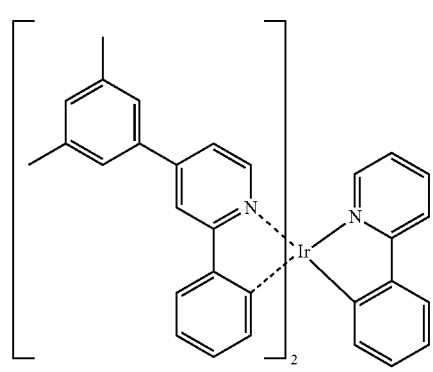
D-119
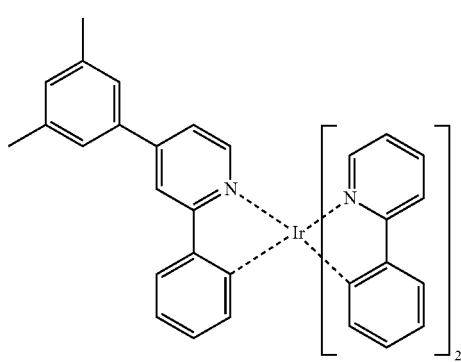
D-120
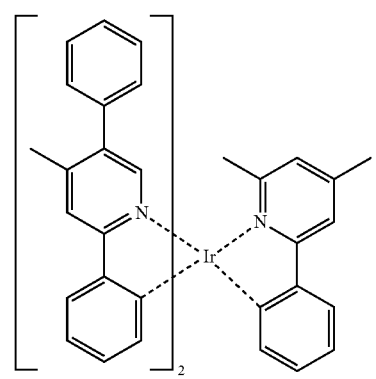
D-121
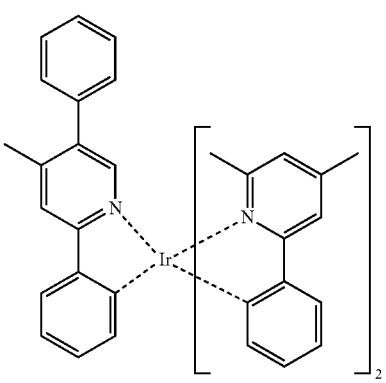
D-122
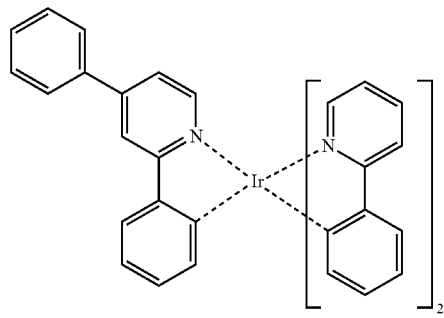
D-123
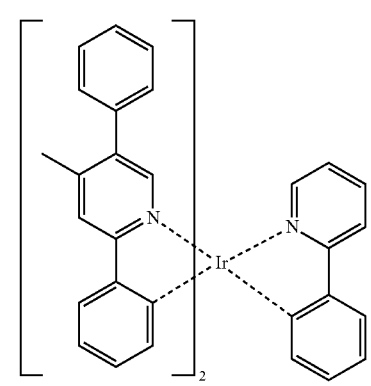

D-124
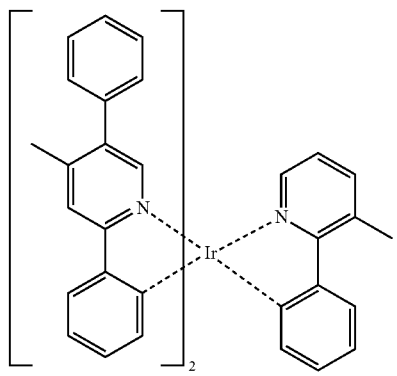
D-125
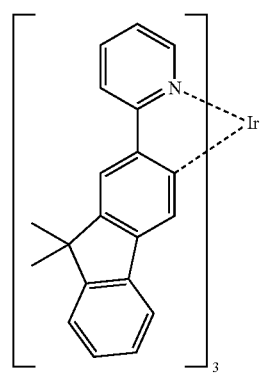
D-126
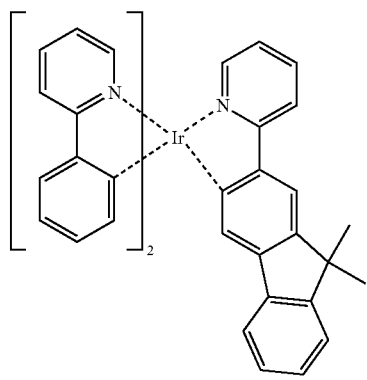
D-127
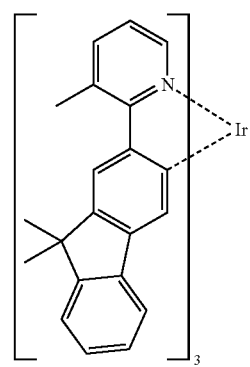
D-128
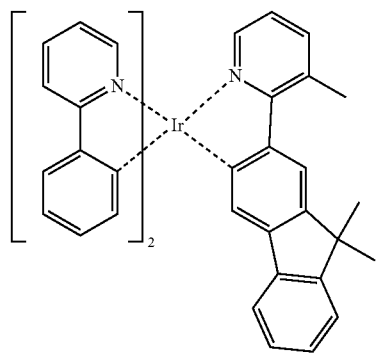
D-129
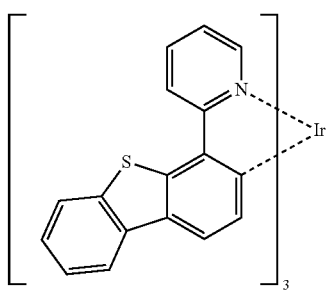
D-130
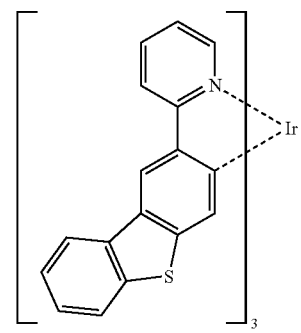
D-131
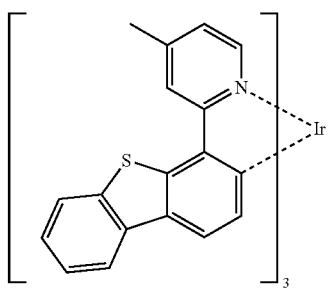
D-132
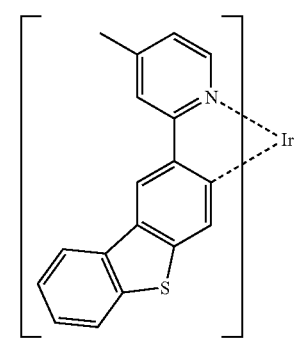

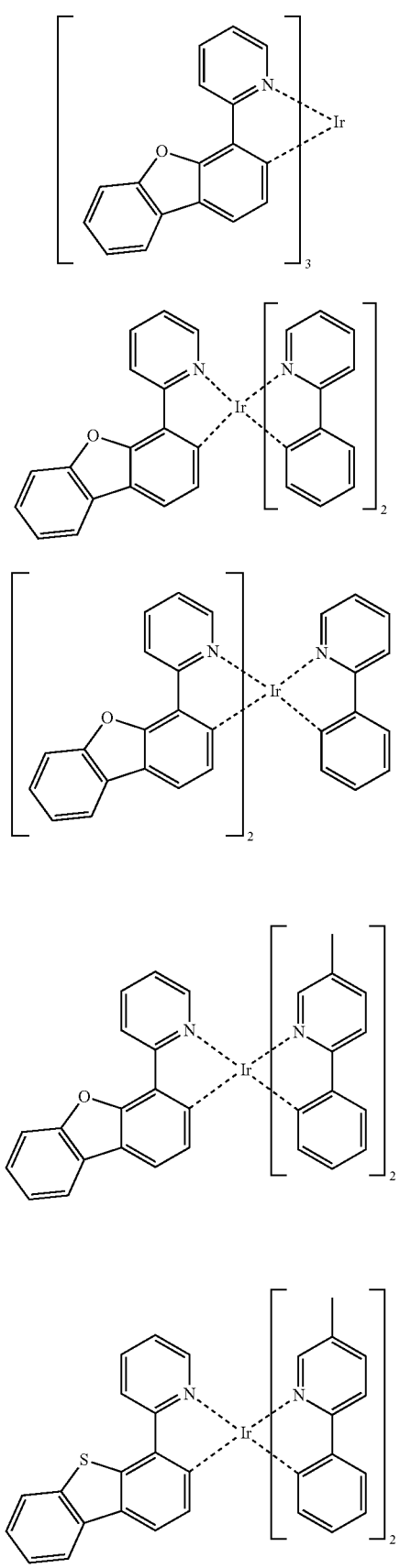
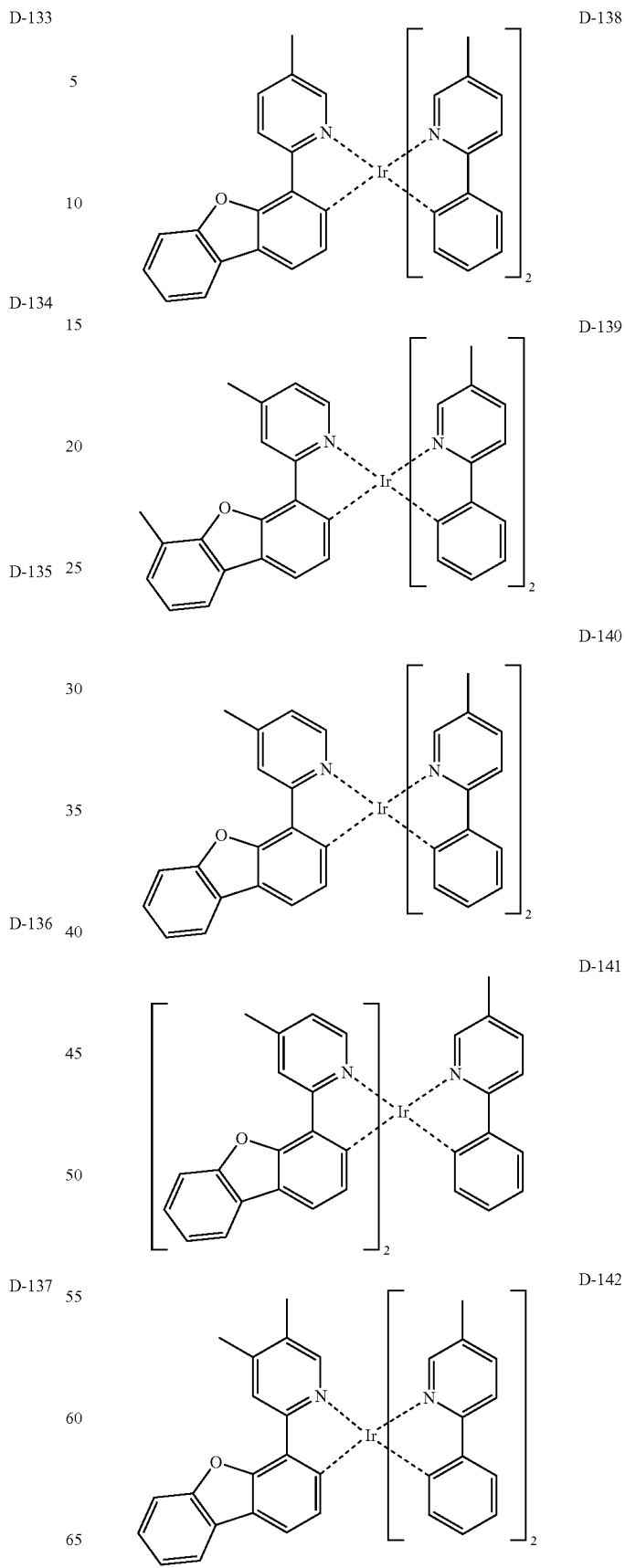

D-143
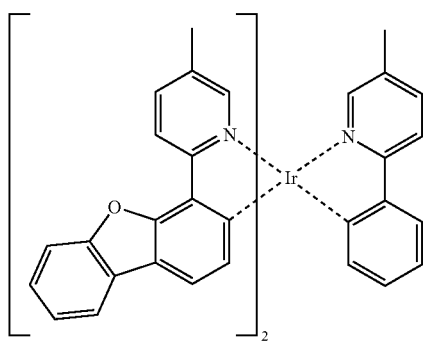
D-144
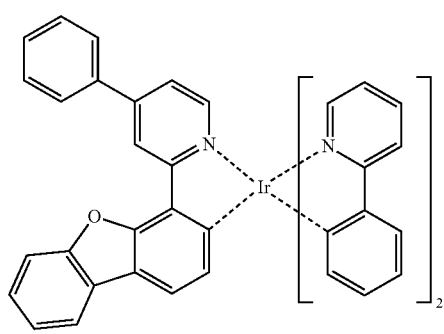
D-145
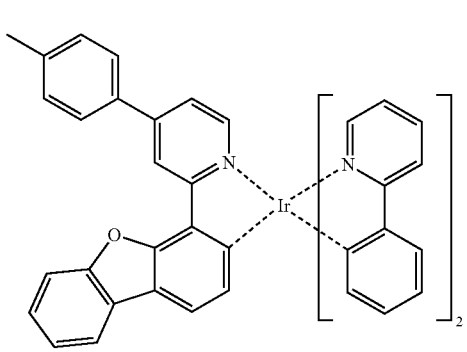
D-146
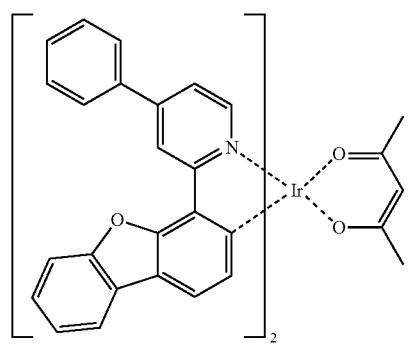
D-147
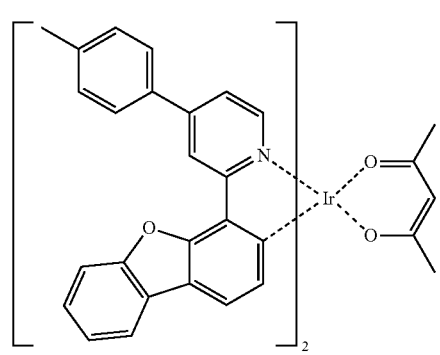
D-148
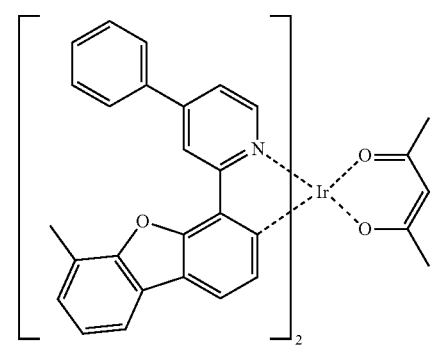
D-149
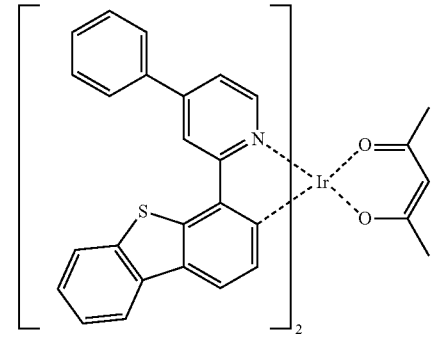
D-150
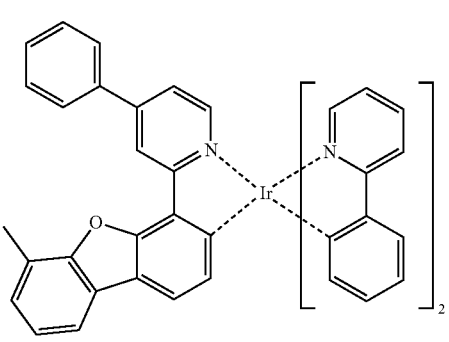

-continued
D-151
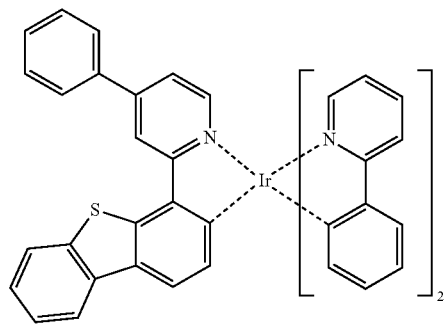
D-152
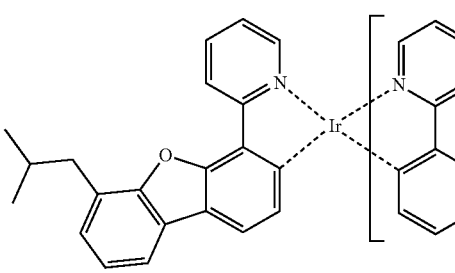
D-153
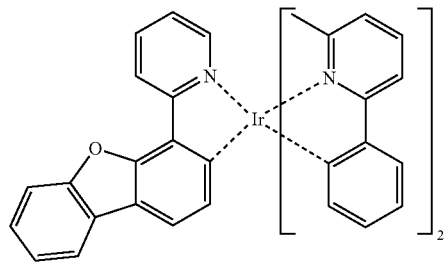
D-154
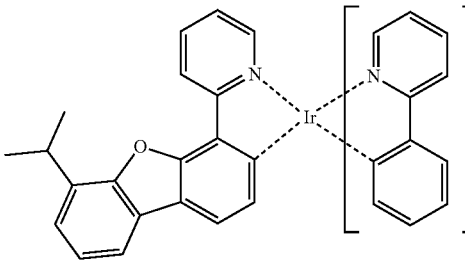
D-155
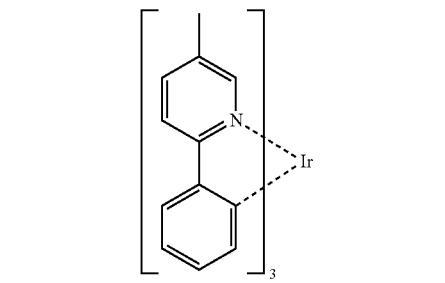
-continued
D-156
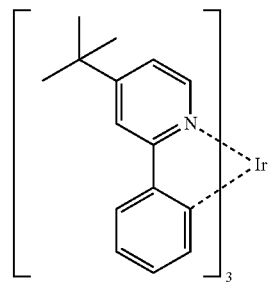
D-157
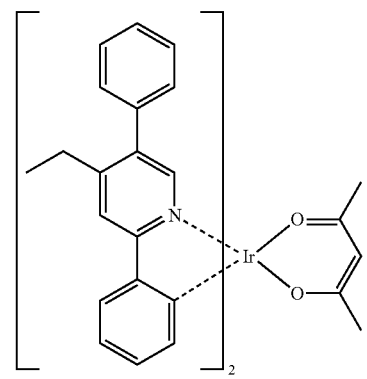
D-158
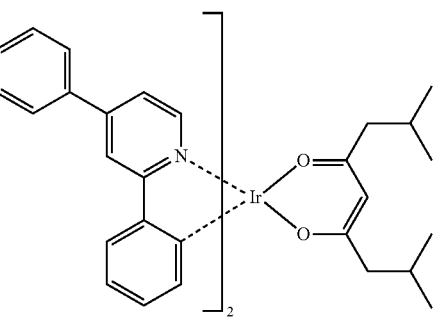
D-159
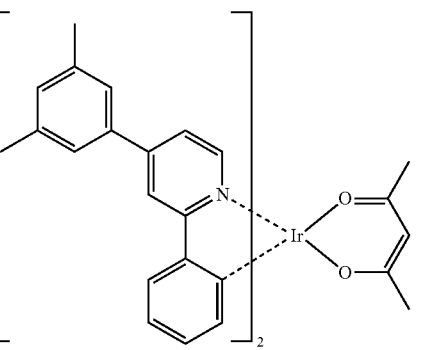
D-160
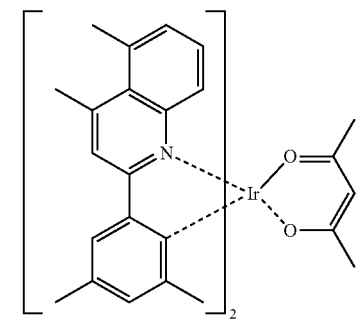

D-161
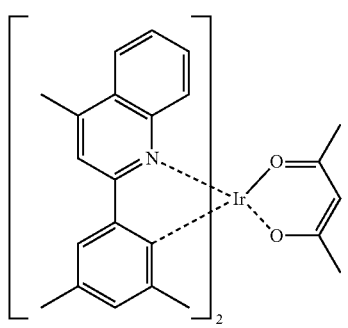
D-165
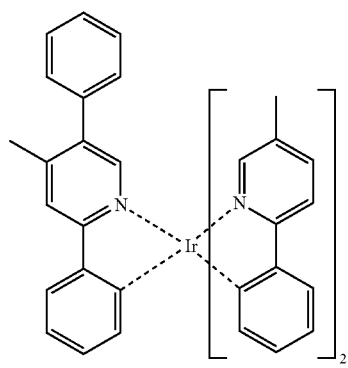
D-162
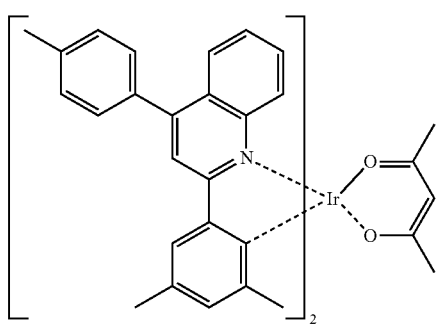
D-166
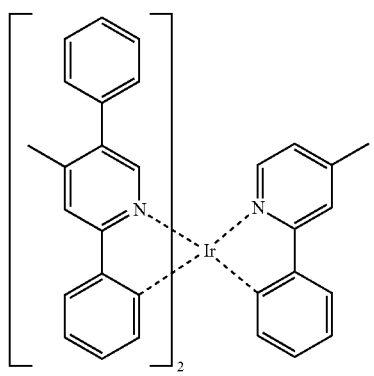
D-163
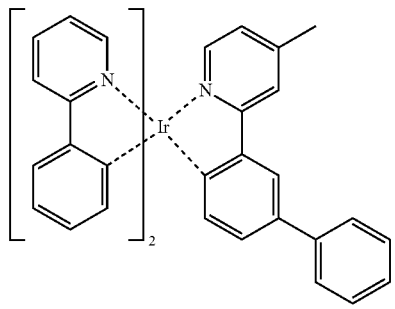
D-167
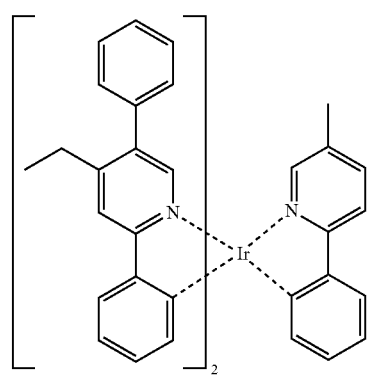
D-164
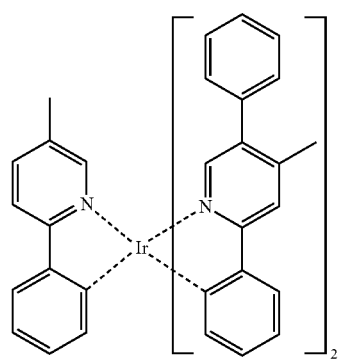
D-168
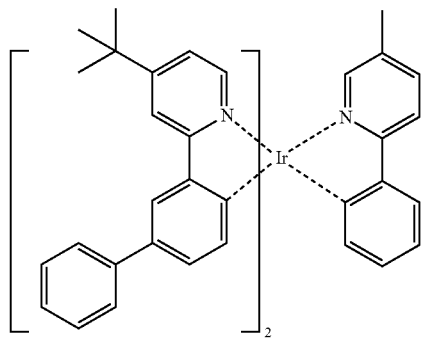

D-169
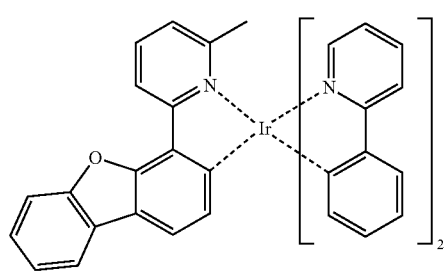
D-170
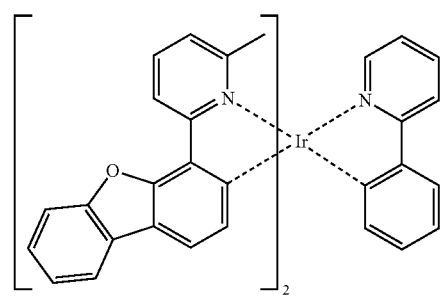
D-171
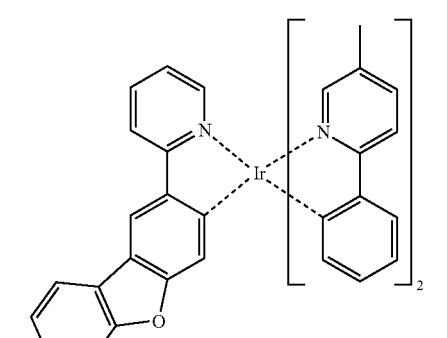
D-172
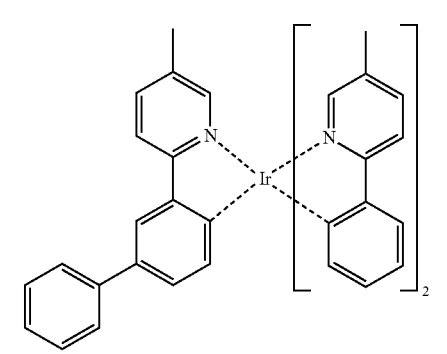
D-173
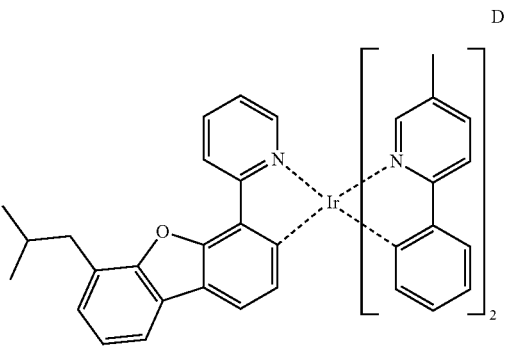
D-174
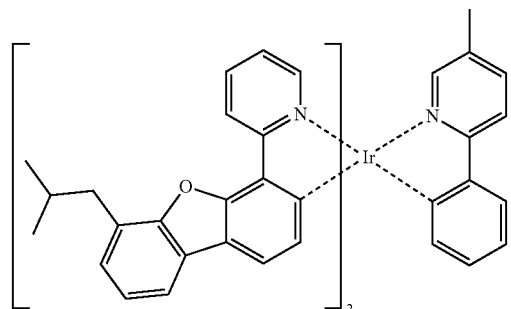
D-175
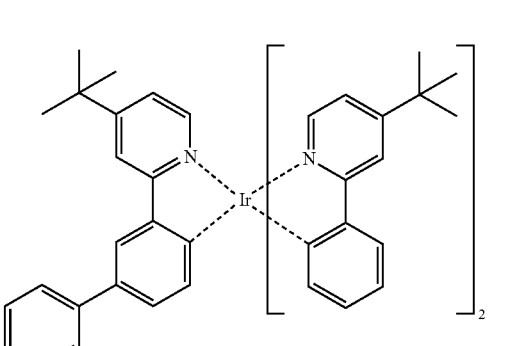
D-176
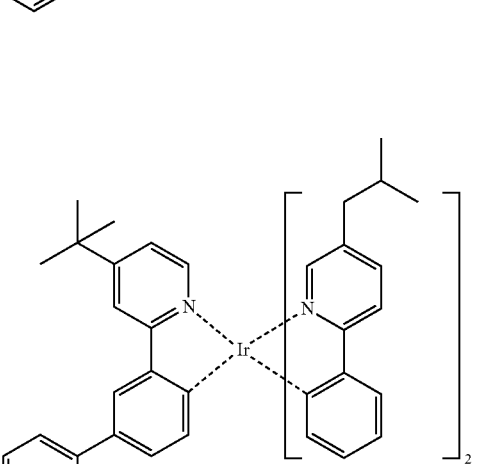
D-177
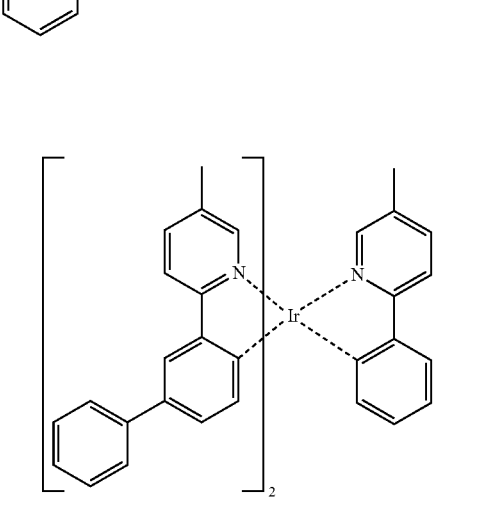

D-178
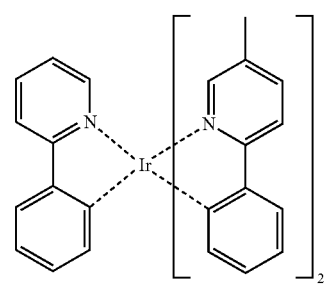
D-182
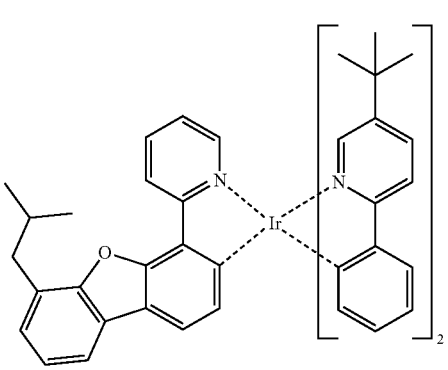
D-179
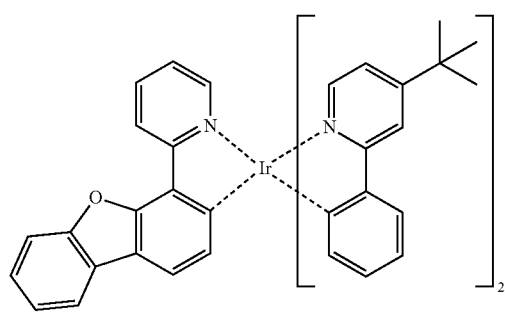
D-183
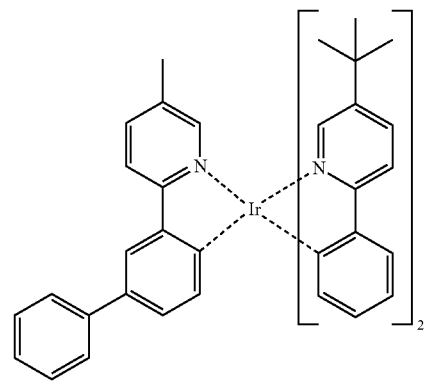
D-180
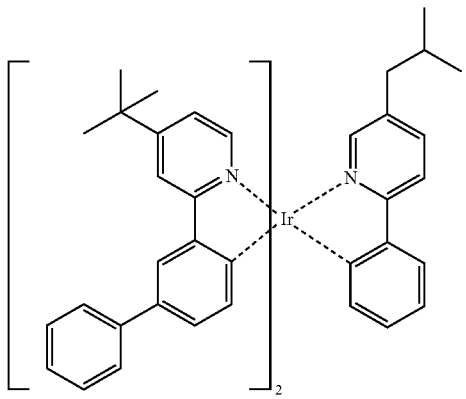
D-184
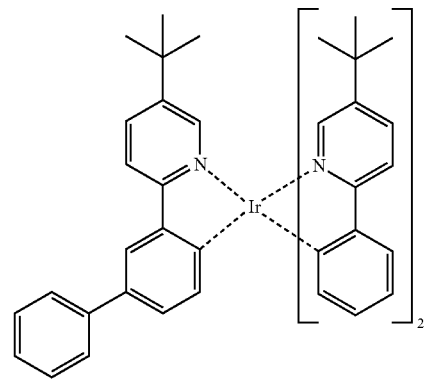
D-181
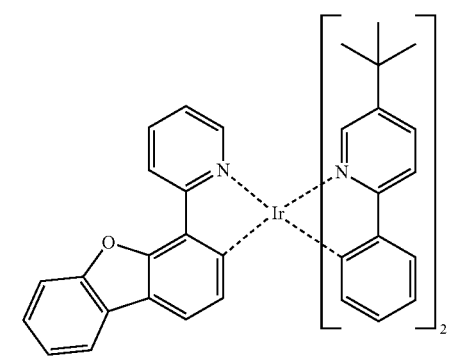
D-185
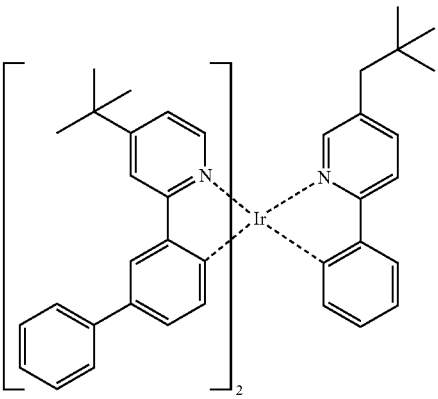

D-186
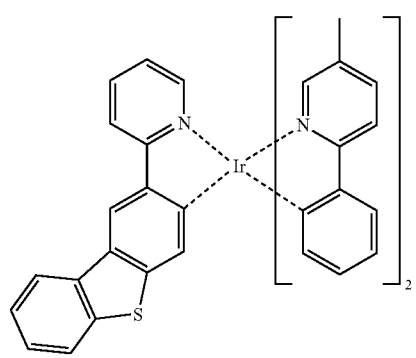
D-187
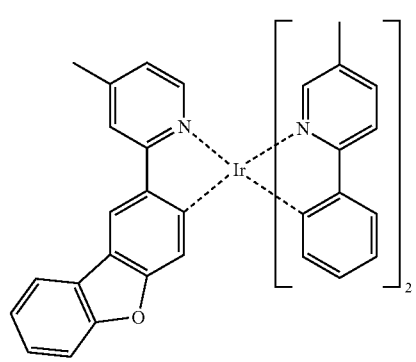
D-188
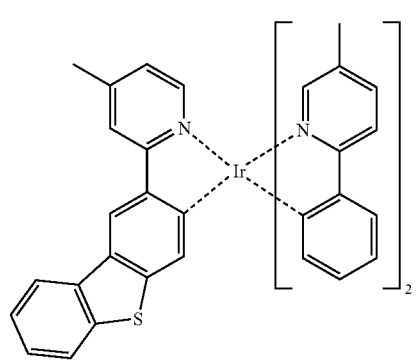
D-189
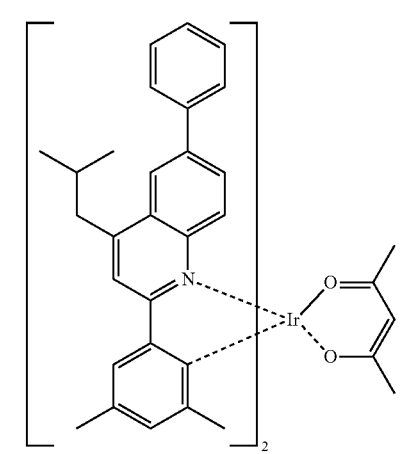
D-190
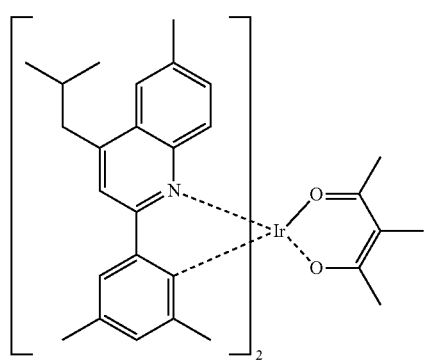
D-191
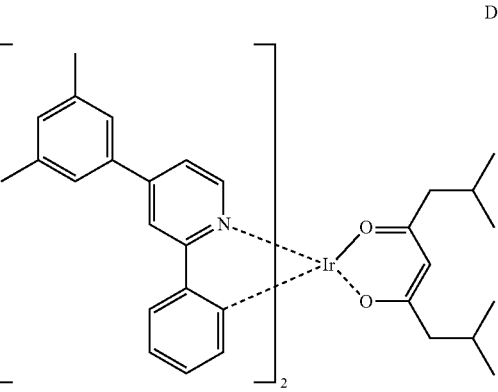
D-192
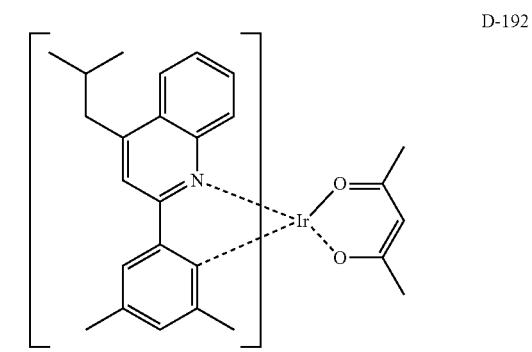
D-199
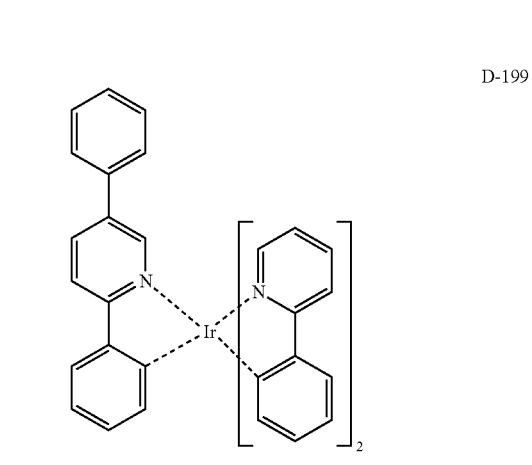

D-200 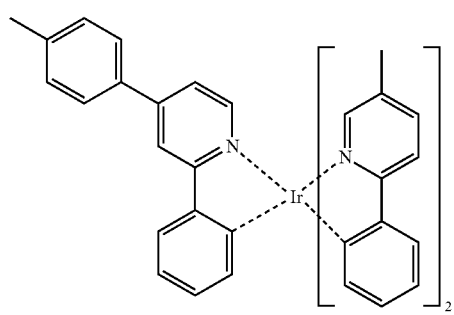
D-201 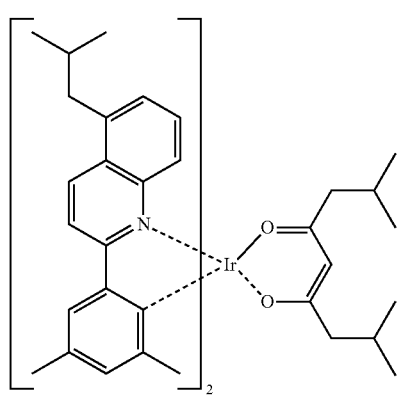
D-202 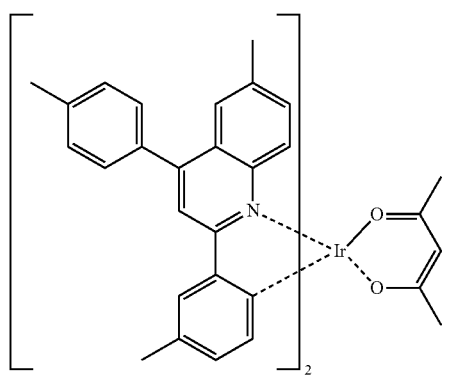
D-203 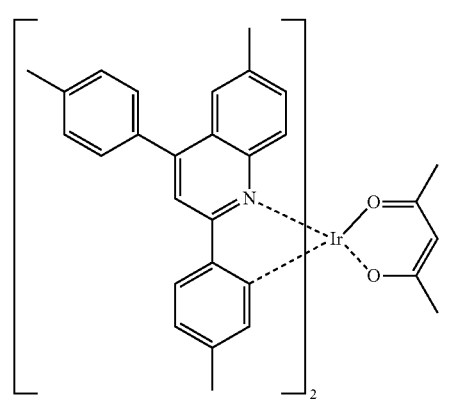
D-204 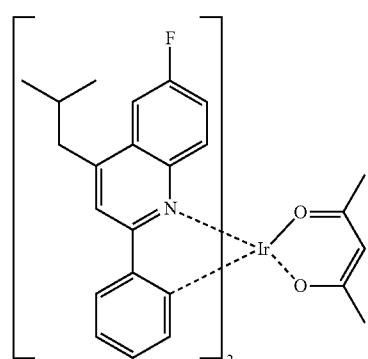
D-205 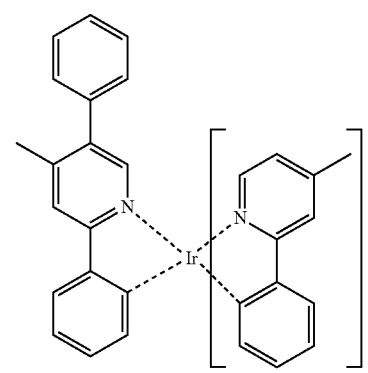
D-206 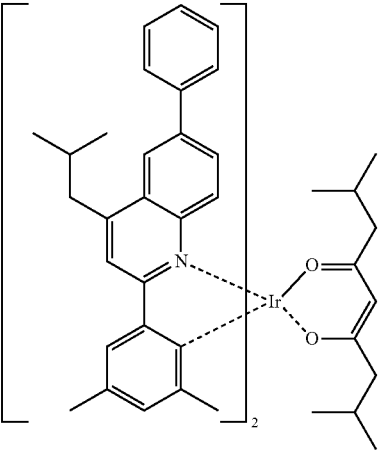
D-207 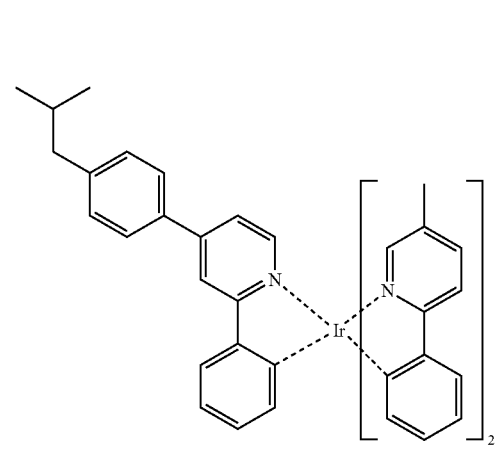

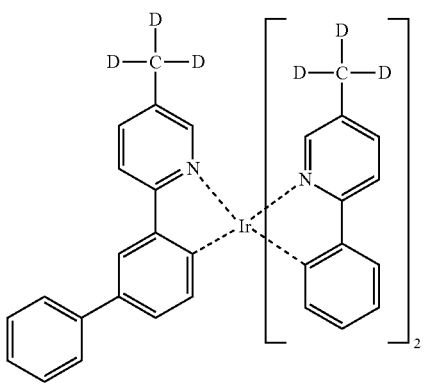

D-208

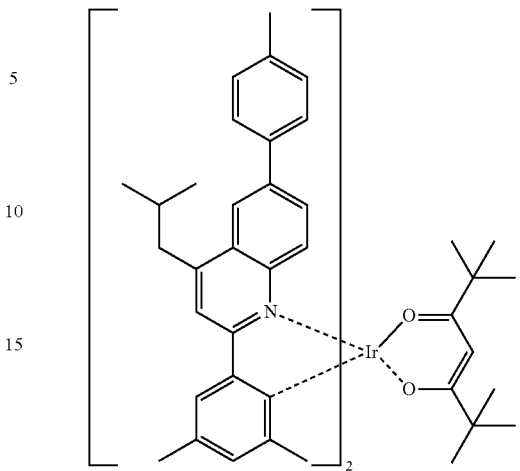

D-211

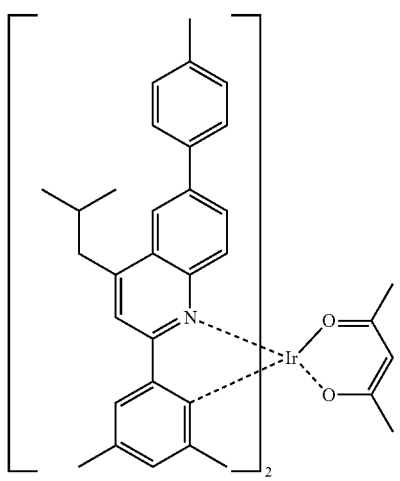

D-209

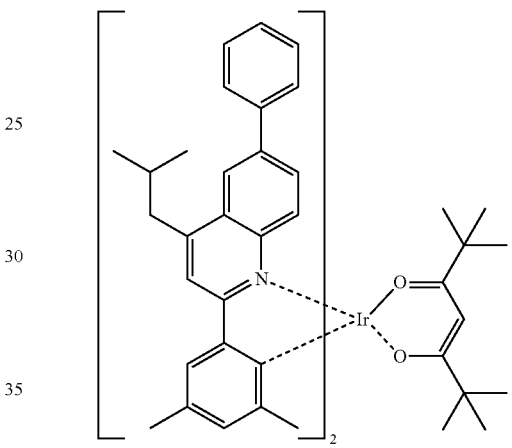

D-212

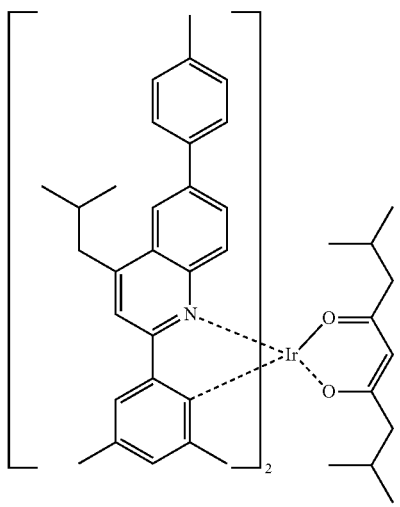

D-210

The organic EL device of the present invention may comprise the organic electroluminescent compound of formula 1 or 2 in an organic layer and further include at least one compound selected from the group consisting of arylamine-based compounds and styrylarylamine-based compounds in the organic layer.

In the organic EL device of the present invention, the organic layer may further comprise at least one metal selected from the group consisting of metals of Group 1, metals of Group 2, transition metals of the 4$^{th}$ period, transition metals of the 5$^{th}$ period, lanthanides, and organic metals of d-transition elements of the Periodic Table, or at least one complex compound comprising the metal, in addition to the organic electroluminescent compound of formula 1 or 2.

In addition, the organic EL device of the present invention may emit white light by further comprising at least one light-emitting layer which comprises a blue electroluminescent compound, a red electroluminescent compound, or a green electroluminescent compound, besides the organic electroluminescent compound of the present invention; and may further include a yellow or orange light-emitting layer, if necessary.

Preferably, in the organic EL device of the present invention, at least one layer (hereinafter, "a surface layer") selected from a chalcogenide layer, a metal halide layer, and a metal oxide layer may be placed on an inner surface(s) of one or both electrode(s). Specifically, it is preferred that a chalcogenide (including oxides) layer of silicon or aluminum is placed on an anode surface of a light-emitting medium layer, and a metal halide layer or metal oxide layer is placed on a cathode surface of a light-emitting medium layer. The surface layer provides operating stability for the organic EL device. Preferably, the chalcogenide includes $SiO_X(1 \leq X \leq 2)$, $AlO_X(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or their combinations can be used between an anode and a light-emitting layer. The hole injection layer may be multi-layers in order to lower a hole injection barrier (or hole injection voltage) from an anode to a hole transport layer or electron blocking layer, wherein each of the multi-layers simultaneously may use two compounds. The hole transport layer or the electron blocking layer may also be multi-layers.

An electron buffer layer, a hole blocking layer, an electron transport layer, an electron injection layer, or their combinations can be used between a light-emitting layer and a cathode. The electron buffer layer may be multi-layers in order to control the injection of an electron and improve interface properties between the light-emitting layer and the electron injection layer, wherein each of the multi-layers simultaneously may use two compounds. The hole blocking layer or the electron transport layer may also be multi-layers, wherein each of the multi-layers may use a multi-component of compounds.

Preferably, in the organic EL device of the present invention, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to a light-emitting medium. Further, the hole transport compound is oxidized to a cation, and thus it becomes easier to inject and transport holes from the mixed region to a light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic EL device having two or more light-emitting layers and emitting white light.

In order to form each layer constituting the organic EL device of the present invention, dry film-forming methods, such as vacuum deposition, sputtering, plasma, ion plating methods, etc., or wet film-forming methods, such as spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents and the solvents do not cause any problems in forming a layer.

Hereinafter, the organic electroluminescent compound of the present invention, the preparation method of the compound, and the luminous properties of the device comprising the compound will be explained in detail with reference to the following examples:

Example 1

Preparation of Compound A-333

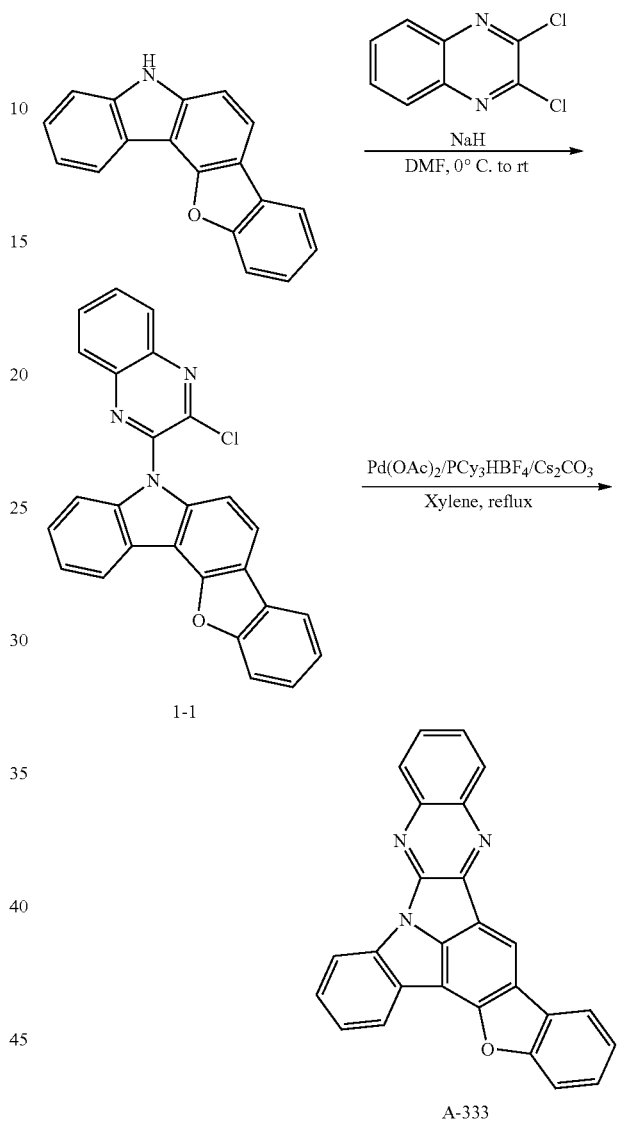

A-333

1) Preparation of Compound 1-1

5H-Benzofuro[3,2-c]carbazole (20.0 g, 77.52 mmol) was dissolved in N,N-dimethylformamide (DMF) (390.0 mL) in a flask, and NaH (60% in a mineral oil) (4.7 g, 116.28 mmol) was then slowly added dropwise to the mixture at 0° C. After stirring the mixture for 30 min, 2,3-dichloroquinoxaline (18.5 g, 93.03 mmol) was slowly added dropwise to the mixture. The mixture was stirred at room temperature for 3 hrs, and methanol and distilled water were added thereto. The obtained solid was filtered under reduced pressure and separated through column chromatography to produce compound 1-1 (20.0 g, Yield: 62%).

2) Preparation of Compound A-333

O-xylene (180.0 mL) was added to compound 1-1 (15.0 g, 35.73 mmol), palladium(II) acetate $(Pd(OAc)_2)$ (1.2 g, 5.36 mmol), tricyclohexylphosphine tetrafluoroborate (PCy$_3$HBF$_4$) (2.0 g, 5.36 mmol), and Cs$_2$CO$_3$ (35.0 g, 107.19 mmol), and the mixture was stirred under reflux at 180° C. for 5 hrs. After completing the reaction, an organic layer was extracted with ethyl acetate and dried by removing the remaining moisture with MgSO$_4$. The product was separated through column chromatography to obtain compound A-333 (4.4 g, Yield: 32%).

|  | MW | UV | PL | M.P |
|---|---|---|---|---|
| A-333 | 383.40 | 404 nm | 497 nm | 306° C. |

Device Example 1

Production of an OLED Device by Using the Organic Electroluminescent Compound According to the Present Invention An OLED device comprising the organic electroluminescent compound of the present invention was produced as follows: A transparent electrode indium tin oxide (ITO) thin film (10 Ω/sq) on a glass substrate for an OLED device (GEOMATEC CO., LTD., Japan) was subjected to an ultrasonic washing with trichloroethylene, acetone, ethanol, and distilled water, sequentially, and was then stored in isopropanol. Next, the ITO substrate was mounted on a substrate holder of a vacuum vapor depositing apparatus. N$^4$,N$^{4'}$-Diphenyl-N$^4$,N$^{4'}$-bis(9-phenyl-9H-carbazole-3-yl)-[1,1'-biphenyl]-4,4'-diamine was introduced into a cell of the vacuum vapor depositing apparatus, and the pressure in the chamber of the apparatus was then controlled to 10$^{-6}$ torr. Thereafter, an electric current was applied to the cell to evaporate the introduced material, thereby forming a first hole injection layer having a thickness of 80 nm on the ITO substrate. Dipyrazino[2,3-f:2',3'-h]quinoxaline-2,3,6,7,10,11-hexacarbonitrile was then introduced into another cell of the vacuum vapor depositing apparatus, and an electric current was applied to the cell to evaporate the introduced material, thereby forming a second hole injection layer having a thickness of 5 nm on the first hole injection layer. N-([1,1'-Biphenyl]-4-yl)-9,9-dimethyl-N-(4-(9-phenyl-9H-carbazole-3-yl)phenyl)-9H-fluorene-2-amine was introduced into a cell of the vacuum vapor depositing apparatus. Afterward, an electric current was applied to the cell to evaporate the introduced material, thereby forming a first hole transport layer having a thickness of 10 nm on the second hole injection layer. N,N-di([1,1'-biphenyl]-4-yl)-4'-(9H-carbazole-9-yl)-[1,1'-biphenyl]-4-amine was introduced into another cell of the vacuum vapor depositing apparatus. Afterward, an electric current was applied to the cell to evaporate the introduced material, thereby forming a second hole transport layer having a thickness of 60 nm on the first hole transport layer. After forming the hole injection layer and the hole transport layer, a light-emitting layer was then deposited as follows. Compound A-333 as a host was introduced into a cell of the vacuum vapor depositing apparatus and compound D-96 was introduced into another cell. The two materials were evaporated at a different rate, and the dopant was deposited in a doping amount of 3 wt %, based on the total weight of the host and dopant, to form a light-emitting layer having a thickness of 40 nm on the hole transport layer. Next, 2,4-bis(9,9-dimethyl-9H-fluorene-2-yl)-6-(naphthalene-2-yl)-1,3,5-triazine and lithium quinolate were evaporated at the rate of 1:1 on another two cells to form an electron transport layer having a thickness of 30 nm on the light-emitting layer. After depositing lithium quinolate having a thickness of 2 nm as an electron injection layer on the electron transport layer, an Al cathode having a thickness of 80 nm was then deposited by another vacuum vapor deposition apparatus on the electron injection layer. Thus, an OLED device was produced.

The produced OLED device showed red emission having an efficiency of 27.3 cd/A at 3.7 V, CIE color coordinate (X,Y) at 1000 cd/m$^2$ of (0.670, 0.330), and the time taken for the light-emission to be reduced from 100% to 90% at a luminance of 5,000 nit of 17 hrs or more.

Comparative Example 1

Production of an OLED Device by Using Conventional Organic Electroluminescent Compound An OLED device was produced in the same manner as in Device Example 1, except that compound B-1 below was used as a host in a light-emitting material.

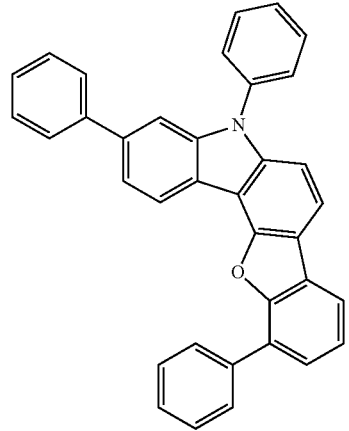

B-1

The produced OLED device showed red emission having an efficiency of 7.7 cd/A at 9.6 V, CIE color coordinate (X,Y) at 1000 cd/m$^2$ of (0.657, 0.336), and the time taken for the light-emission to be reduced from 100% to 90% at a luminance of 5,000 nit of 1 hr or more.

The organic electroluminescent compounds according to the present invention have high luminous efficiency, in particular current efficiency and power efficiency compared with conventional compounds, and give colors having high purity.

The invention claimed is:

1. An organic electroluminescent compound represented by the following formula 1 or formula 2:

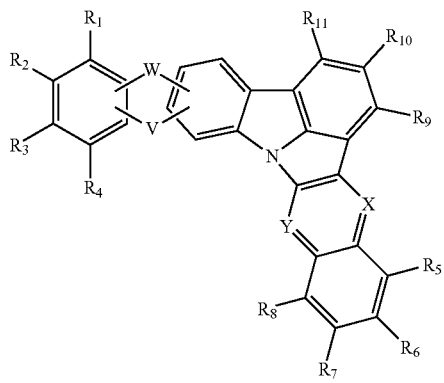

(1)

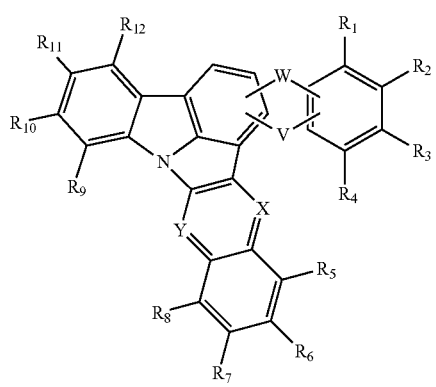

(2)

wherein
X and Y each independently represent —CR$_{13}$— or —N—, with the proviso that X and Y do not simultaneously represent —CR$_{13}$—;
W and V each independently represent a single bond, O or S; and
R$_1$ to R$_{13}$ each independently represent hydrogen, deuterium, a halogen, a cyano group, a substituted or unsubstituted (C1-C30)alkyl group, a substituted or unsubstituted (C6-C30)aryl group, a substituted or unsubstituted 3- to 30-membered heteroaryl group, a substituted or unsubstituted (C3-C30)cycloalkyl group, a substituted or unsubstituted (C1-C30)alkoxy group, a substituted or unsubstituted tri(C1-C30)alkylsilyl group, a substituted or unsubstituted di(C1-C30)alkyl (C6-C30)arylsilyl group, a substituted or unsubstituted (C1-C30)alkyldi(C6-C30)arylsilyl group, a substituted or unsubstituted tri(C6-C30)arylsilyl group, a substituted or unsubstituted mono- or di(C1-C30)alkylamino group, a substituted or unsubstituted mono- or di(C6-C30)arylamino group, or a substituted or unsubstituted (C1-C30)alkyl(C6-C30)arylamino group; or are linked to an adjacent substituent(s) to form a substituted or unsubstituted mono- or polycyclic (C3-C30) alicyclic or aromatic ring whose carbon atom(s) may be replaced with at least one hetero atom selected from nitrogen, oxygen, and sulfur.

2. The organic electroluminescent compound according to claim 1, wherein R$_1$ to R$_{13}$ in formulae 1 and 2 each independently represent hydrogen, a substituted or unsubstituted (C6-C20)aryl group, or a substituted or unsubstituted 5- to 20-membered heteroaryl group.

3. The organic electroluminescent compound according to claim 1, wherein R$_1$ to R$_{13}$ in formulae 1 and 2 each independently represent hydrogen, or a substituted or unsubstituted (C6-C12)aryl group.

4. The organic electroluminescent compound according to claim 1, wherein the substituents of the substituted alkyl group, the substituted cycloalkyl group, the substituted aryl group, the substituted heteroaryl group, the substituted alkoxy group, the substituted alkylsilyl group, the substituted arylsilyl group, the substituted alkylamino group, the substituted arylamino group, or the substituted mono- or polycyclic (C3-C30) alicyclic or aromatic ring in formulae 1 and 2 are each independently at least one selected from the group consisting of deuterium; a halogen; a cyano group; a carboxyl group; a nitro group; a hydroxyl group; a (C1-C30)alkyl group; a halo(C1-C30)alkyl group; a (C2-C30)alkenyl group; a (C2-C30)alkynyl group; a (C1-C30)alkoxy group; a (C1-C30)alkylthio group; a (C3-C30)cycloalkyl group; a (C3-C30)cycloalkenyl group; a 3- to 7-membered heterocycloalkyl group; a (C6-C30)aryloxy group; a (C6-C30)arylthio group; a 3- to 30-membered heteroaryl group which is unsubstituted or substituted with a (C6-C30)aryl group; a (C6-C30)aryl group which is unsubstituted or substituted with a 3- to 30-membered heteroaryl group; a tri(C1-C30)alkylsilyl group; a tri(C6-C30)arylsilyl group; a di(C1-C30)alkyl(C6-C30)arylsilyl group; a (C1-C30)alkyldi(C6-C30)arylsilyl group; an amino group; a mono- or di(C1-C30)alkylamino group; a mono- or di(C6-C30)arylamino group; a (C1-C30)alkyl(C6-C30)arylamino group; a (C1-C30)alkylcarbonyl group; a (C1-C30)alkoxycarbonyl group; a (C6-C30)arylcarbonyl group; a di(C6-C30)arylboronyl group; a di(C1-C30)alkylboronyl group; a (C1-C30)alkyl(C6-C30)arylboronyl group; a (C6-C30)aryl(C1-C30)alkyl group; and a (C1-C30)alkyl(C6-C30)aryl group.

5. The organic electroluminescent compound according to claim 1, wherein the compound represented by formula 1 or 2 is selected from the group consisting of the following compounds:

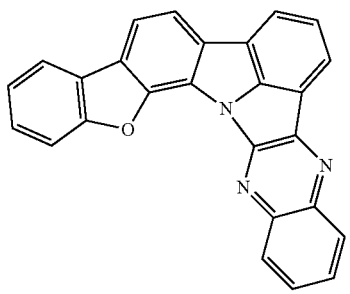

A-1

A-2
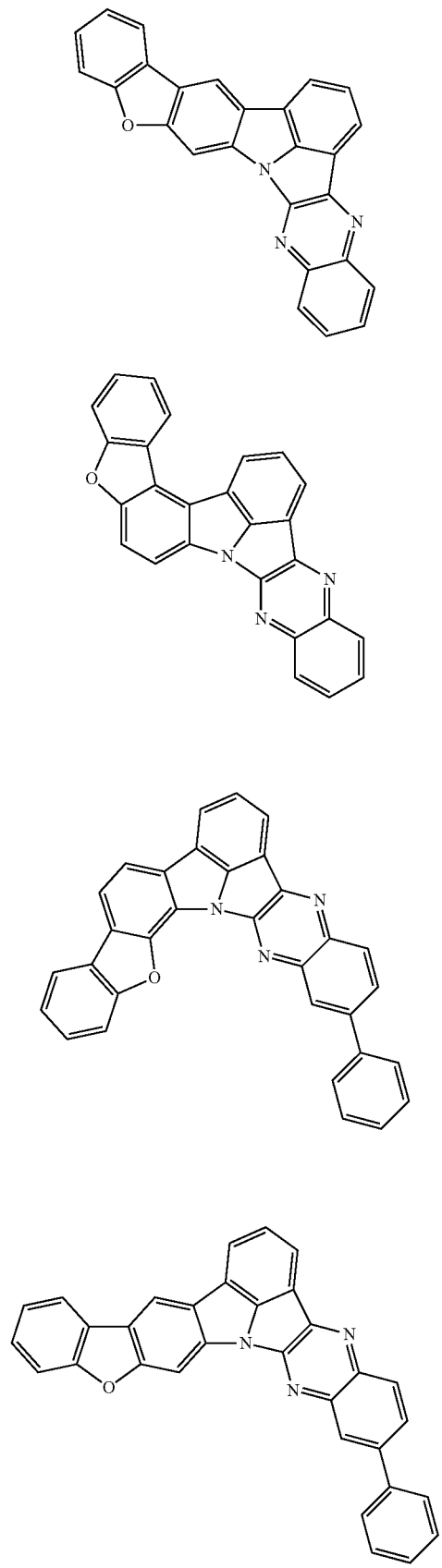
A-3
A-4
A-5
A-6
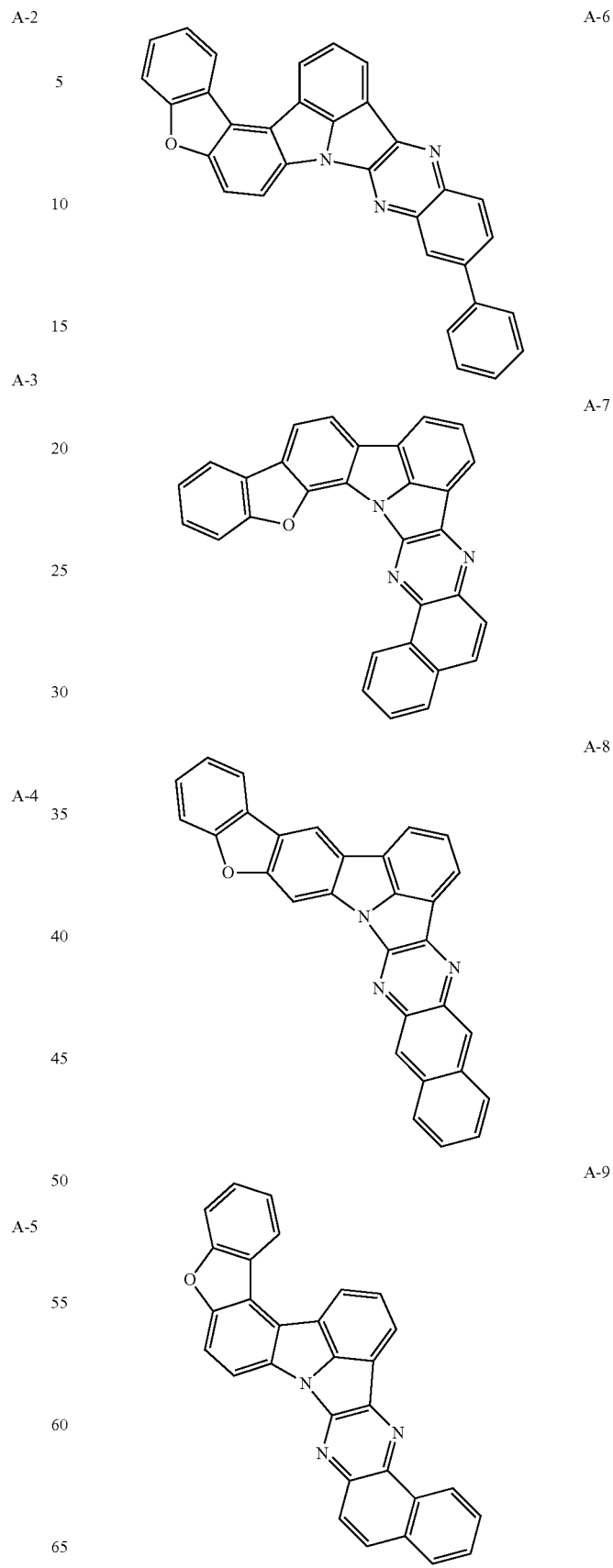
A-7
A-8
A-9

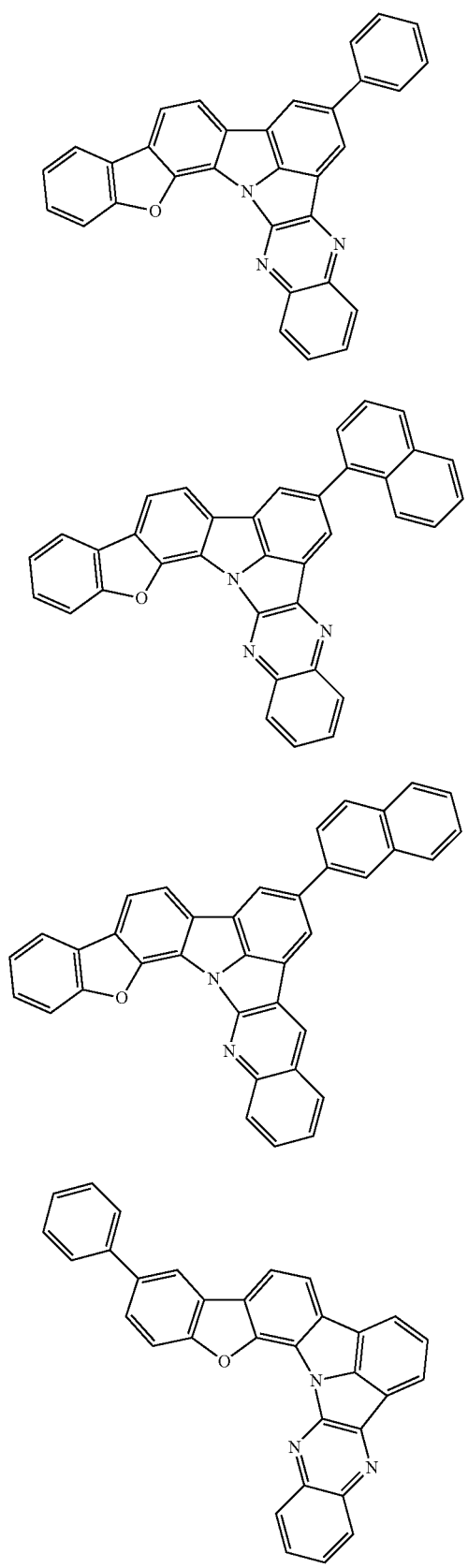
A-10
A-11
A-12
A-13
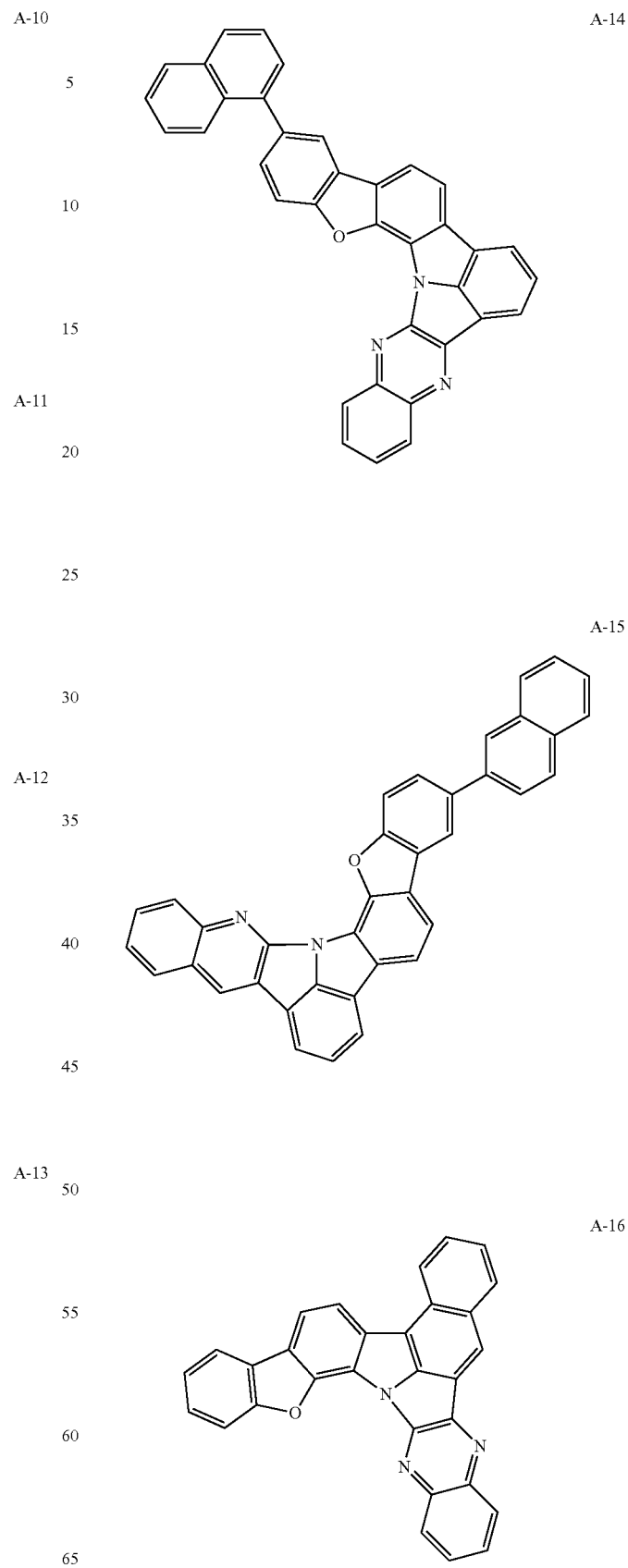
A-14
A-15
A-16

-continued
A-17
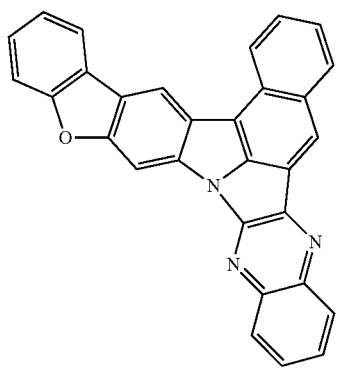
A-18
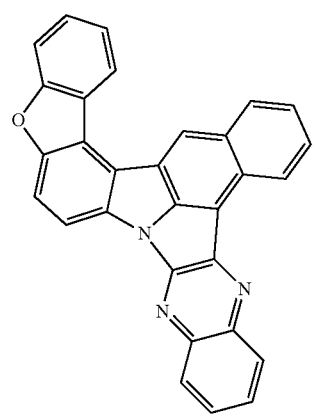
A-19
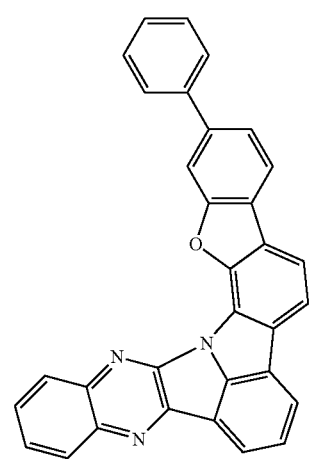
-continued
A-20
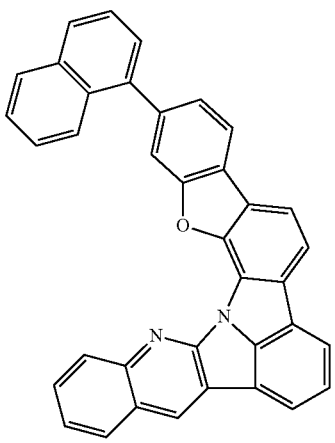
A-21
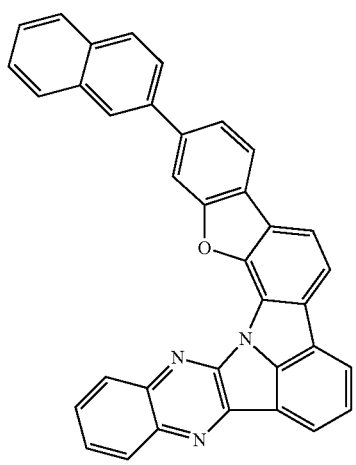
A-22
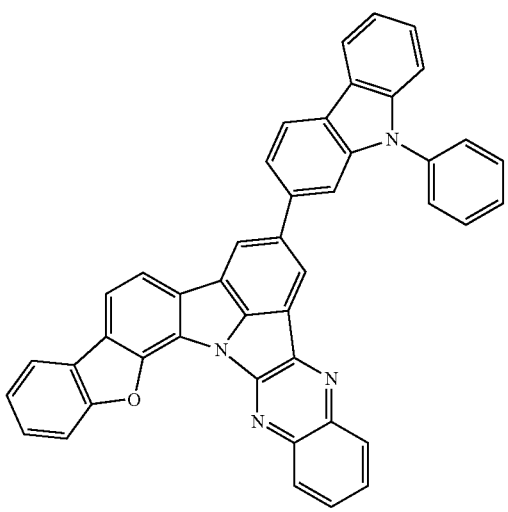

-continued
A-23
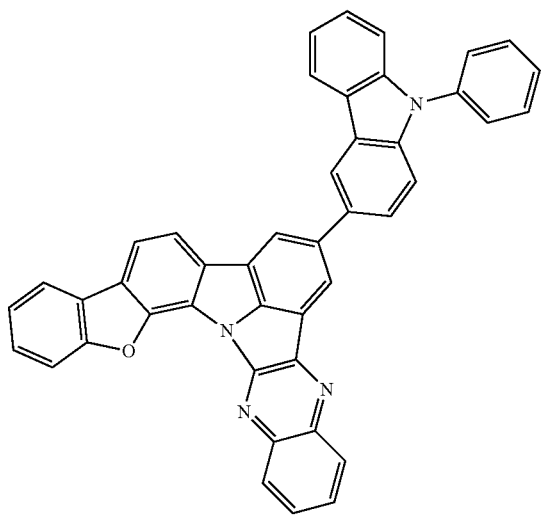
A-24
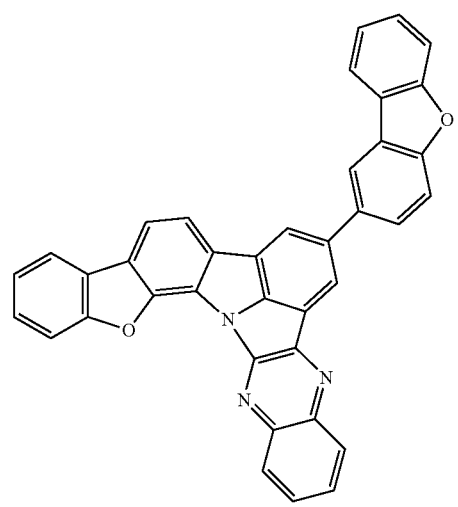
A-25
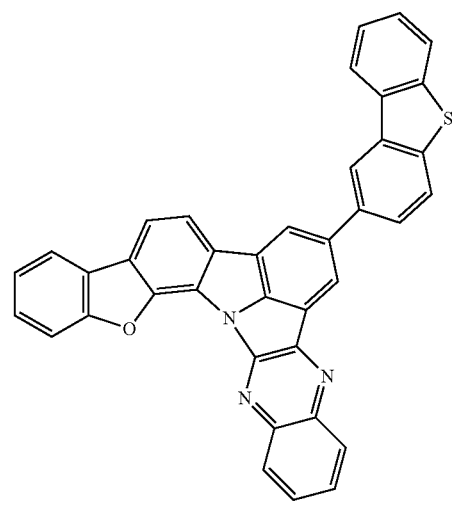
-continued
A-26
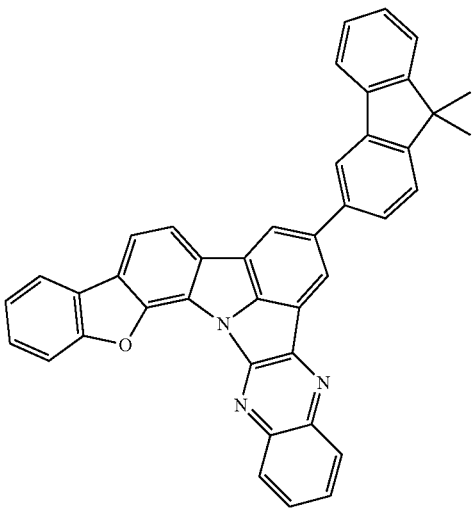
A-27
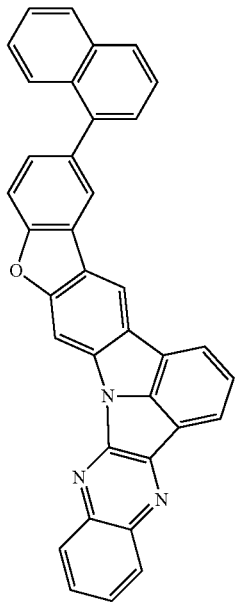
A-28
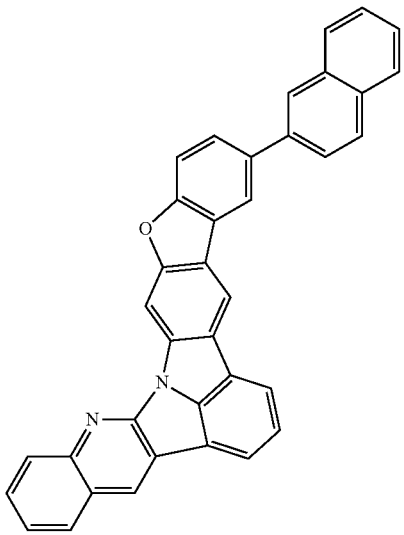

-continued
A-29
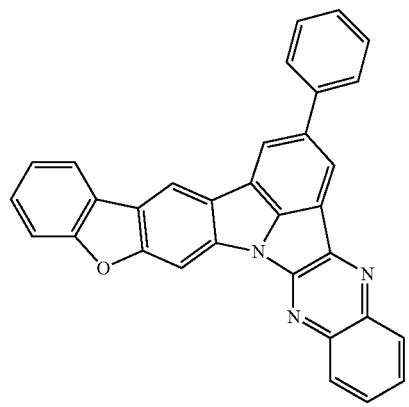
A-30
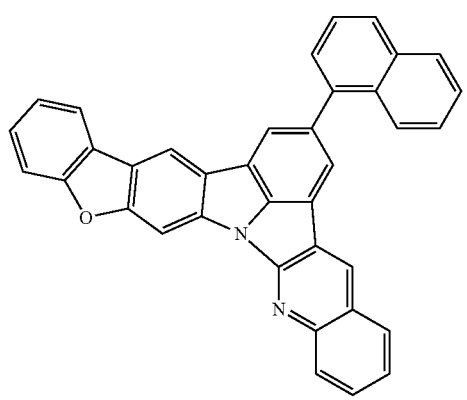
A-31
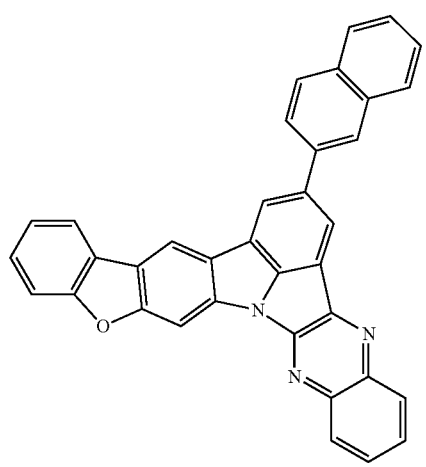
-continued
A-32
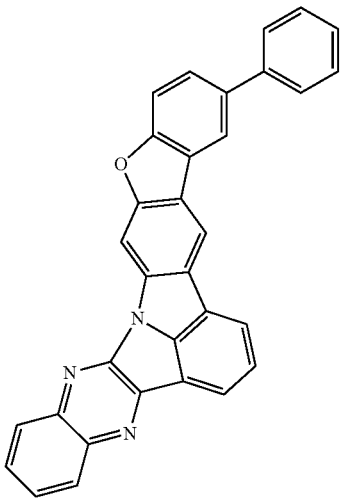
A-33
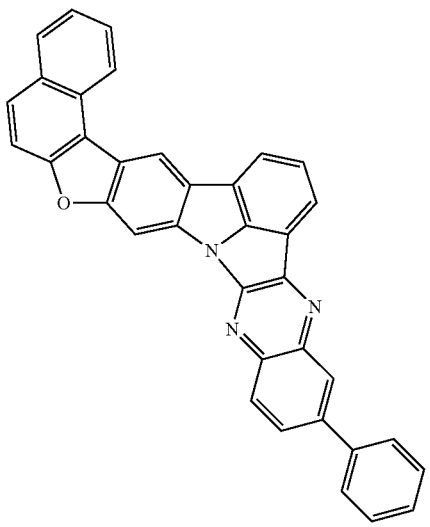
A-34
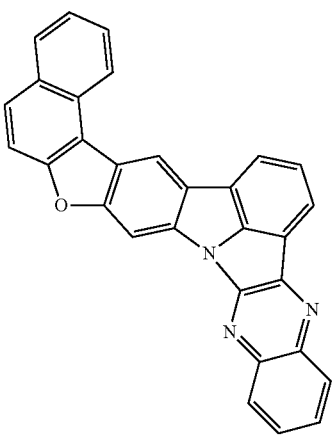

A-35
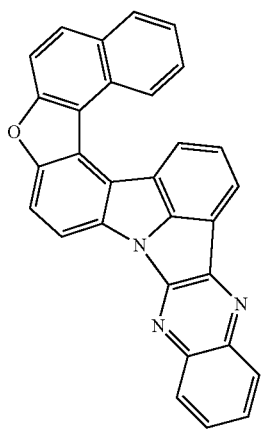
A-38
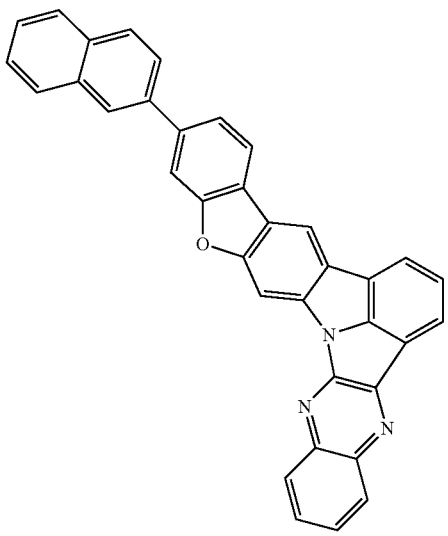
A-36
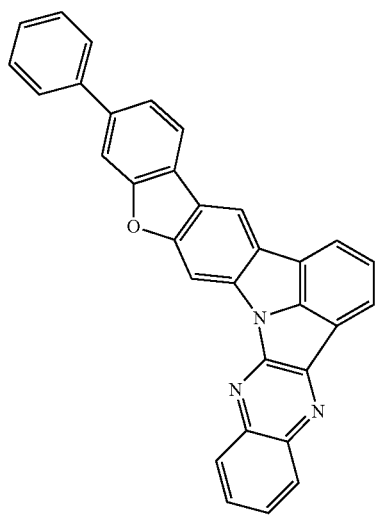
A-39
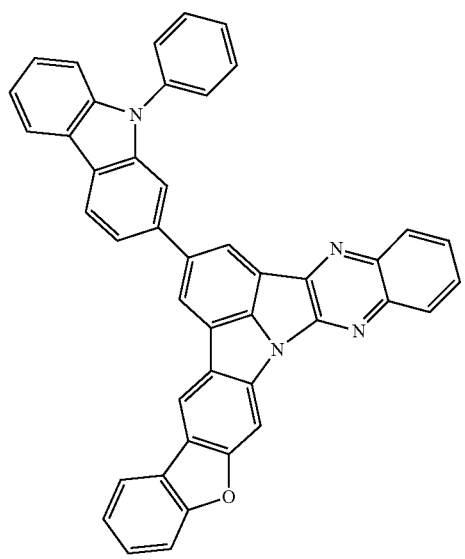
A-37
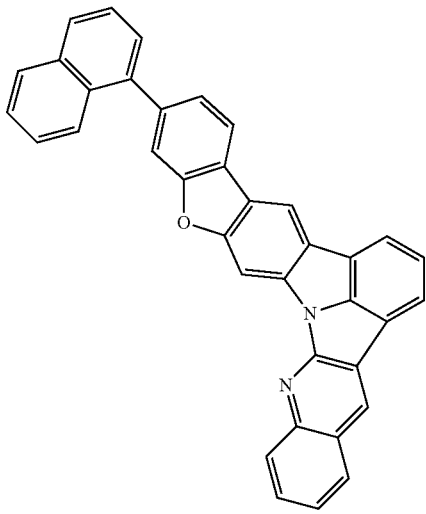
A-40
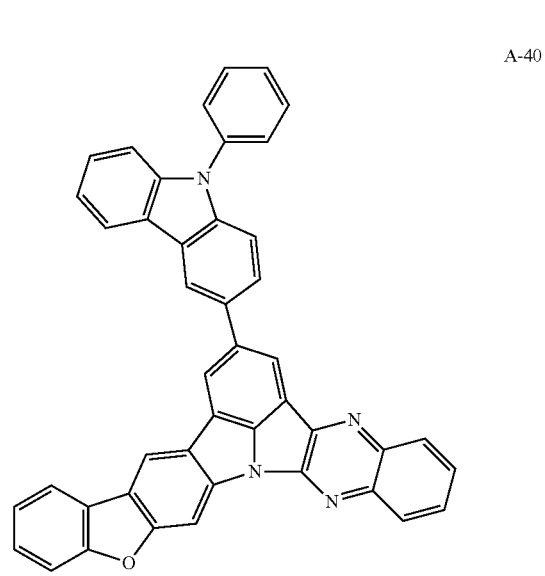

A-41
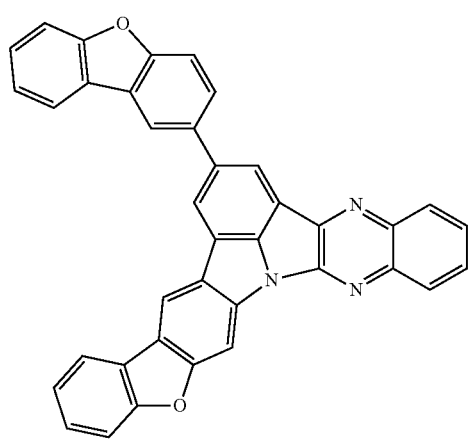
A-44
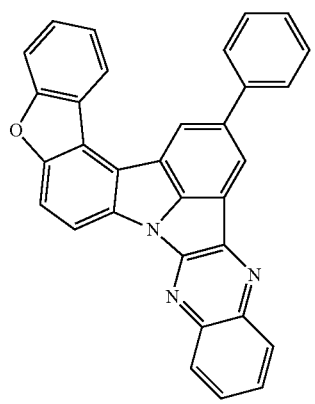
A-42
A-45
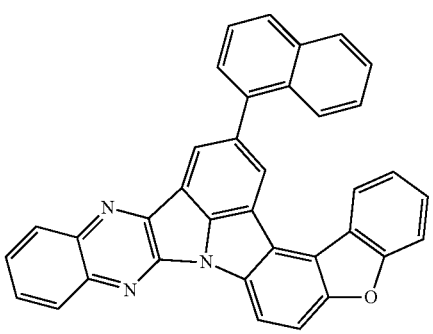
A-46
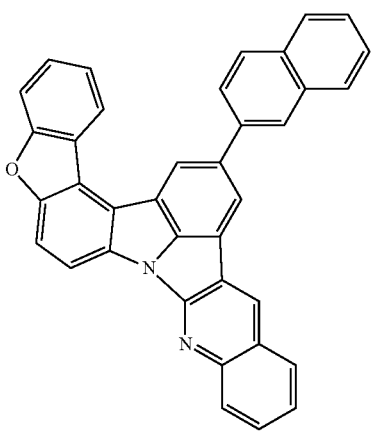
A-43
A-47
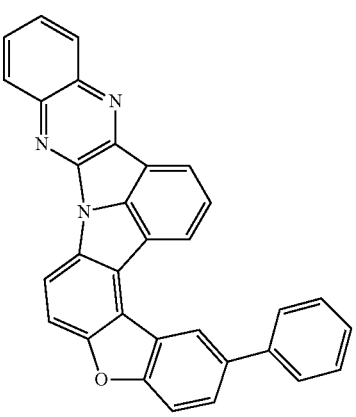

A-48
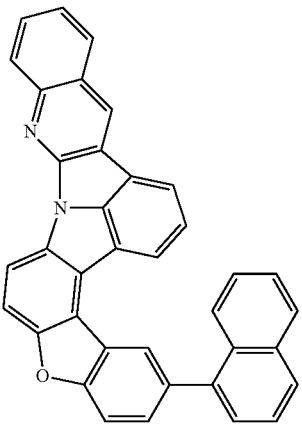
A-49
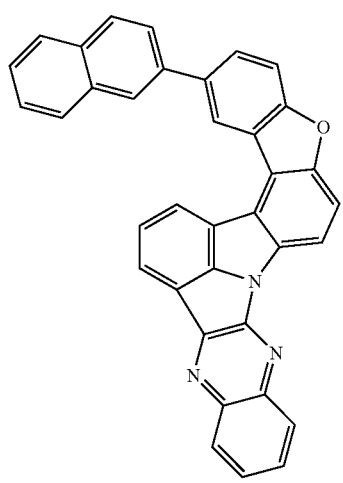
A-50
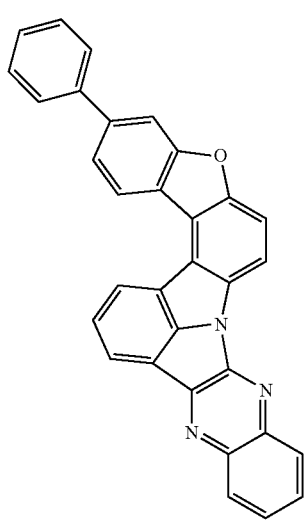
A-51
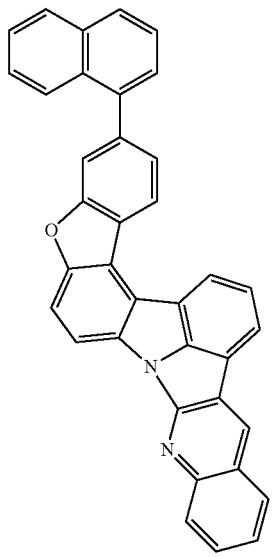
A-52
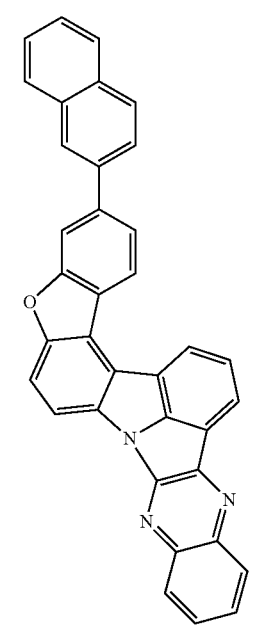
A-53
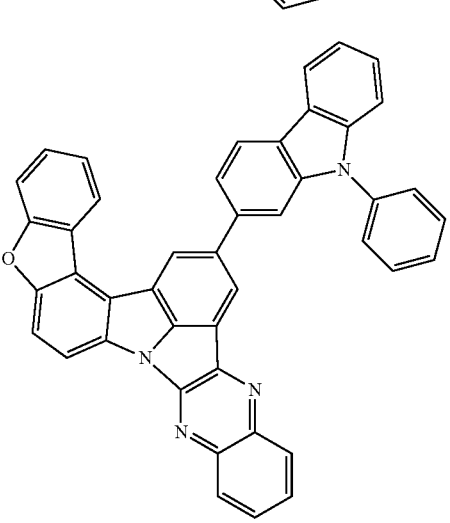

A-54
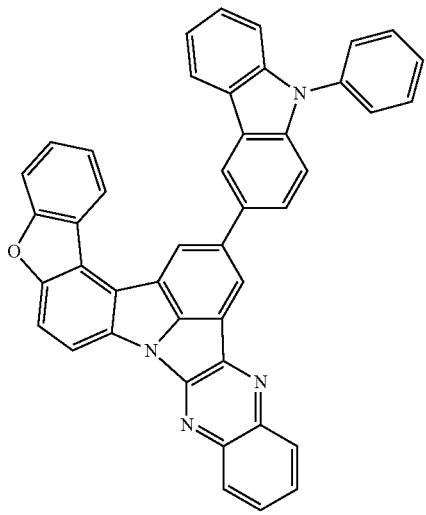
A-55
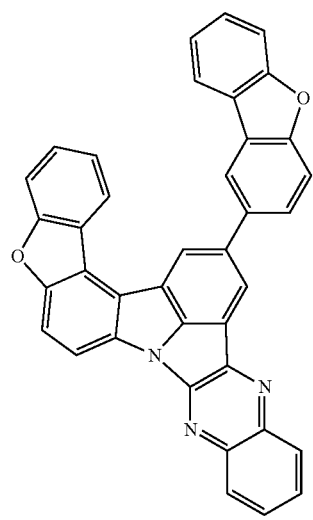
A-56
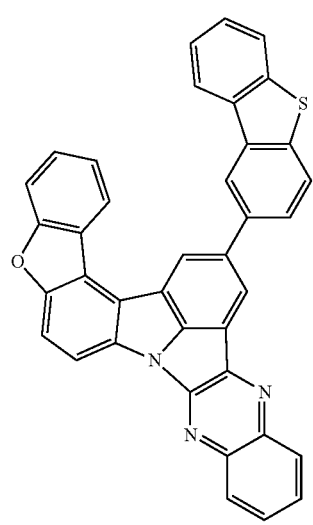
A-57
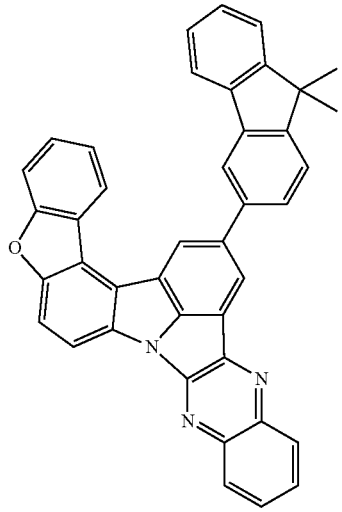
A-58
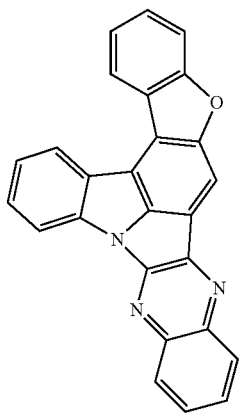
A-59
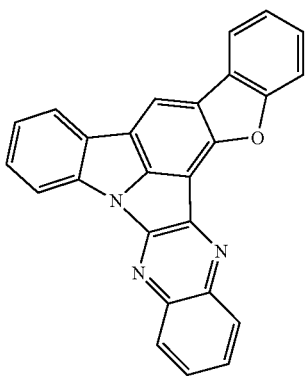

A-60
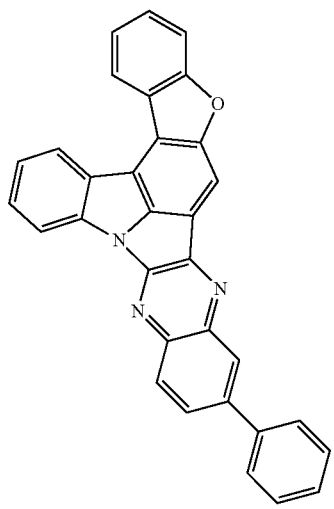
A-61
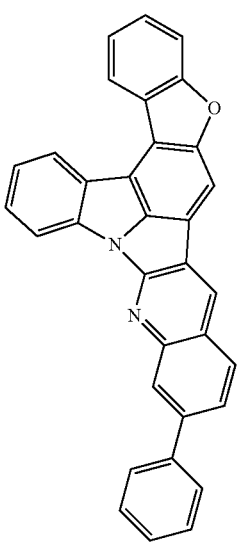
A-62
A-63
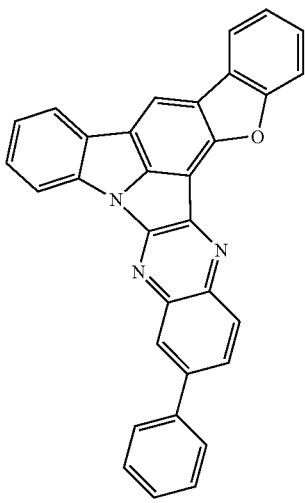
A-64
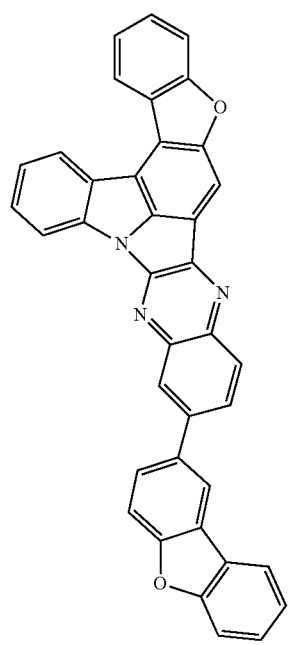

A-65
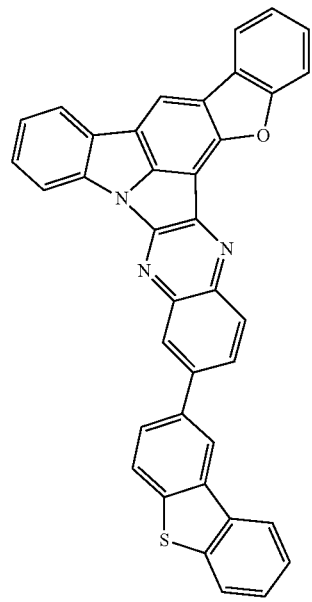
A-66
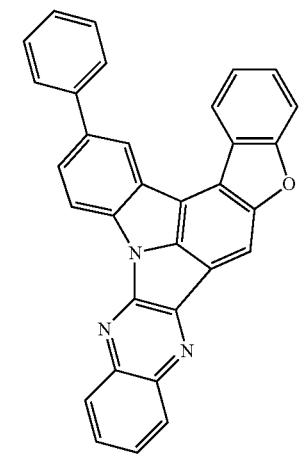
A-67
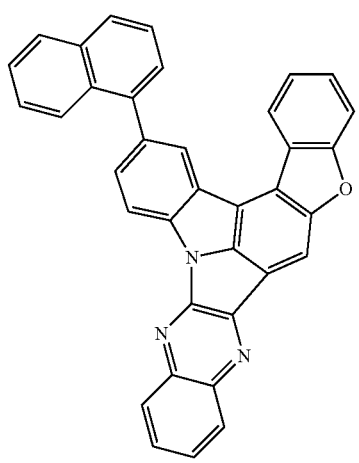
A-68
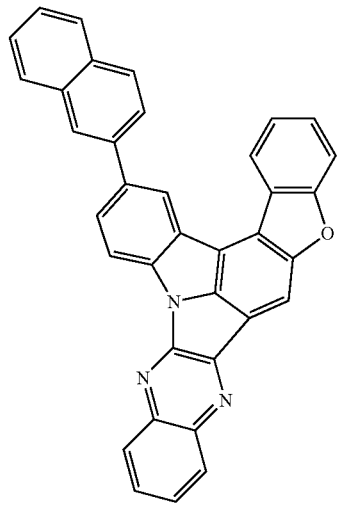
A-69
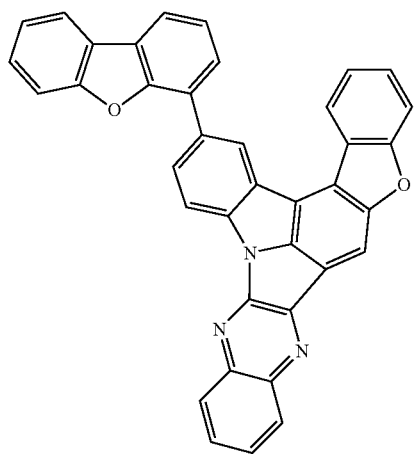
A-70
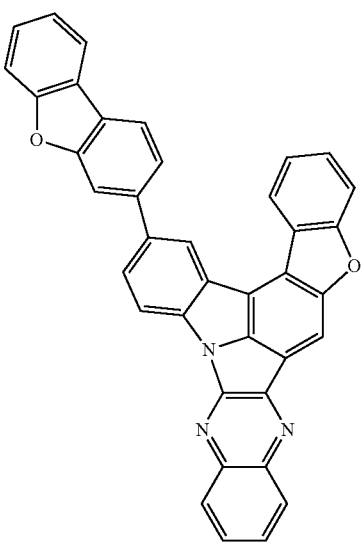

A-71
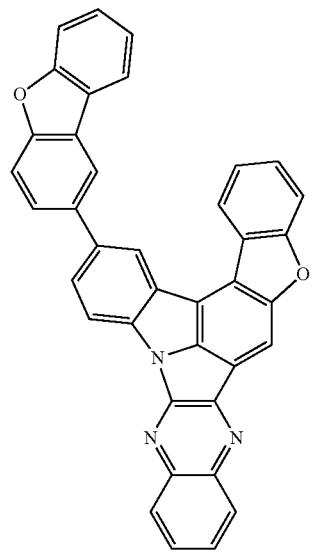
A-72
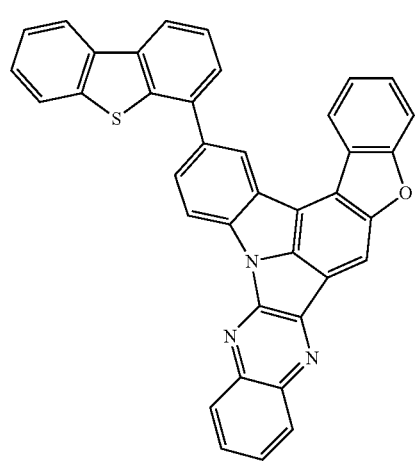
A-73
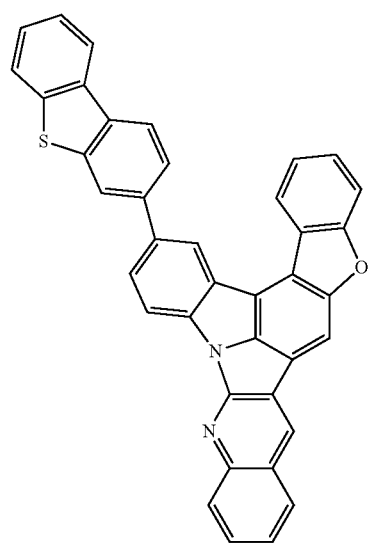
A-74
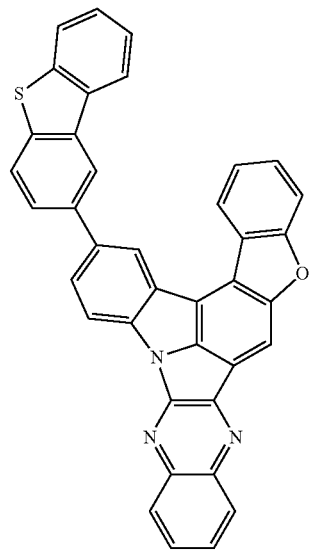
A-75
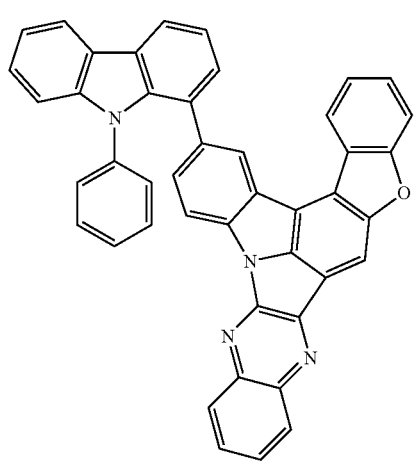
A-76
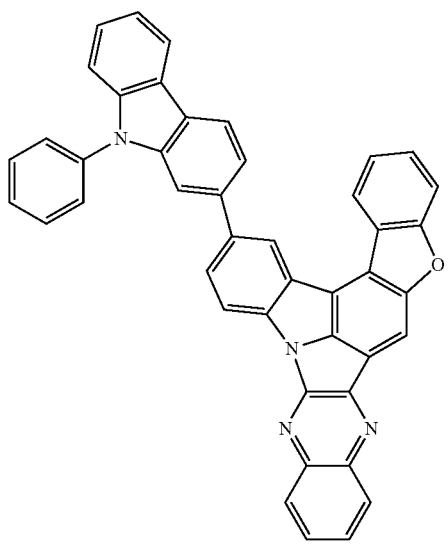

-continued
A-77
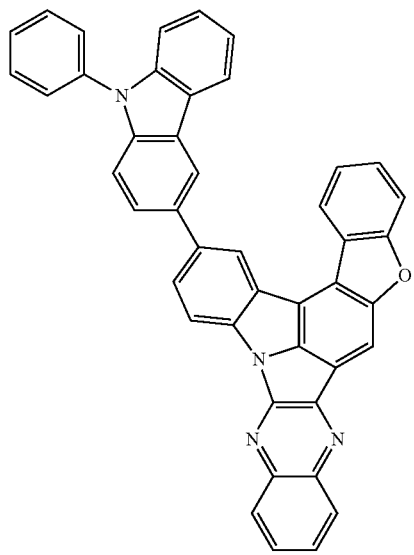
A-78
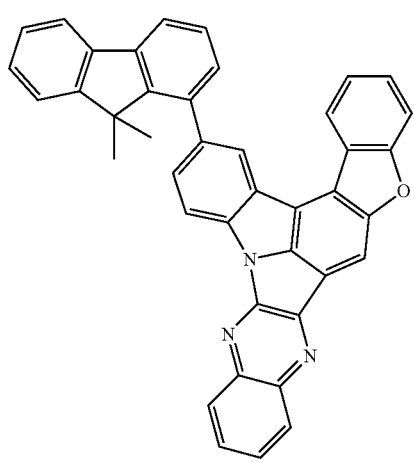
A-79
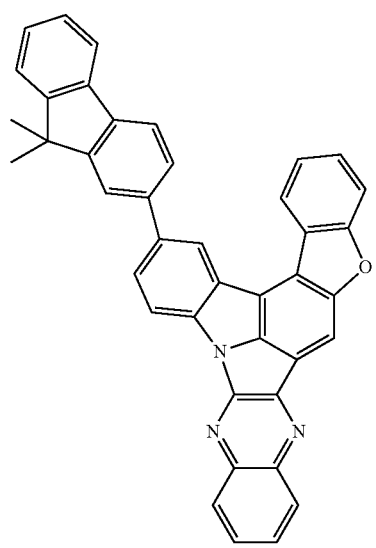
-continued
A-80
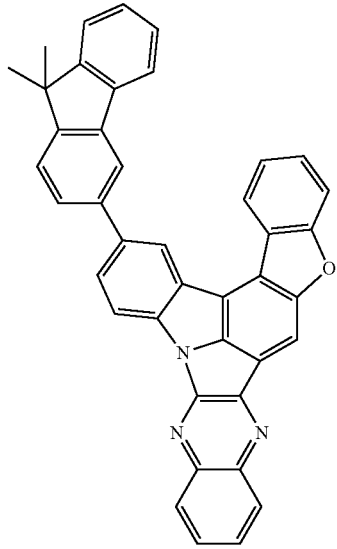
A-81
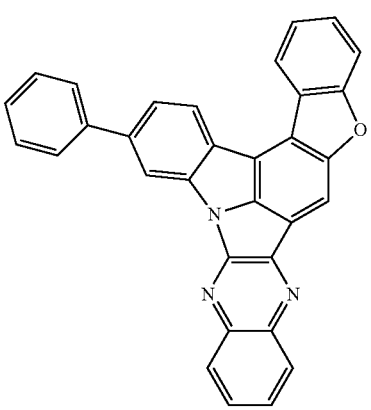
A-82
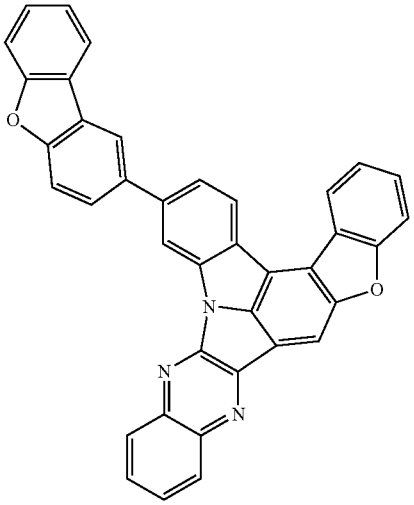

A-83
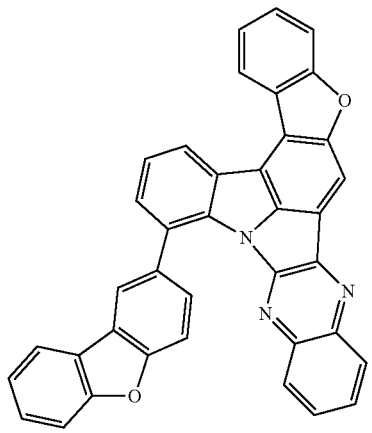
A-86
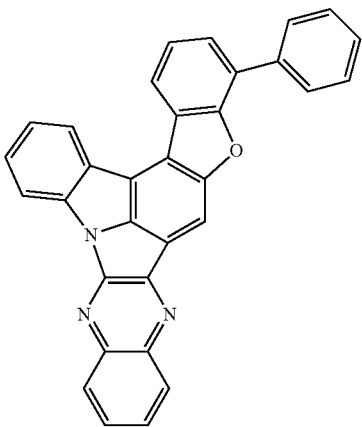
A-84
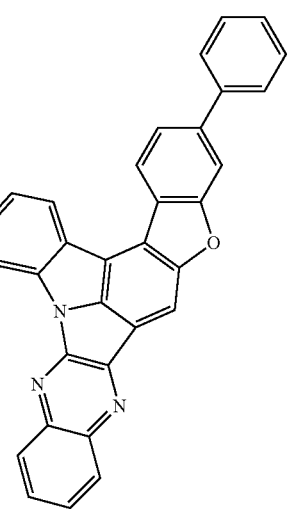
A-87
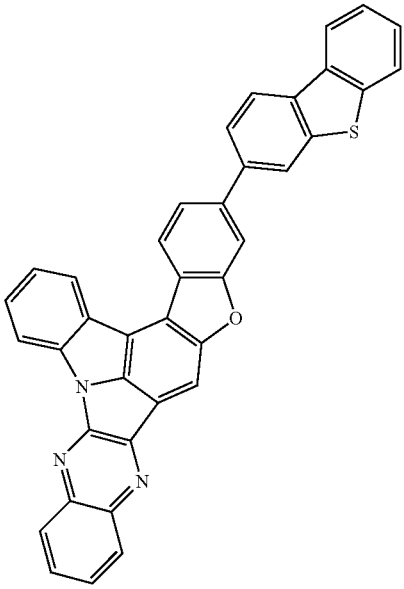
A-85
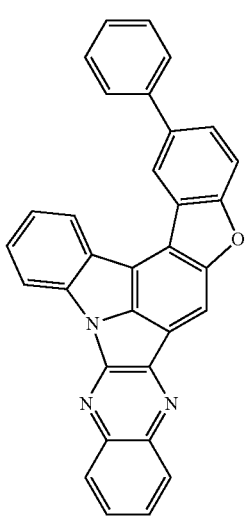
A-88
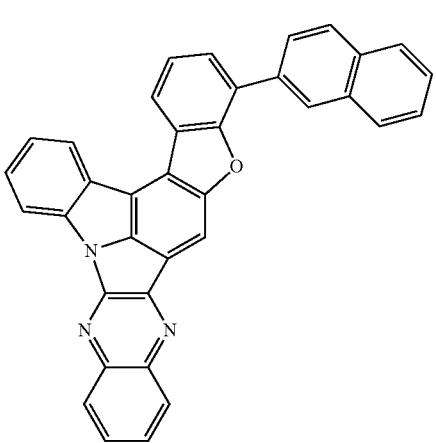

-continued
A-89
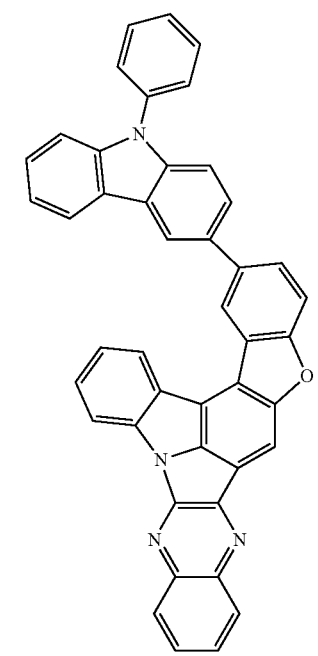
A-90
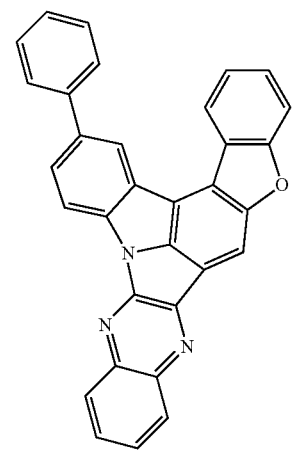
A-91
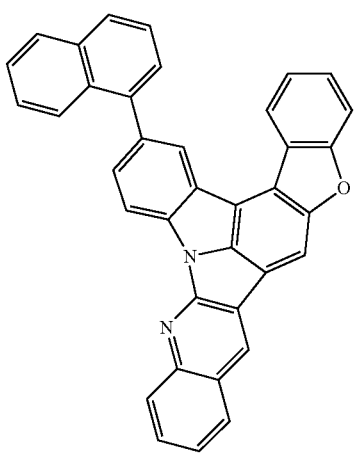
-continued
A-92
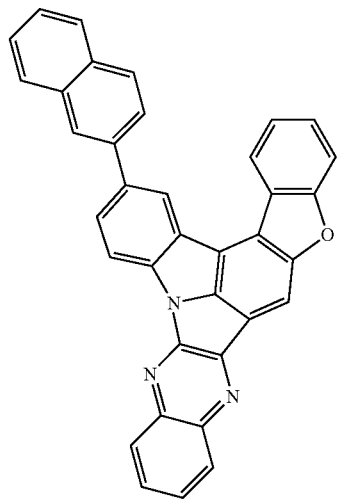
A-93
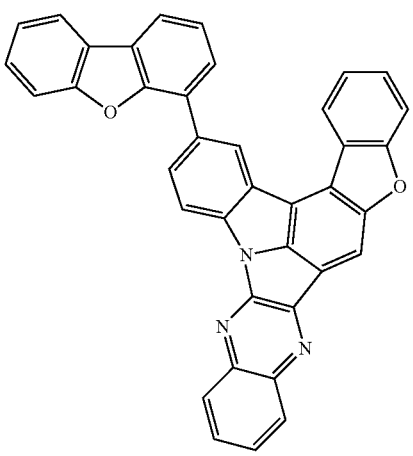
A-94
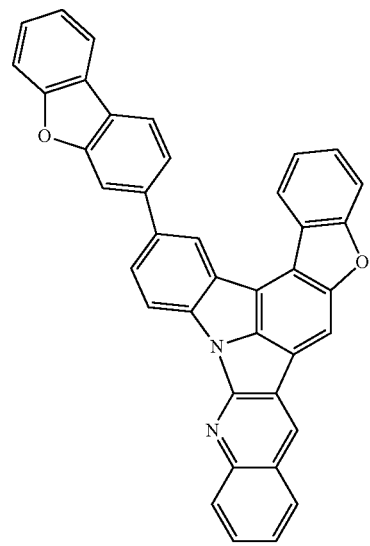

A-95
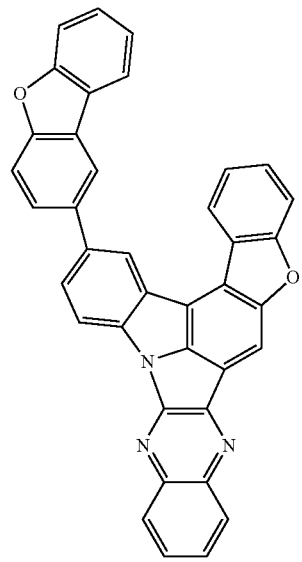
A-96
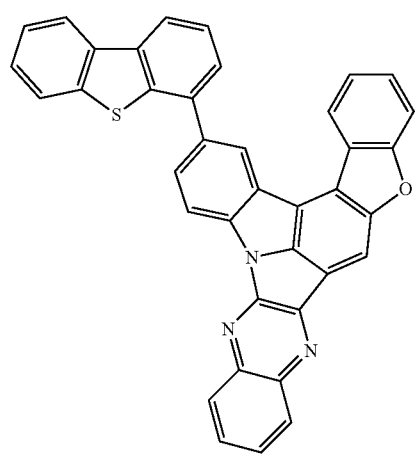
A-97
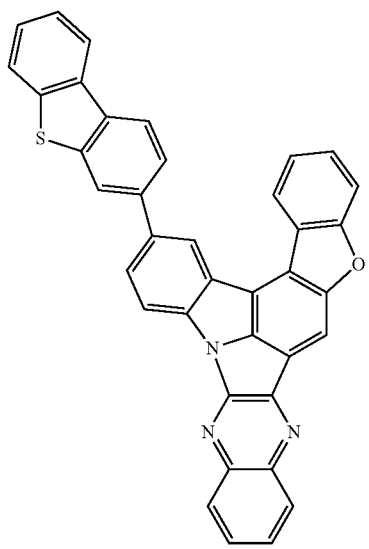
A-98
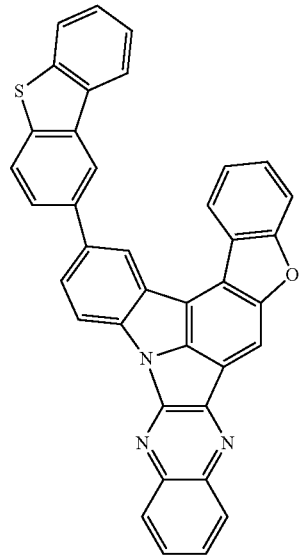
A-99
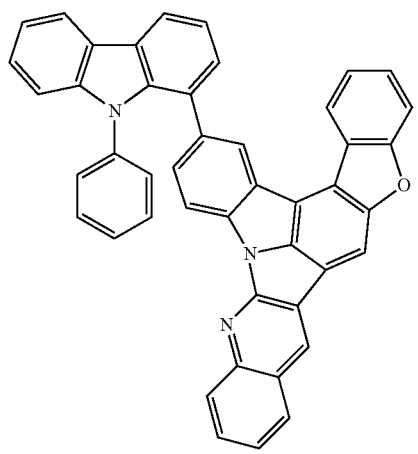
A-100
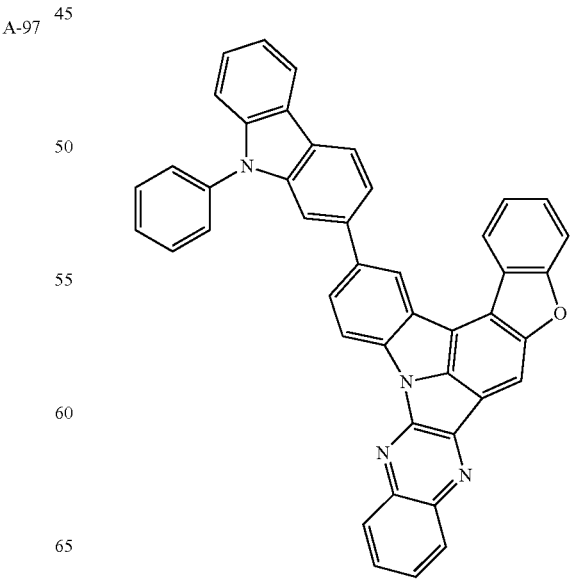

-continued
A-101
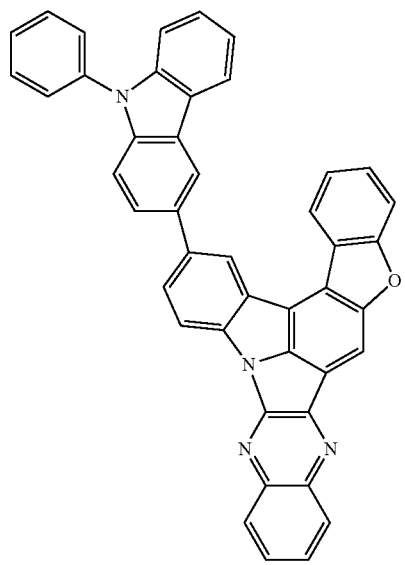
A-102
A-103
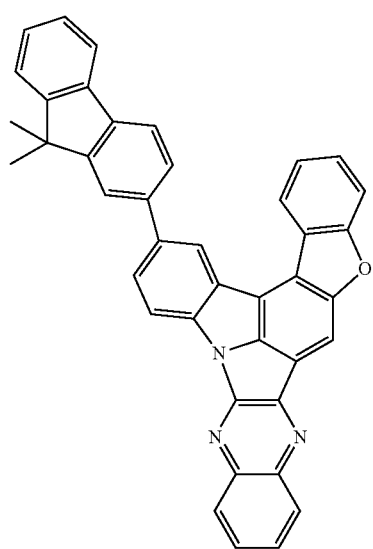
-continued
A-104
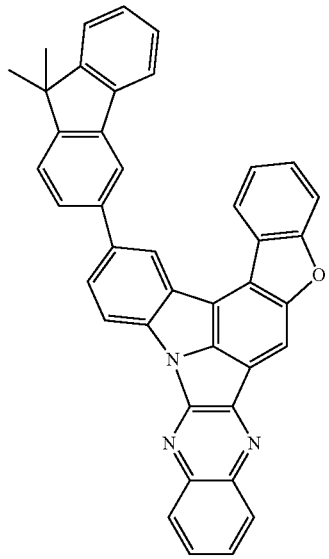
A-105
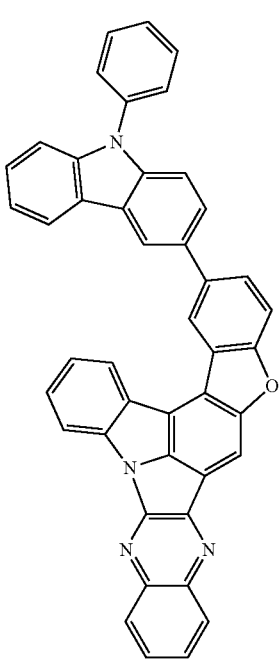
A-106
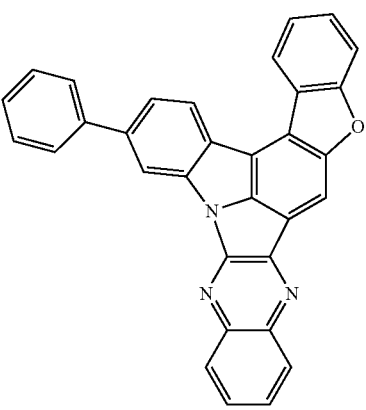

A-107
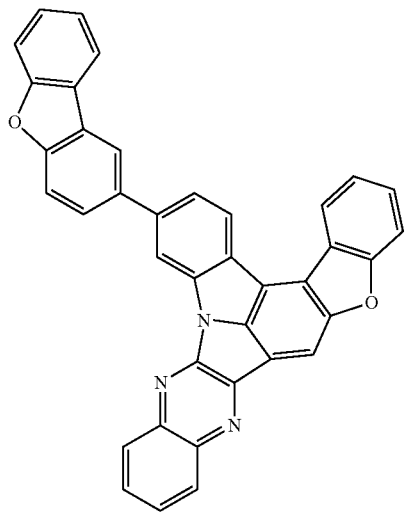
A-108
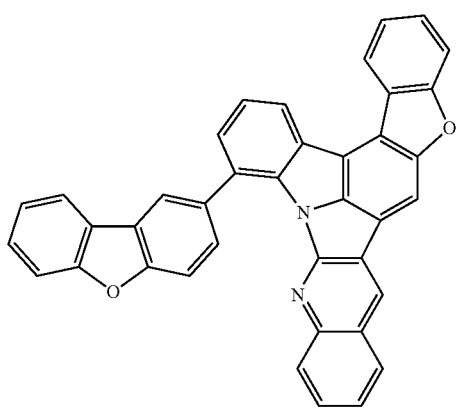
A-109
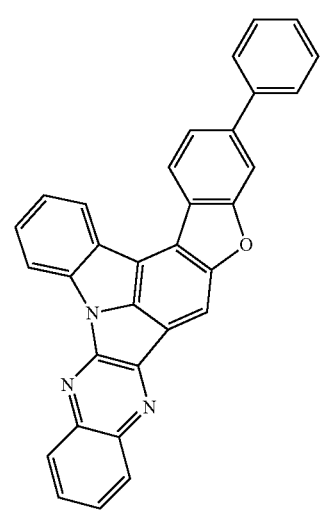
A-110
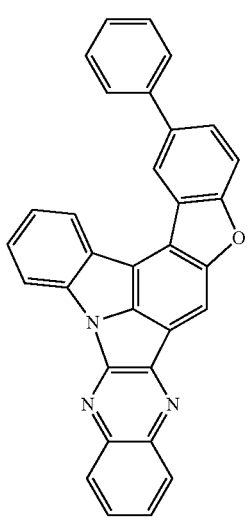
A-111
A-112
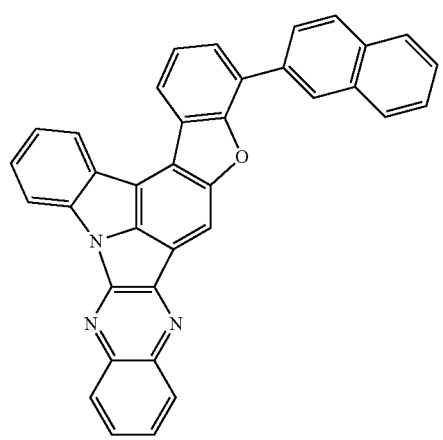

A-113
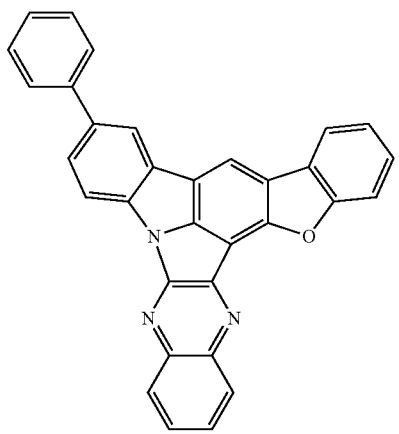
A-116
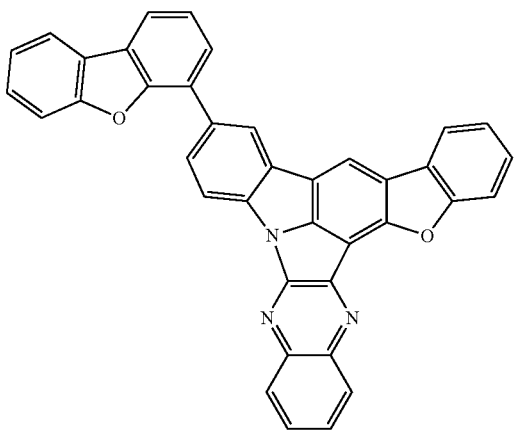
A-114
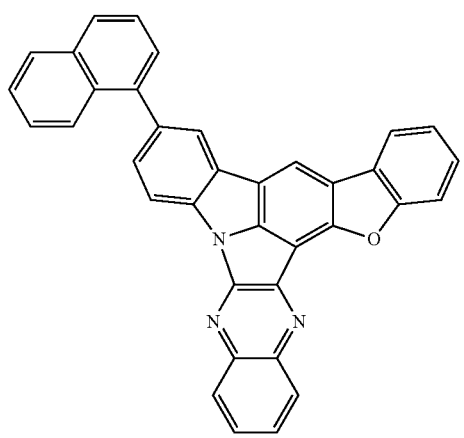
A-117
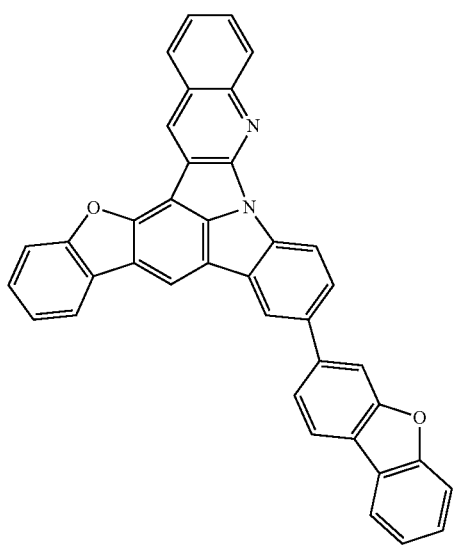
A-115
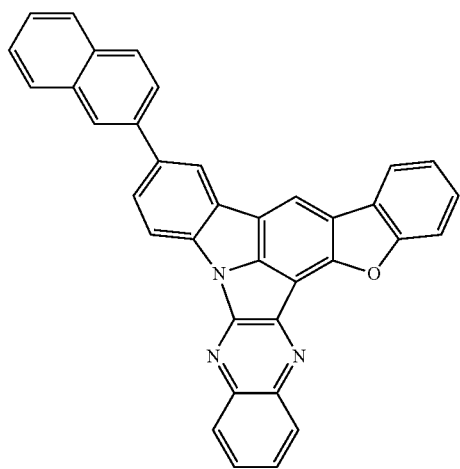
A-118
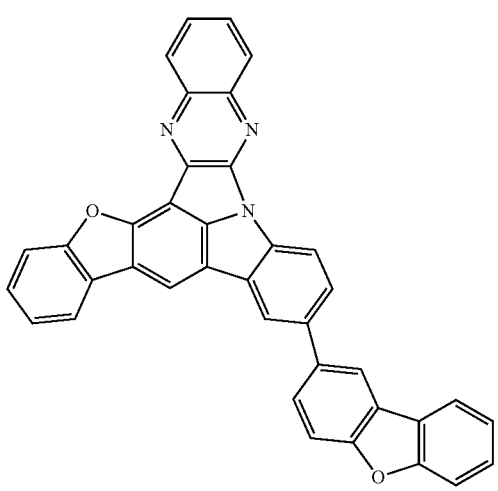

-continued
A-119
A-120
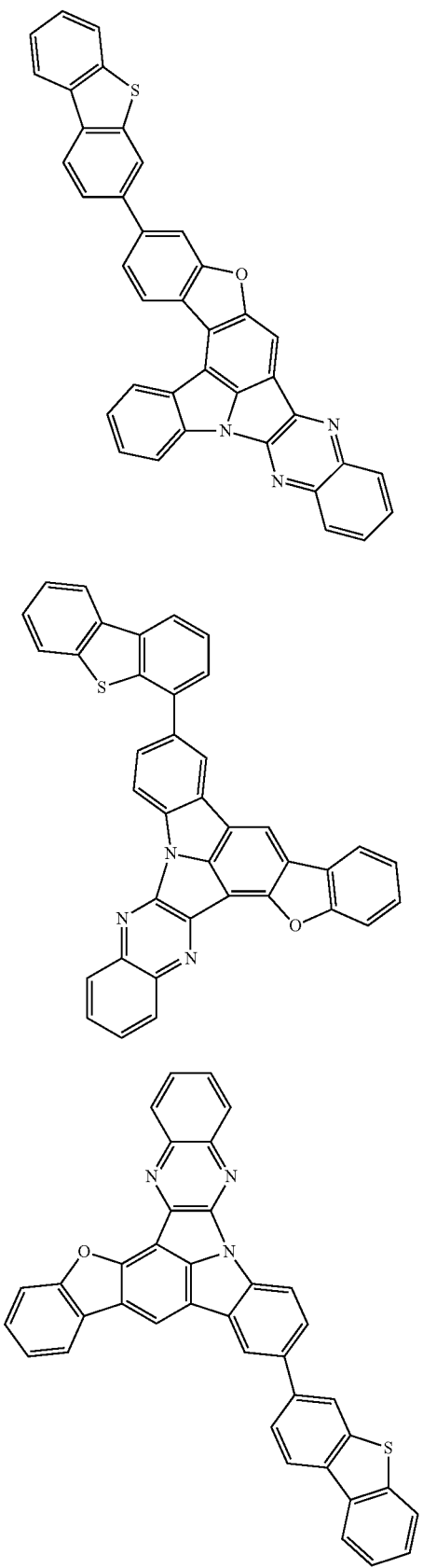
A-122
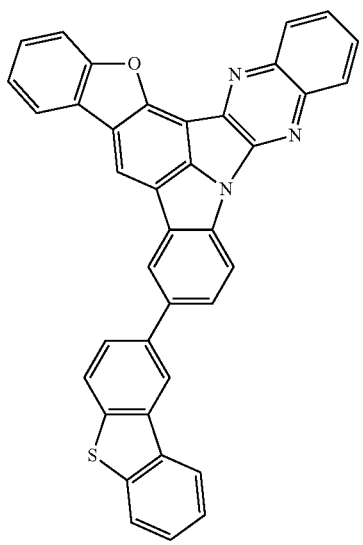
A-121
A-123
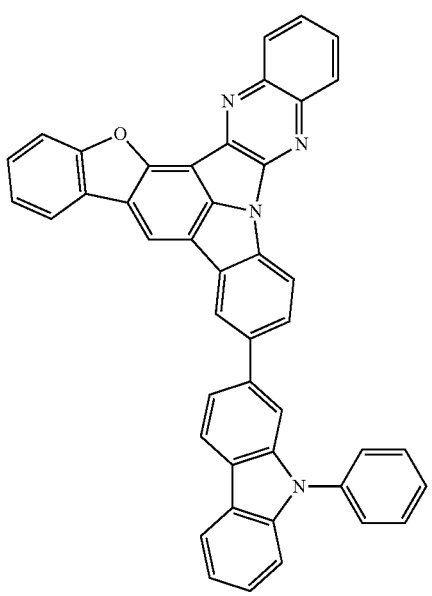

A-124
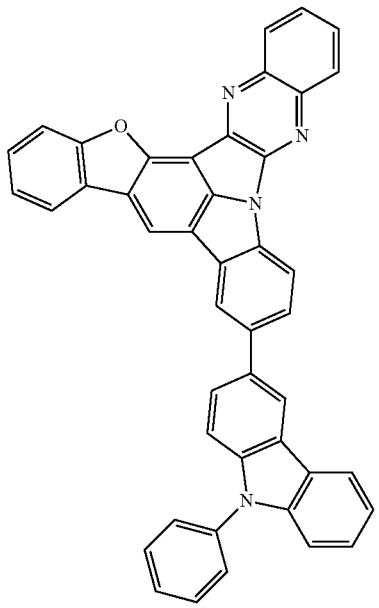
A-125
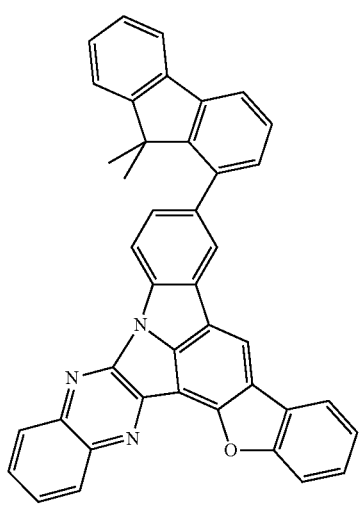
A-126
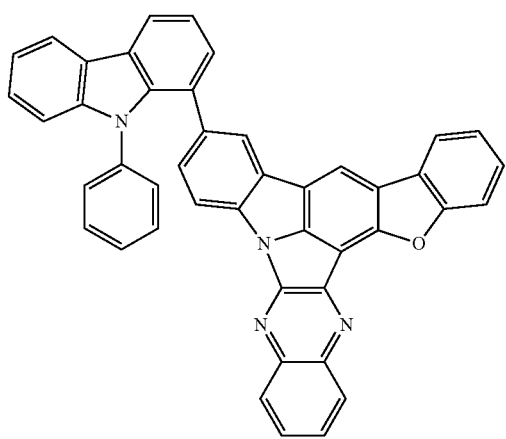
A-127
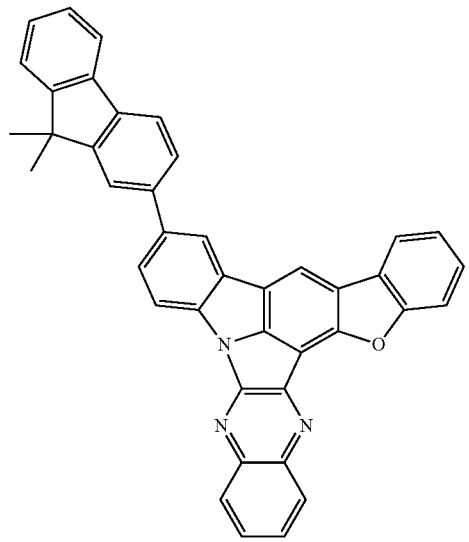
A-128
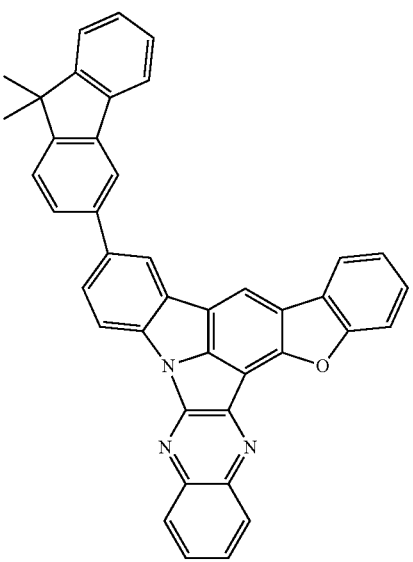
A-129
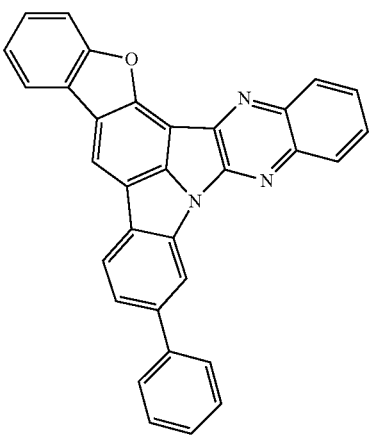

A-130
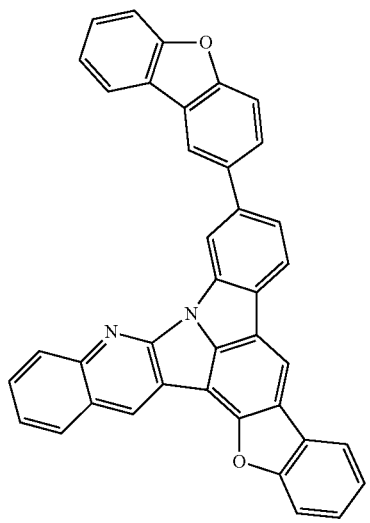
A-131
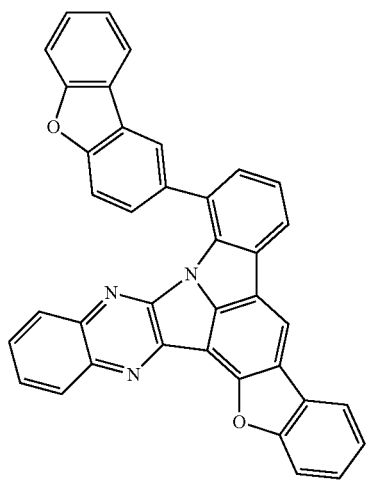
A-132
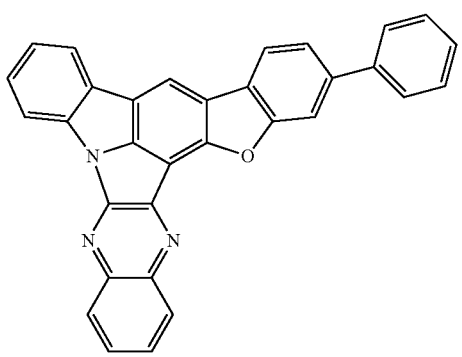
A-133
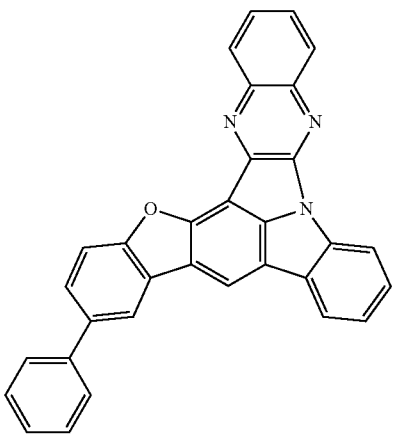
A-134
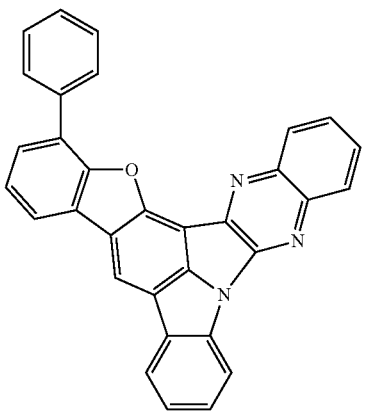
A-135
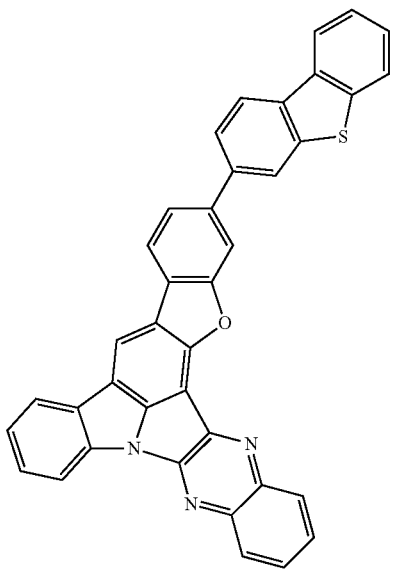

A-136
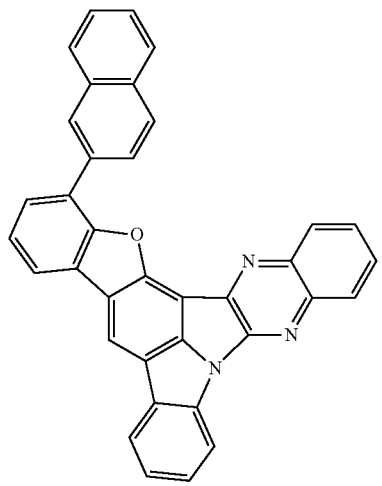
A-137
A-138
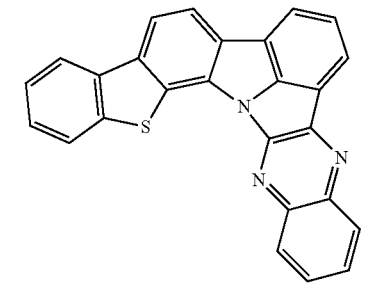
A-139
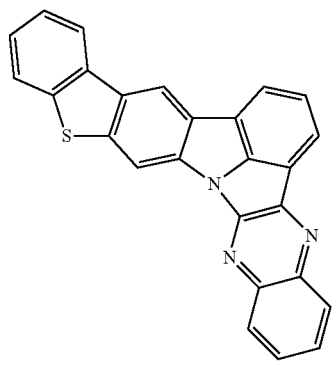
A-140
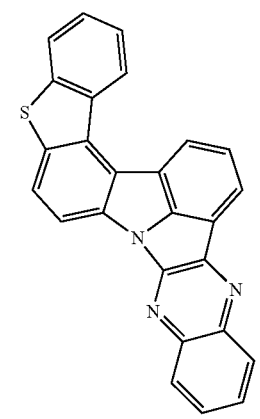
A-141
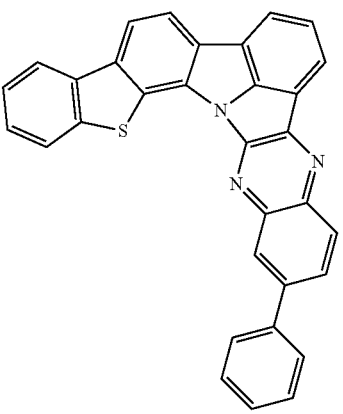

-continued
A-142
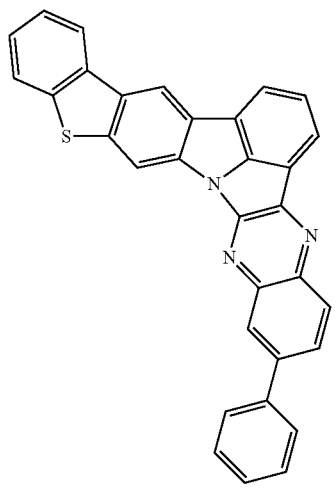
A-143
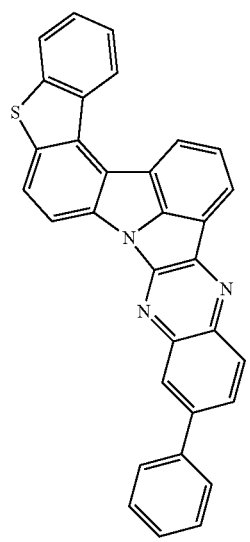
A-144
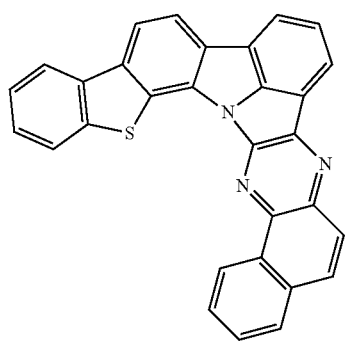
-continued
A-145
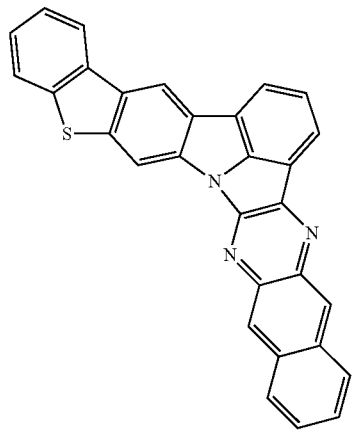
A-146
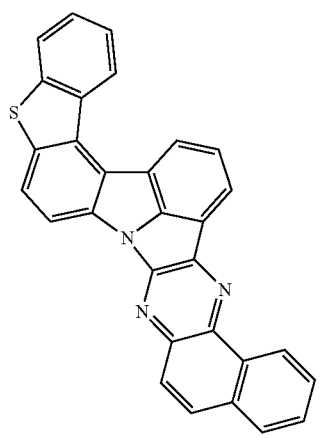
A-147
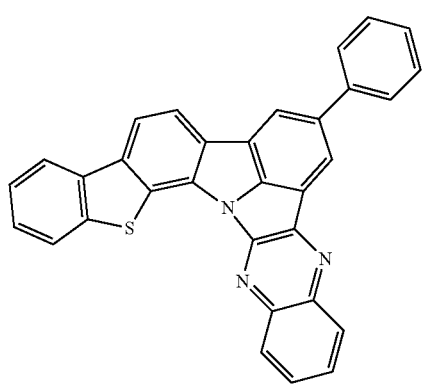
A-148

-continued
A-149
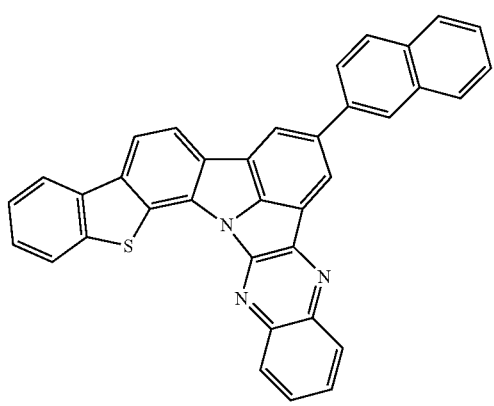
A-150
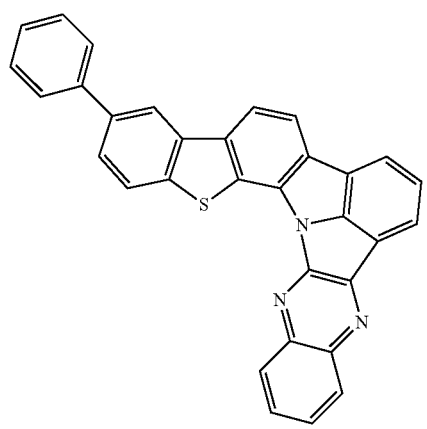
A-151
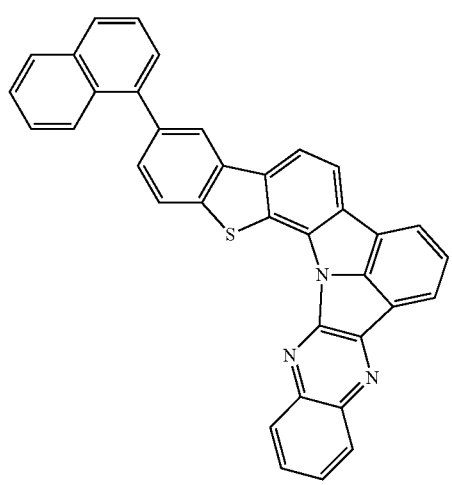
-continued
A-152
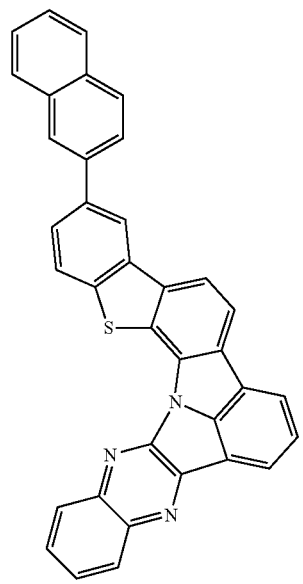
A-153
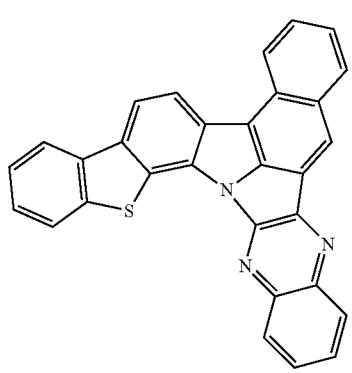
A-154
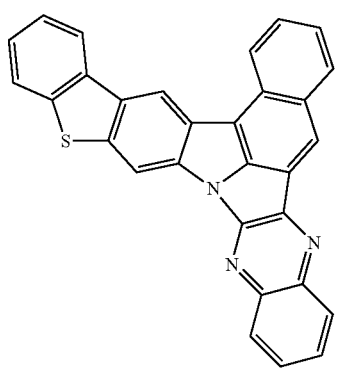

-continued
A-155
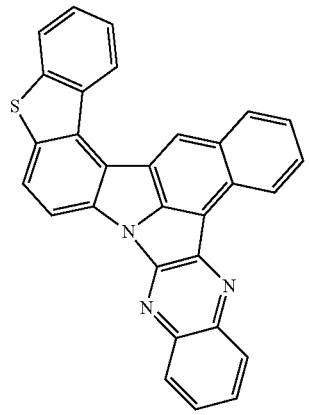
A-156
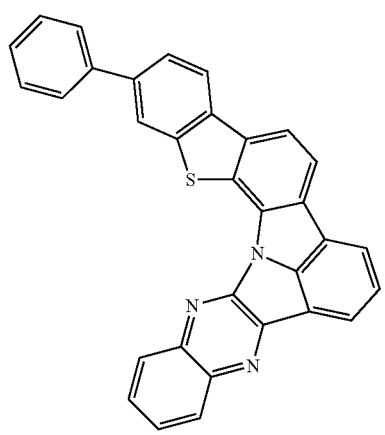
A-157
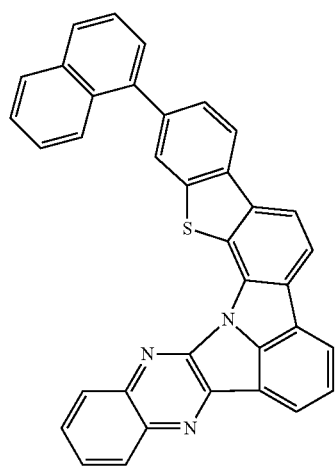
-continued
A-158
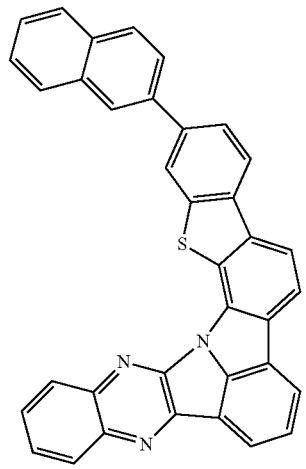
A-159
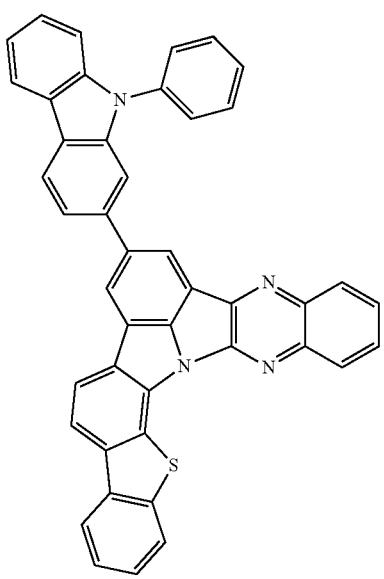
A-160
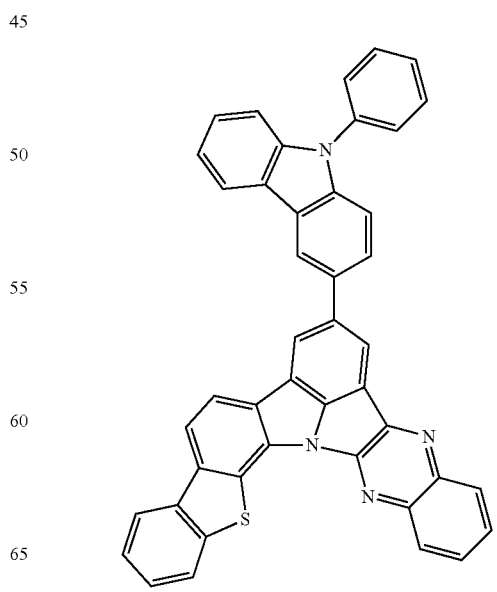

-continued
A-161
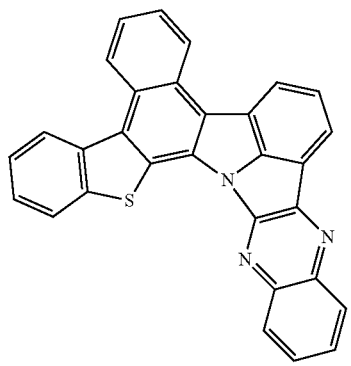
A-162
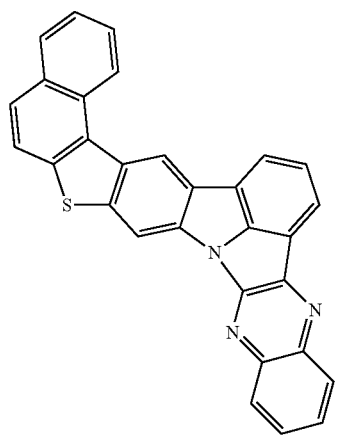
A-163
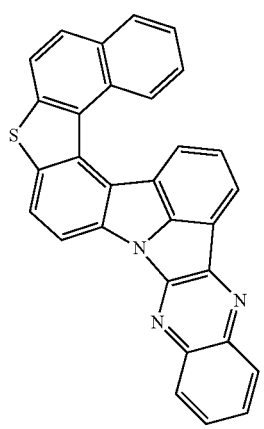
-continued
A-164
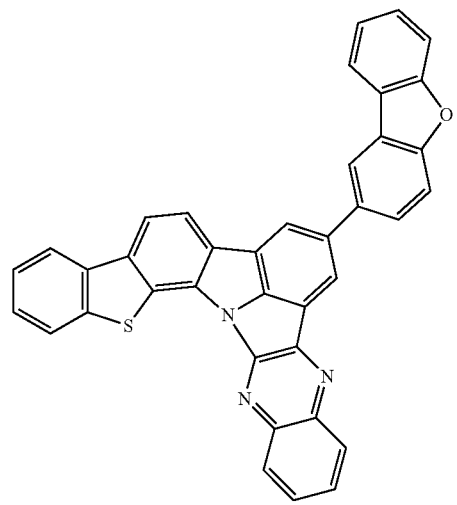
A-165
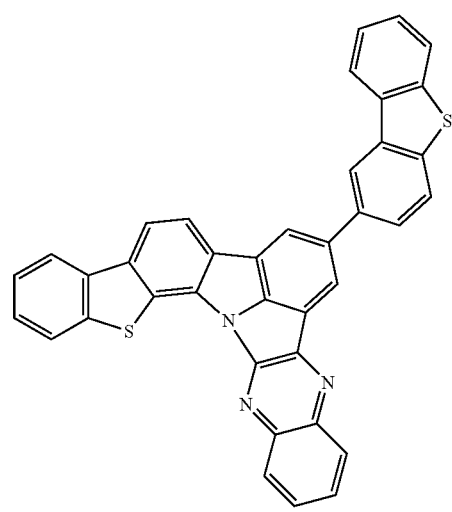
A-166
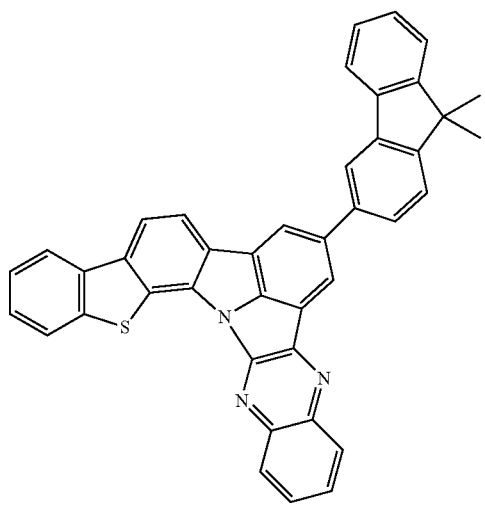

A-167
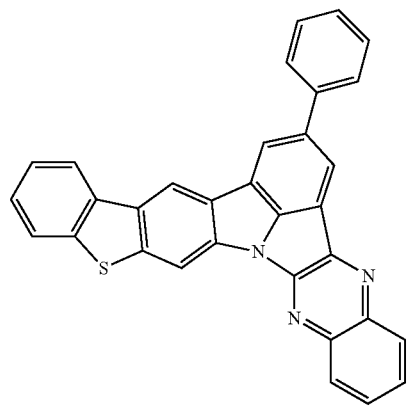
A-168
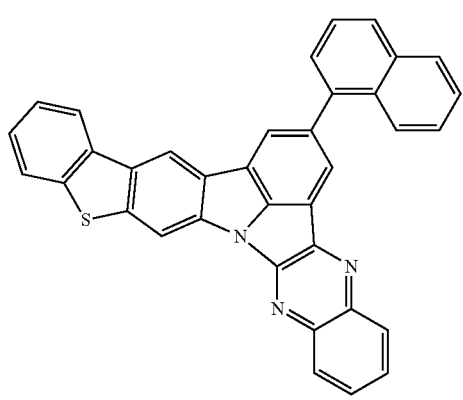
A-169
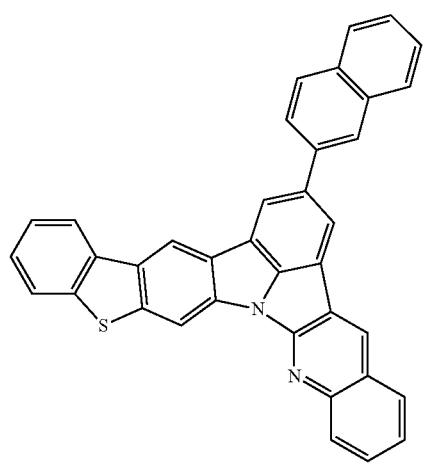
A-170
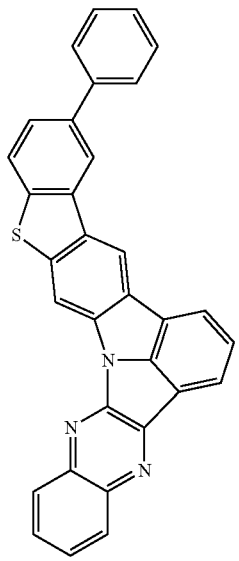
A-171
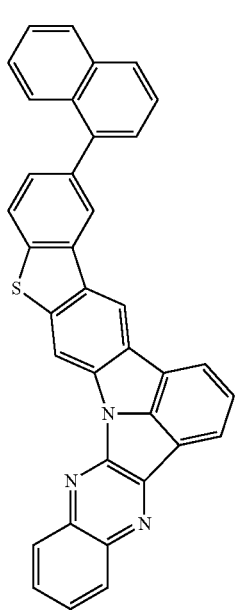

A-172
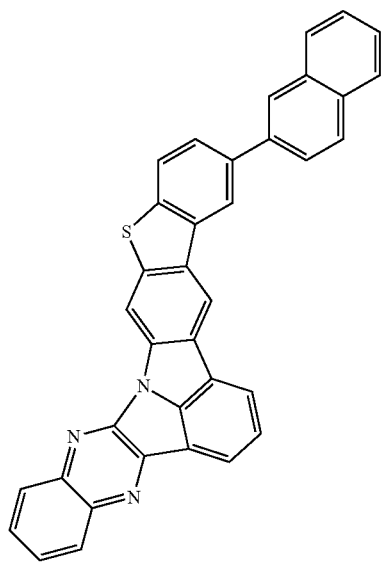
A-173
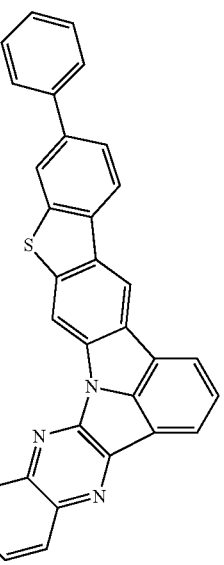
A-174
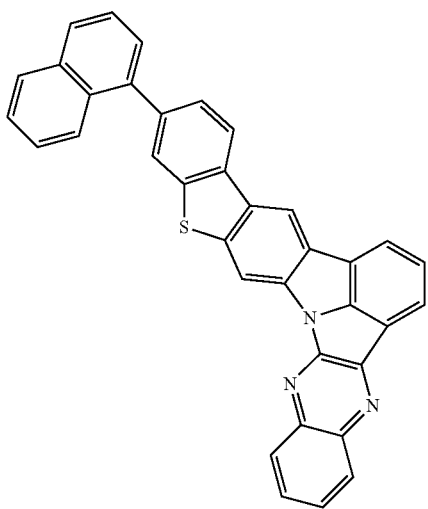
A-175
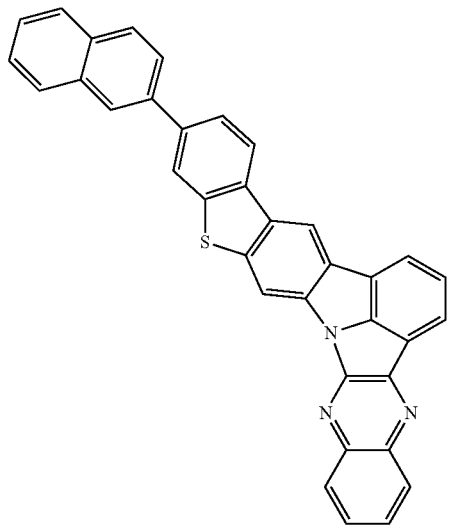
A-176
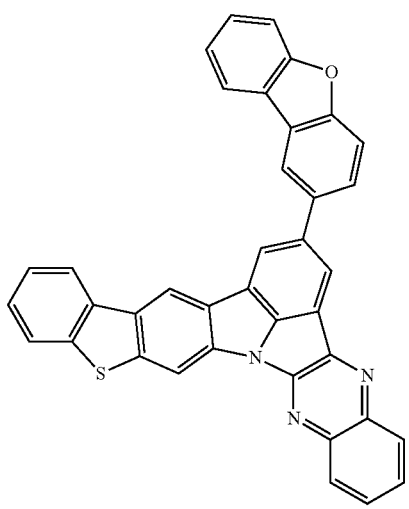
A-177
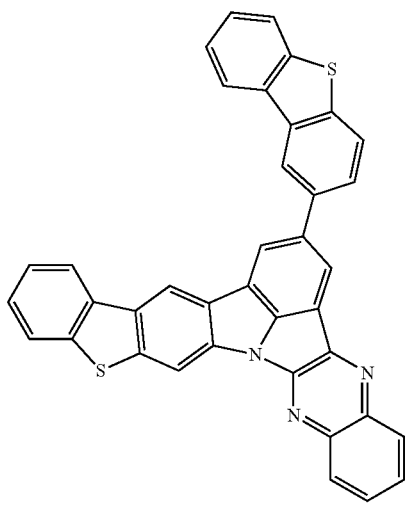

-continued
A-178
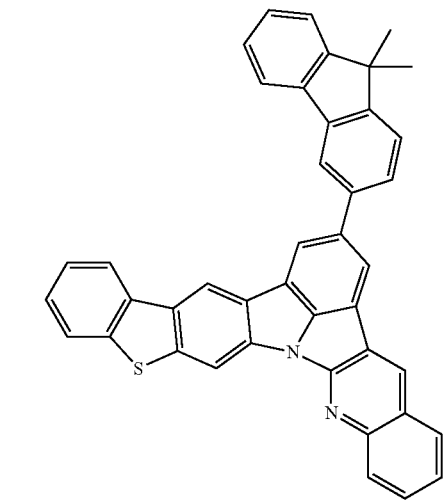
A-179
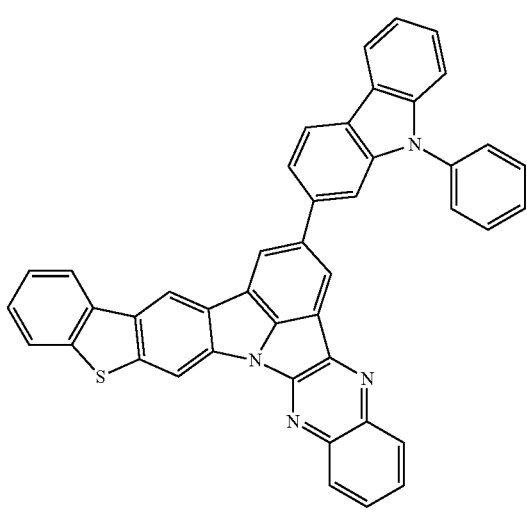
A-180
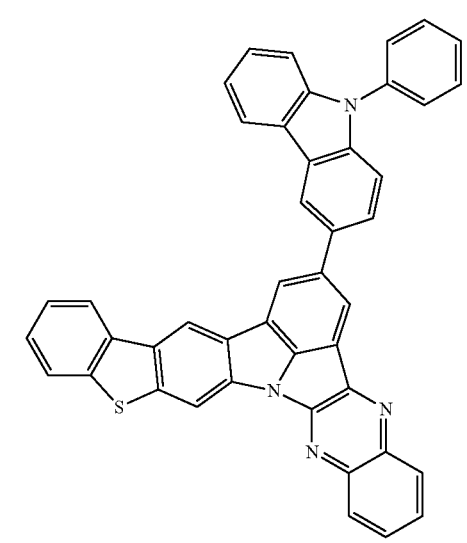
-continued
A-181
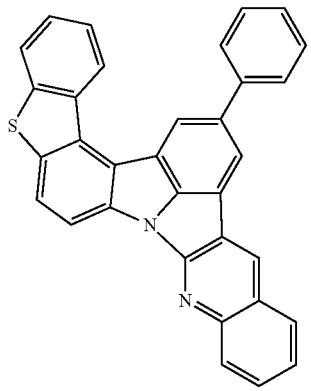
A-182
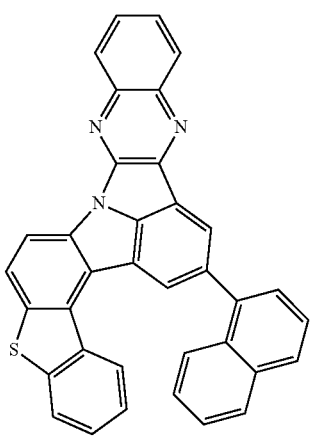
A-183
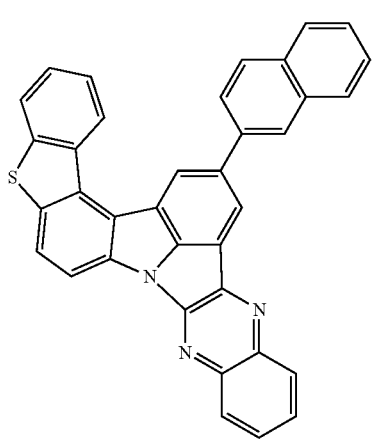
A-184
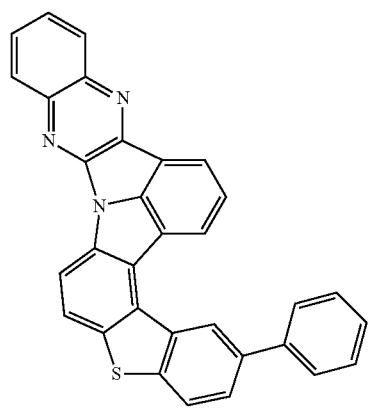

-continued
A-185
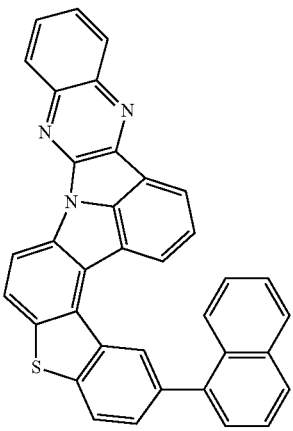
A-186
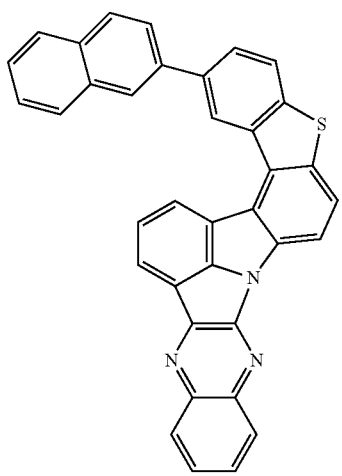
A-187
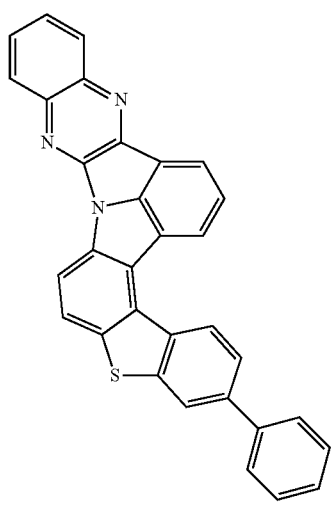
-continued
A-188
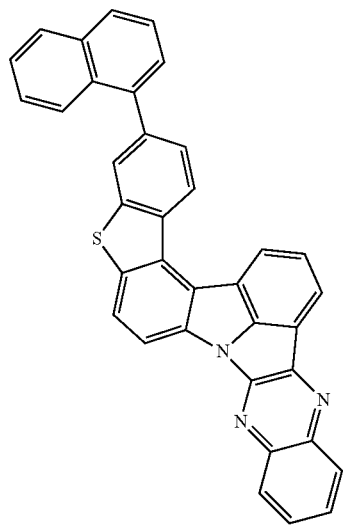
A-189
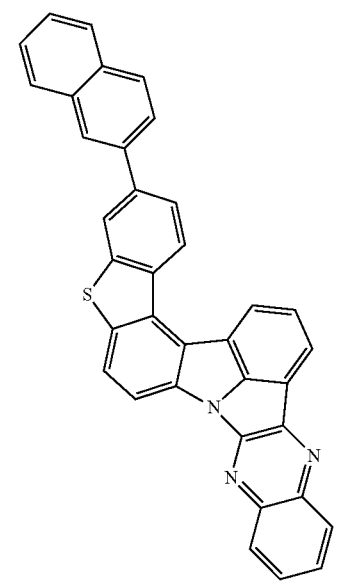
A-190
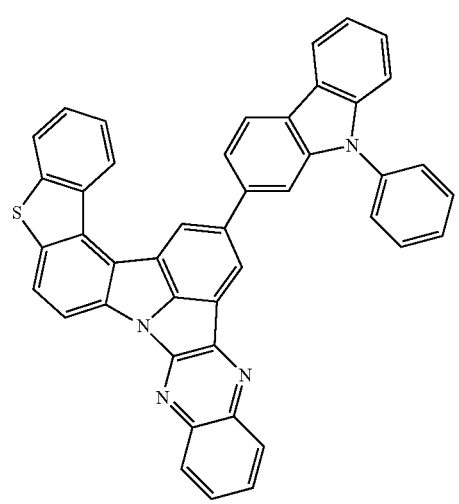

A-191
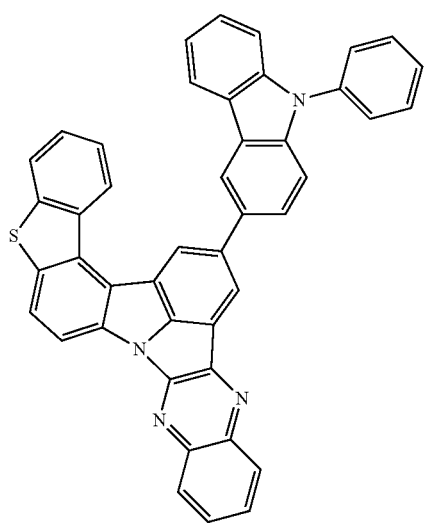
A-192
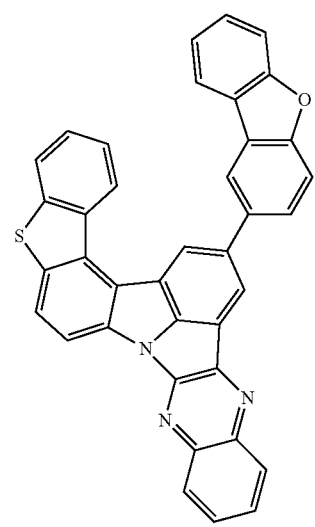
A-193
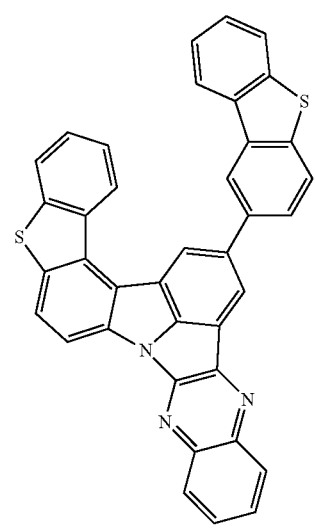
A-194
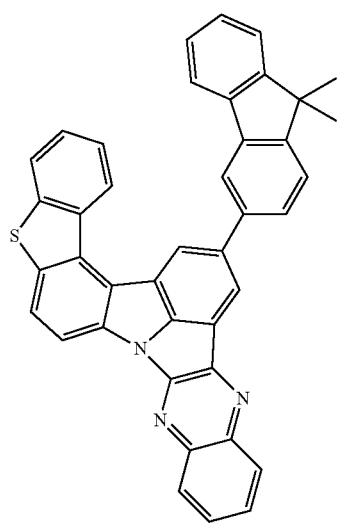
A-195
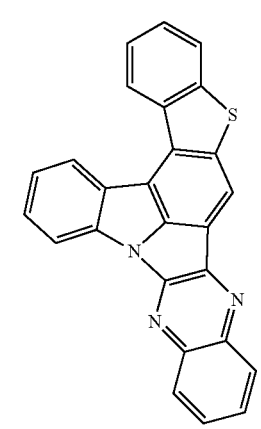
A-196
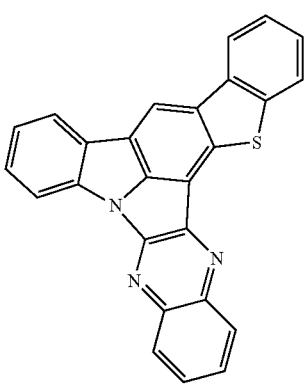

-continued
A-197
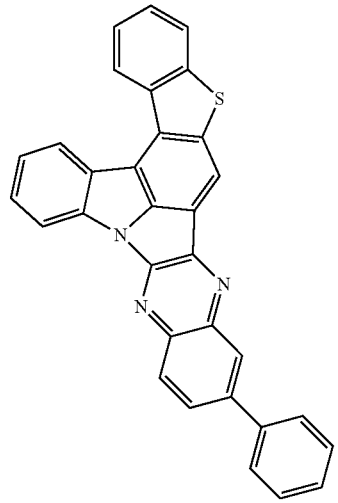
A-198
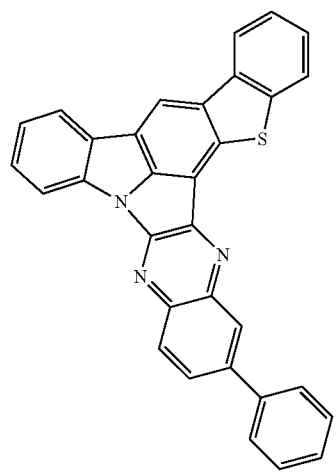
A-199
-continued
A-200
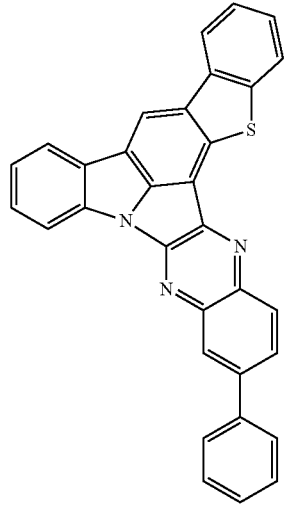
A-201
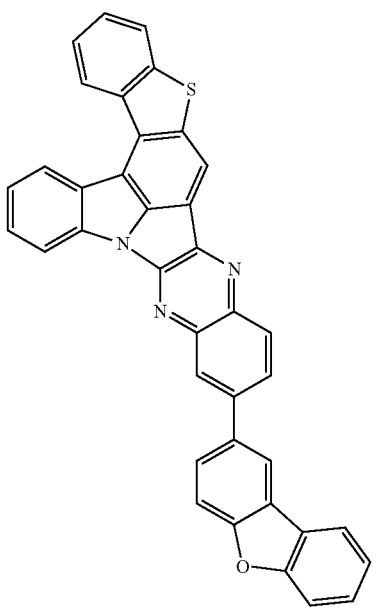

A-202
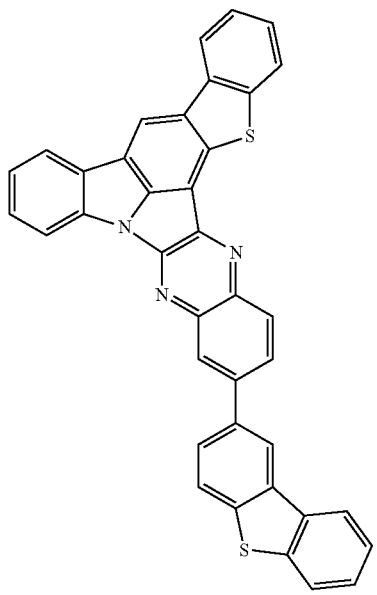
A-203
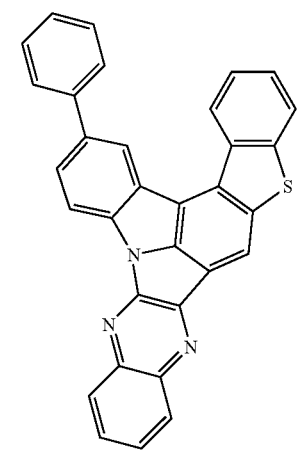
A-204
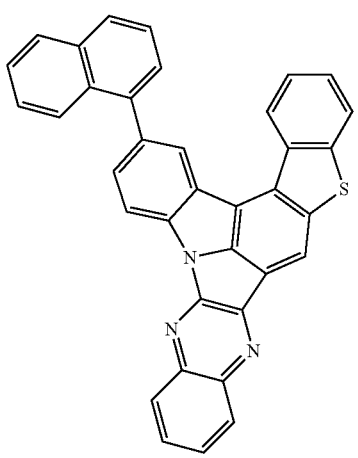
A-205
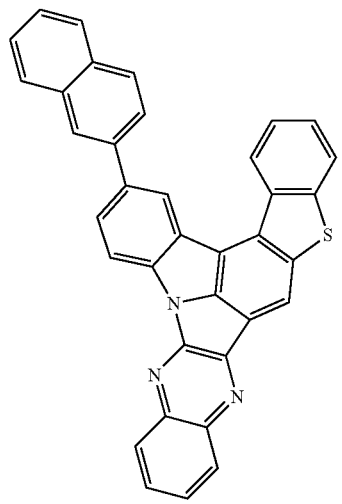
A-206
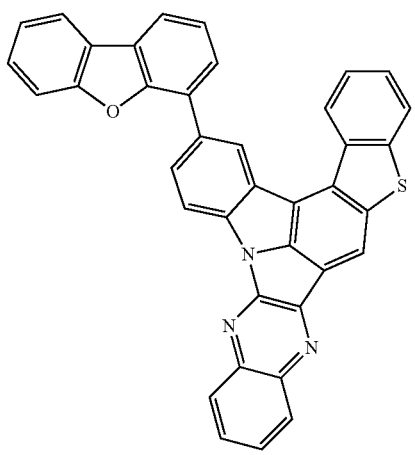
A-207
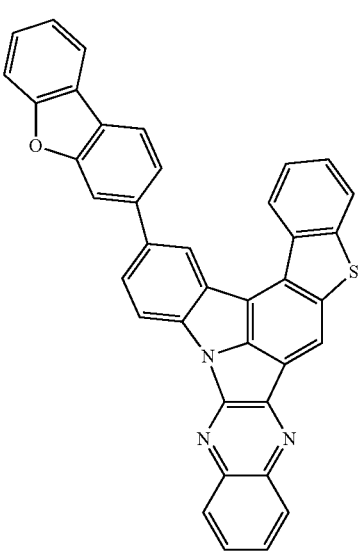

-continued
A-208
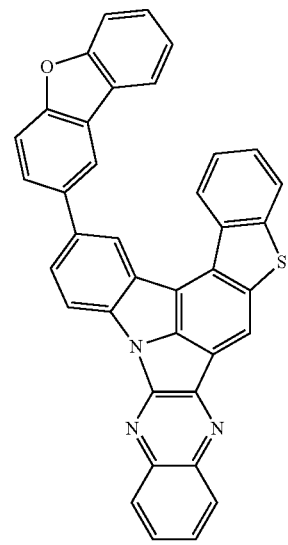
A-209
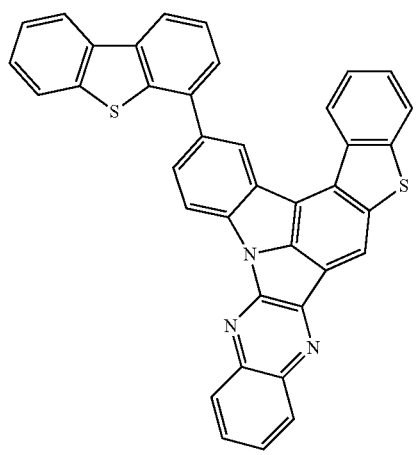
A-210
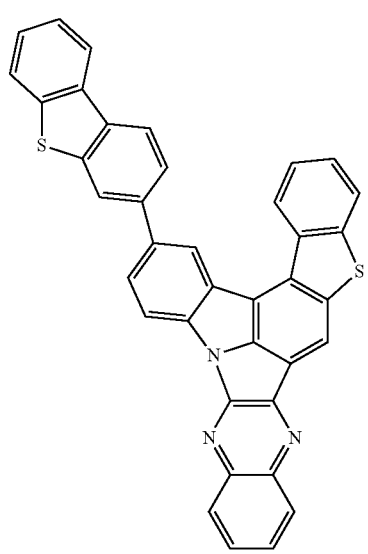
-continued
A-211
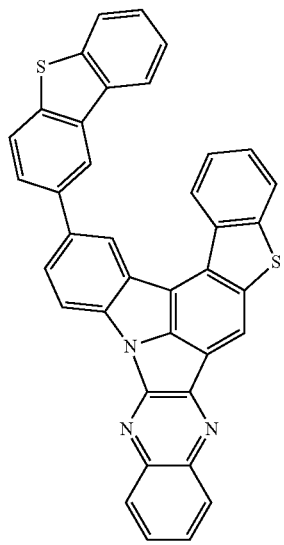
A-212
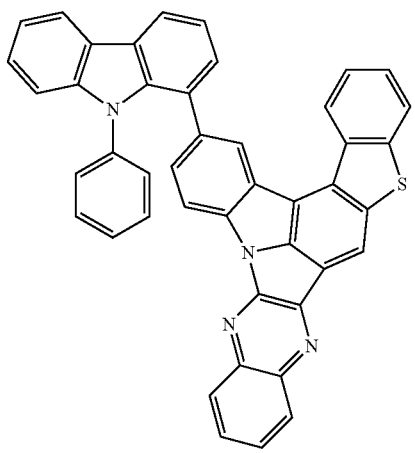
A-213
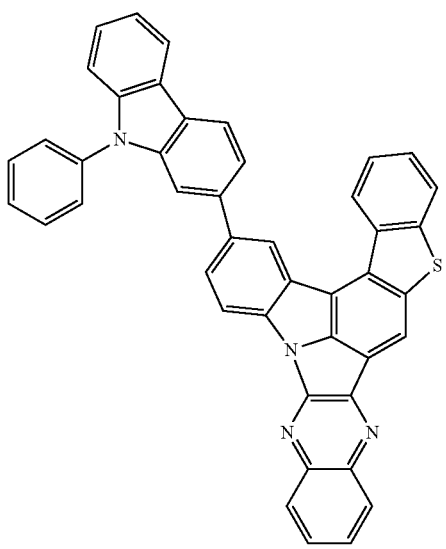

A-214
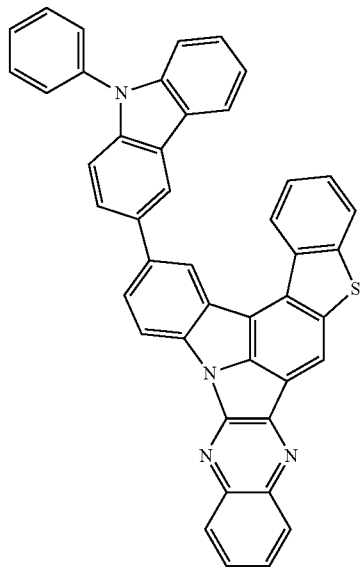
A-215
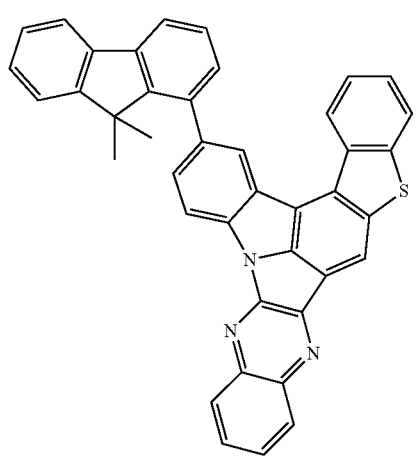
A-216
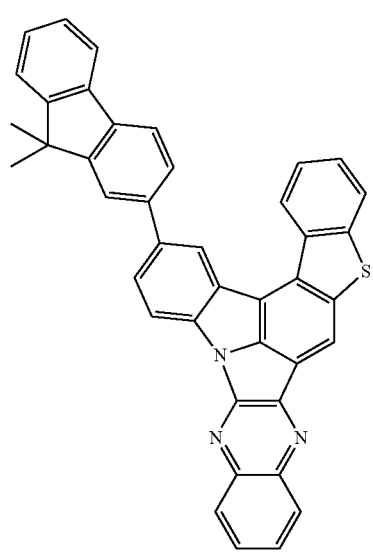
A-217
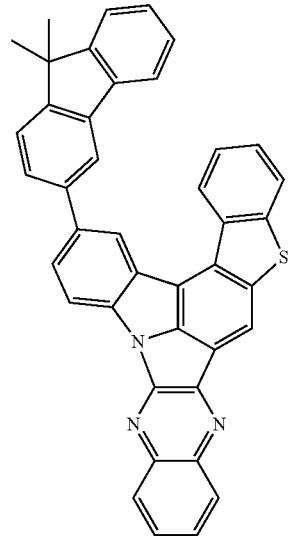
A-218
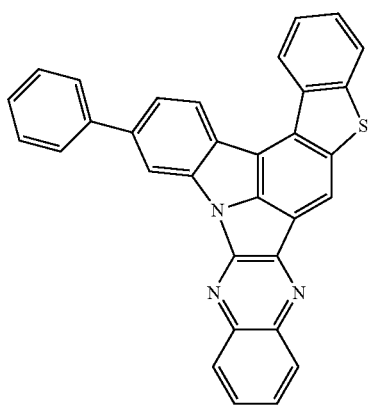
A-219
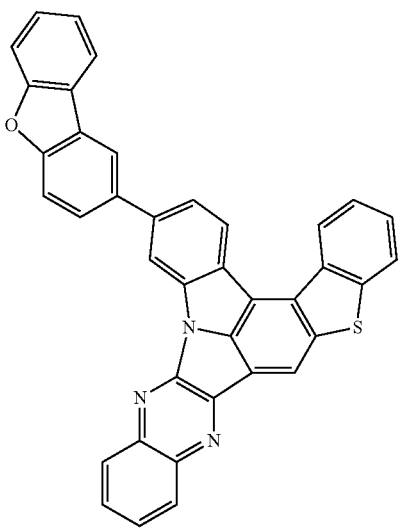

A-220
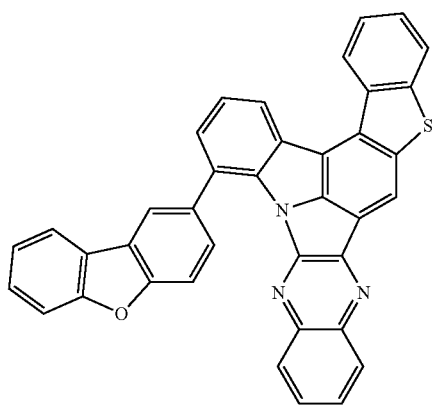
A-221
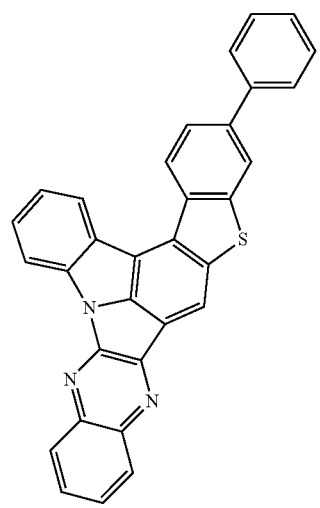
A-223
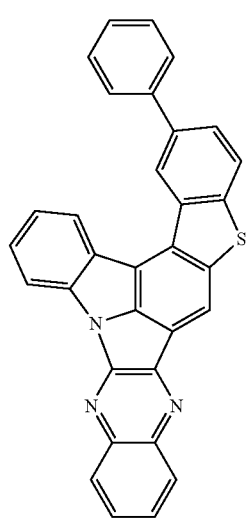
A-224
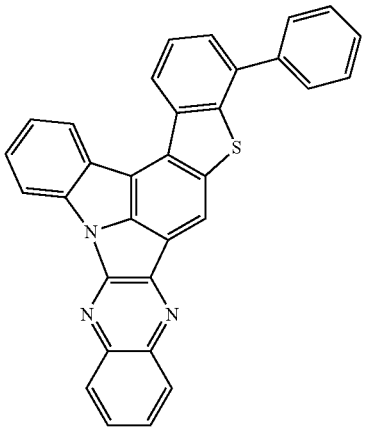
A-225
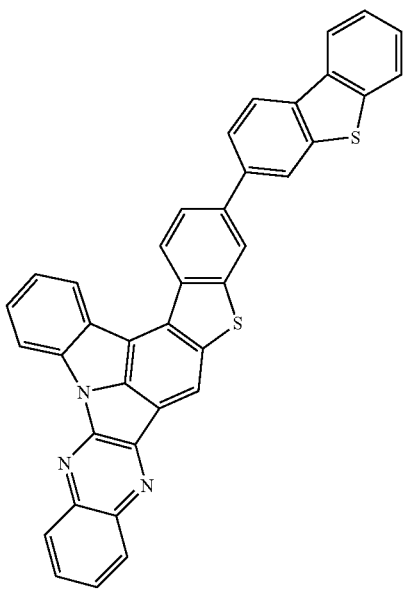
A-226
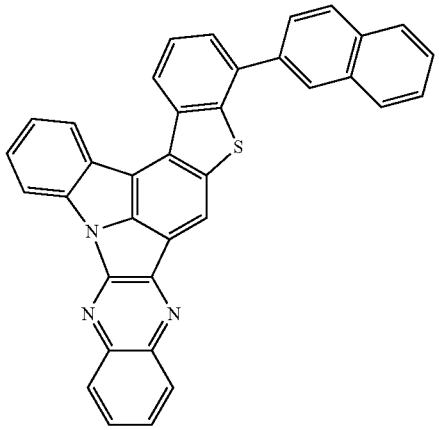

A-227
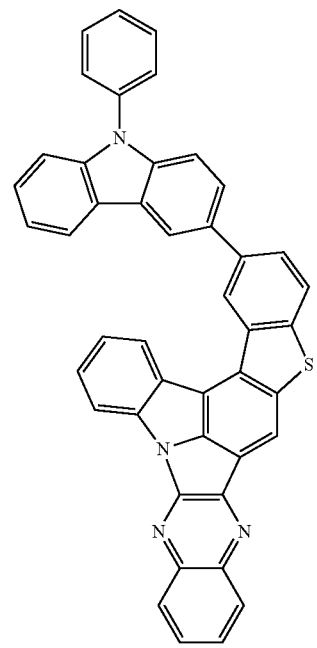
A-228
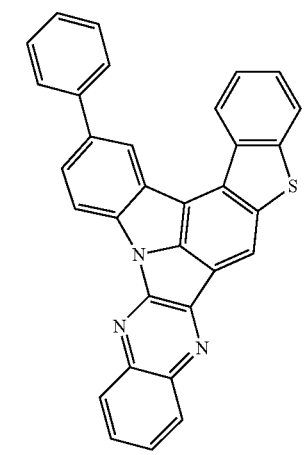
A-229
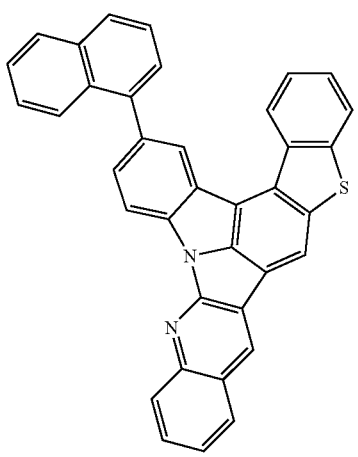
A-230
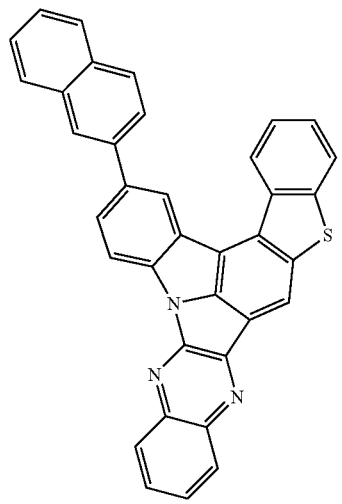
A-231
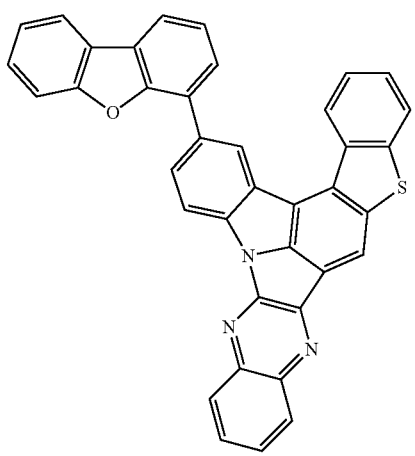
A-232
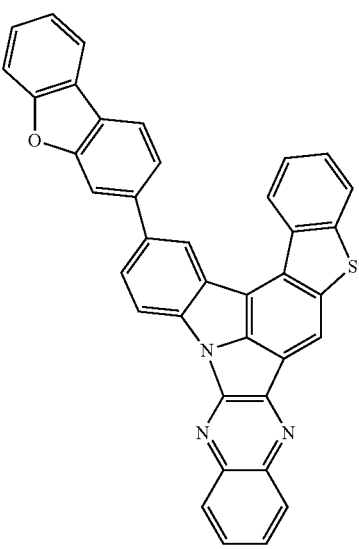

A-233
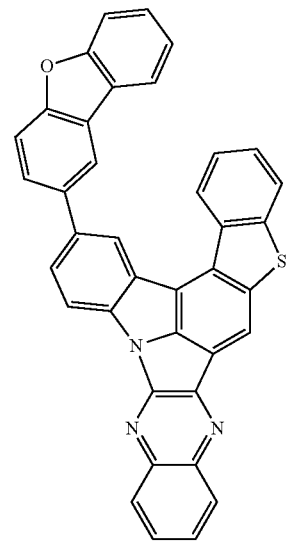
A-234
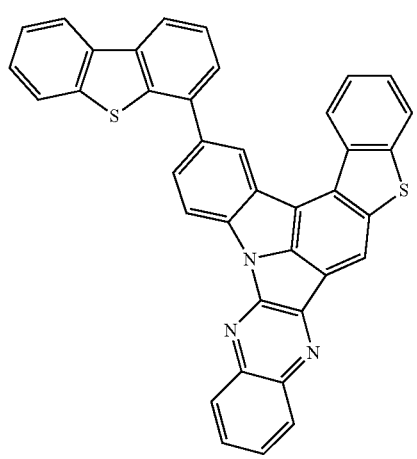
A-235
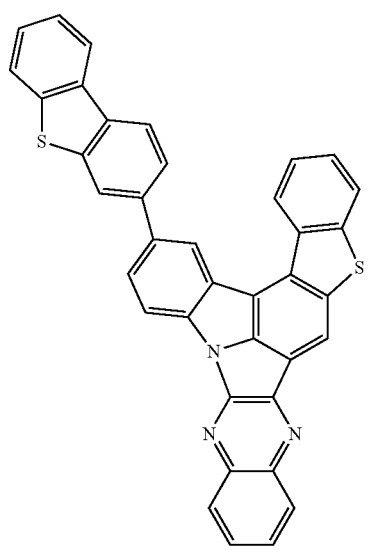
A-236
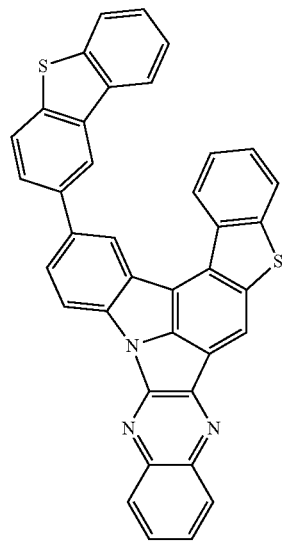
A-237
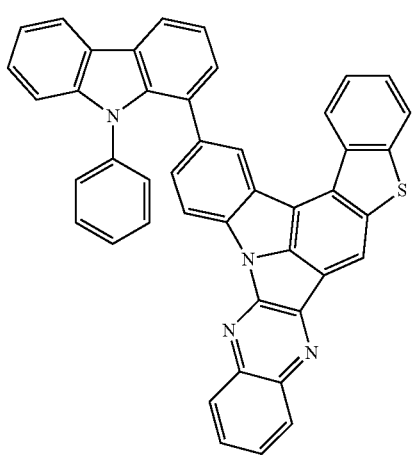
A-238
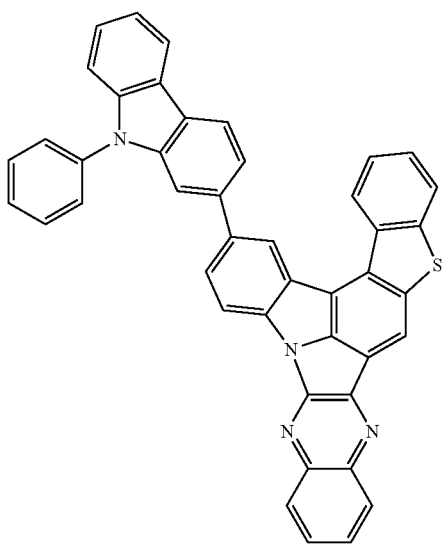

-continued
A-239
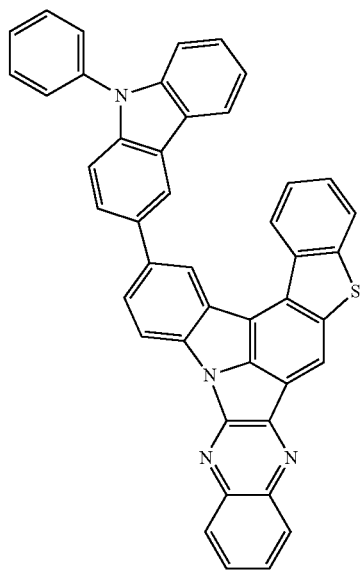
A-240
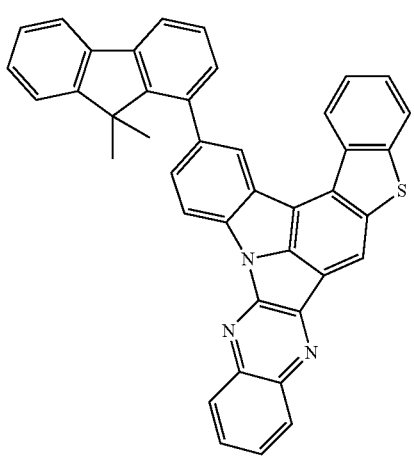
A-241
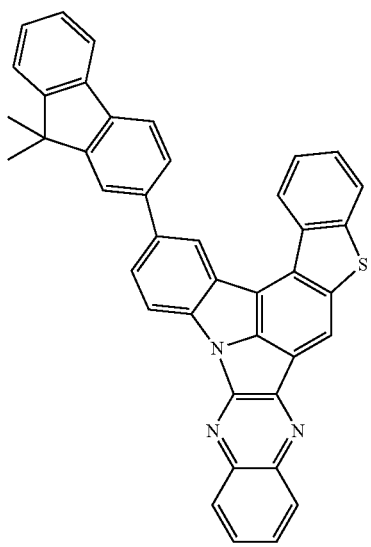
-continued
A-242
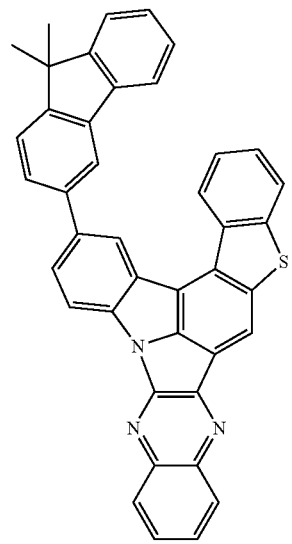
A-243
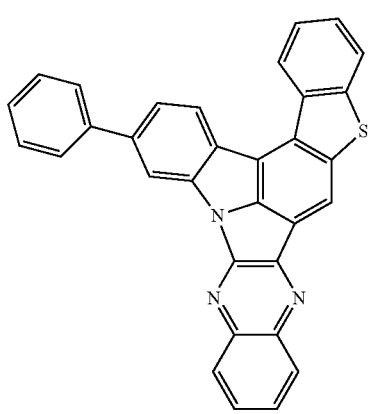
A-244
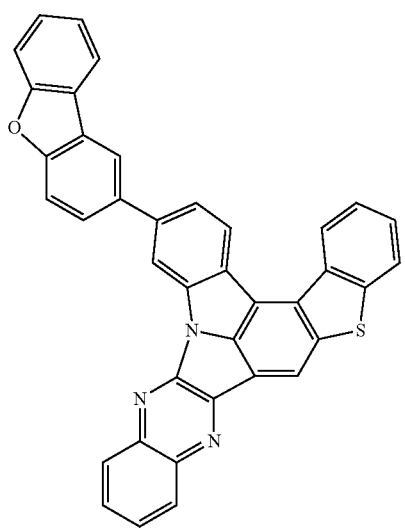

-continued
A-245
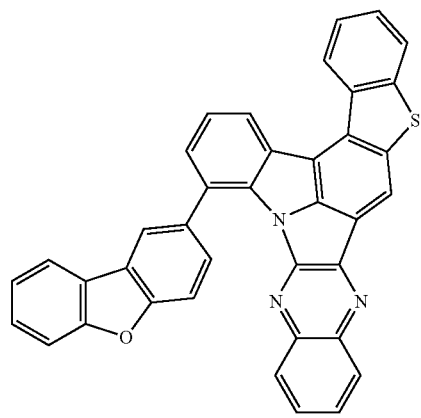
A-246
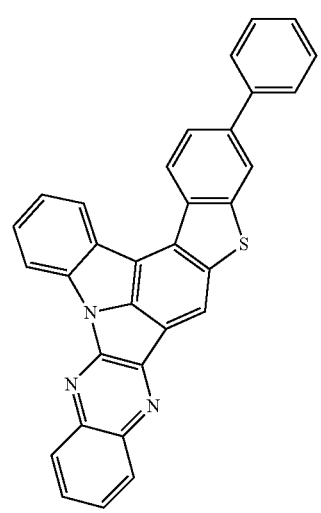
A-247
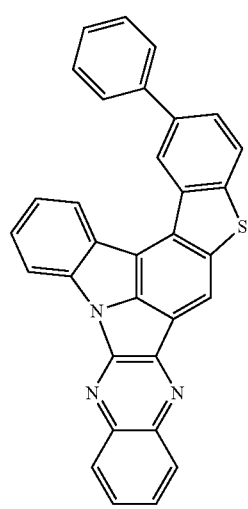
-continued
A-248
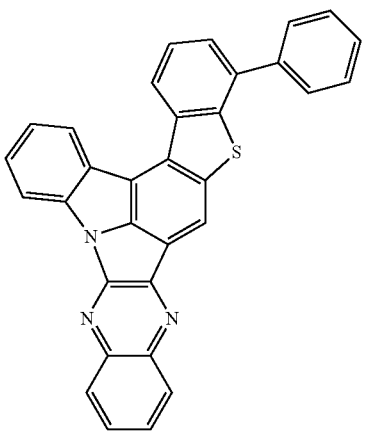
A-249
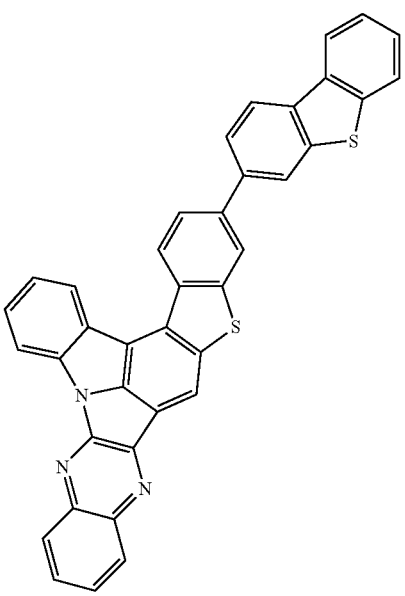
A-250
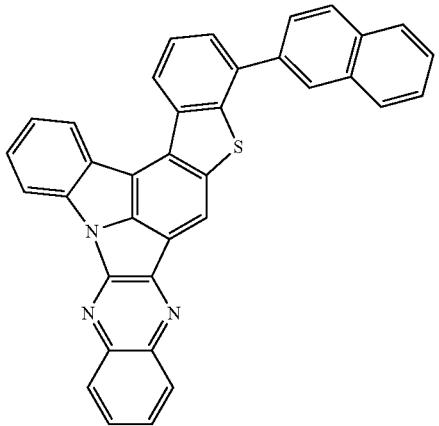

A-251
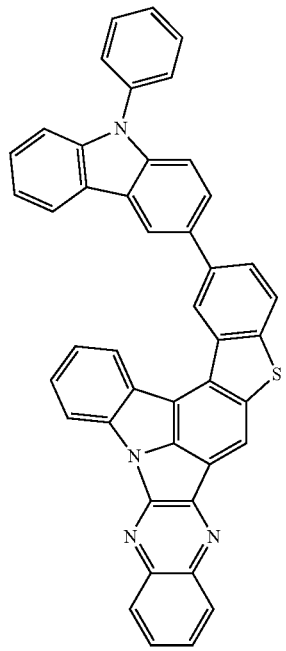
A-252
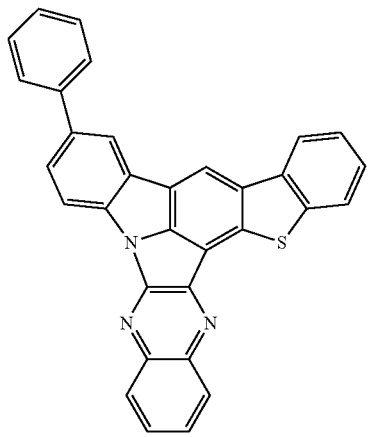
A-253
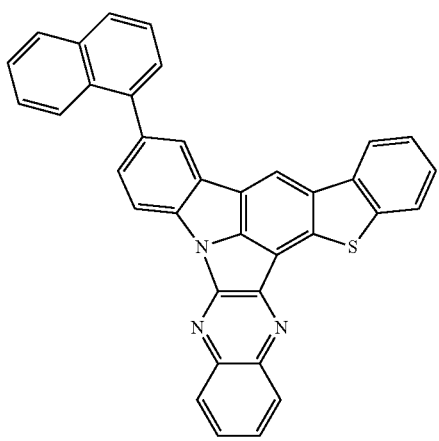
A-254
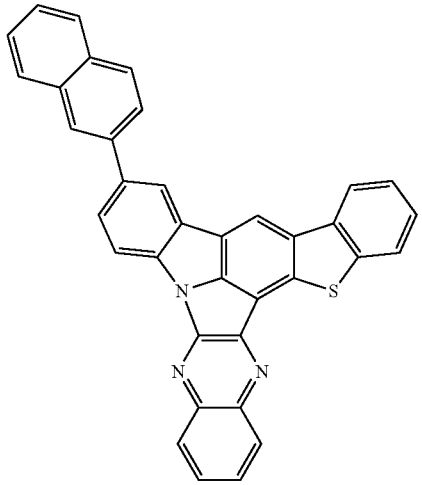
A-255
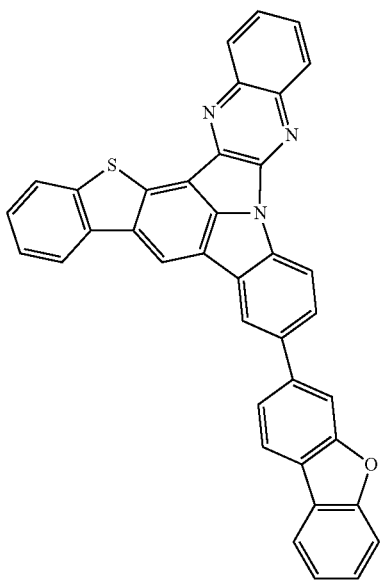
A-256

A-257
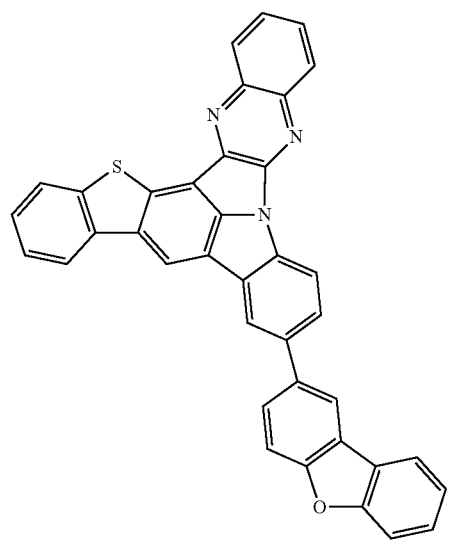
A-258
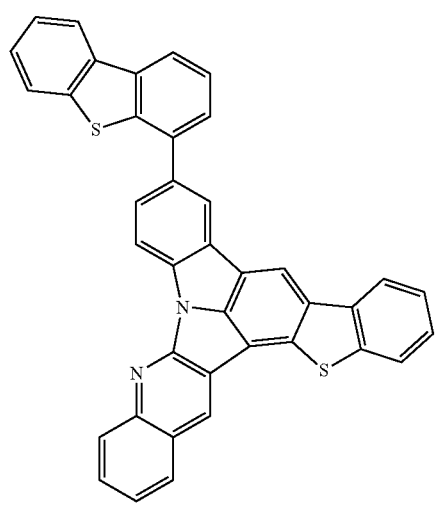
A-259
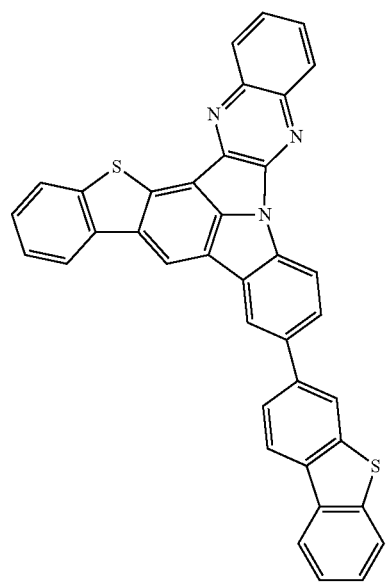
A-260
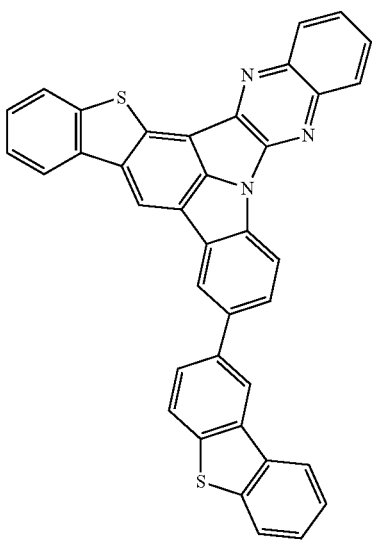
A-261
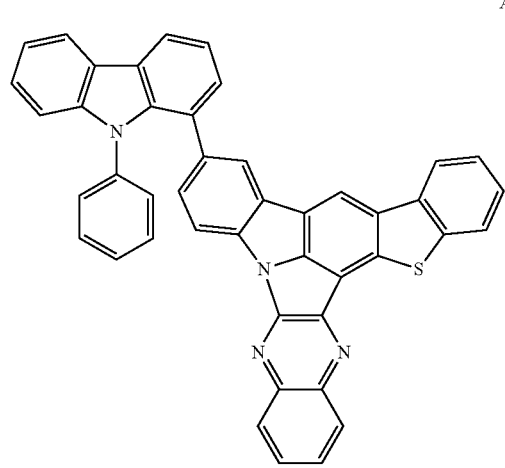
A-262
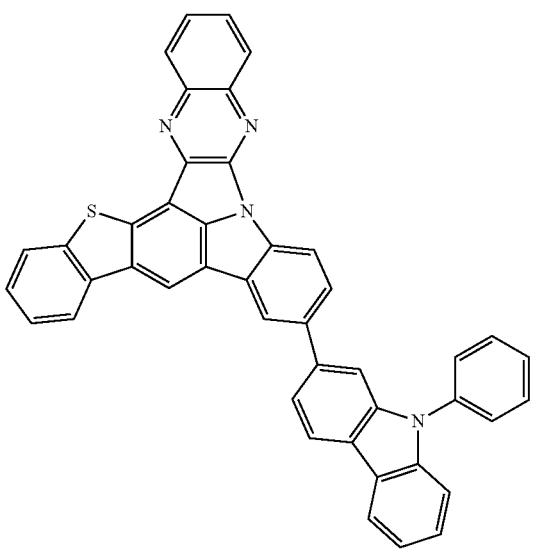

A-263
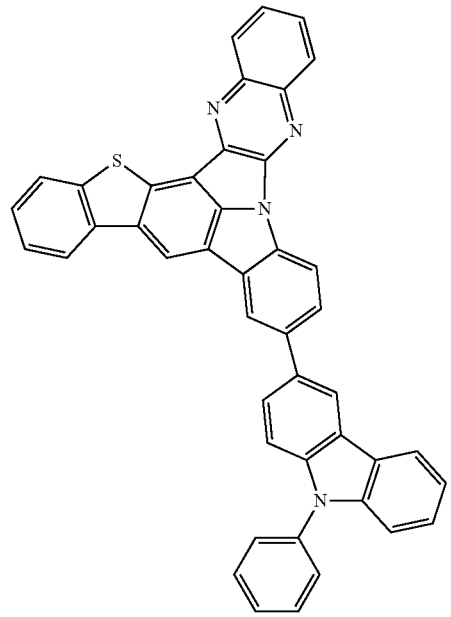
A-264
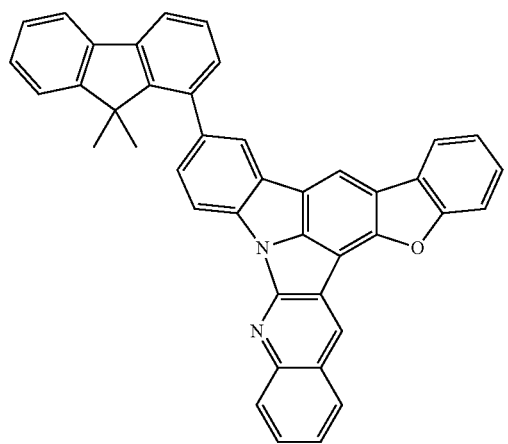
A-265
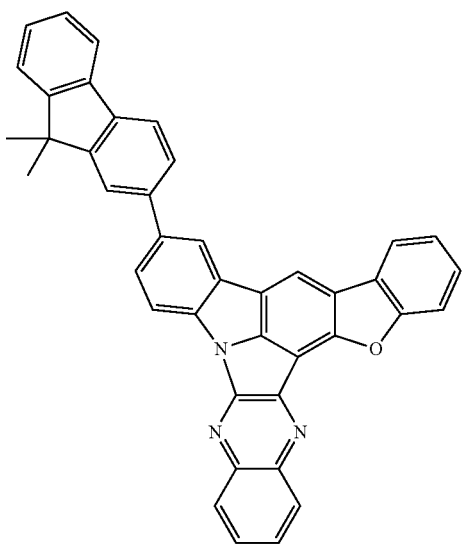
A-266
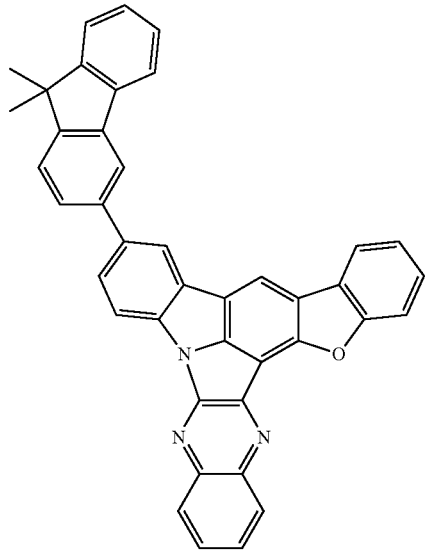
A-267
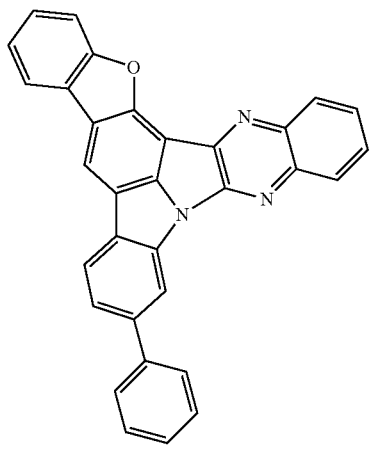
A-268
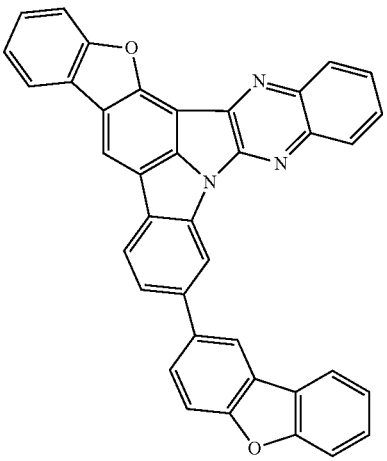

-continued
A-269
A-270
A-271
A-272
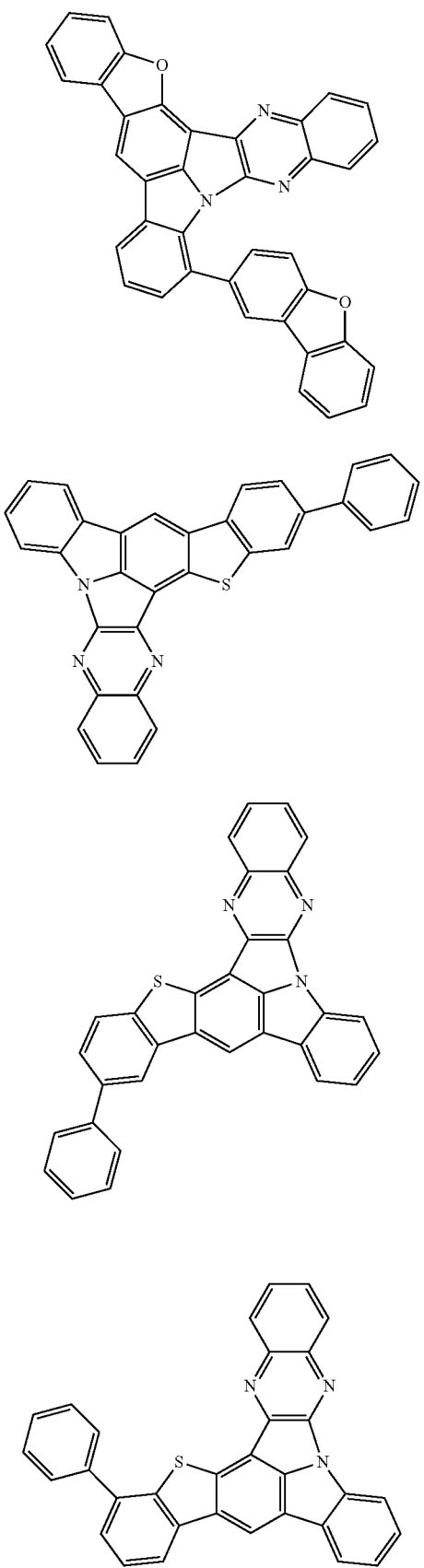
-continued
A-273
A-274
A-275
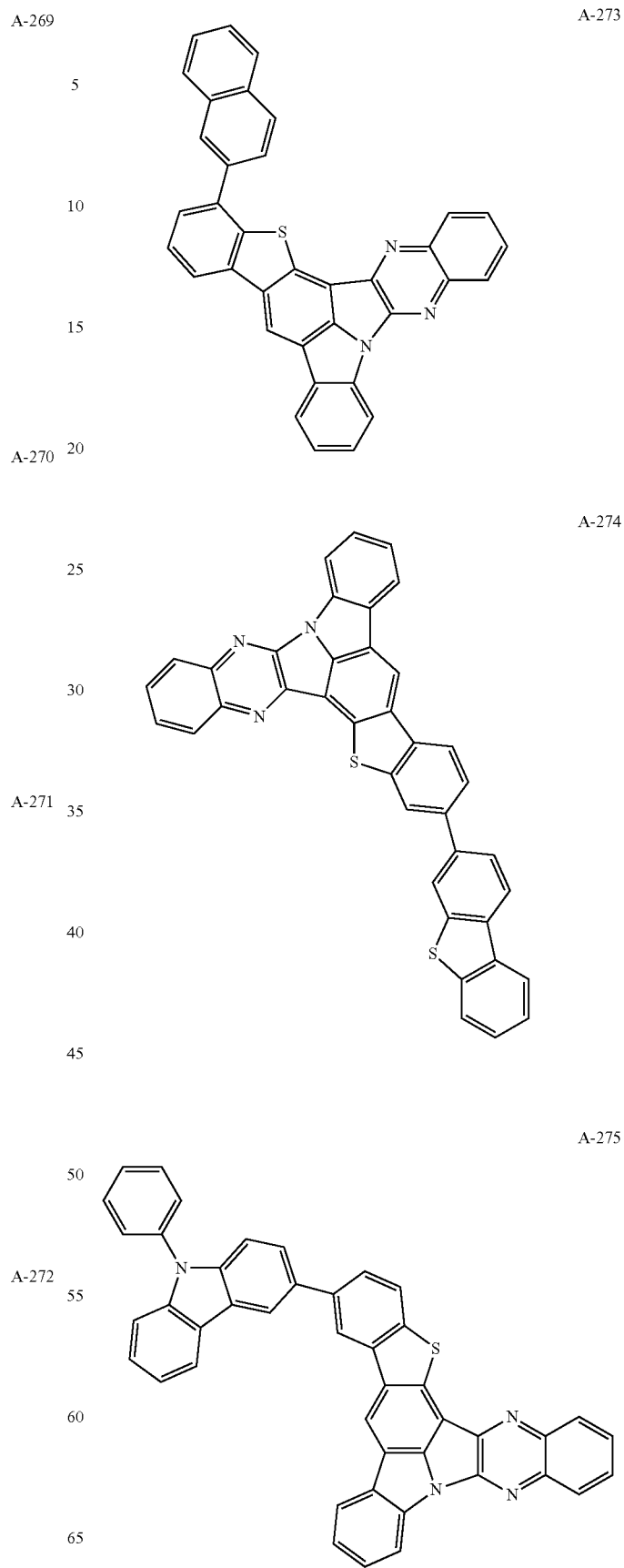

-continued
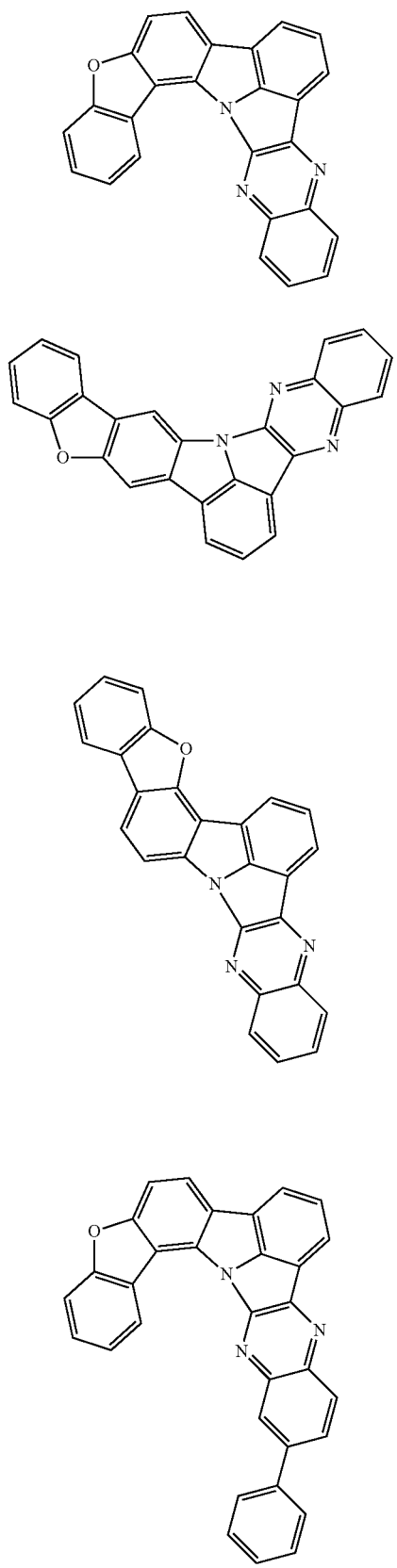
A-276
A-277
A-278
A-279
-continued
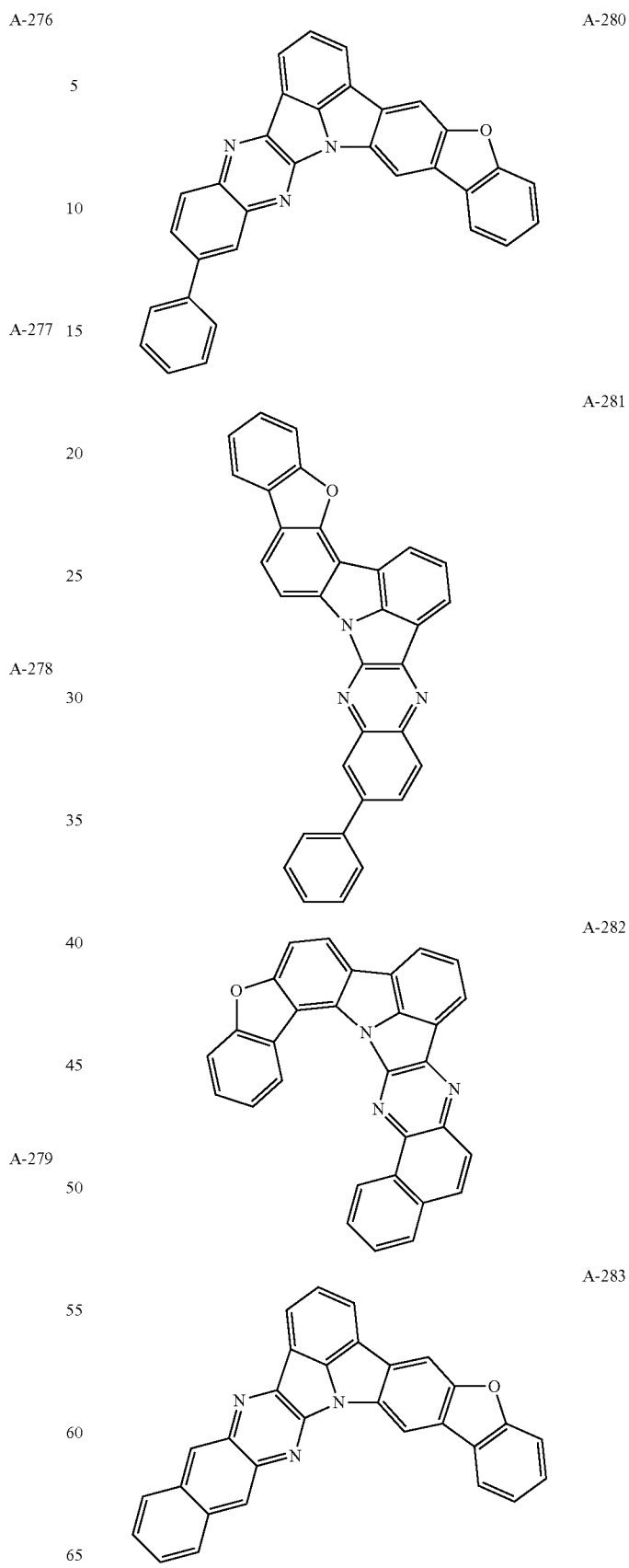
A-280
A-281
A-282
A-283

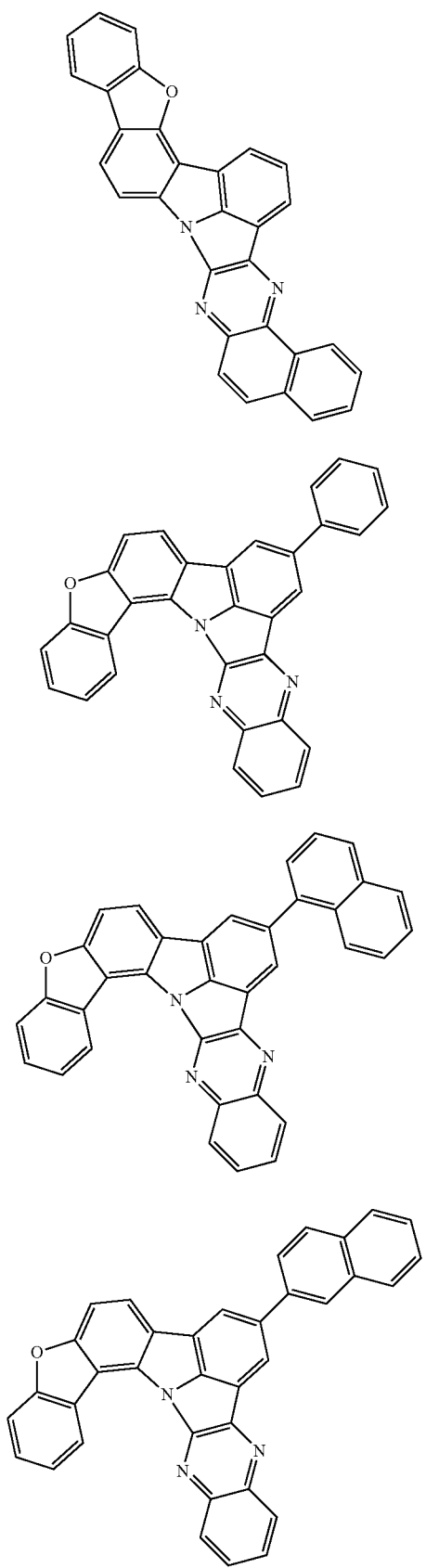
A-284
A-285
A-286
A-287
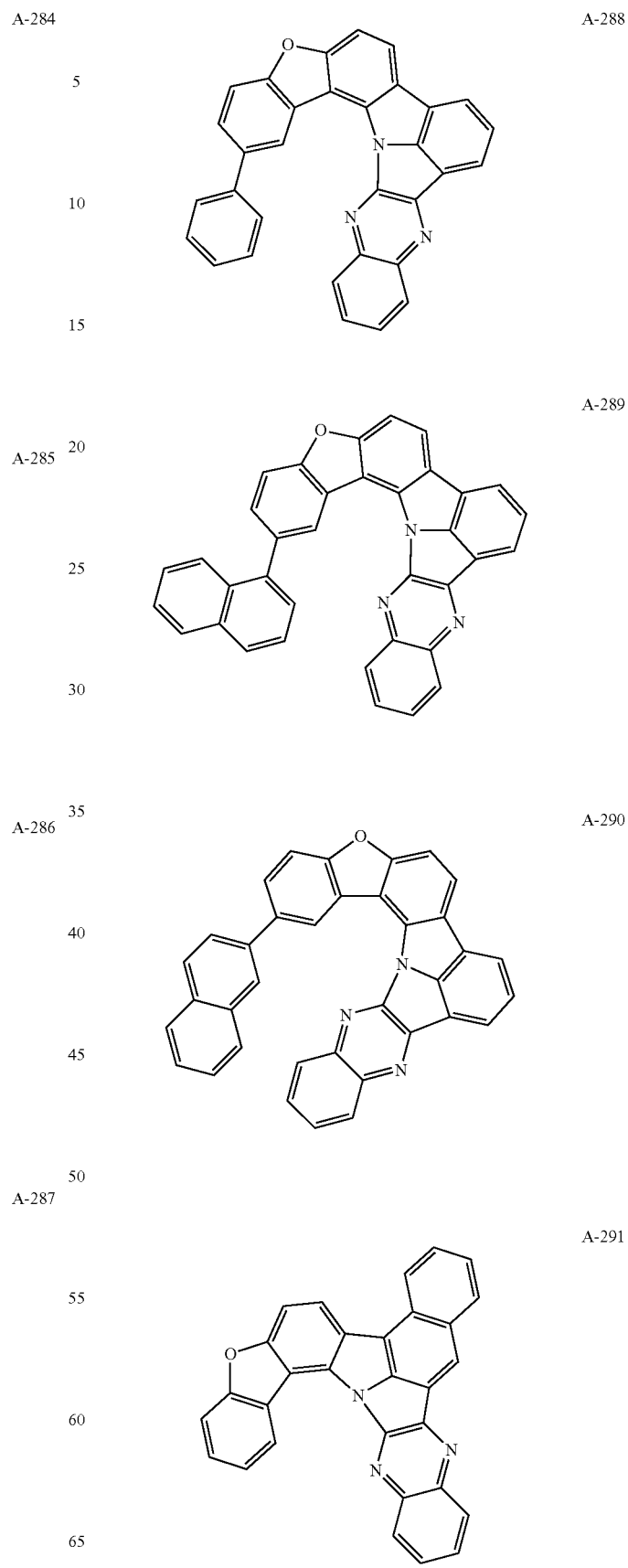
A-288
A-289
A-290
A-291

A-292
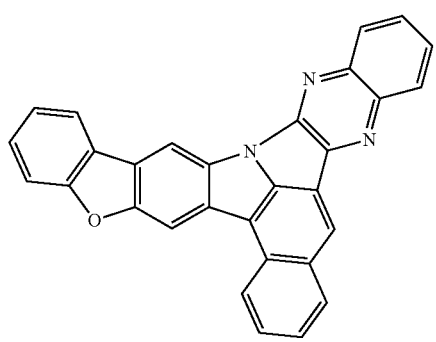
A-293
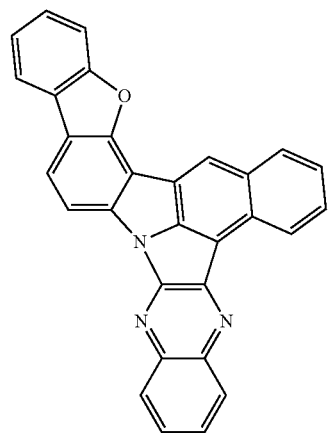
A-294
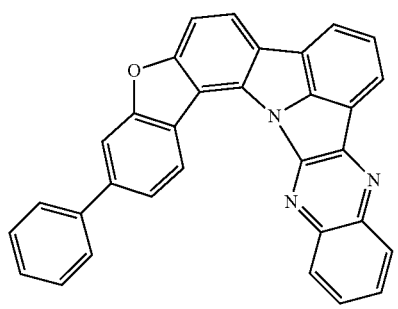
A-295
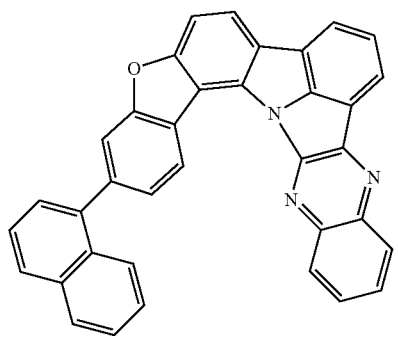
A-296
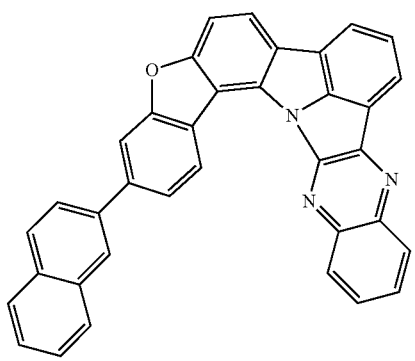
A-297
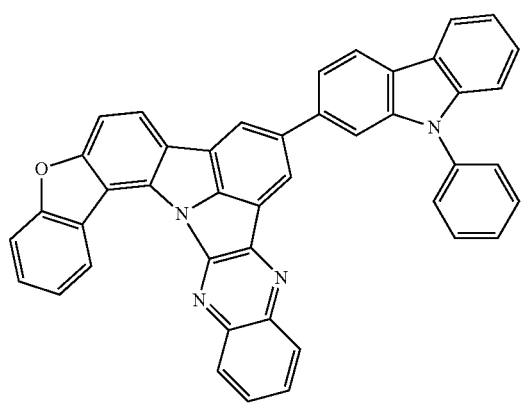
A-298
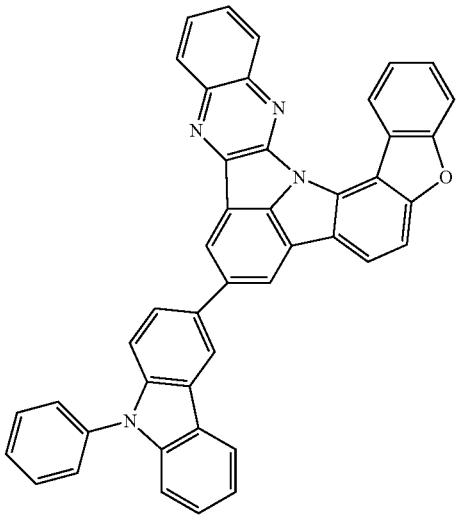
A-299
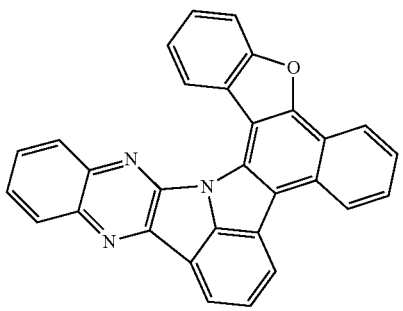

-continued
A-300
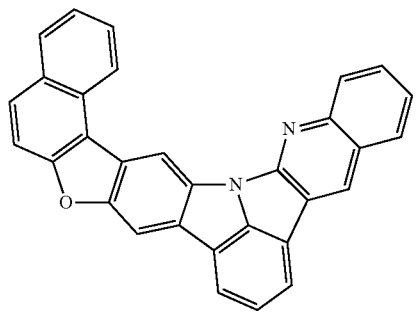
A-301
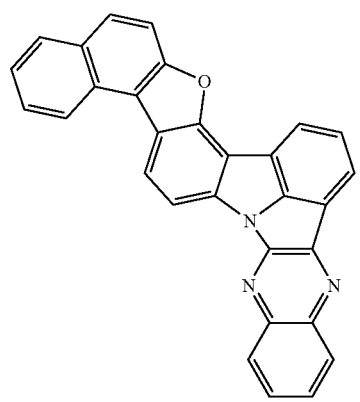
A-302
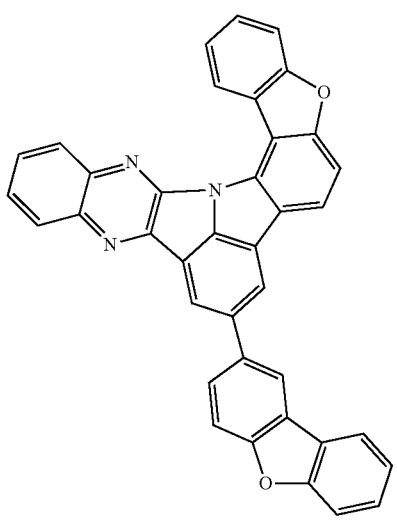
-continued
A-303
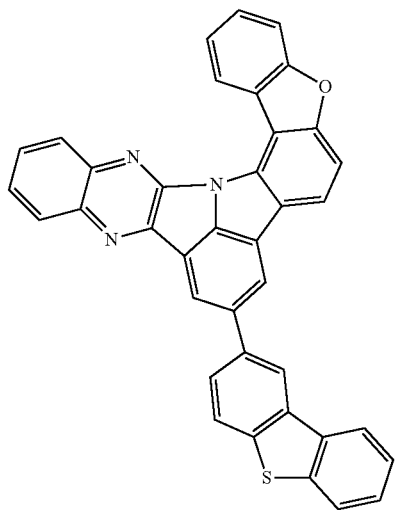
A-304
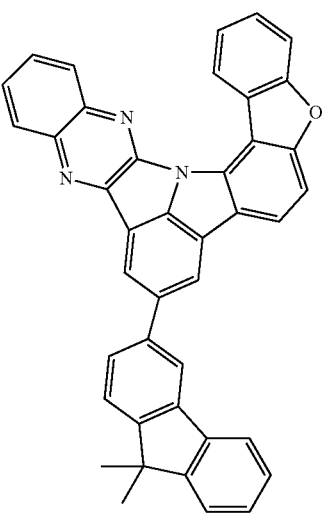
A-305
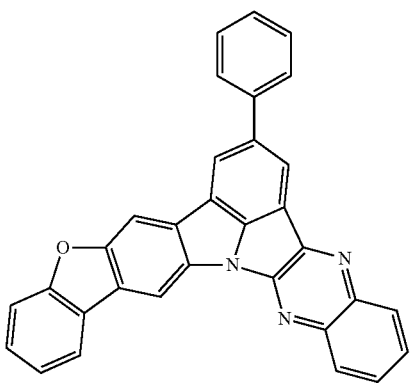

A-306
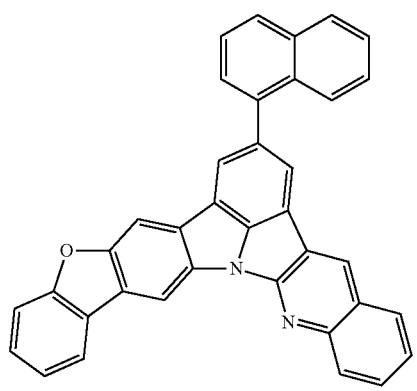
A-307
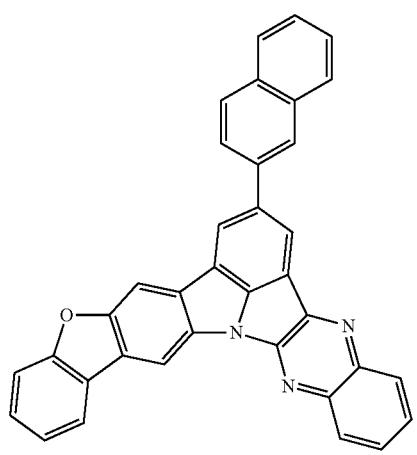
A-308
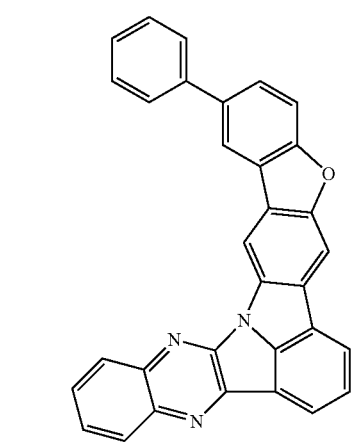
A-309
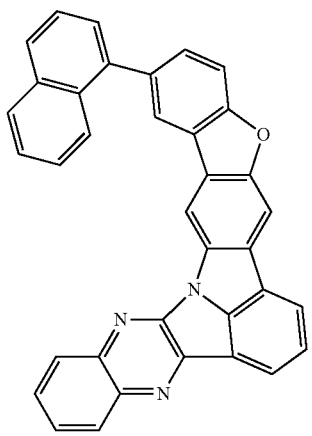
A-310
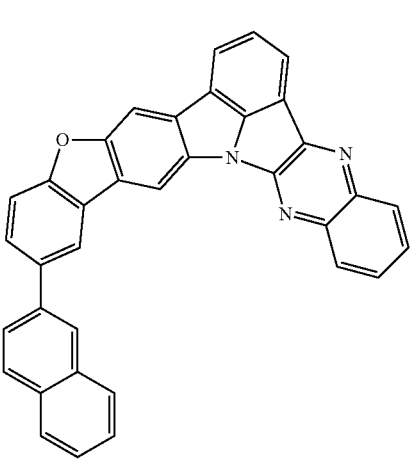
A-311
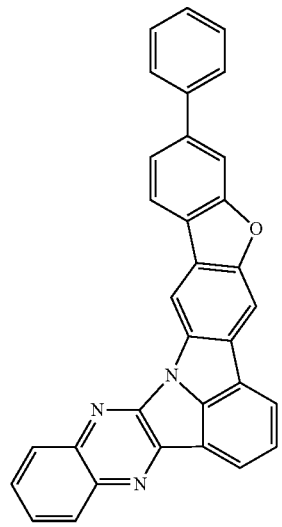

-continued
A-312
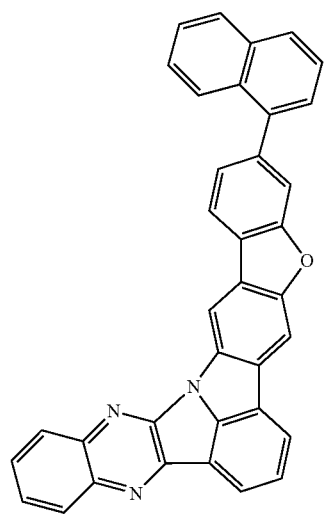
A-313
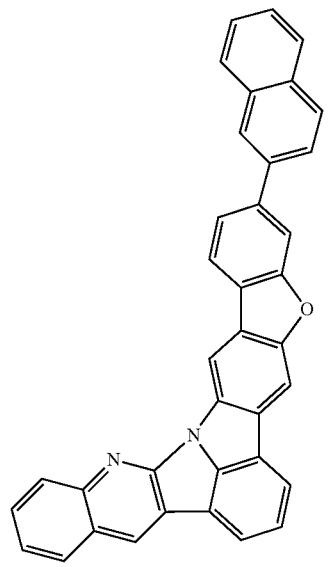
A-314
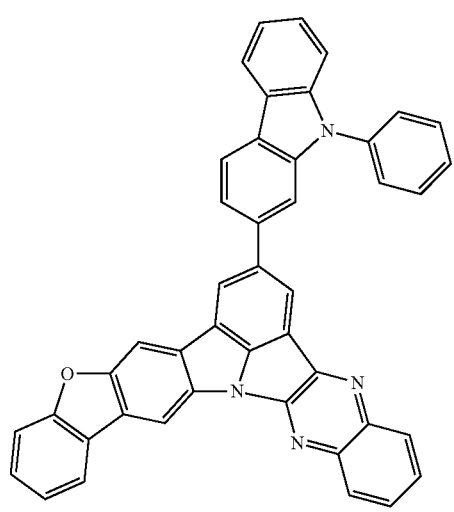
-continued
A-315
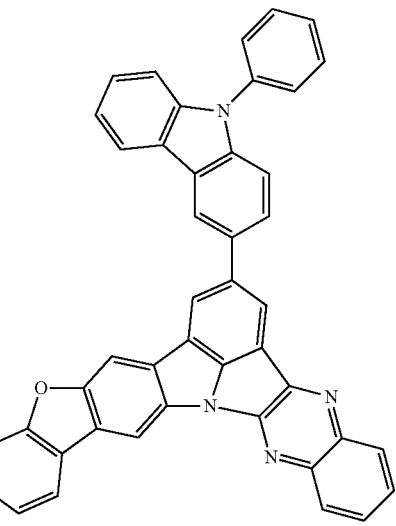
A-316
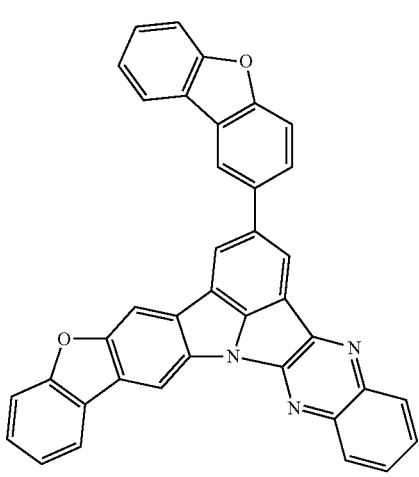
A-317
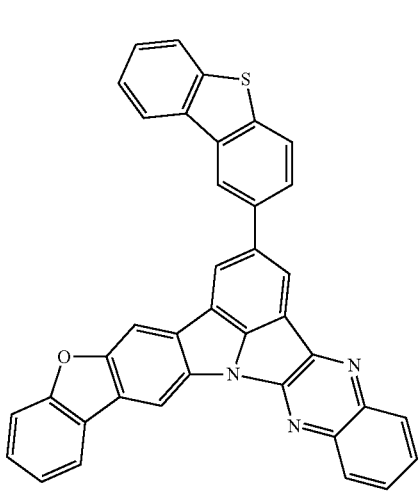

-continued
A-318
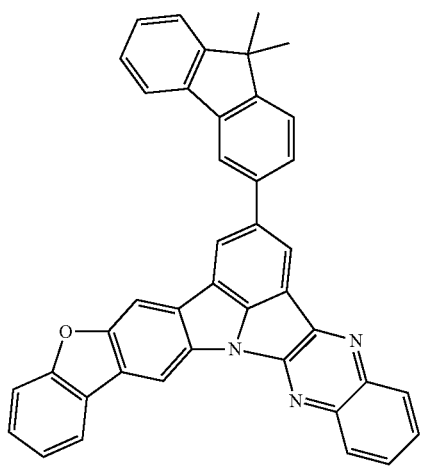
A-319
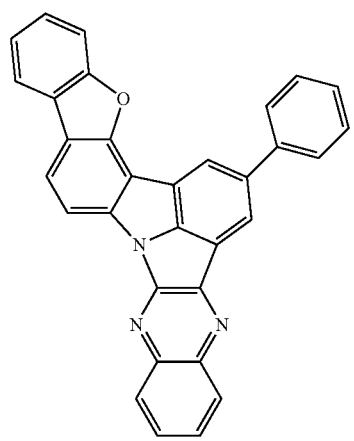
A-320
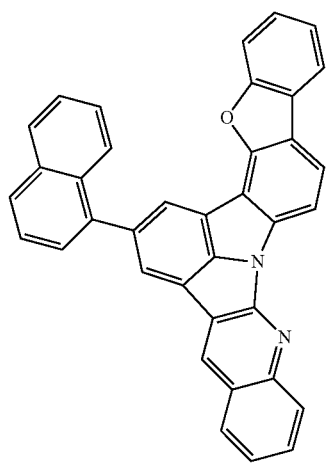
-continued
A-321
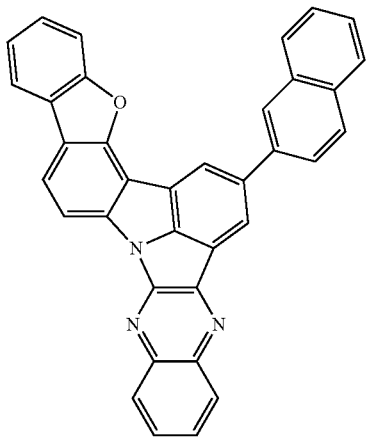
A-322
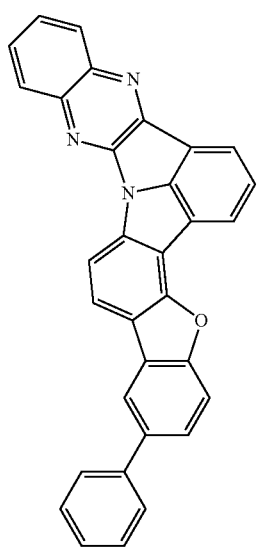
A-323
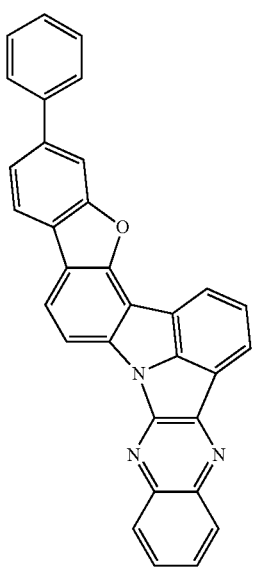

-continued
A-324
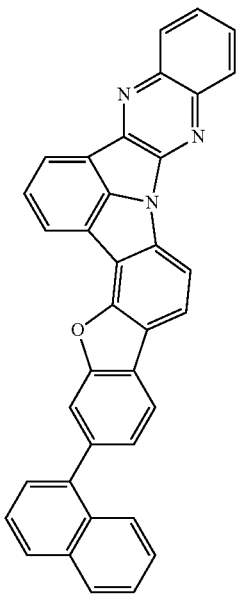
A-325
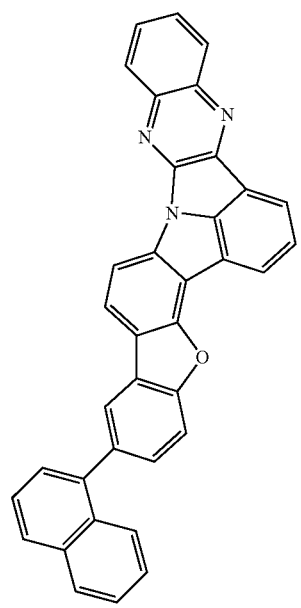
A-326
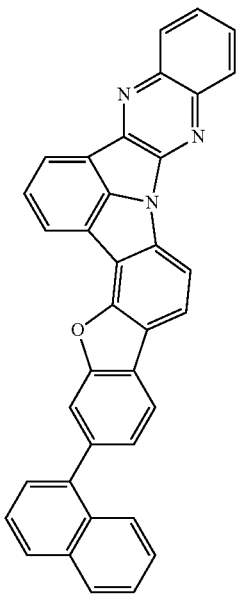
A-327
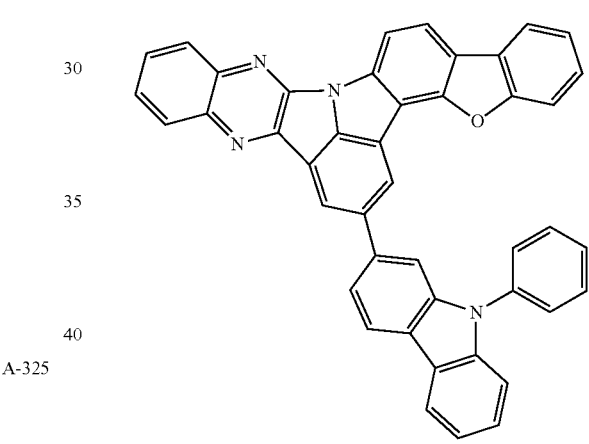
A-328
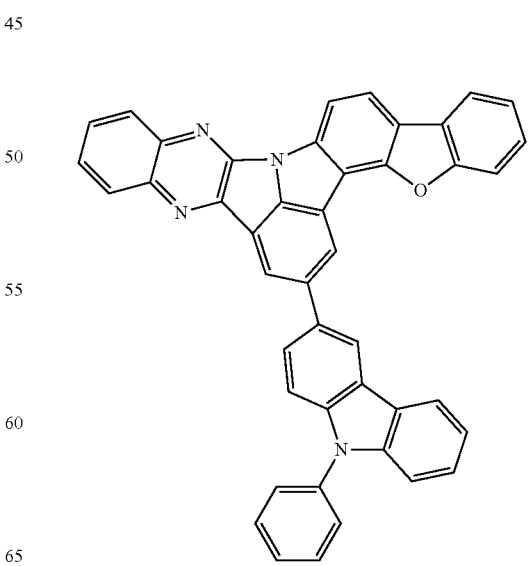

A-329
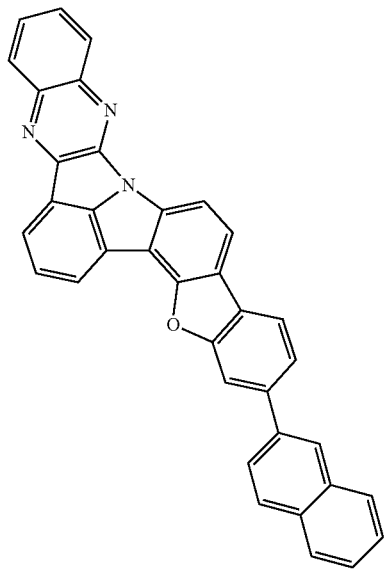
A-330
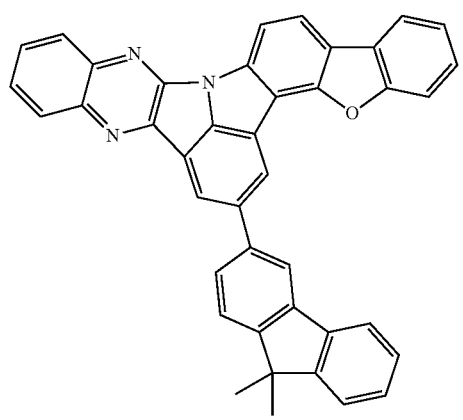
A-331
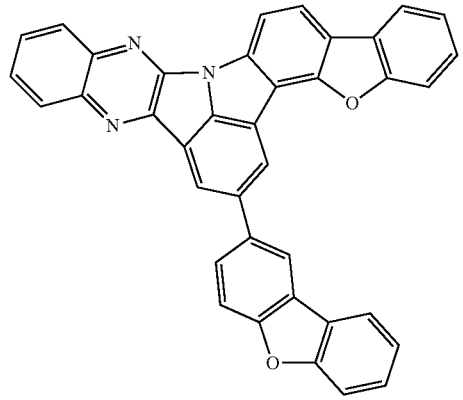
A-332
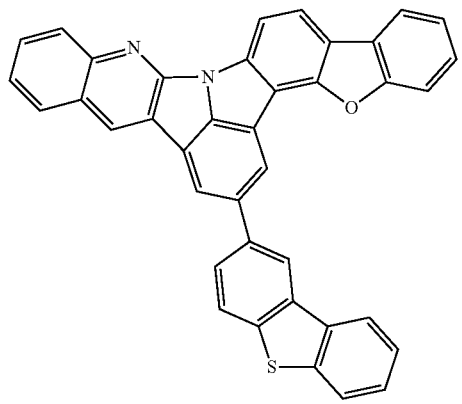
A-333
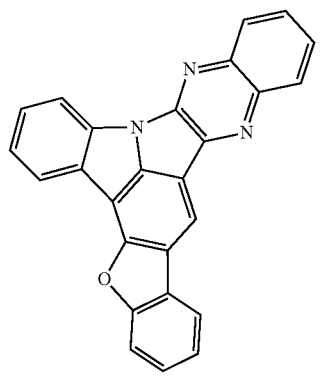
A-334
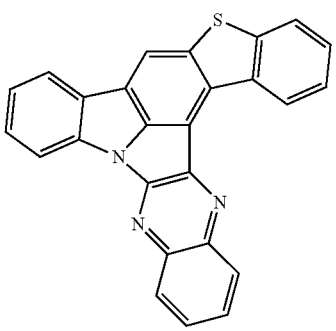
A-335
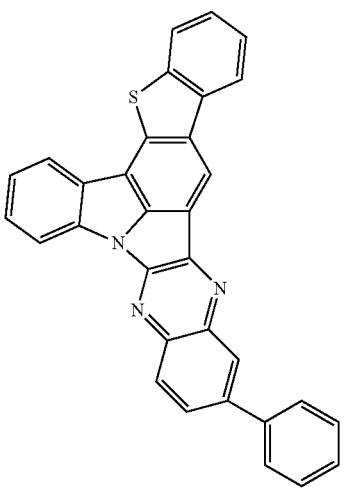

A-336
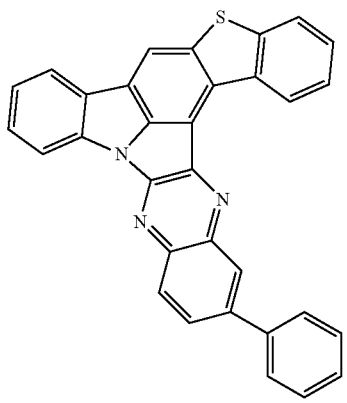
A-337
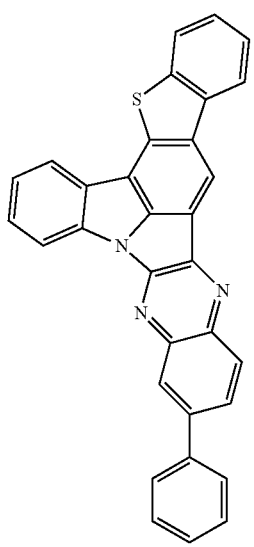
A-338
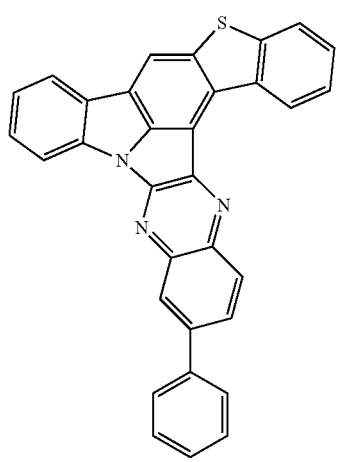
A-339
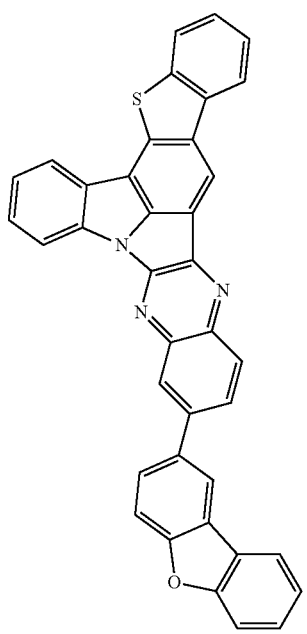
A-339-1
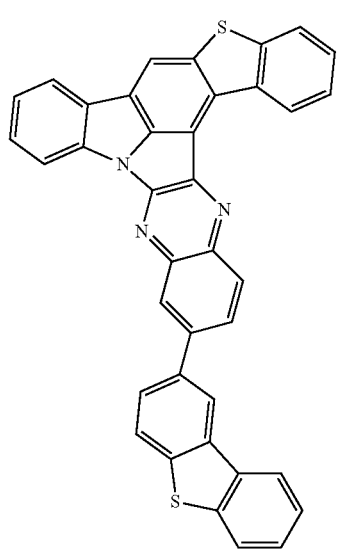
A-340
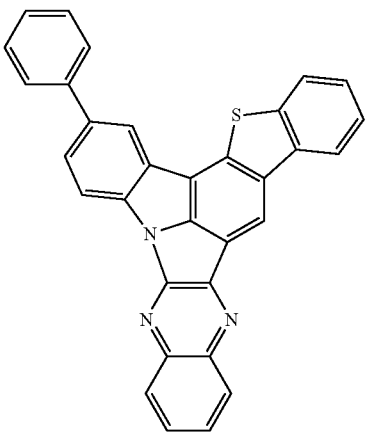

A-341
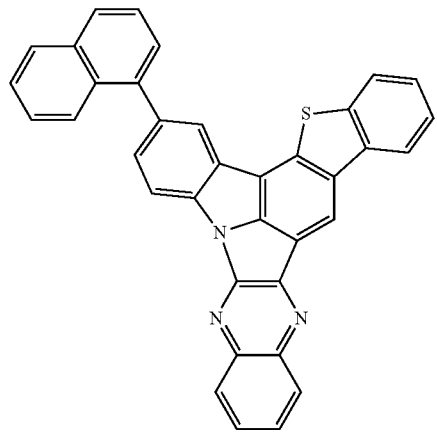
A-342
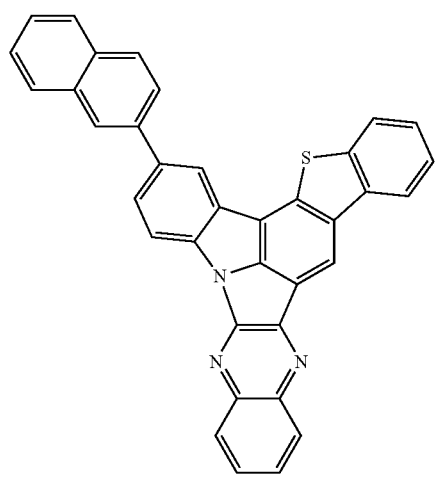
A-343
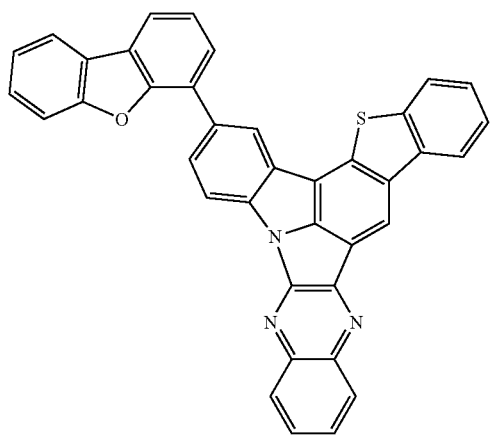
A-344
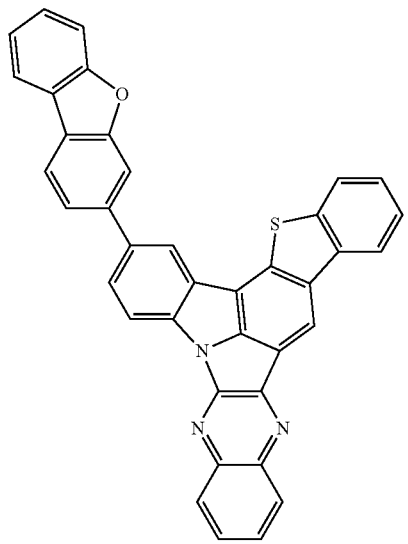
A-345
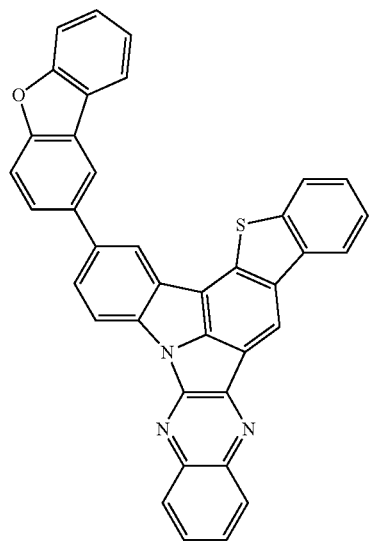
A-346
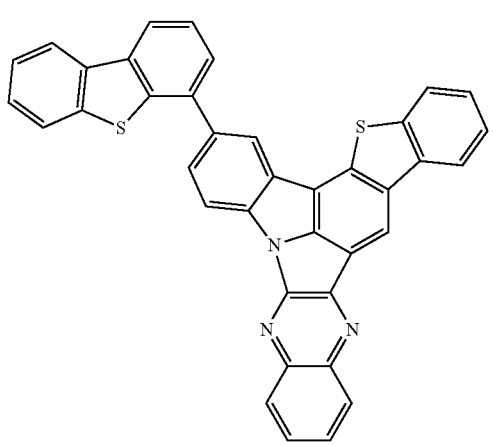

-continued
A-347
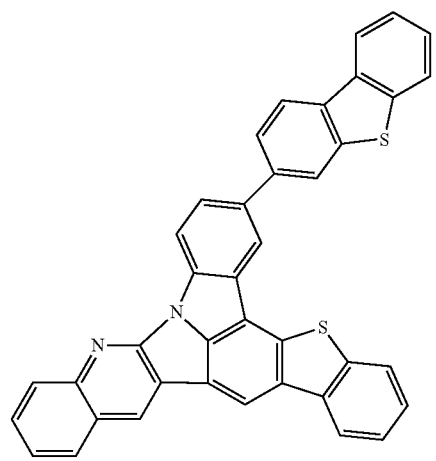
A-348
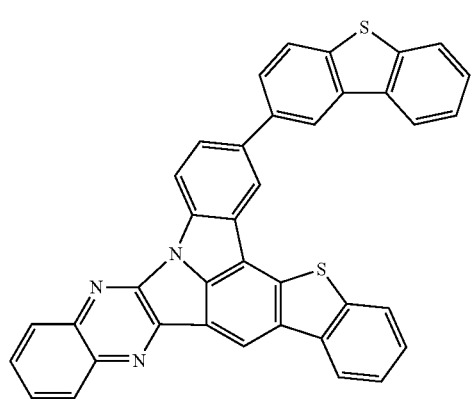
A-349
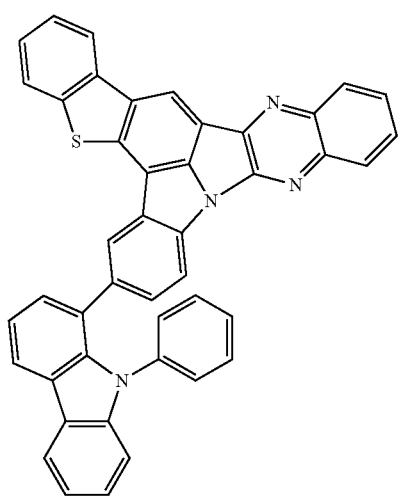
-continued
A-350
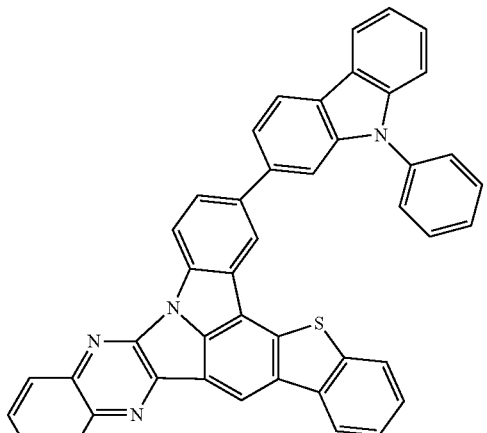
A-351
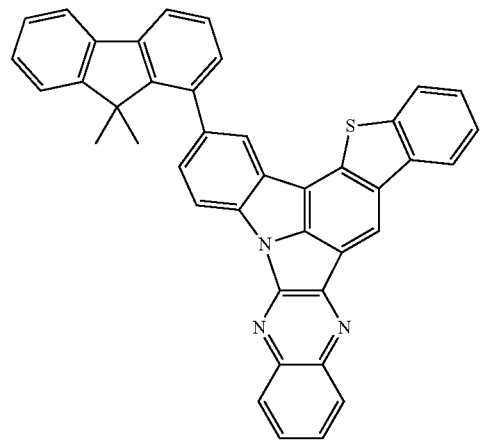
A-352
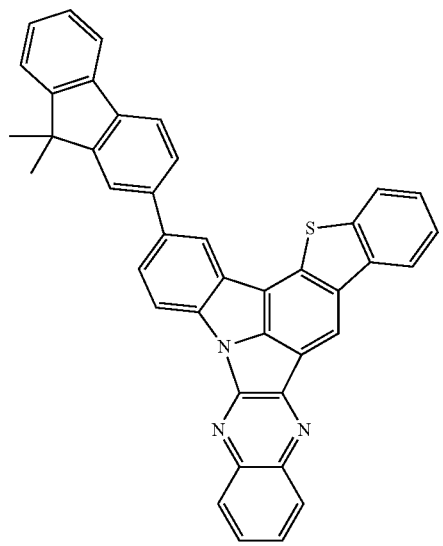

357
-continued
A-353
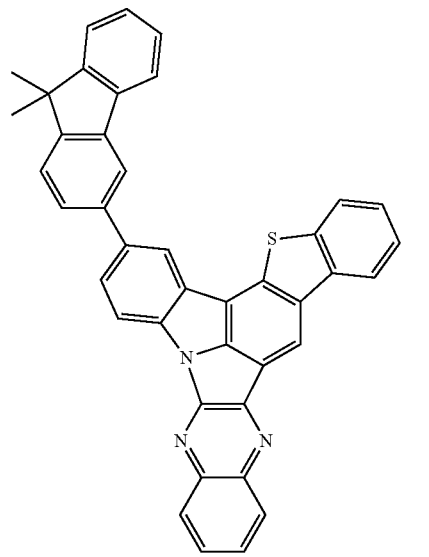
A-354
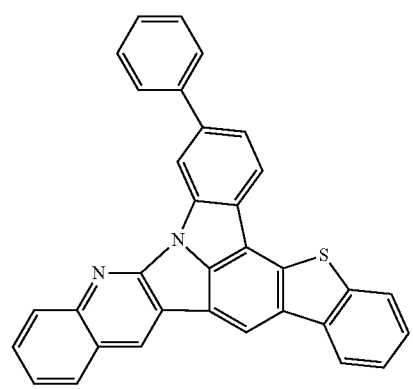
A-355
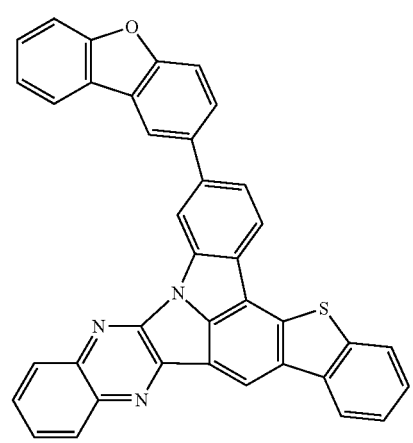
A-356
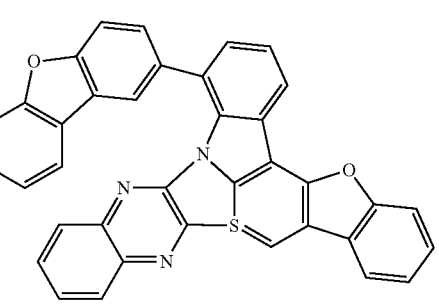
358
-continued
A-357
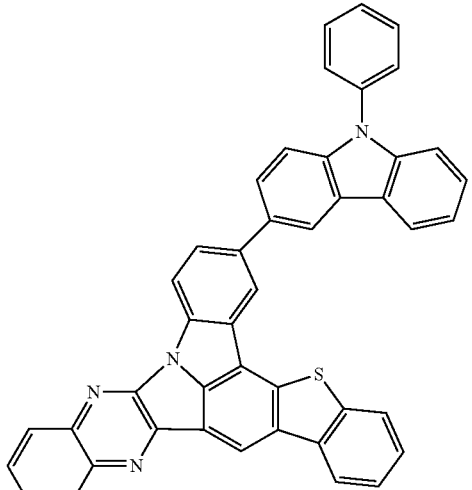
A-358
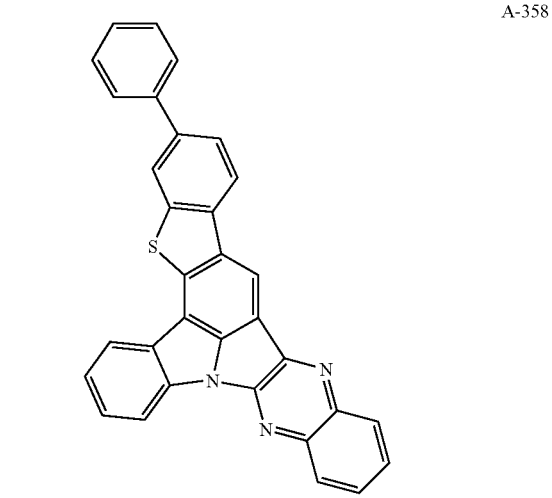
A-359
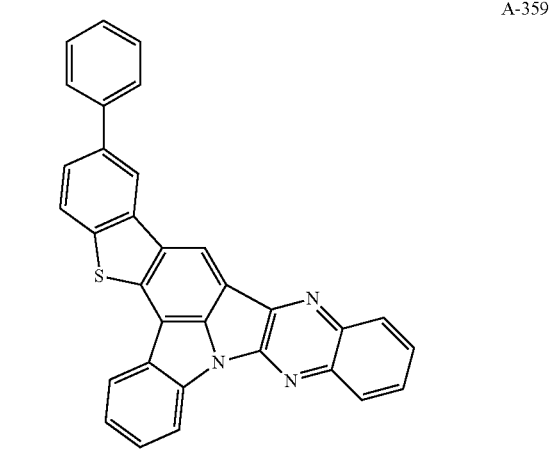

-continued
A-360
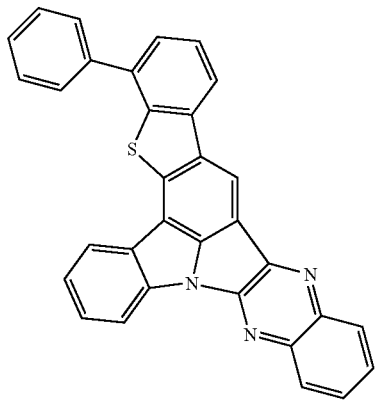
A-361
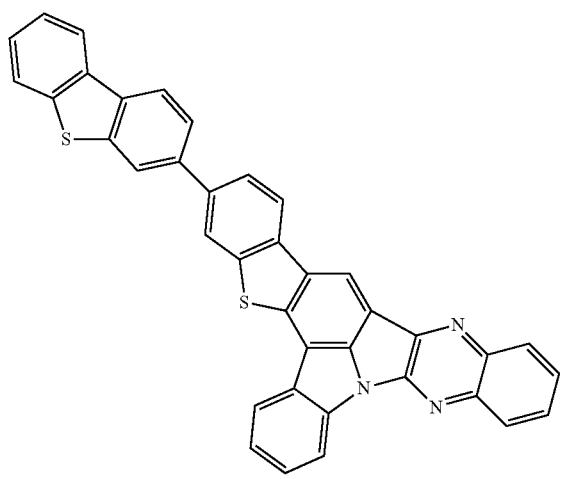
A-362
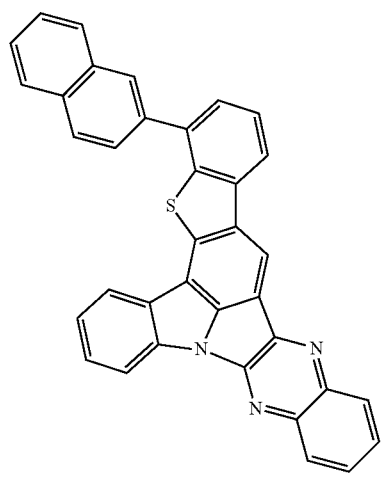
-continued
A-363
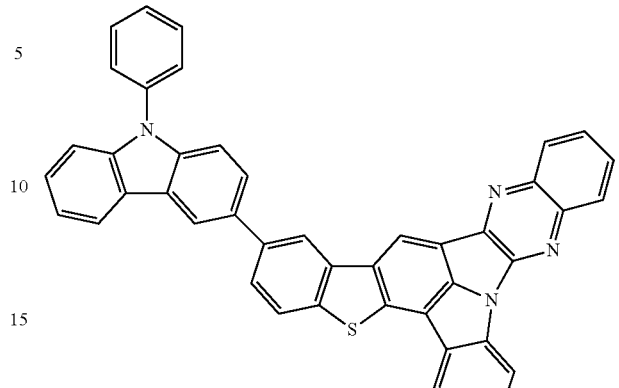
A-364
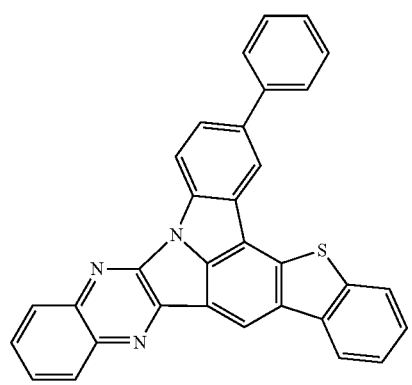
A-365
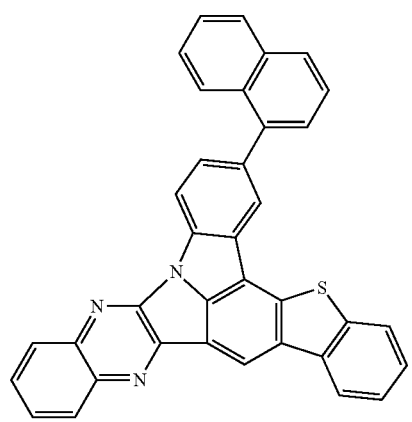
A-366
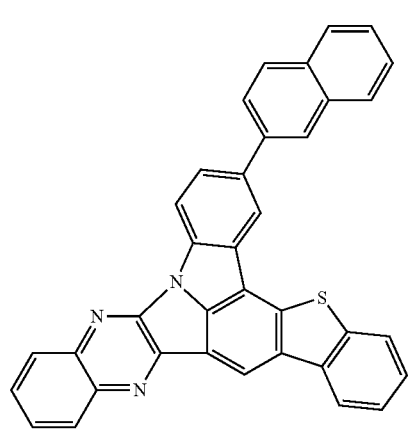

-continued
A-367
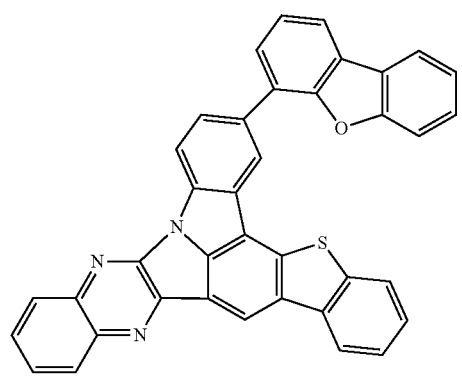
A-368
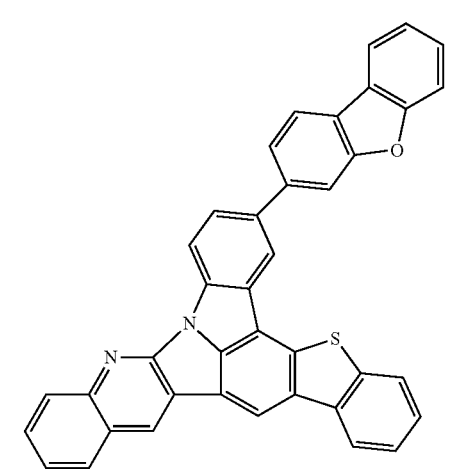
A-369
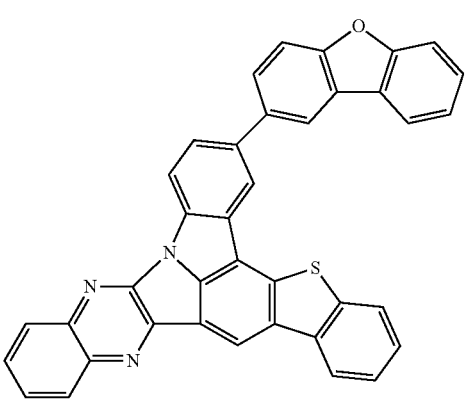
A-370
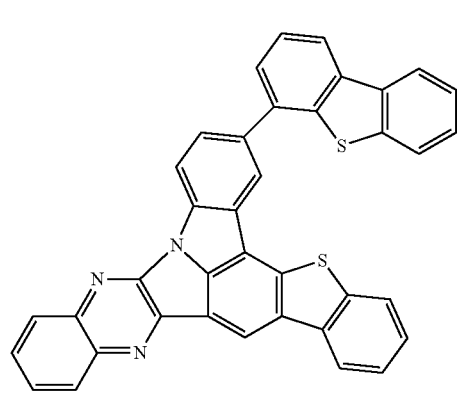
-continued
A-371
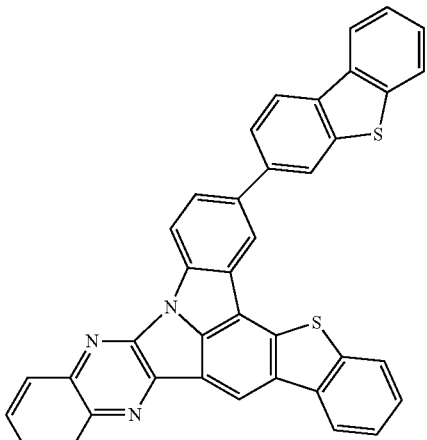
A-372
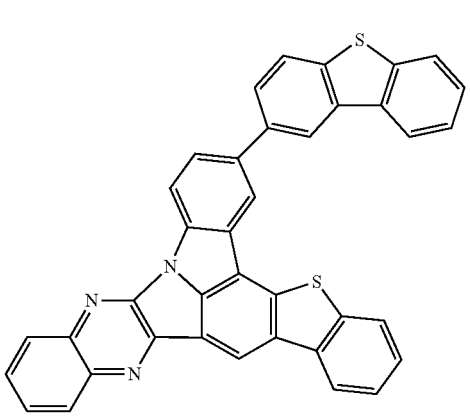
A-373
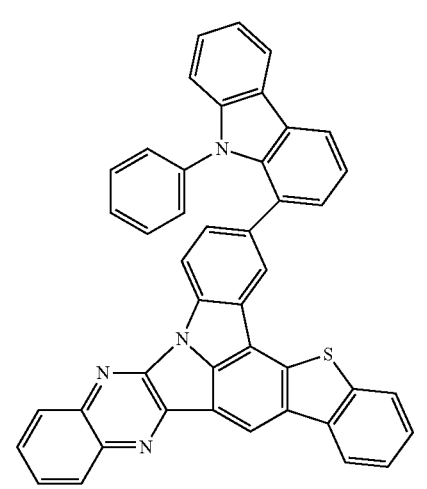

-continued
A-374
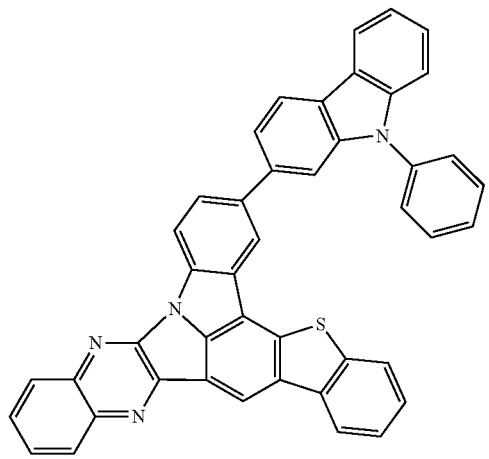
A-375
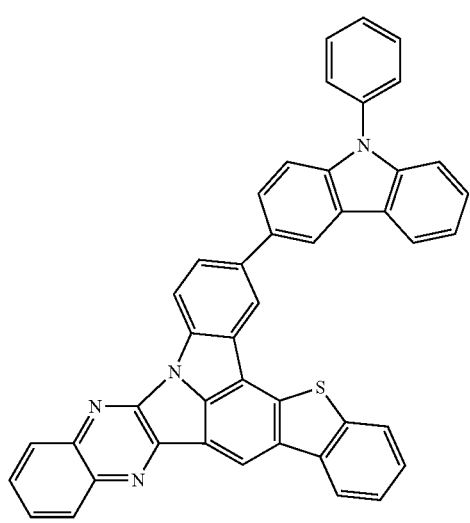
A-376
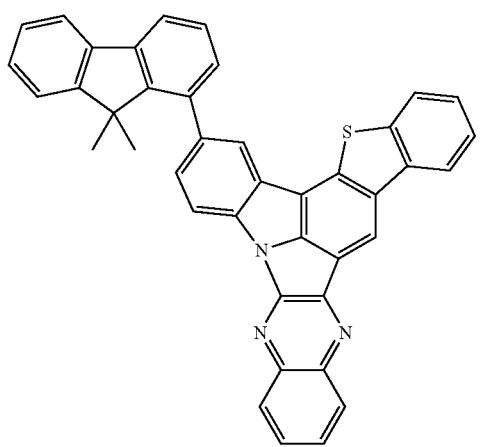
-continued
A-377
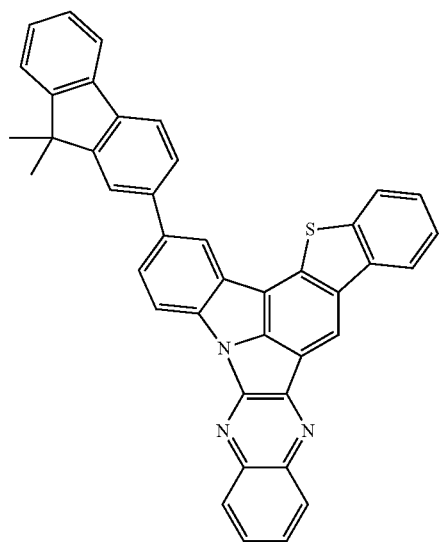
A-378
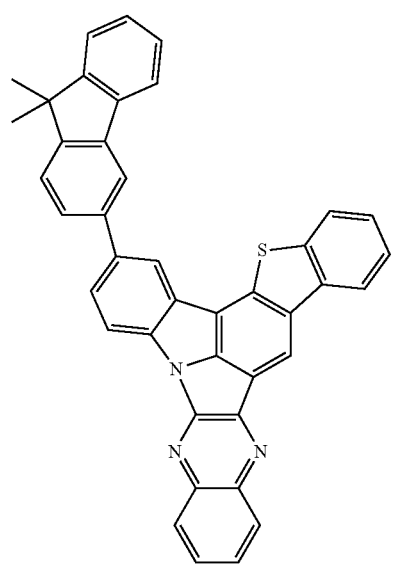
A-379
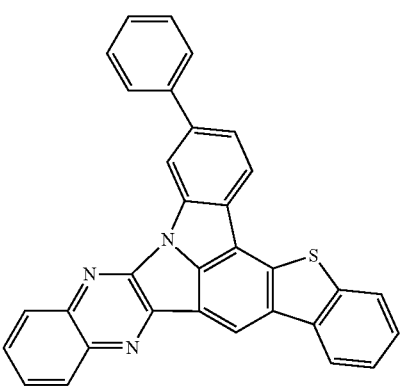

A-380
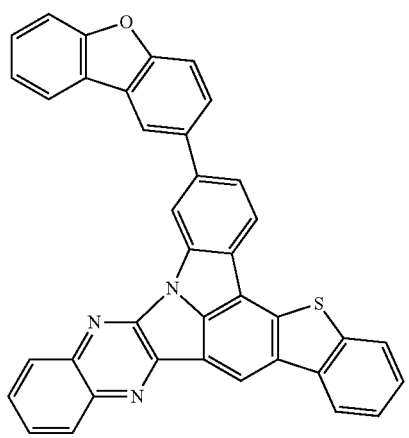
A-381
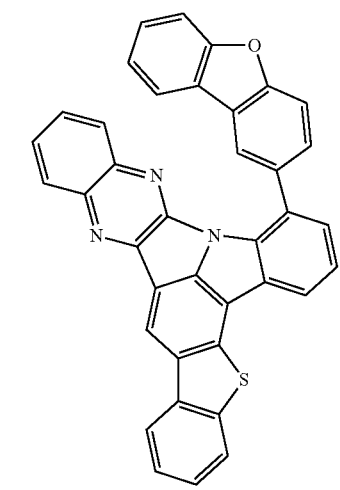
A-382
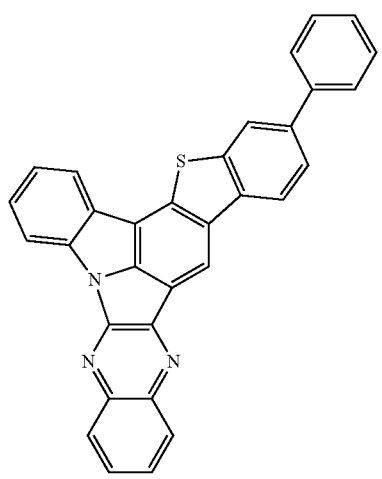
A-383
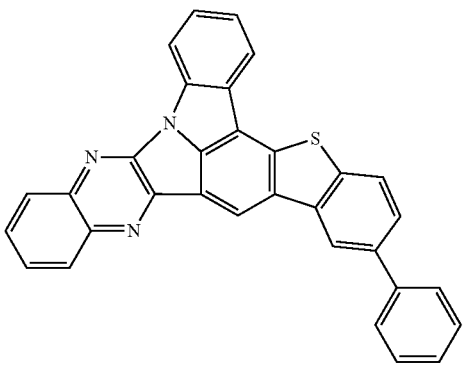
A-384
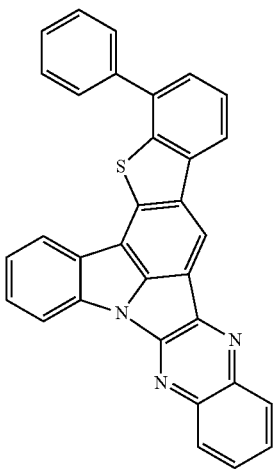
A-385
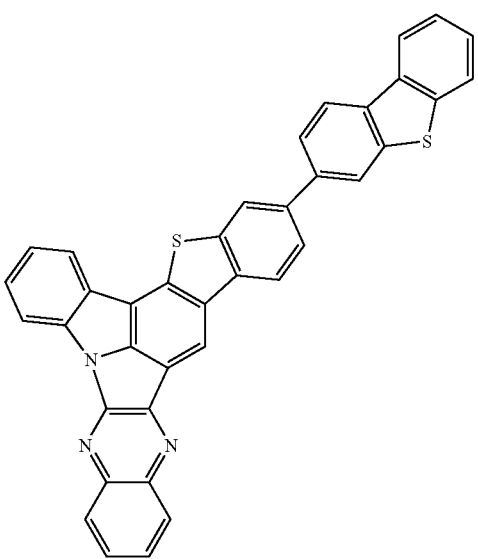

A-386
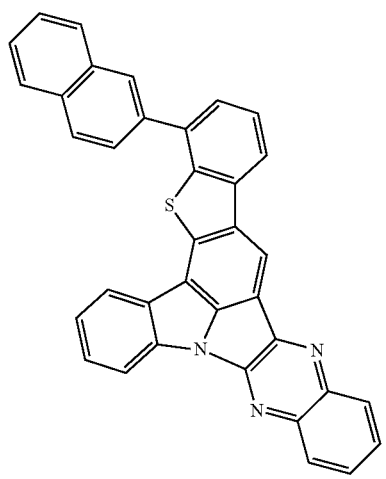
A-387
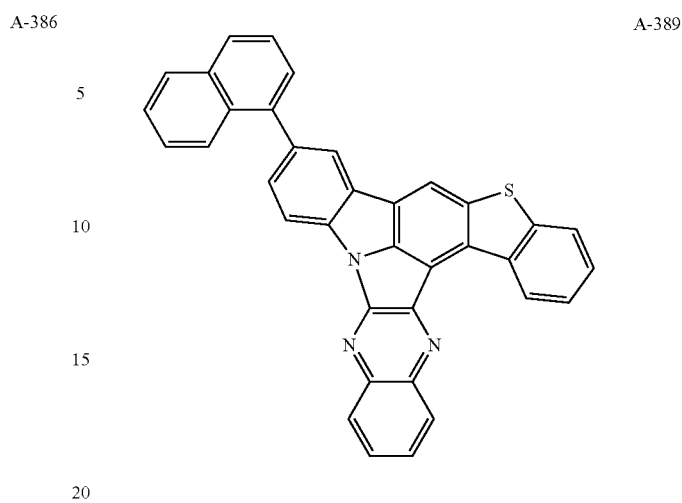
A-388
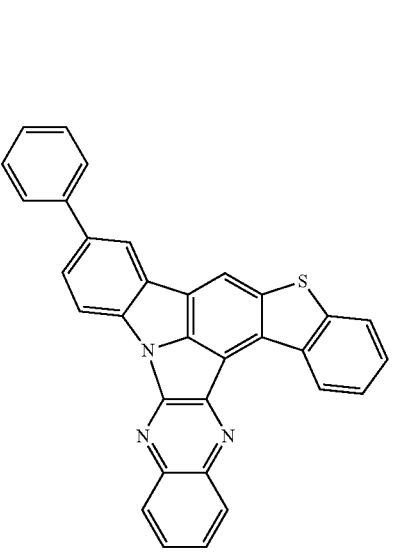
A-389
A-390
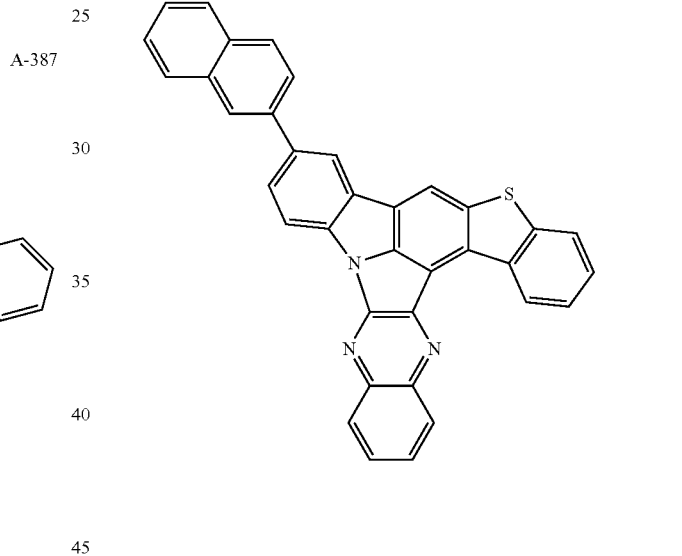
A-391
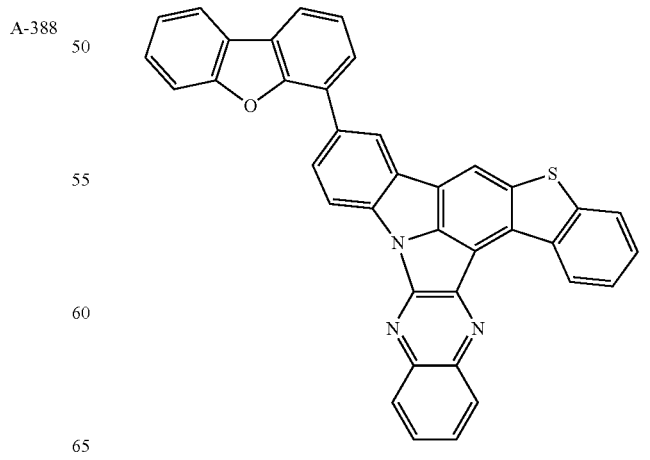

-continued
A-392
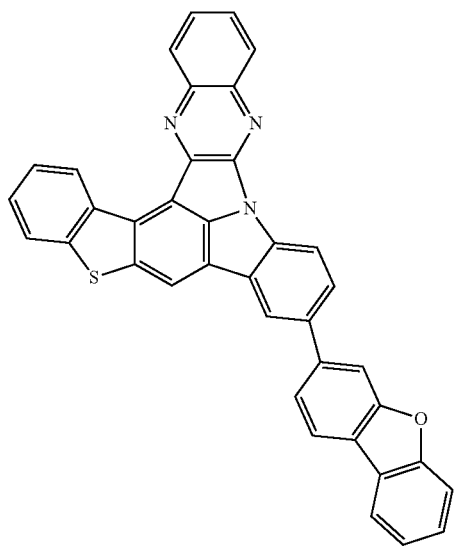
A-393
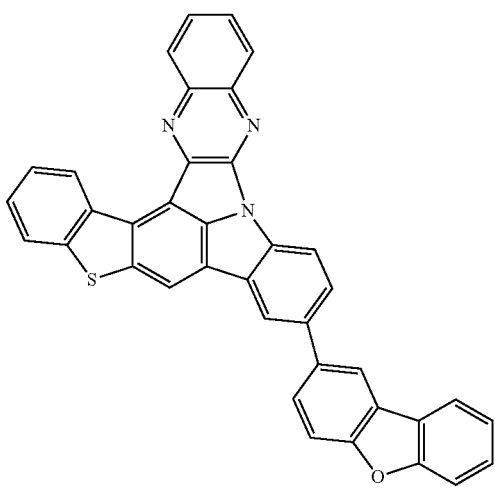
A-394
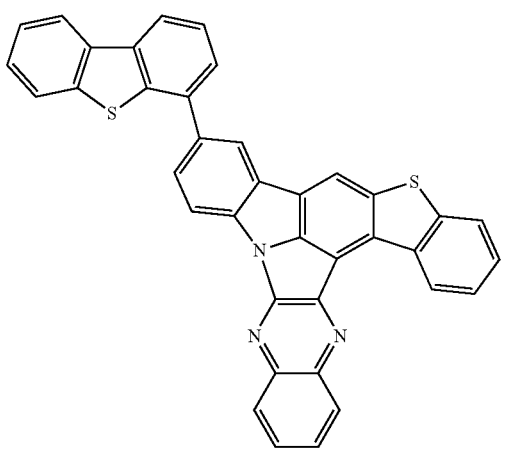
-continued
A-395
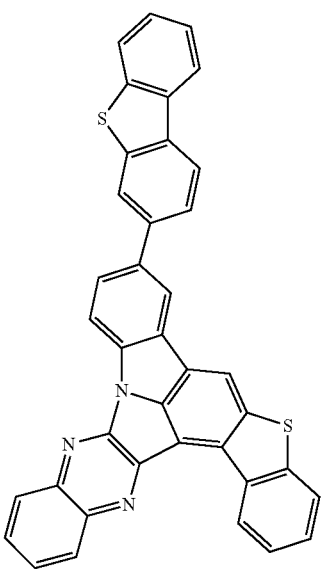
A-396
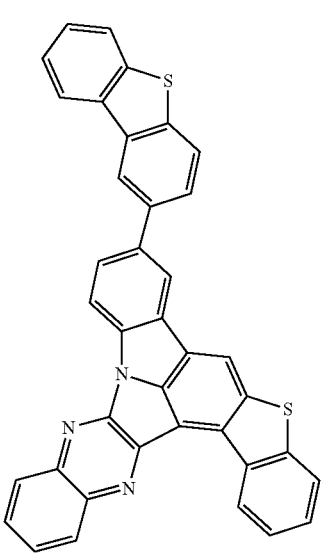
A-397
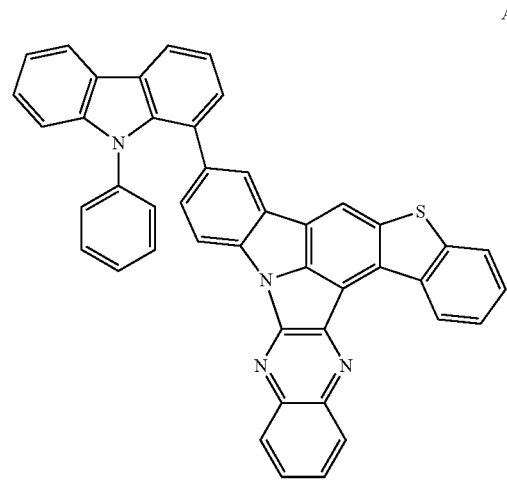

A-398
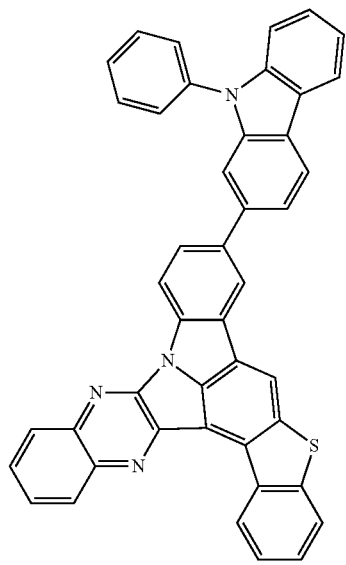
A-399
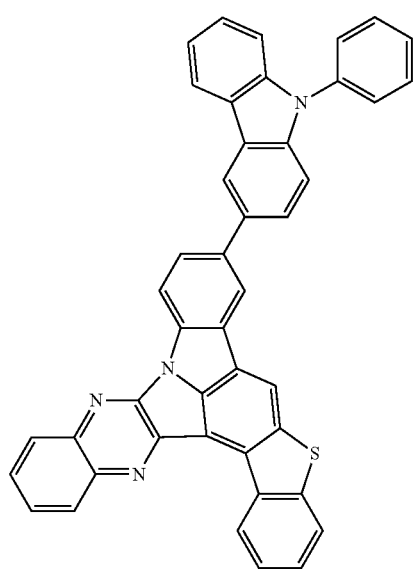
A-400
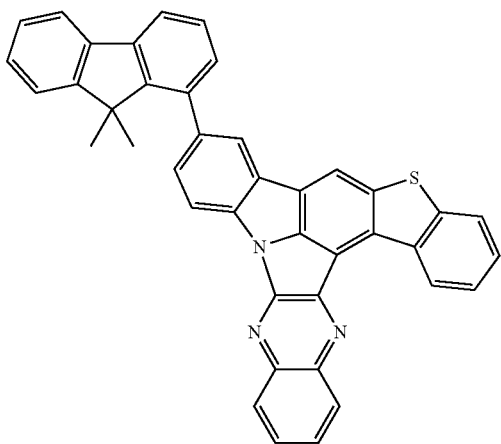
A-401
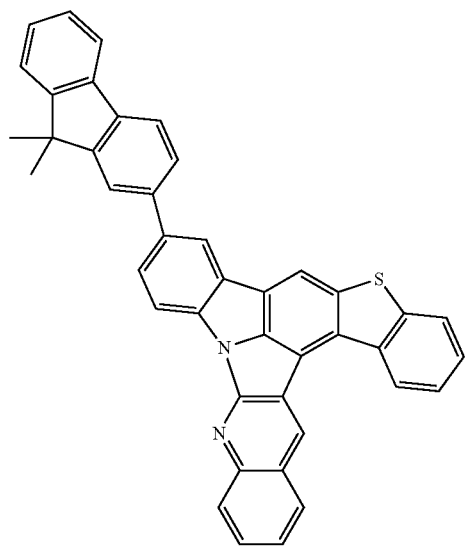
A-402
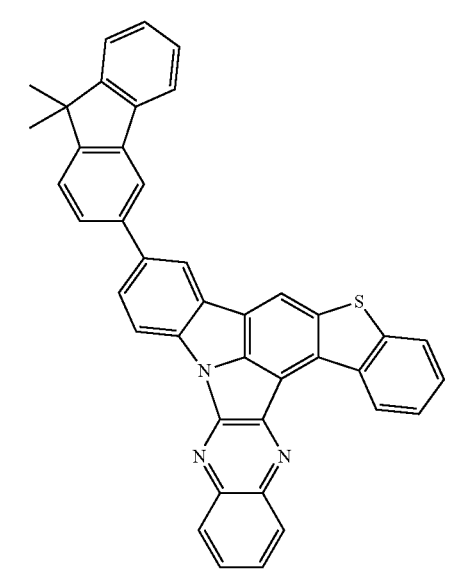
A-403
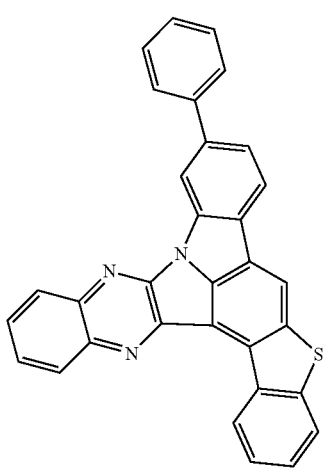

A-404
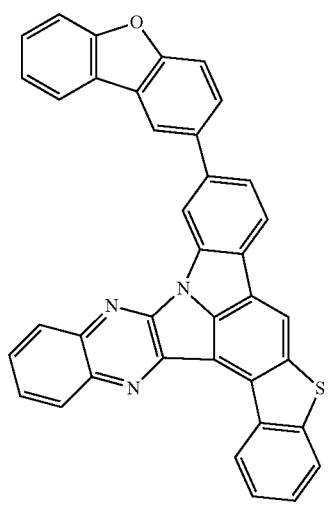
A-405
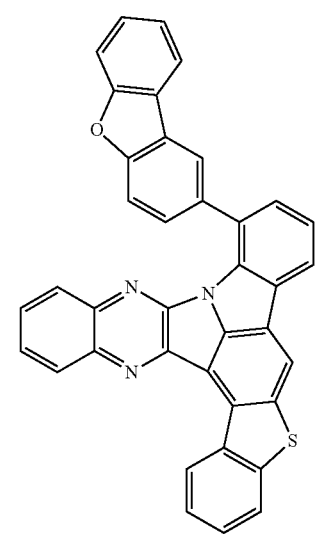
A-406
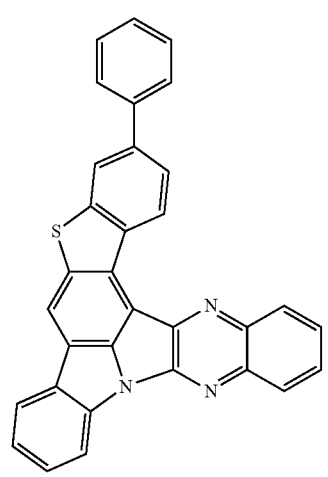
A-407
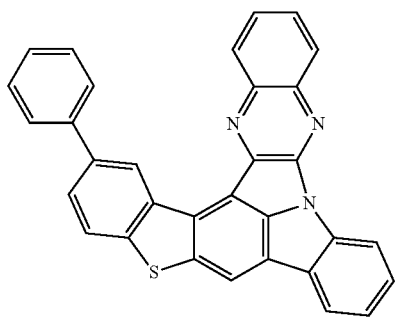
A-408
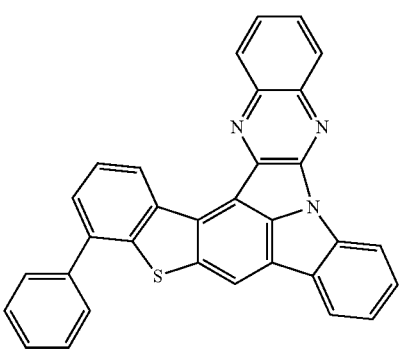
A-409
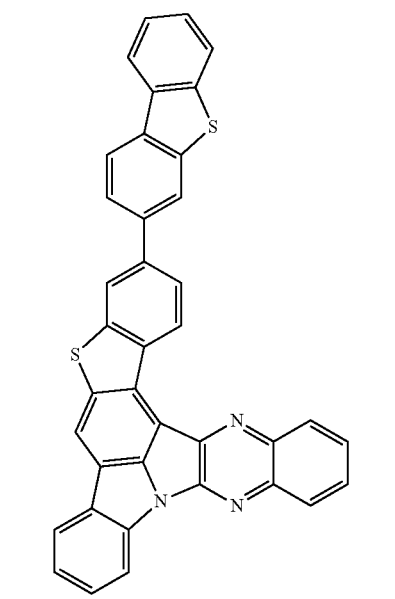

A-410
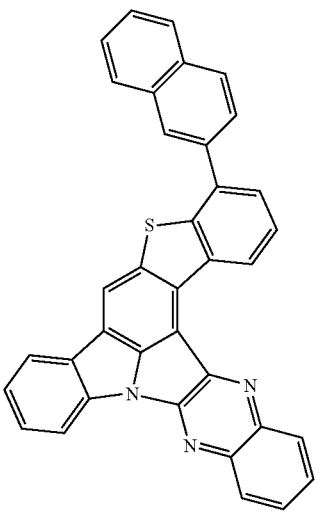
A-411
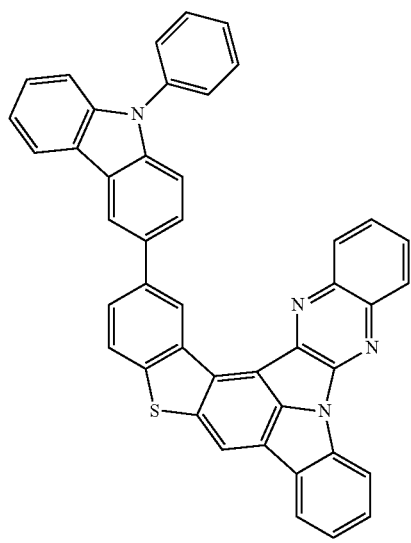
A-412
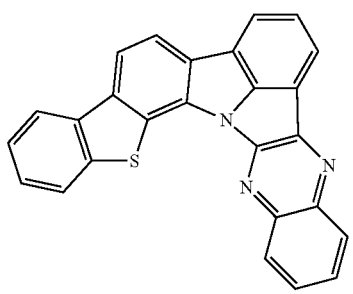
A-413
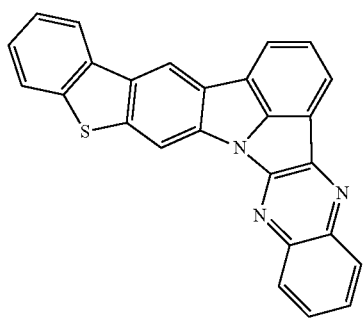
A-414
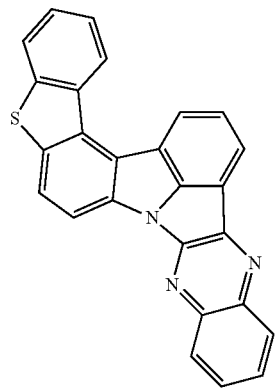
A-415
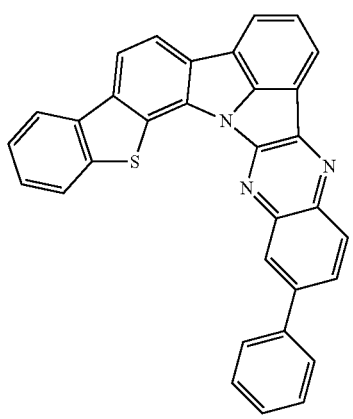
A-416
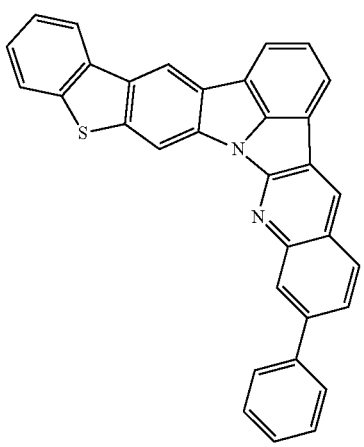

-continued
A-417
A-418
A-419
A-420
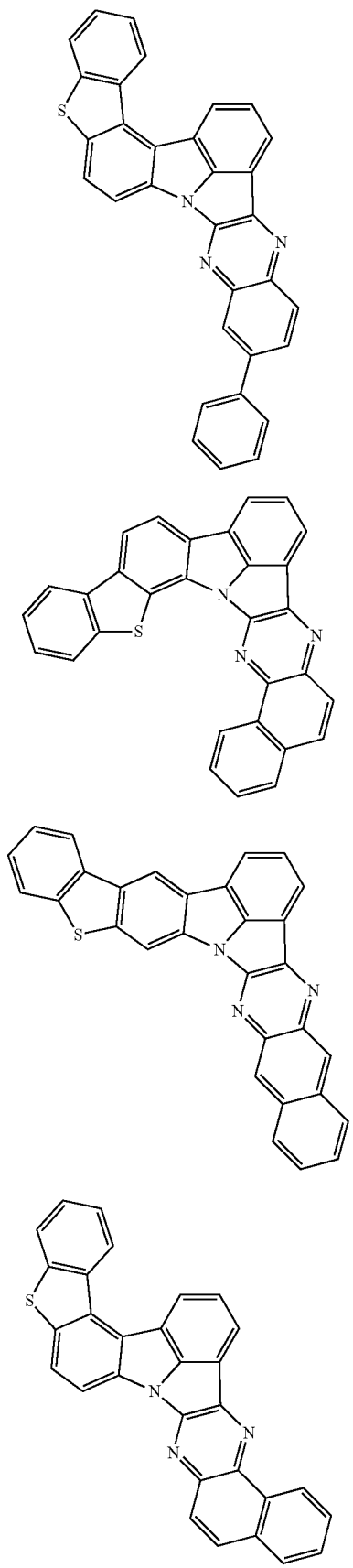
-continued
A-421
A-422
A-423
A-424
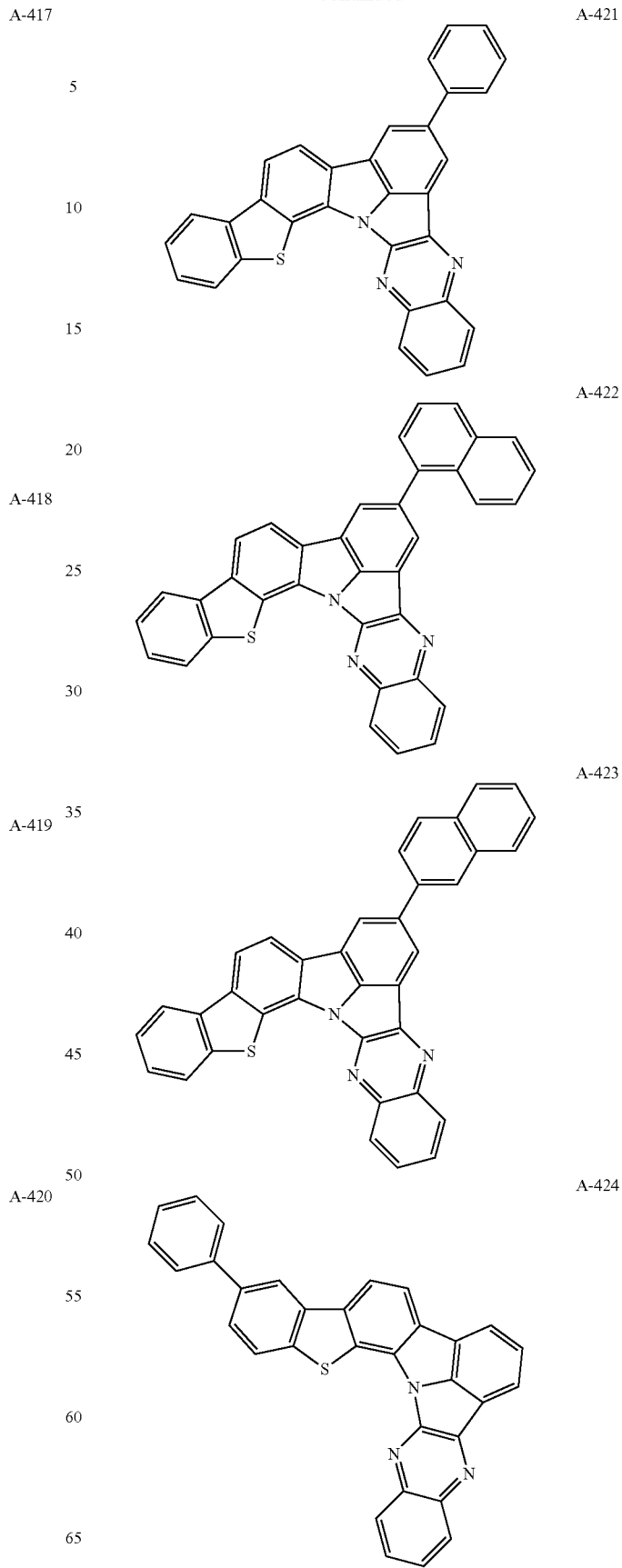

-continued
A-425
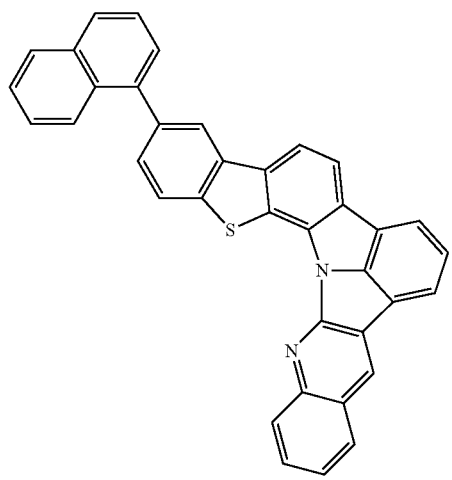
A-426
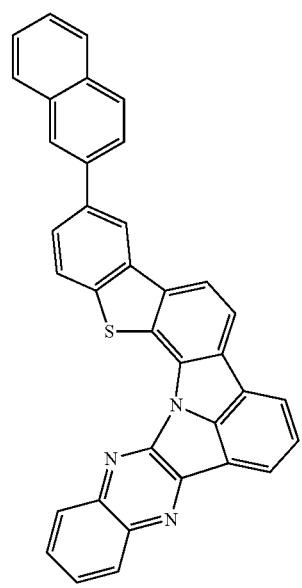
A-427
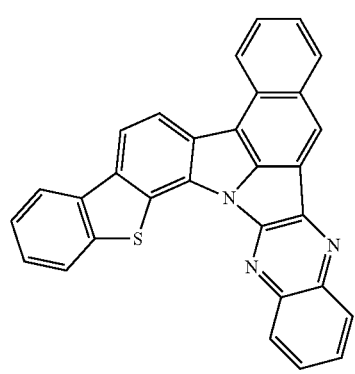
-continued
A-428
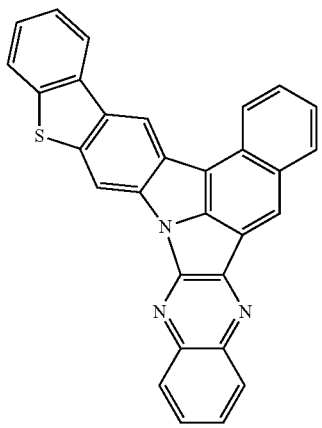
A-429
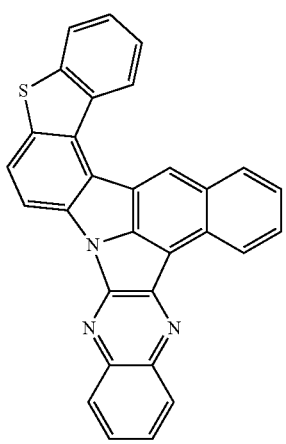
A-430
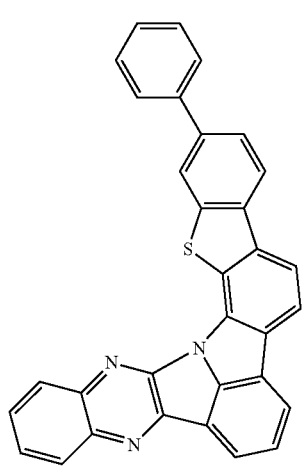

A-431
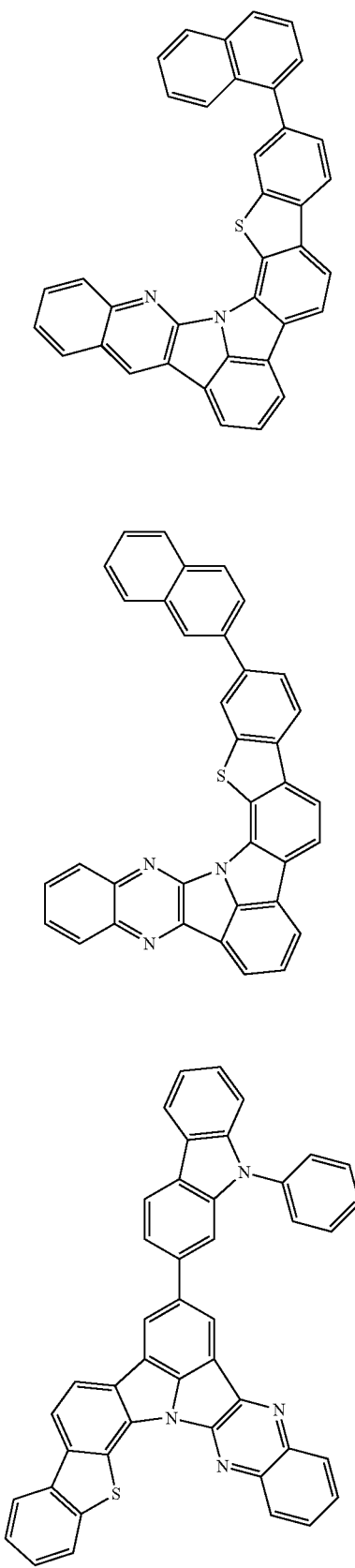
A-432
A-434
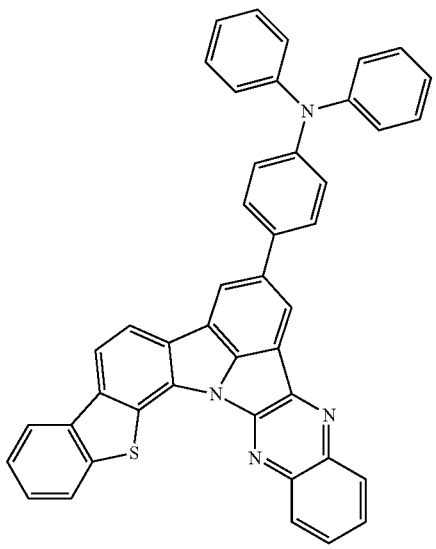
A-435
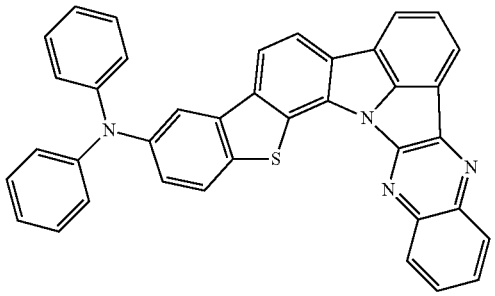
A-436
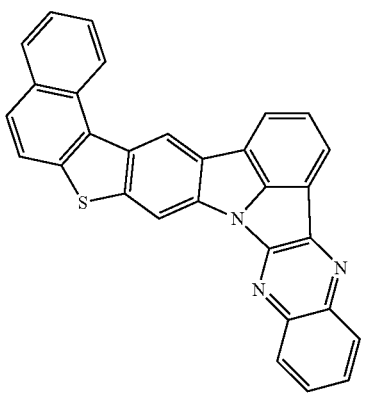
A-433
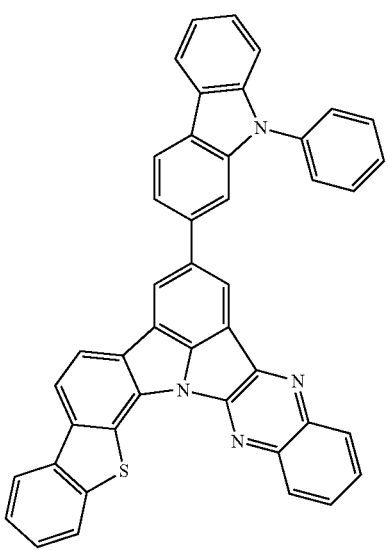
A-437
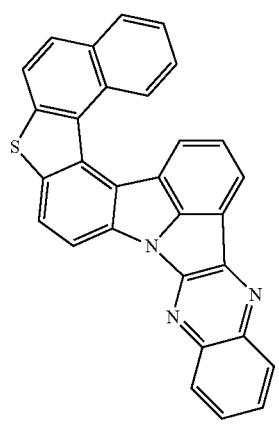

A-438
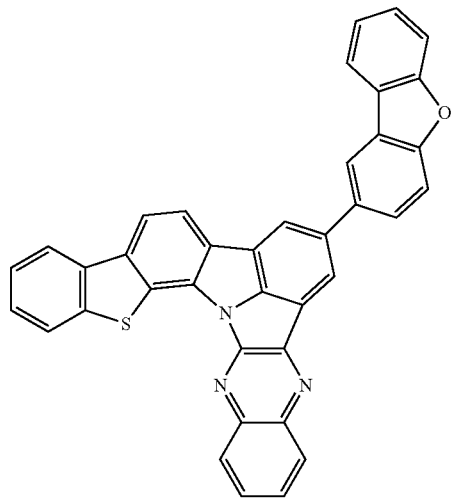
A-441
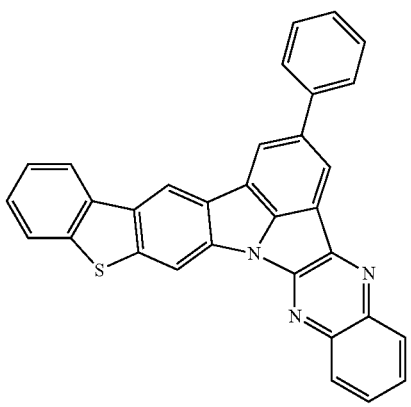
A-439
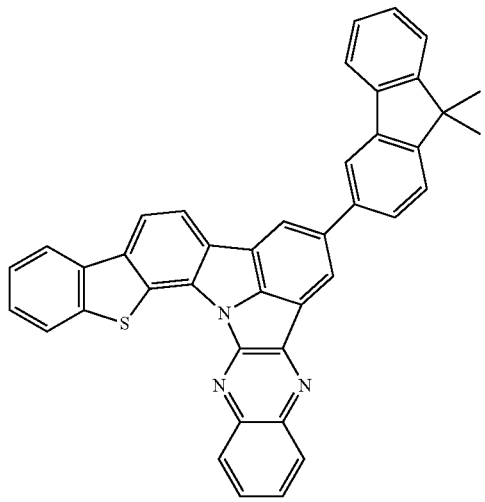
A-442
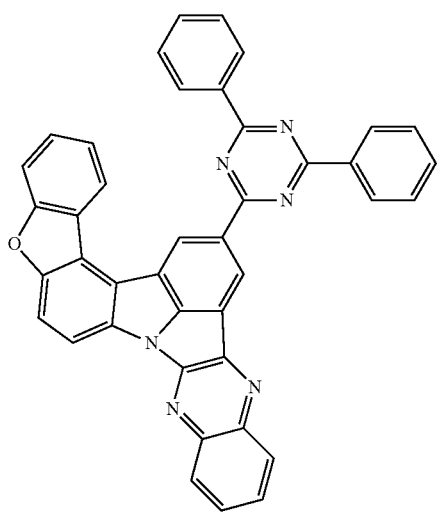
A-440
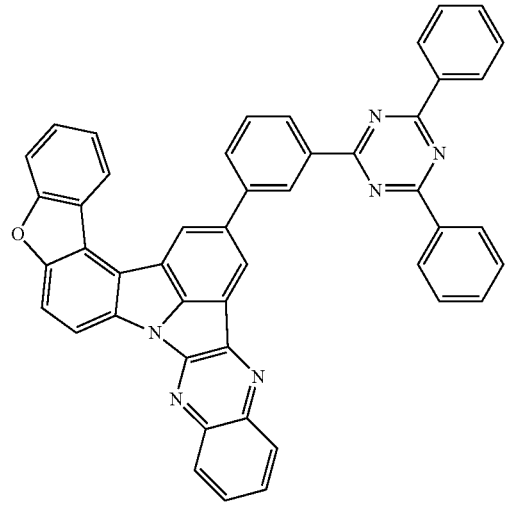
A-443

A-444
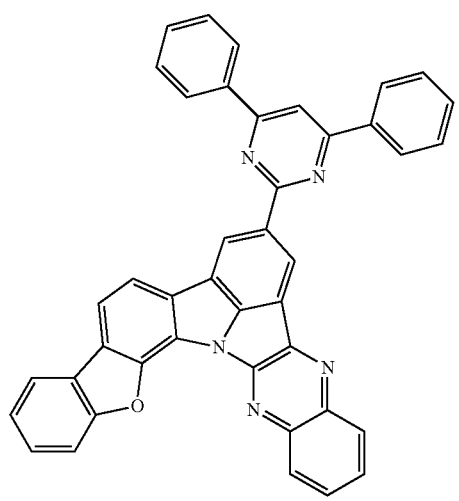
A-445
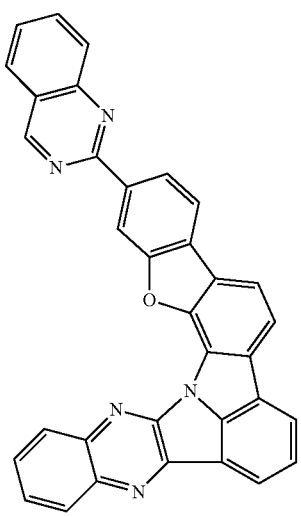
A-446
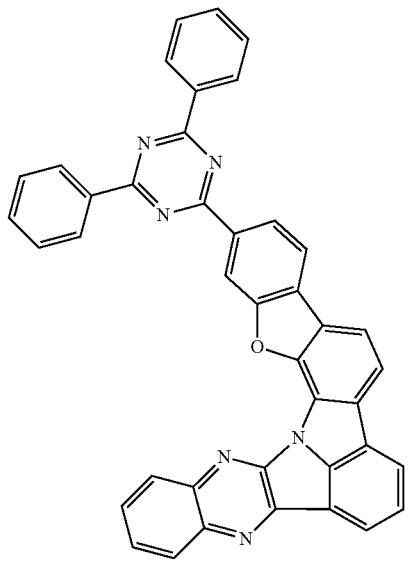
A-447
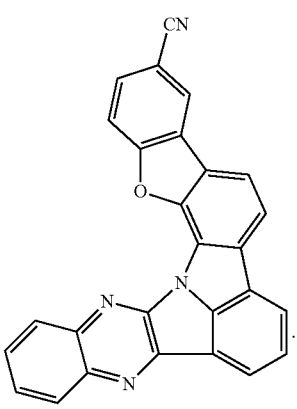
6. An organic electroluminescent device comprising the organic electroluminescent compound according to claim 1.
* * * * *